United States Patent
Dylla et al.

(10) Patent No.: US 9,778,264 B2
(45) Date of Patent: *Oct. 3, 2017

(54) IDENTIFICATION AND ENRICHMENT OF CELL SUBPOPULATIONS

(71) Applicant: STEM CENTRX, INC., South San Francisco, CA (US)

(72) Inventors: Scott J. Dylla, Emerald Hills, CA (US); Marianne Santaguida, Redwood City, CA (US); Wade C. Anderson, Fairfield, CA (US); Bob Y. Liu, South San Francisco, CA (US); Samuel A. Williams, San Mateo, CA (US)

(73) Assignee: ABBVIE STEMCENTRX LLC, North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/454,107

(22) Filed: Aug. 7, 2014

(65) Prior Publication Data

US 2015/0030636 A1    Jan. 29, 2015

Related U.S. Application Data

(63) Continuation of application No. PCT/US2013/025361, filed on Feb. 8, 2013, and a continuation-in-part of application No. 13/820,061, said application No. PCT/US2013/025361 is a continuation of application No. 13/414,666, filed on Mar. 7, 2012, now abandoned, and a continuation-in-part of application No. 13/369,277, filed on Feb. 8, 2012, now abandoned, said application No. 13/820,061 is a continuation of application No. PCT/US2011/050451, filed on Sep. 2, 2011.

(60) Provisional application No. 61/510,413, filed on Jul. 21, 2011, provisional application No. 61/380,181, filed on Sep. 3, 2010.

(51) Int. Cl.
| A61K 38/00 | (2006.01) |
| G01N 33/574 | (2006.01) |
| A61K 39/00 | (2006.01) |
| C12N 5/09 | (2010.01) |
| A61K 49/00 | (2006.01) |

(52) U.S. Cl.
CPC .... G01N 33/57492 (2013.01); A61K 39/0011 (2013.01); C12N 5/0693 (2013.01)

(58) Field of Classification Search
None
See application file for complete search history.

(56) References Cited

U.S. PATENT DOCUMENTS

| 5,552,381 A | 9/1996 | Atkinson et al. |
| 6,004,528 A | 12/1999 | Bergstein |
| 6,107,540 A | 8/2000 | Sawyer et al. |
| 6,117,985 A | 9/2000 | Thomas et al. |
| 6,984,522 B2 | 1/2006 | Clarke et al. |
| 7,148,038 B2 | 12/2006 | Mather |
| 7,563,619 B2 | 7/2009 | Williams et al. |
| 7,632,678 B2 | 12/2009 | Hansford et al. |
| 7,744,878 B2 | 6/2010 | Mather |
| 7,781,179 B2 | 8/2010 | Weissman et al. |
| 8,038,996 B2 | 10/2011 | Mahadevan |
| 8,038,998 B2 | 10/2011 | Bergstein |
| 8,044,259 B2 | 10/2011 | Clarke et al. |
| 8,148,147 B2 | 4/2012 | Simeone et al. |
| 8,153,421 B2 | 4/2012 | Maitland et al. |
| 8,168,586 B1 | 5/2012 | Fang et al. |
| 8,309,354 B2 | 11/2012 | Mather |
| 2002/0115065 A1 | 8/2002 | Logtenberg et al. |
| 2002/0165188 A1 | 11/2002 | Herlyn et al. |
| 2003/0119080 A1 | 6/2003 | Mangano |
| 2003/0129677 A1 | 7/2003 | Martens et al. |
| 2004/0038281 A1 | 2/2004 | Hung |
| 2006/0019256 A1 | 1/2006 | Clarke et al. |
| 2006/0281136 A1 | 12/2006 | Nishikawa et al. |
| 2007/0128202 A1 | 6/2007 | Mather |
| 2007/0134794 A1 | 6/2007 | Mangano |
| 2007/0248628 A1 | 10/2007 | Keller et al. |
| 2008/0038770 A1 | 2/2008 | Hansford et al. |
| 2008/0064049 A1* | 3/2008 | Clarke ............... C12N 5/0093 435/7.23 |
| 2008/0118432 A1 | 5/2008 | Bergstein et al. |
| 2008/0118518 A1 | 5/2008 | Cirrito et al. |
| 2008/0132423 A1 | 6/2008 | Kondo |
| 2008/0175870 A1* | 7/2008 | Mather ............... C12N 5/0695 424/277.1 |
| 2010/0003265 A1 | 1/2010 | Scheffler et al. |
| 2010/0015046 A1 | 1/2010 | Govindan et al. |

(Continued)

FOREIGN PATENT DOCUMENTS

| CN | 1795379 A | 6/2006 |
| CN | 1940062 B | 4/2010 |

(Continued)

OTHER PUBLICATIONS

Zhong et al (Cancer Letters, 2010, vol. 299, pp. 150-160).*

(Continued)

*Primary Examiner* — Karen Canella

(74) *Attorney, Agent, or Firm* — Womble Carlyle Sandridge & Rice, LLP

(57) ABSTRACT

Markers useful for the identification, characterization and, optionally, the enrichment or isolation of tumorigenic cells or cell subpopulations are disclosed.

24 Claims, 54 Drawing Sheets

(56) References Cited

U.S. PATENT DOCUMENTS

| | | |
|---|---|---|
| 2010/0162416 A1 | 6/2010 | Krtolica et al. |
| 2010/0169990 A1 | 7/2010 | Clarke et al. |
| 2010/0255471 A1 | 10/2010 | Clarke et al. |
| 2010/0272636 A1 | 10/2010 | Byrd et al. |
| 2010/0273160 A1 | 10/2010 | Donahoe et al. |
| 2011/0020221 A1 | 1/2011 | Berman et al. |
| 2011/0191868 A1 | 8/2011 | Gupta et al. |
| 2012/0039885 A1 | 2/2012 | Mahadevan |
| 2013/0061340 A1 | 3/2013 | Dylla et al. |
| 2013/0061342 A1 | 3/2013 | Dylla et al. |
| 2013/0260385 A1 | 10/2013 | Dylla et al. |
| 2014/0105888 A1 | 4/2014 | Foord et al. |

FOREIGN PATENT DOCUMENTS

| | | |
|---|---|---|
| CN | 101802616 | 8/2010 |
| EP | 2078732 | 7/2009 |
| EP | 2295537 | 3/2011 |
| EP | 2385370 | 9/2011 |
| EP | 2517555 | 10/2012 |
| JP | 2001-057828 | 3/2001 |
| WO | WO 01/88537 | 11/2001 |
| WO | WO 02/12477 | 2/2002 |
| WO | WO 02/18948 | 3/2002 |
| WO | WO 03/032814 | 4/2003 |
| WO | WO 2004/058298 | 7/2004 |
| WO | WO 2008/007648 | 1/2008 |
| WO | WO 2008/008284 | 1/2008 |
| WO | WO 2008/091908 | 7/2008 |
| WO | WO 2008/149803 | 12/2008 |
| WO | WO 2009/045201 | 4/2009 |
| WO | WO 2009/070767 | 6/2009 |
| WO | WO 2009/126558 | 10/2009 |
| WO | WO 2009/157623 | 12/2009 |
| WO | WO 2010/011893 | 1/2010 |
| WO | WO 2011/057034 | 5/2011 |
| WO | WO 2011/089004 | 7/2011 |
| WO | WO 2012/027723 | 3/2012 |
| WO | WO 2012/031280 | 3/2012 |
| WO | WO 2012/040824 | 4/2012 |
| WO | WO 2012/044992 | 4/2012 |
| WO | WO 2012/046064 | 4/2012 |
| WO | WO 2013/119964 | 8/2013 |
| WO | WO 2015/031698 | 3/2015 |
| WO | WO 2016/064749 | 4/2016 |

OTHER PUBLICATIONS

Ulasov et al (Human Gene Therapy, 2006, vol. 17, pp. 556-564).*
Schraivogel et al (The EMBO Journal, 2011, vol. 30, pp. 4309-4322).*
Andrew et al (Cancer Research, 1990, vol. 50, pp. 5225-5230).*
Acloque, Hervé et al. "The physiology and pathology of the EMT. Meeting on the epithelial-mesenchymal transition." *EMBO Rep.* (2008) vol. 9, No. 4, pp. 322-326.
Bae et al. E-cadherin plasticity in prostate cancer stem cell invasion, Am J Cancer Res. 1(1):71-84 (2011).
Berezhnaya et al. Expression of E-cadherin in drug resistant human breast cancer cells and their sensitivity to lymphokine-activated lymphocyts action, Exp Oncol. 31(4):242-245 (2007).
Botchkina et al. Phenotypic subpopulations of metastatic colon cancer stem cells: genomic analysis,*Cancer Genomics Proteomics*. 6(1):19-29 (2009).
Buettner, Ralf et al., "Activated Signal Transducers and Activators of Transcription 3 Signaling Induces CD46 Expression and Protects Human Cancer Cells from Complement-Dependent Cytotoxicity", *Mol Cancer Res* (2007) 5:823-832.
Bui, Matthew H.T. et al "Carbonic Anhydrase IX Is an Independent Predictor of Survival in Advanced Renal Clear Cell Carcinoma Implications for Prognosis and Therapy", *Clinical Cancer Research* (2003) vol. 9, 802-811.
Cao L et al, "Omental milky spots—highly efficient "natural filter" for screening gastric cancer stem cells", *Medical Hypotheses*, (2009) vol. 73, Issue 6, pp. 1017-1018.
Cardone, John et al., "Complement regulator CD46 temporally regulates cytokine production by conventional and unconventional T cells," *Nature Immunology*, vol. 11, No. 9, Sep. 2010, pp. 862-872.
Carter, Paul et al. "Identification and validation of cell surface antigens for antibody targeting in oncology." *Endocr Relat Cancer* (2004) 11, 659-687.
Cattaneo, Roberto "Four viruses, two bacteria, and one receptor: membrane cofactor protein (CD46) as pathogens' magnet," *Journal of Virology*, May 2004, vol. 78, No. 9 pp. 4385-4388.
Cavard, Catherine et al. "Gene expression profiling provides insights into the pathways involved in solid pseudopapillary neoplasm of the pancreas," *J Pathol.*, 2009; 218: 201-209.
Chen, Taotao et al. "E-Cadherin-Mediated Cell-Cell Contact Is Critical for Induced Pluripotent Stem Cell Generation," *Stem Cells* (2010) 28:1315-1325.
"Centocor returns rights to anti-CD46 to Crucell" *Crucell* press release Dec. 24, 2002.
Dalerba, Piero et al. "Phenotypic characterization of human colorectal cancer stem cells." *PNAS* (Jun. 12, 2007) vol. 104, No. 24, pp. 10158-10163.
Dalerba, Piero et al. "Single-cell dissection of transcriptional heterogeneity in human colon tumors." *Nature Biotechnology* 2011 vol. 29(12):1120-1127.
*Definition of transcriptome*—National Human Genome Research Institute—NIH [online] https://www.genome.gov/13014330, downloaded on Apr. 18, 2013.
Devemy, Emmanuelle et al. "Identification of a novel dual E- and N-cadherin antagonist," *Peptides* 30 (2009) 1539-1547.
Dick, John "Stem cell concepts renew cancer research." *Blood* (2008) vol. 112, No. 13, pp. 4793-4807.
Dylla, Scott J. et al. "Colorectal Cancer Stem Cells Are Enriched in Xenogeneic Tumors Following Chemotherapy." *PLoS ONE* (Jun. 2008) vol. 3, Issue 6, e2428, pp. 1-13.
Eramo, A. et al,"Identification and expansion of the tumorigenic lung cancer stem cell population," *Cell Death and Differentiation* (2008) 15, 504-514.
Fishelson et al., "Cancer resistance to complement dependent cytotoxicity (CDC): problem-oriented research and development", *Mol Immunol.* 46:2794-2800 (2009).
Fishelson, Z. et al., "Obstacles to cancer immunotherapy: expression of membrane complement regulatory proteins (mCRPs) in tumors," *Molecular Immunology* 40 (2003) 109-123.
Frixen, Uwe H. et al., "E-Cadherin-mediated Cell-Cell Adhesion Prevents Invasiveness of Human Carcinoma Cells." *J Cell Biol.*, (1991) 113:173-85.
Gancz, Dana et al., "Cancer resistance to complement dependent cytotoxicity (CDC): problem-oriented research and development", *Mol Immunol.* (2009) 46:2794-2800.
Garvalov, Boyan K. "Cancer stem cells: a new framework for the design of tumor therapies" *J. Mol. Med* (2011) 89; 95-107.
Goslings, Willem R.O. et al., Membrane-Bound Regulators of Complement Activation in Uveal Melanomas CD46, CD55, and CD59 in Uveal Melanomas, *Investigative Ophthalmology & Visual Science*, Aug. 1996, vol. 37, No. 9, pp. 1884-1891.
Green, Shane K. et al. Antiadhesive antibodies targeting E-cadherin sensitize multicellular tumor spheroids to chemotherapy in vitro, *Mol Cancer Ther* 2004;3:149-159.
Hara T. et al., "Soluble forms of membrane cofactor protein (CD46, MCP) are present in plasma, tears, and seminal fluid in normal subjects", *Clin. exp. Immunol.* (1992) 89,490-494.
Hara, T. et al., "High expression of membrane cofactor protein of complement (CD46) in human leukaemia cell lines: implication of an alternatively spliced form containing the STA domain in CD46 up-regulation", *Scand J Immunol.* (1995) 42(6):581-90.
Ho, Maria M. et al. "Side population in human lung cancer cell lines and tumors is enriched with stem-like cancer cells," *Cancer Res* 2007; 67:4827-4833.
Hong, Soonjin et al., "Cadherin exits the junction by switching its adhesive bond", *J Cell Biol.* (2011) 192(6):1073-1083.

(56) References Cited

OTHER PUBLICATIONS

Jamieson, Catriona H.M. et al. "Granulocyte—Macrophage Progenitors as Candidate Leukemic Stem Cells in Blast-Crisis CML". *N Engl J Med.*(2004) 351:657-667.
Jantscheff, Peter et al. "Expression of CEACAM6 in Resectable Colorectal Cancer: A Factor of Independent Prognostic Significance", *Journal of Clinical Oncology*, vol. 21, No. 19, Oct. 1, 2003: pp. 3638-3646.
Johnstone, R.W. et al., "Identification and quantification of complement regulator CD46 on normal human tissues", *Immunology* (1993) 79; 341-347.
Jurianz, Katrin et al., "Neutralization of complement regulatory proteins augments lysis of breast carcinoma cells targeted with rhumAb anti-HER2", *Immunopharmacology* (1999) 42; 209-218.
Kuefer, R. et al., "Assessment of a fragment of e-cadherin as a serum biomarker with predictive value for prostate cancer", *British Journal of Cancer* (2005) 92, 2018-2023.
Lee, Hyuk-Joon et al. "Tumor specificity and in vivo targeting of an antibody against exon 9 deleted E-cadherin in gastric cancer", *J Cancer Res Clin Oncol* (2007) 133:987-994.
Lee, Jeongwu et al. "Tumor stem cells derived from glioblastomas cultured in bFGF and EGF more closely mirror the phenotype and genotype of primary tumors than do serum-cultured cell lines", *Cancer Cell*, 2006, 9:391-403.
Liu et al, "Adenovirus-mediated intratumoral expression of immunostimulatory proteins in combination with systemic Treg Inactivation induces tumor-destructive immune responses in mouse models", *Cancer Gene Therapy*(2011) 18, 407-418.
Luo et al, "Mammary Epithelial-Specific Ablation of the Focal Adhesion Kinase Suppresses Mammary Tumorigenesis by Affecting Mammary Cancer Stem / Progenitor Cells", *Cancer Res*(2009) 69:466-474.
Madjd, Zahra et al., "Do poor-prognosis breast tumours express membrane cofactor proteins (CD46)?", *Cancer Immunol Immunother* (2005) 54: 149-156.
Maisner, Andrea et al., "Membrane Cofactor Protein (CD46) Is a Basolateral Protein That Is Not Endocytosed. Importance of the Tetrapeptide FTSL At the Carboxyl Terminus*" *J Biol Chem* (1997) vol. 272, No. 33, pp. 20793-20799, 1997.
Mohamet, Lisa et al. "Loss of Function of E-Cadherin in Embryonic Stem Cells and the Relevance toModels of Tumorigenesis", *Journal of Oncology*, vol. 2011, Article ID 352616, 19 pages.
O'Brien, Catherine A. et al, "A human colon cancer cell capable of initiating tumour growth in immunodeficient mice", *Nature* 445, 106-110 (Jan. 4, 2007).
Patel, Saurabh D et al. "Type II Cadherin Ectodomain Structures: Implications for Classical Cadherin Specificity", *Cell* (Mar. 24, 2006) 124, pp. 1255-1268.
Peng et al., "Intraperitoneal Therapy of Ovarian Cancer Using an Engineered Measles Virus." *Cancer Res* 2002; 62:4656-4662.
Persson, David B. et al., "Structure of extracellular portion of CD46 provides insights into its interactions with complement proteins and pathogens" *PLoS Pathog*, (Sep. 2010) vol. 6, Issue 9, pp. 1-12.
Pinter, Claudia et al., "Presence of autoantibodies against complement regulatory proteins in relapsing-remitting multiple sclerosis", *J NeuroVirol* (2000) 6 Suppl 2:S42-S46.
PlusCellect™ Catalog No. PLS748 package insert (2009).
Ravindranath, Naren M. et al., "Cell-surface density of complement restriction factors (CD46,CD55, and CD59): oral squamous cell carcinoma versus other solid tumors", *Oral Surg Oral Med Oral Pathol Oral Radiol Endod.* (2007) vol. 103, No. 2, p. 231-239.
Richmond et al., Dis. Model. Mech. Sep./Oct. 2008, doi: 10.1242/dmm.000976 vol. 1 No. 2-3 78-82 Mouse xenograft models vs GEM models for human cancer therapeutics.
Riley-Vargas, Rebecca C. et al., "CD46: expanding beyond complement regulation," *Trends Immunol.* (2004) vol. 25, No. 9, pp. 496-503.
Riley-Vargas, Rebecca C. et al., "Expression of Membrane Cofactor Protein (MCR; CD46) on spermatozoa: Just a complement inhibitor?", *Mod. Asp. Immunobiol.* (2003) 3(2):75-78.

Said, Jonathan, "Biomarker discovery in urogenital cancer", *Biomarkers* Nov. 2005; 10 Suppl 1:S83-6.
Sansone, Pasquale. et al "IL-6 triggers malignant features in mammospheres from human ductal breast carcinoma and normal mammary gland", *The Journal of Clinical Investigation* (Dec. 2007) vol. 117, No. 12, pp. 3988-4002.
Schmitt, C.A. et al., "Expression and regulation by interferon-gamma of the membrane-bound complement regulators CD46 (MCP), CD55 (DAF) and CD59 in gastrointestinal tumours," *European Journal of Cancer* (1999) vol. 35, No. 1, pp. 117-124.
Schölzel, Stefan et al. "Carcinoembryonic antigen family members CEACAM6 and CEACAM7 are differentially expressed in normal tissues and oppositely deregulated in hyperplastic colorectal polyps and early adenomas", *American Journal of Pathology* (Feb. 2000) vol. 156, No. 2, pp. 595-605.
Seya, Tsukasa et al., "Complement-mediated tumor cell damage induced by antibodies against membrane cofactor protein (MCP, CD46)", *J Exp Med* (1990) 172(6):1673-80.
Seya, Tsukasa et al., "Human membrane cofactor protein (MCP, CD46): multiple isoforms and functions," *IJBCB* (1999) 31; 1255-1260.
Shiozaki, Hitoshi et al. "E-Cadherin mediated adhesion system in cancer cells", *Cancer Supplement* (Apr. 15, 1996) vol. 77, No. 8 pp. 1605-1613.
Soyuer, Serdar et al. "Prognostic significance of CD9 expression in locally advanced gastric cancer treated with surgery and adjuvant chemoradiotherapy", *Pathology—Research and Practice* 206 (2010) 607-610.
Surowiak, Pawel et al., "CD46 Expression is Indicative of Shorter Revival-free Survival for Ovarian Cancer Patients", *Anticancer Research* (2006) 26: 4943-4948.
Takeichi, Masatoshi, "Cadherin Cell Adhesion Receptors as a Morphogenetic Regulator", *Science*, vol. 251, No. 5000 (Mar. 22, 1991), pp. 1451-1455.
Todaro, Matilde et al., "Colon Cancer Stem Cells: Promise of Targeted Therapy", *Gastroenterology* (2010)138:2151-2162.
Tomschy, Andrea et al., "Homophilic adhesion of E-cadherin occurs by a homophilic adhesion of E-cadherin occurs by a co-operative two-step interaction of N-terminal domains", *The EMBO Journal* (1996) vol. 15 No. 14 pp. 3507-3514.
Tuve, Sebastian et al: "A New Group B Adenovirus Receptor Is Expressed at High Levels on Human Stem and Tumor Cells", *J Virol*. Dec. 2006; 80 (24): 12109-12120.
Van Der Flier, Laurens G. et al. "Stem Cells, Self-Renewal, and Differentiation in the Intestinal Epithelium", *Annu. Rev. Physiol.* (2009) 71:241-260.
Van Roy, F. et al., "The cell-cell adhesion molecule E-cadherin", *Cell. Mol. Life Sci.* 65 (2008) 3756-3788.
Varela, Juan Carlos et al, "Upregulated expression of complement inhibitory proteins on bladder cancer cells and anti-MUC1 antibody immune selection." *Int. J. Cancer*, Sep. 15, 2008; 123(6): 1357-1363.
Von Kleist, S. et al., "Identification of an Antigen from Normal Human Tissue That Crossreacts with the Carcinoembryonic Antigen", *Proc. Nat. Acad. Sci. USA* (Sep. 1972) vol. 69, No. 9, pp. 2492-2494.
Wang et al, "In Vitro and in Vivo Properties of Adenovirus Vectors with Increased Affinity to CD46", *Journal of Virology* (2008), pp. 10567-10579.
Woodward, Wendy A. "On mammary stem cells", *J. Cell Sci*, 2005, 118:3585-3594.
Wu, A. et al. "Persistence of CD133[+] cells in human and mouse glioma cell lines: detailed characterization of GL261 glioma cells with cancer stem cell-like properties", *Stem Cells and Development* (2008)17:173-184.
Yu et al.,"Enhanced c-erbB-2/neu Expression in Human Ovarian Cancer Cells Correlates with More Severe Malignancy That Can Be Suppressed by E1A" *Cancer Res* 1993;53:891-898.
Zell, S. et al., "Down regulation of CD55 and CD46 expression by anti-sense phosphorothioate oligonucleotides (S-ODNs) sensitizes tumor cells to complement attack", *Clin Exp Immunol.* (2007) 150(3): 576-584.

(56) References Cited

OTHER PUBLICATIONS

International Search Report dated May 18, 2012 issued in PCT application (No. PCT/US2011/050451).
Written Opinion dated May 18, 2012 issued in PCT application (No. PCT/US2011/050451).
IPRP issued in PCT application (No. PCT/US2011/050451).
International Search Report dated Sep. 24, 2013 issued in PCT application (No. PCT/US2013/025361).
Written Opinion dated Sep. 24, 2013 issued in PCT application (No. PCT/US2013/025361).
IPRP issued on Aug. 12, 2014 in PCT application (No. PCT/US2013/025361).
Extended European Search Report dated Nov. 26, 2013 issued in European application (No. 13190308.0).
Official Action datedJun. 19, 2014 issued in Australian application (No. 2011295722).
Official Action dated Feb. 7, 2014 issued in Chinese application (No. 201180053062.3).
Office Action dated Jul. 15, 2013 issued in (U.S. Appl. No. 13/369,277).
Office Action dated Sep. 24, 2014 issued in (U.S. Appl. No. 13/369,277).
Office Action dated Nov. 29, 2012 issued in (U.S. Appl. No. 13/414,666).
Office Action dated Apr. 25, 2013 issued in (U.S. Appl. No. 13/414,666).
Office Action dated Jul. 15, 2014 issued in (U.S. Appl. No. 13/414,666).
Galli et al "Isolation and Characterization of Tumorigenic,Stem-like Neural Precursors fromHuman Glioblastoma" *Cancer Research*, (2004) 64; 7011-7021.
Howard et al "Effect of butyrate and corticosteroids on retinoblastoma in vitro and in vivo." Invest Ophthalmol Vis Sci. May 1991; 32(6):1711-3.
Maurer et al "CD46 Is a Cellular Receptor for Bovine Viral Diarrhea Viurus" *Journal of Virol*, (Feb. 2004) 78:1792-1799.
Melotti et al "In vitro and in vivo characterization of highly purified Human Mesothelioma derived cells" *BMC Cancer* (2010) 10:54 pp. 1-10.
Ni et al "Evaluation of adenovirus vectors containing serotype 35 fibers for tumer targeting." *Cancer Gene Therapy* (2006) 13:1072-1081.
Y79 (ATCC® HTB™), 2014, 1 page, http://www.atcc.org/products/all/HTB-18.aspx#characteristics.
Official Action dated Nov. 2, 2014 issued in Chinese application (No. 201180053062.3).
Official Action dated May 27, 2015 issued in Chinese application (No. 201180053062.3).
Search Report dated Nov. 2, 2014 issued in Chinese application (No. 201180053062.3).
Official Action dated Oct. 13, 2015 issued in Chinese application (No. 201180053062.3).
Official Action dated Jan. 23, 2015 issued in EP Application (No. 13190308.0).
Official Action dated Mar. 8, 2016 issued in EP Application (No. 13190308.0).
Official action dated Sep. 2, 2015 issued in Japanese application (No. 2013-527364).
Office Action dated Dec. 24, 2014 issued in (U.S. Appl. No. 13/820,061).
Office Action dated Aug. 14, 2015 issued in (U.S. Appl. No. 13/820,061).
May definition printout from Google.google.com/search?q=matrix+definition&sourceis=ie7&ris=com, printed Dec. 25, 2016, pp. 1-2.
Official Action dated Jun. 17, 2016, issued in (U.S. Appl. No. 13/820,061).
Official Action dated Aug. 2, 2016, issued in (U.S. Appl. No. 13/414,666).
Official action dated Jul. 14, 2016, issued in Japanese application (No. 2013-527364).
Varsano et al., "Human lung cancer cell lines express cell membrane complement inhibitory proteins and are extremely resistant to complement-mediated lysis; a comparison with normal human respiratory epithelium in vitro, and an insight into mechanism(s) of resistance," *Clin Exp Immunol*. (Aug. 1998) 113(2):173-182.
Official Action dated May 15, 2014, issued in (U.S. Appl. No. 13/369,277).
Official Action dated Feb. 19, 2016, issued in (U.S. Appl. No. 13/369,277).
Official Action dated Oct. 12, 2016, issued in (U.S. Appl. No. 13/369,277).
Official Action dated Aug. 24, 2015, issued in (U.S. Appl. No. 13/414,666).
Official Action dated Mar. 4, 2016, issued in (U.S. Appl. No. 13/414,666).
Official Action dated Jan. 12, 2017, issued in AU application (No. 2016201730).
Official Action dated Dec. 13, 2016, issued in JP application (No. 2016-40197).
Official Action dated Apr. 25, 2017, issued in JP application (No. 2013-527364).
Official action dated Jun. 13, 2017, issued in (U.S. Appl. No. 13/820,061).
Hartigan-O'Conor et al., Human CD4+ regulatory T cells express lower levels of the IL-7 receptor alpha chain (CD127), allowing consistent identification and sorting of live cells, *Journal of Immunological Methods*(2007) 319:41-52.
Tung et al., "New approaches to fluorescence compensation and visualization of FACS data," *Clinical Immunology*(2004) 110:277-283.

\* cited by examiner

CD46 Is Heterogeneously
Expressed on Solid Tumor Cells

Colorectal Tumorigenicity is Associated With CD46$^{hi}$ CD324$^+$ Tumor Cell Subpopulations Pancreatic Tumorigenicity is Associated
With CD46$^{hi}$ CD324$^+$ Tumor Cell Subpopulations

Non-Small Cell Lung Cancer Tumorigenicity is Associated with CD46$^{hi}$ CD324$^+$ Tumor Cell Subpopulations

Breast Tumorigenicity is Associated With CD46$^{hi}$ CD324$^+$ Tumor Cell Subpopulations

Ovarian Tumorigenicity is Associated With CD46hi CD324+ Tumor Cell Subpopulations

OV45

OV45

Small-Cell Lung Cancer Tumorigenicity is Associated With CD46$^{hi}$ CD324$^+$ Tumor Cell Subpopulations

LU64

LU64

Melanoma Tumorigenicity is Associated With
CD46$^{hi}$ CD324$^+$ Tumor Cell Subpopulations

CD46$^{hi}$ CD324$^+$ Cell Subpopulations Are Highly Tumorigenic With Regard to Different Cancers

|  |  | 500+ cells | | 200-499 cells | | 50-199 cells | | <50 cells | |
|---|---|---|---|---|---|---|---|---|---|
| SCRx-CR05 | CD46$^{-/lo}$CD324- |  |  | 0/5 | 0% | 1/5 | 20% | 1/5 | 20% |
|  | CD46$^{hi}$ CD324- |  |  | 5/5 | 100% | 7/9 | 78% |  |  |
|  | CD46$^{hi}$ CD324+ |  |  | 5/5 | 100% | 14/14 | 100% | 18/25 | 72% |
| SCRx-CR10 | CD46$^{-/lo}$CD324- |  |  | 0/5 | 0% |  |  |  |  |
|  | CD46$^{hi}$ CD324- |  |  | 1/5 | 20% |  |  |  |  |
|  | CD46$^{hi}$ CD324+ |  |  | 3/5 | 60% |  |  |  |  |
| SCRx-CR14 | CD46$^{-/lo}$CD324- | 0/5 | 0% | 3/15 | 20% | 0/5 | 0% | 0/5 | 0% |
|  | CD46$^{hi}$ CD324- |  |  | 8/15 | 53% |  |  | 0/5 | 0% |
|  | CD46$^{hi}$ CD324+ | 10/10 | 100% | 20/20 | 100% | 4/5 | 80% | 6/10 | 60% |
| SCRx-CR16 | CD46$^{-/lo}$CD324- |  |  | 0/5 | 0% |  |  |  |  |
|  | CD46$^{hi}$ CD324- |  |  | 1/5 | 20% |  |  |  |  |
|  | CD46$^{hi}$ CD324+ |  |  | 4/9 | 44% |  |  |  |  |
| SCRx-LU37 | CD46$^{-/lo}$CD324- | 0/5 | 0% |  |  |  |  |  |  |
|  | CD46$^{hi}$ CD324- | 0/5 | 0% |  |  |  |  |  |  |
|  | CD46$^{hi}$ CD324+ | 6/10 | 60% |  |  |  |  |  |  |
| SCRx-LU49 | CD46$^{-/lo}$CD324- |  |  |  |  | 0/5 | 0% |  |  |
|  | CD46$^{hi}$ CD324+ |  |  |  |  | 5/5 | 100% |  |  |
| SCRx-PA03 | CD46$^{-/lo}$CD324- |  |  | 0/5 | 0% |  |  |  |  |
|  | CD46$^{hi}$ CD324- |  |  | 3/5 | 60% |  |  |  |  |
|  | CD46$^{hi}$ CD324+ |  |  | 5/5 | 100% |  |  |  |  |
| SCRx-PA04 | CD46$^{-/lo}$CD324- | 0/5 | 0% |  |  |  |  |  |  |
|  | CD46$^{hi}$ CD324- | 0/5 | 0% |  |  |  |  |  |  |
|  | CD46$^{hi}$ CD324+ | 5/5 | 100% |  |  |  |  |  |  |

FIG. 11A

CD46$^{hi}$ CD324$^+$ Cell Subpopulations Are Highly Tumorigenic With Regard to Different Cancers

|  |  | 500+ cells | | 200-499 cells | | 50-199 cells | | <50 cells | |
|---|---|---|---|---|---|---|---|---|---|
| SCRx-BR22 | CD46$^{hi}$CD324- | | | 10/10 | 100% | | | 1/10 | 10% |
| | CD46$^{hi}$CD324+ | | | 10/10 | 100% | | | 10/10 | 100% |
| SCRx-BR31 | CD46$^{hi}$CD324- | | | | | | | 0/5 | 0% |
| | CD46$^{hi}$CD324+ | | | | | | | 4/10 | 40% |
| SCRx-BR56 | CD46$^{hi}$CD324- | | | | | | | 6/15 | 40% |
| | CD46$^{hi}$CD324+ | | | | | | | 17/19 | 89% |
| SCRx-OV11 | CD46$^{hi}$CD324- | | | 1/10 | 10% | | | | |
| | CD46$^{hi}$CD324+ | | | 2/4 | 50% | | | | |
| SCRx-OV26 | CD46$^{hi}$CD324- | 0/6 | 0% | | | | | | |
| | CD46$^{hi}$CD324+ | 7/10 | 70% | | | | | | |
| SCRx-OV45 | CD46$^{hi}$CD324- | 0/13 | 0% | 0/6 | 0% | | | | |
| | CD46$^{hi}$CD324+ | 20/30 | 67% | 8/13 | 62% | | | | |
| SCRx-OV55 | CD46$^{hi}$CD324- | | | | | 0/12 | 0% | | |
| | CD46$^{hi}$CD324+ | | | | | 28/30 | 93% | | |
| SCRx-SK22* | CD46$^{hi}$CD324- | | | 0/5 | 0% | | | | |
| | CD46$^{hi}$CD324+ | | | 5/5 | 100% | | | | |

*Primary sort out of freshly resected patient tumor

FIG. 11B

Selected Proteins Co-Expressed on CD46$^{hi}$ CD324$^+$ cells
and Associated with Tumor Initiating Cell Populations

| | Colorectal | Breast | NSCLC | Ovarian | Pancreatic | SCLC | Melanoma |
|---|---|---|---|---|---|---|---|
| CCR10 | x | | | x | | x | |
| CD9 | x | | x | | | | |
| CD13 | | | x | | x | | |
| CD15 | | | x | x | x | | |
| CD24 | | | x | x | | | |
| CD26 | | | x | | x | | |
| CD29 | | | x | | x | | x |
| CD32 | | | | x | | | |
| CD49a | x | | x | | | | |
| CD49b | x | x | x | | x | | |
| CD49c | x | | x | | | x | |
| CD49f | x | | x | | x | | |
| CD51 | x | x | x | | x | x | |
| CD54 | | x | | | x | | |
| CD55 | x | x | | | x | | |
| CD56 | | | | x | | | |
| CD58 | | | x | | | | |
| CD63 | x | x | | | | | |
| CD66 | | | | x | x | | |
| CD66a | | | x | | x | | |
| CD66a/c/e | | | | x | x | | |
| CD66c | | | x | x | x | | |
| CD66e | | | x | | x | x | |
| CD71 | | x | x | x | x | | |
| CD73 | x | | x | | | | |
| CD91 | x | | x | | | | |
| CD82 | x | | | | | | |
| CD91 | | | x | x | | | |
| CD98 | x | | x | | | | |
| CD99 | x | | x | | x | x | |
| CD102 | | | | x | | | |
| CD104 | x | | x | | x | | |
| CD105 | | | x | | | | |
| CD108 | | | | | x | | |
| CD111 | | | x | x | | x | |
| CD117 | | | | x | | x | |
| CD118 | | | | | | x | |
| CD130 | | x | x | | | | |
| CD131 | | x | | | | | |

FIG. 12A

Selected Proteins Co-Expressed on CD46$^{hi}$ CD324$^+$ cells and Associated with Tumor Initiating Cell Populations

| | Colorectal | Breast | NSCLC | Ovarian | Pancreatic | SCLC | Melanoma |
|---|---|---|---|---|---|---|---|
| CD133 | | | | x | | x | |
| CD136 | x | | | | | | |
| CD141 | | | | x | | | |
| CD146 | | | | x | | | |
| CD147 | | | | | | | x |
| CD148 | | x | | | | | |
| CD151 | x | x | x | x | | | |
| CD155 | x | x | x | | x | | |
| CD157 | | | | x | | | |
| CD164 | | | | x | | x | |
| CD166 | | | | x | x | | |
| CD167a | | | | x | | | |
| CD172a | | x | | | x | | |
| CD177 | | | | x | | | |
| CD186 | | x | | | | | |
| CD196 | | | | x | | | |
| CD221 | | x | x | x | | | |
| CD230 | | x | x | | | | |
| CD234 | | | | x | | | |
| CD244 | | x | | | | | |
| CD245 | | x | | | | | |
| CD262 | | | x | | x | | |
| CD265 | | | | x | | | |
| CD273 | | | | | x | | |
| CD275 | x | x | x | x | x | | |
| CD295 | | | x | x | | | x |
| CD298 | | | x | | | | |
| CD299 | | | | x | | | |
| CD317 | | | | x | | | |
| CD318 | | x | x | | | | |
| CD340 | | | x | | | | |
| BMPR-1B | | | | x | | | |
| Cadherin-11 | | | | x | | | |
| c-Met | x | | x | | | | |
| Claudin-3 | | | | x | | | |
| DLL-1 | | | | x | | x | |
| DLL-3 | | | | x | | | |
| EphB2 | | | x | | | | |
| EphB4 | x | x | x | | | | |
| FOLR1 | | | | x | | | |

FIG. 12B

Selected Proteins Co-Expressed on CD46$^{hi}$ CD324$^{+}$ cells
and Associated with Tumor Initiating Cell Populations

| | Colorectal | Breast | NSCLC | Ovarian | Pancreatic | SCLC | Melanoma |
|---|---|---|---|---|---|---|---|
| Frizzled-3 | | | | x | | | |
| Glut-1 | | | | | | x | |
| Glut-2 | | | | | x | | |
| Glypican 5 | | | x | | | | |
| HLA-A/B/C | | | | x | | | |
| HLA-A2 | | | | x | | | |
| HER3 | | x | x | | | x | x |
| IL-15R | | x | | | | | |
| IL-20 Ra | | | | | x | | |
| Jagged-2 | | | | x | | | |
| Integrin a8 | | x | | | | | |
| Integrin a9b1 | | | x | x | | x | |
| Integrin b5 | | x | | | x | | |
| LAG-3 | | | | x | | | |
| Leukotriene B4R | | x | | | | | |
| LOX-1 | | | | x | | x | |
| LDL-R | | x | | | x | | |
| MCSP | | | | x | | | x |
| Mer | | | | | x | | |
| Nectin-4 | | x | | x | | | |
| Notch2 | | x | | | | | |
| NPC | | | | x | | | |
| PD-L2 | | | | x | | | |
| Plexin B1 | | x | | | | | |
| Semaphorin 4B | | | x | | | | |
| Somatostatin-R2 | | | | x | | | |
| TROP-2 | | x | x | | | | |
| ULBP2 | | x | | | | | |
| Vb9 | | | | | x | | |
| VEGFR2 | | | | x | | | |

FIG. 12C (Part 1)

(Part 2)

(Part 1)

(Part 2)

(Part 3)

(Part 4)

(Part 1)

(Part 2)

Selected Proteins Are Associated With
Non-Small Cell Lung Tumor Initiating Cell Populations (Part 3)

(Part 4)

(Part 5)

Selected Proteins Are Associated With
Non-Small Cell Lung Tumor Initiating Cell Populations (Part 6)

(Part 7)

(Part 1)

(Part 2)

(Part 3)

(Part 4)

Selected Proteins Are Associated With Ovarian Tumor Initiating Cell Populations (Part 1)

(Part 2)

(Part 3)

(Part 4)

(Part 5)

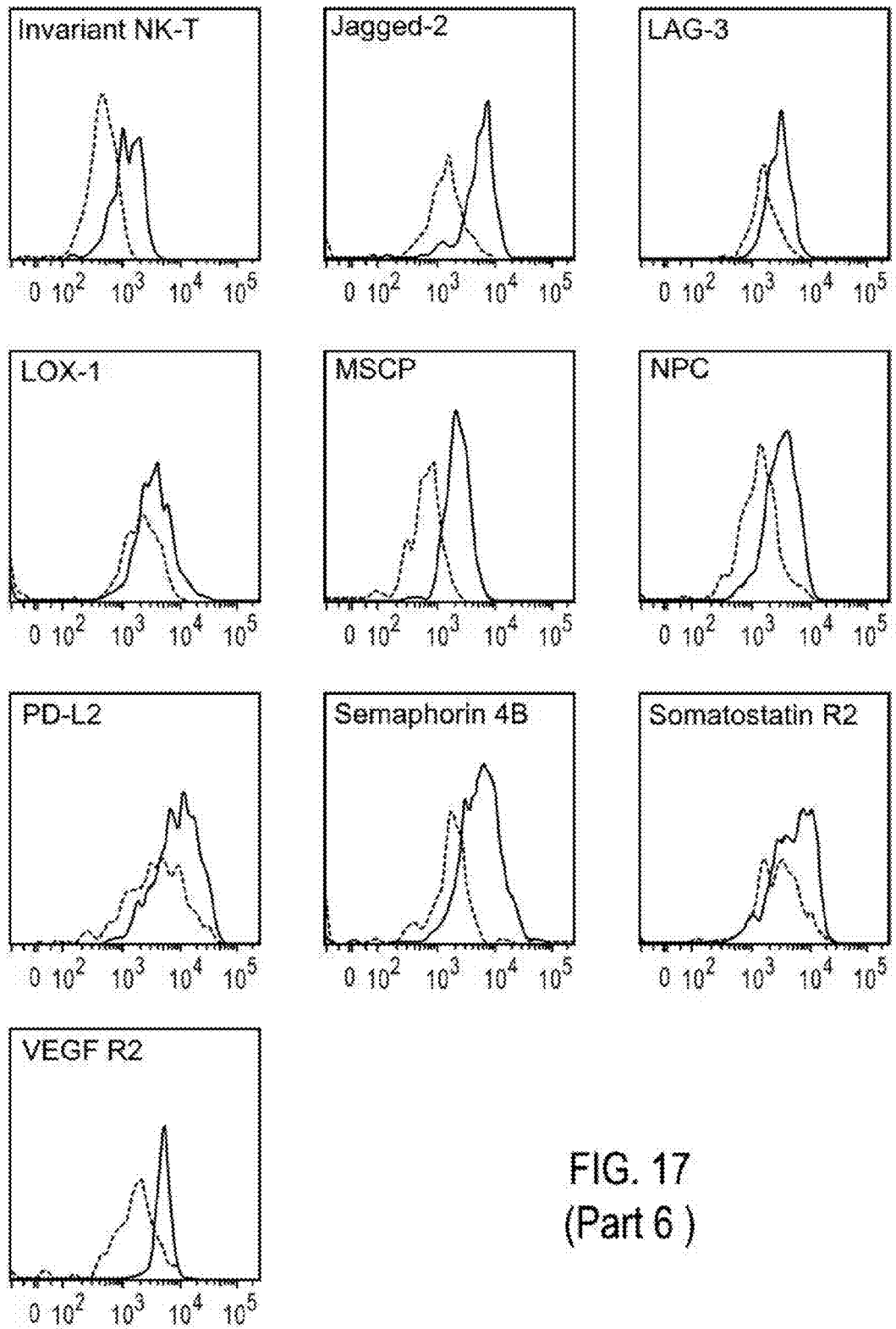
FIG. 17 (Part 6)

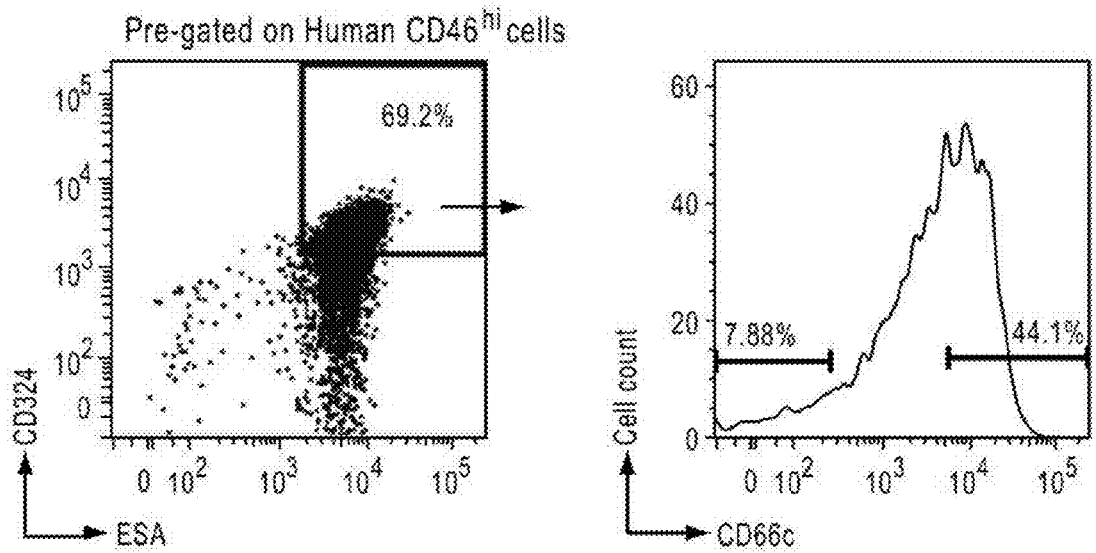
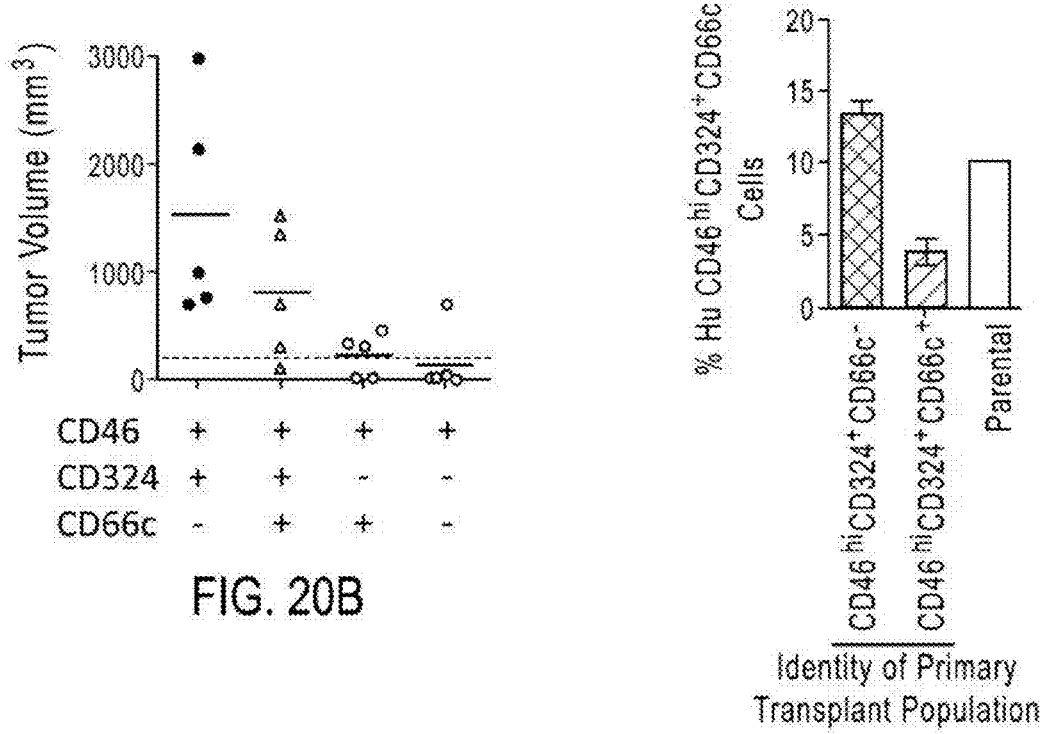

Colorectal CD46$^{hi}$ CD324$^+$ CD66c$^-$ Cells Reconstitute Heterogeneous Tumors in Primary and Secondary Transplants

Distribution of cells expressing CD66 in Tumor Derived from

CD46$^{hi}$ CD324$^+$ CD66c- Enriched Cell Populations Demonstrate Robust Tumorigenicity
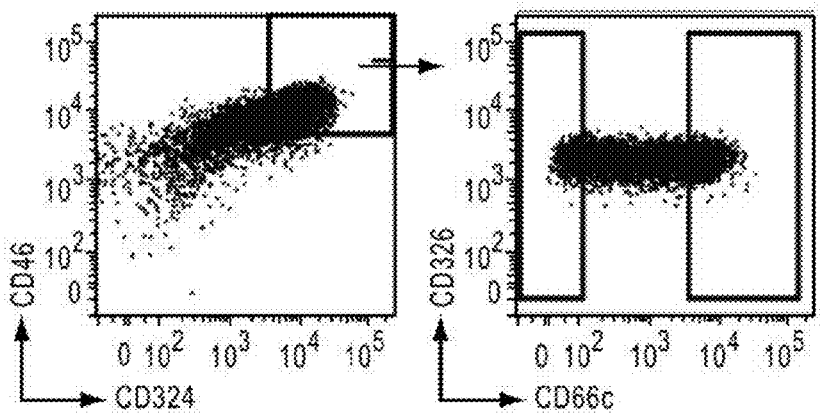
FIG. 22A
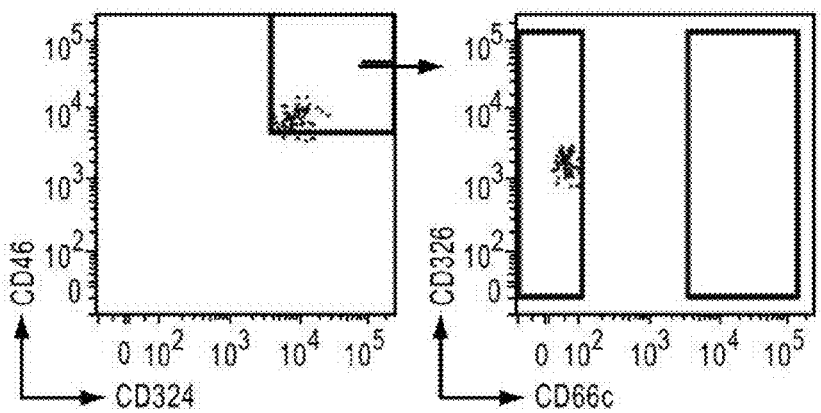
FIG. 22B
| # of CD46$^{hi}$ CD324+ CD66c- Cells Injected | Tumors/Animals Injected (%) |
|---|---|
| 1,000 | 19/19 (100%) |
| 200 | 5/5 (100%) |
| 50 | 9/9 (100%) |
| 20 | 5/5 (100%) |
| 8 | 3/5 (60%) |
| 3 | 3/5 (60%) |
FIG. 22C Differential Expression of CD46, CD324 and CD66 Is Indicative of Proliferation and Differentiation Potential Chemotherapeutic Agents Increase Relative Frequency of CD46$^{hi}$ CD324$^+$ CD66c$^-$ Cells in Residual Tumors Chemotherapeutic Agents Increase Relative Frequency
of CD46$^{hi}$ Tumorigenic Cells in Residual Pancreatic Tumors Gene Expression of Selected Markers Among Tumor Cell Subpopulations

IDENTIFICATION AND ENRICHMENT OF CELL SUBPOPULATIONS

CROSS REFERENCED APPLICATIONS

This application claims priority from U.S. patent application Ser. No. 13/369,277, filed Feb. 8, 2012 and U.S. patent application Ser. No. 13/414,666 filed Mar. 7, 2012 each of which is incorporated herein by reference in their entirety.

FIELD OF THE INVENTION

The present invention relates generally to the identification, characterization and, optionally, the isolation or enrichment of cells or cell subpopulations, particularly tumor initiating cells derived from various neoplasia. In selected aspects the invention also relates to methods of isolating tumor initiating cells and the resulting preparations, as well as various methods for using tumor initiating cells and cell populations, and in vitro and in vivo models comprising such cells, in research and development and in diagnostic, therapeutic and other clinical and non-clinical applications.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. Differentiation and proliferation decisions are often controlled by numerous factors and signals that are balanced to maintain cell fate decisions and tissue architecture. Normal tissue architecture is largely maintained by cells responding to microenvironmental cues that regulate cell division and tissue maturation. Accordingly, cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combinations thereof. When normal cellular proliferation and/or differentiation is disturbed or somehow disrupted it can lead to various diseases or disorders including proliferative disorders such as cancer.

Conventional treatments for cancer include chemotherapy, radiotherapy, surgery, immunotherapy (e.g., biological response modifiers, vaccines or targeted therapeutics) or combinations thereof. Sadly, far too many cancers are non-responsive or minimally responsive to such conventional treatments leaving few options for patients. For example, in some patients certain cancers exhibit gene mutations that render them non-responsive despite the general effectiveness of selected therapies. Moreover, depending on the type of cancer some available treatments, such as surgery, may not be viable alternatives. Limitations inherent in current standard of care therapeutics are particularly evident when attempting to care for patients who have undergone previous treatments and have subsequently relapsed. In such cases the failed therapeutic regimens and resulting patient deterioration may contribute to refractory tumors which often manifest themselves as a relatively aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies that kill residual tumor cells ultimately responsible for tumor recurrence and metastasis (i.e. cancer stem cells).

One promising area of research involves the use of targeted therapeutics to go after the tumorigenic "seed" cells that appear to underlie many cancers. To that end, most solid tissues are now known to contain adult, tissue-resident stem cell populations generating the differentiated cell types that comprise the majority of that tissue. Tumors arising in these tissues similarly consist of heterogeneous populations of cells that also ultimately arise from stem cells, but differ markedly in their overall proliferation, organization and response to microenvironmental cues. While it is increasingly recognized that the majority of tumor cells have a limited ability to proliferate, a minority population of cancer cells (commonly known as cancer stem cells or CSC) have the exclusive ability to extensively self-renew thereby enabling an inherent tumor perpetuating capacity. More specifically, the cancer stem cell hypothesis proposes that there is a distinct subset of cells (i.e. CSC) within each tumor (typically 0.1-10%) that is capable of indefinite self-renewal and of generating tumor cells progressively limited in their replication capacity as a result of differentiation to tumor progenitor cells and, subsequently, to terminally differentiated tumor cells.

In recent years it has become more evident these CSC (also known as tumor perpetuating cells or TPC) might be more resistant to traditional chemotherapeutic agents or radiation and thus persist after standard of care clinical therapies to later fuel the growth of refractory tumors, secondary tumors and promote metastases. Moreover, growing evidence suggests that pathways that regulate organogenesis and/or the self-renewal of normal tissue-resident stem cells are deregulated or altered in CSC, resulting in the continuous expansion of self-renewing cancer cells and tumor formation. See generally Al-Hajj et al., 2004, PMID: 15378087; and Dalerba et al., 2007, PMID: 17548814; each of which is incorporated herein in its entirety by reference. Thus, the effectiveness of traditional, as well as more recent targeted treatment methods, has apparently been limited by the existence and/or emergence of resistant cancer cells that are capable of perpetuating the cancer even in face of these diverse treatment methods. Huff et al., European Journal of Cancer 42: 1293-1297 (2006) and Zhou et al., Nature Reviews Drug Discovery 8: 806-823 (2009) each of which is incorporated herein in its entirety by reference. Such observations are confirmed by the consistent inability of traditional debulking agents to substantially increase patient survival when suffering from solid tumors, and through an increasingly sophisticated understanding as to how tumors grow, recur and metastasize. Accordingly, recent strategies for treating neoplastic disorders have recognized the importance of eliminating, depleting, silencing or promoting the differentiation of tumor perpetuating cells so as to diminish the possibility of tumor recurrence or metastasis leading to patient relapse.

Efforts to develop such strategies have incorporated non-traditional xenograft (NTX™) models, wherein primary human solid tumor specimens are implanted and passaged exclusively in immunocompromised mice. In numerous cancers such techniques confirm the existence of a subpopulation of cells with the unique ability to generate heterogeneous tumors in vivo and fuel their growth indefinitely. As previously hypothesized, work in NTX models has confirmed that identified CSC subpopulations of tumor cells appear more resistant to debulking regimens such as chemotherapy and radiation, potentially explaining the disparity between clinical response rates and overall survival. Further, employment of NTX models in CSC research has sparked a fundamental change in drug discovery and preclinical evaluation of drug candidates that may lead to CSC-targeted therapies having a major impact on tumor recurrence and metastasis thereby improving patient survival rates. While progress has been made, inherent technical difficulties associated with handling primary and/or xenograft tumor tissue, along with a lack of experimental platforms and tools to characterize CSC identity and differentiation potential, pose major challenges. As such, there remains a substantial need for compounds, compositions, methods, devices and models (both in vitro and in vivo) to selectively target, stratify, enrich, analyze and characterize cancer stem cells and cancer stem cell subpopulations for use in the development of clinically useful compounds, compositions and methods.

SUMMARY OF THE INVENTION

These and other objectives are provided for by the present invention which, in a broad sense, is directed to methods, compounds, compositions and articles of manufacture that may be used to identify or characterize, and, optionally, to isolate, partition, separate or enrich certain tumorigenic cells or cell subpopulations associated with proliferative or neoplastic disorders. In preferred embodiments the subject cell or cell subpopulation will comprise tumor initiating cells and/or tumor perpetuating cells and/or tumor progenitor cells.

More specifically, in accordance with the teachings herein the inventors have discovered a series of markers that may be used independently, in combination or collectively to accurately interrogate, identify, characterize, enrich, isolate and/or sort cancer stem cells from a wide variety of tumors. Using selected techniques, the novel association of the disclosed markers with specific, self-renewing malignant cells in the tumor architecture provides for identification, enrichment, isolation, or purification of phenotypically distinct cells or tumor cell subpopulations that are capable of perpetual self-renewal and tumor recapitulation. In contrast to the prior art, and as evidenced by the Examples below, the disclosed markers are capable of interrogating, recognizing or identifying tumor initiating cells from a variety of tumors. The enrichment or isolation of these marker-defined, relatively homogeneous cell populations in turn allows for extensive characterization of the constituent cancer stem cells, including elucidation of proteins and/or nucleic acids with diagnostic utility as well as potential genotypic or phenotypic therapeutic targets. Moreover, as discussed in some detail below such refined cell populations may advantageously be used for the screening of pharmaceutical compounds. In other preferred embodiments the cells and compositions of the instant invention may be used in conjunction with animals such as immunocompromised mice to facilitate research, discovery and drug development efforts comprising novel in vivo models. Additionally it will be appreciated that the disclosed markers may further be used in clinical and non-clinical settings for the diagnosis, classification, monitoring and management of proliferative disorders as well as providing associated kits, devices or other articles of manufacture.

In particularly preferred embodiments the present invention provides for the identification, characterization, enrichment and/or isolation of, respectively, tumor initiating cells (TIC), tumor perpetuating cells (TPC), tumor progenitor cells (TProg) and non-tumorigenic (NTG) cells through the novel use of selected marker or marker combinations as set forth herein. With respect to the cancer stem cell paradigm, the TIC, TPC and TProg tumor cell subpopulations are each tumorigenic to a greater or lesser extent and, as such, are responsible for tumor growth, maintenance, recurrence and metastasis. Significantly, the instant invention allows such cell subpopulations to be interrogated, identified, characterized and optionally derived from a variety of different tumor types and stages of cancer. That is, through the identification of specific cancer stem cell markers, including tumor initiating cell associated markers (TICAM), tumor perpetuating cell associated markers (TPCAM) and tumor progenitor cell associated markers (TProgAM), the present invention provides, among other aspects, for the uniform and reproducible recognition, characterization, enrichment or isolation of highly pure tumorigenic cell subpopulations that, in turn, allow for the identification of cancer stem cell specific therapeutic targets and nucleic acids or proteins of prospective diagnostic and/or prognostic utility. In this regard these cells or enriched cell subpopulations, as defined by the disclosed markers alone or in combination, can be effectively employed in pharmaceutical research and development activities to identify novel therapeutic targets optimized for the inhibition, silencing, depletion or eradication of tumor initiating cells.

Accordingly, in preferred embodiments the present invention provides an isolated tumorigenic cell population enriched for expression of at least one TICAM. In a related embodiment the present invention will comprise a method for enriching a tumorigenic cell population comprising the steps of:

contacting a tumor cell population with a binding agent which preferably associates with at least one TICAM; and sorting said cells associated with at least one TICAM to provide an enriched tumorigenic cell population. Preferably the process will comprise a cell dissociation step prior to the contacting step. In other preferred embodiments the binding agent will comprise a genotypic binding agent or a phenotypic binding agent.

In particularly preferred embodiments the sorting step comprises fluorescence activated cell sorting (FACS), magnetic-assisted cell sorting (MACS), substrate-assisted cell sorting, laser capture microdissection, fluorometry, flow cytometry, mass cytometry or microscopy techniques. In other preferred embodiments the sorting step will comprise contacting the tumor cell population with a plurality of binding agents. In such embodiments the cell subpopulations may be interrogated, sorted, enriched, characterized or isolated by more than one TICAM.

Also provided by the invention are enriched tumor cell subpopulations derived from a heterogeneous tumor mass as well as tumor initiating cells derived from these tumors. It will be appreciated that the disclosed methods of enriching or isolating tumor initiating cells along with in vivo cell passaging and in vitro culture techniques result in populations of cells compatible with a wide variety of uses, as further described below.

Another aspect of the invention comprises personalized methods of treatment in a subject in need there comprising the characterization and, optionally, manipulation of tumorigenic cells or cell populations derived from the subject's own tumor using methods in accordance with the invention.

In this respect another embodiment of the invention comprises a method of treating, diagnosing or monitoring or predicting the results of a particular course of therapy in a subject in need thereof comprising the steps of;

accessing a sample from a subject; and contacting the sample with at least one binding agent that preferably associates with a TICAM.

In preferred embodiments the binding agent will comprise a phenotypic agent such as an antibody or immunoreactive fragment thereof. In other preferred embodiments the binding agent will comprise a genotypic agent such as a nucleic acid or related construct such as a labeled oligonucleotide probe, anti-sense construct, miRNA, intercalating dye, etc. In yet other embodiments the tumor sample will comprise a solid tumor sample. In other preferred embodiments the method will further comprise the step of characterizing or assessing tumorigenic cells associated with said tumor sample. In still other embodiments accessing the sample will occur in vivo. In others accessing the sample will occur in vitro. Preferred embodiments may further comprise the step of obtaining a tumor sample from the subject.

As described below such methods may further be used to determine if a subject is susceptible to tumor recurrence or metastatic events.

Yet another aspect of the instant invention will comprise a method of determining if a cell obtained from a tumor sample is tumorigenic comprising the step of contacting the tumor cell with at least one TICAM binding agent.

Again, in preferred embodiments the binding agent will comprise a phenotypic agent such as an antibody or immunoreactive fragment thereof or a genotypic agent such as a nucleic acid or an RNA or DNA construct. In still other embodiments the cell will be interrogated or tested to determine the ability of said cell to initiate a tumor when transplanted in vivo. In yet other embodiments the tumor cell will be interrogated or tested to determine the ability of the cell to initiate a colony in vitro. It will further be appreciated that the cell may be included in an enriched or isolated cell subpopulation.

Yet another aspect of the present invention provides methods of treating a subject suffering from cancer wherein the method comprises interrogating, assessing or characterizing TICAM positive cells (e.g., via genotypic or phenotypic binding agents) from the subject. Optionally the assessment may occur following treatment of the subject and, in other embodiments, the assessment will occur after the subject has been treated with one or more anti-cancer agents. In yet other embodiments the assessment will be undertaken prior to the patient being treated. Moreover, such interrogation may be conducted in vitro on tissue samples obtained from the patient or in vivo. In particularly preferred embodiments the method will comprise interrogating circulating tumor cells.

Another embodiment of the present invention relates to methods to determine if a subject is at risk of recurrence wherein the method comprising assessing the presence of TICAM positive cells, through the introduction of a binding agent (genotypic or phenotypic) that preferably associates with at least one TICAM, wherein the detection of tumor cells at the original tumor site, elsewhere in the body, or circulating in the blood is indicative that the subject is at risk of recurrent cancer and/or metastasis. In such embodiments, a subject at risk of recurrence or metastasis may be treated using art recognized clinical techniques.

In a similar vein the present invention also provides kits or devices that are useful in the diagnosis and monitoring of tumor initiating cell-associated disorders such as cancer. In one preferred embodiment the present invention preferably provides an article of manufacture useful for diagnosing or treating such disorders comprising a receptacle or receptacles comprising one or more genotypic or phenotypic binding agents that preferably associate with a tumor initiating cell associated marker and instructional materials for using the same. In other embodiments the disclosed TICAM binding agents may be associated with a solid support (e.g., a filter, matrix, surface, catheter, etc.) that is then contacted with patient tissue in vivo or in vitro.

Still another embodiment of the instant invention comprises a method of conducting genotypic or phenotypic analysis comprising the steps of:

providing a tumorigenic cell or enriched tumorigenic cell population comprising one or more TICAM;

treating said cell or cell population to obtain genetic or proteomic material; and analyzing said genetic or proteomic material.

In preferred embodiments the analyzing step will comprise transcriptome analysis (including whole transcriptome analysis) using Next-Gen sequencing. In other embodiments, the analyzing step will comprise genotyping via exome arrays or epigenetics analysis via ChiP-seq, expression analysis using quantitative PCR or microarray, microRNA analysis, or focused proteomics analysis using FACS or protein microarrays.

In yet other preferred embodiments, the analyzing step will comprise protein expression analysis using massively parallel mass cytometry. In yet other embodiments the analyzing step will comprise mass spectrometry-based analysis of the protein repertoire on TIC and other tumor cell subpopulations of interest.

Still another embodiment of the instant invention comprises a method for the diagnosis and monitoring of tumor initiating cell-associated disorders by detecting, characterizing and/or quantifying TIC identity and frequency within patient specimens (e.g., blood, serum or undissociated tumor) comprising nucleic acid expression analysis.

Yet another embodiment of the instant invention comprises a method for the diagnosis and monitoring of tumor initiating cell-associated disorders by identifying and/or quantifying TIC identity and frequency in patients using methods that include imaging or light/energy detection methodologies. In preferred embodiments the analysis will comprise Next-Gen whole genome sequencing or exon/SNP array analysis.

In yet another embodiment the present invention will comprise a method of screening potential pharmaceutical compounds comprising the steps of:

exposing a tumorigenic cell or tumorigenic cell population to a candidate compound; and contacting the tumorigenic cell or tumorigenic cell population with at least one TICAM binding agent.

In selected embodiments the exposing step will be conducted in vivo. In other preferred embodiments the exposing step will be conducted in vitro. In yet other preferred embodiments the method will further comprise characterizing the tumorigenic cell or tumorigenic cell population. In still other embodiments the TICAM binding agent will comprise a phenotypic binding agent or a genotypic binding agent.

In another embodiment, the instant invention provides a method of inducing cancer comprising the steps of:

providing a tumorigenic cell population enriched for one or more TICAM; and introducing the tumorigenic cell population into a subject.

In yet another preferred embodiment the instant invention comprises a method of inducing cancer comprising the steps of:

isolating a tumorigenic cell exhibiting one or more TICAM; and introducing the isolated tumorigenic cell into a subject.

Preferably the cell is isolated by contacting said cell with one or more binding agents that preferably associate with one or more TICAM. In selected embodiments the binding agent will comprise a phenotypic binding agent or a genotypic binding agent.

The instant invention further provides a method of generating a tumor or tumor samples comprising the steps of:

providing a tumorigenic cell or enriched tumorigenic cell population comprising one or more TICAM;

introducing the tumorigenic cell or enriched tumorigenic cell population into a subject;

allowing for the tumorigenic cell or cell population to generate a tumor.

In preferred embodiments the generated tumor will be interrogated, characterized, sampled, biopsied, harvested or collected to provide a tumor sample. In particularly preferred embodiments the biopsied or harvested tumor will be frozen and banked using art-recognized techniques. In yet other preferred embodiments cells derived from the generated tumors will be implanted or passaged in a subject. Still other preferred embodiments of the instant invention comprise a tumor bank comprising such generated tumors or tumor cells.

In still another preferred embodiment the present invention provides an animal model for the analysis of pharmaceutical compounds comprising a subject implanted with a tumorigenic cell or cell population purified or enriched for one or more TICAM. In particularly preferred embodiments the subject will comprise an immunocompromised mouse. A related preferred embodiment comprises a method of producing an animal model for the analysis of pharmaceutical compounds comprising the step of introducing a tumorigenic cell or cell population isolated, purified or enriched for one or more TICAM.

Yet another preferred embodiment provides for the quantification of TIC within a specimen by serially transplanting said specimen serially into another host subject in varying cell dilutions and enumerating the frequency of binary tumor growth events independent of rate.

Still yet another preferred embodiment provides for the quantification of TIC within a specimen by plating varying cell dilutions in vitro and enumerating the frequency of colony forming events.

Another preferred embodiment provides for the quantification and characterization of TIC within a specimen by obtaining cells from a sample and analyzing the constituent cells by flow cytometry, mass cytometry or by imaging modalities.

Yet another preferred embodiment provides for the quantification and characterization of TIC within a specimen by obtaining genetic material (DNA or RNA) from a sample, and analyzing the expression of TIC and/or NTG cell-associated gene/microRNA expression by qRT-PCR.

Other embodiments will comprise a method of immunizing a subject comprising the steps of:

providing a tumorigenic cell population enriched for one or more TICAM; and introducing the tumorigenic cell population into said subject.

Preferably the subject comprises a competent immune system and exhibits an immune response to the tumorigenic cell population. In other preferred embodiments the immune response will generate binding agents that preferably associate with TICAM or to therapeutic targets associate with the TICAM positive cells.

Another embodiment of the instant invention comprises vaccinating a subject with one or more TICAM to generate a protective immune response directed to cancer stem cells. In this respect the present invention comprises a method of vaccinating a subject in need thereof comprising the step of exposing said subject's immune system to one or more TICAM wherein the subject develops a protective immune response. Preferably the TICAM will be administered to the subject in a soluble form. In other embodiments the TICAM may be expressed on a cell. Such embodiments may comprise, for instance, inactivated TIC populations or cells engineered to express one or more TICAM. In other embodiments the exposure may take place in vitro wherein cell populations comprising immune components from the subject are exposed to the TICAM and reinfused into the patient to stimulate an immune response.

In other embodiments the invention provides a method for the detection and/or enumeration of tumorigenic potential comprising the step of detecting secreted proteins or immunoreactive fragments thereof wherein said proteins are associated with tumor-initiating cells sorted from NTG cells.

Preferably the detection may take place in vivo or in vitro and further comprises the step of quantifying the secreted proteins.

In another embodiment the invention comprises a method for identifying novel TICAMs comprising the steps of:

exposing a tumor-bearing subject to chemotherapy;

collecting tumor cell populations from said subject; and analyzing the cell populations for TICAM expression.

In preferred embodiments the TICAM expression is elevated. In other embodiments the collected tumor cell populations will comprise composite tumor cell populations.

Besides the aforementioned aspects selected embodiments of the invention provide a method of analyzing or monitoring cancer progression and/or pathogenesis in vivo, comprising the steps of:

introducing one or more tumor initiating cells comprising one or more TICAM into a subject; and monitoring cancer progression and/or pathogenesis in the subject.

In preferred embodiments the subject will be treated with one or more anti-cancer agents following the introduction of the one or more tumor initiating cells. In other embodiments the subject will comprise a non-human mammal. In still other preferred embodiments the non-human mammal will comprise an immunocompromised mouse or a primate.

In still other preferred embodiments the TICAM of the instant invention may be used to identify tumorigenic cells in regenerative medicine compositions. As will be appreciated regenerative medicine products comprising stem cell compositions such as embryonic, iPS, or adult stem cell derived cells are becoming more common and increasingly being used for therapeutic intervention. Unfortunately such products may unintentionally comprise cancer stem cells that could proved dangerous for the intended patients. Using the methods, compositions and articles of manufacture of the instant invention those skilled in the art will appreciate that such regenerative medicine products could readily be screened for presence of unwanted cancer stem cells. Moreover, the teachings herein are also compatible with depleting or eliminating any cancer stem cells that may be present in the regenerative medicine product comprising stem cells.

Accordingly, in one embodiment the instant invention provides a method for detecting the presence of cancer stem cells in a regenerative medicine product comprising stem cells comprising the step of contacting said regenerative medicine product with at least one TICAM binding agent. In another preferred embodiment the present invention provides for the depletion or elimination of cancer stem cells from a regenerative medicine product comprising stem cells comprising the step of contacting said regenerative medicine product with at least one TICAM binding agent. It will further be appreciated that the contacting step may be conducted using any one of a number of art-recognized techniques and commercially available devices or articles of manufacture that are readily apparent in view of the instant disclosure.

As discussed in more detail below, preferred TICAMs compatible with the instant invention comprise CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

In another particularly preferred embodiment compatible TICAMs comprise CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

In particularly preferred embodiments cells and cell populations enriched or isolated as set forth herein shall comprise a phenotypic or genotypic marker or determinant comprising one or more TICAM. As discussed extensively below and illustrated by the appended Examples, binding agents for each of the aforementioned makers may be used in accordance with the teachings herein to interrogate, identify, characterize and, optionally, separate, enrich or isolate tumorigenic cell populations including cancer stem cell populations.

Moreover, the present invention provides TICAM subsets that preferentially associate with discrete tumor types and may be particularly useful for enriching, characterizing, monitoring or detecting such tumorigenic cells or cell subpopulations or in conjunction with diagnostic or therapeutic procedures related to such tumors. That is, as set forth in FIGS. 12A-12C, the present invention provides colorectal associated TICAM, breast associated TICAM, non-small cell lung cancer associated (NSCLC) TICAM, ovarian associated TICAM, pancreatic associated TICAM, small cell lung cancer (SCLC) TICAM and melanoma associated TICAM. Of course it will be appreciated that the identified tumor associated TICAM subsets may be used with selected tumors and in conjunction with the teachings herein to practice all aspects of the invention generally set forth in the context of the broader population of identified TICAM.

With regard to all the aforementioned embodiments it will be appreciated that a particularly preferred TICAM comprises a TICAM selected from the group consisting of CD46, CD324 and CD66c. In this respect it will be appreciated that particularly preferred tumorigenic cells or enriched cell populations will comprise a $CD46^{hi}$ phenotype. In other preferred embodiments the disclosed cells or cell populations will comprise a $CD324^+$ phenotype. In yet other especially preferred embodiments the cells or cell compositions of the instant invention will comprise a $CD46^{hi}$ $CD324^+$ phenotype. In still other preferred embodiments the disclosed cells will have a $CD46^{hi}$ $CD324^+$ $CD66c^-$ phenotype while in yet other embodiments the cells will exhibit a $CD46^{hi}$ $CD324^+$ $CD66c^+$. Of course it will be appreciated that cells or cell populations comprising the aforementioned phenotypes may be derived using genotypic or phenotypic binding agents that preferentially associate or react with each of the specified markers.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent by reference to the figures and in the teachings set forth herein.

BRIEF DESCRIPTION OF THE FIGURES

FIGS. 11A and 11B are tabular overviews of representative colorectal (CR), non-small cell lung (LU37 and LU49), pancreatic (PA), triple-negative breast (BR), ovarian (OV) and melanoma (SK) tumor cell transplant experiments using isolated tumor cell subpopulations expressing various combinations of CD46 and CD324.

FIGS. 12A-12C provide a tabular overview of markers observed to be co-expressed on CD46$^{hi}$ CD324$^+$ cells in the respective solid tumor types denoted.

FIGS. 20A-20C are graphical representations depicting the ability of colorectal tumor-derived cell populations enriched for CD46$^{hi}$, CD324 and/or CD66 expression to reconstitute heterogeneous tumors reflecting the parental tumor from which they were obtained.

FIGS. 22A-22C provide scatter plots and a tabular summary showing the robust tumorigenicity demonstrated by isolated colorectal CD46$^{hi}$ CD324$^+$ CD66c$^-$ cell populations through serial transplantation.

DETAILED DESCRIPTION OF THE INVENTION

I. Introduction

Figure 1A:
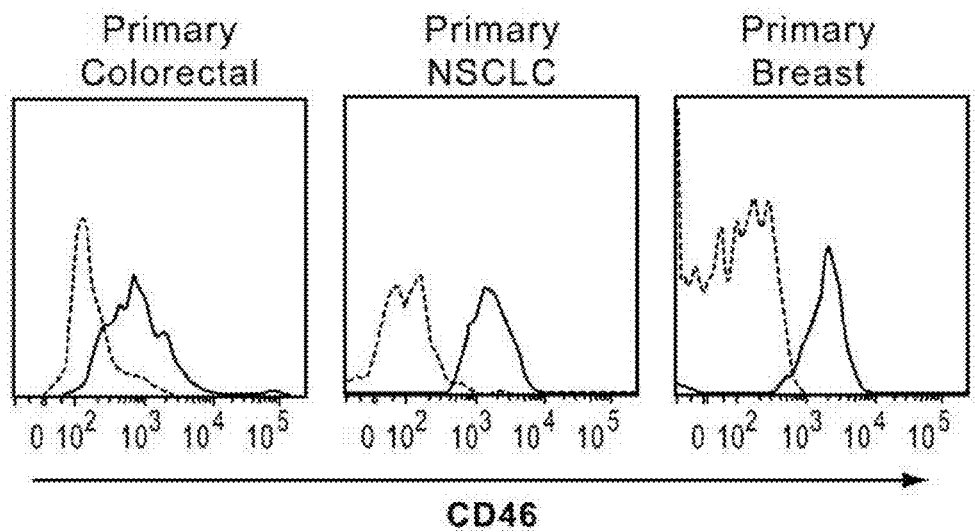
FIGS. 1A-1D depict flow cytometry-based protein expression data for various individual tumor cells displayed as histogram plots, wherein the background staining of isotype control antibodies is shown in gray, filled histograms and CD46 expression is displayed using the bold, black line.
Figure 1B:
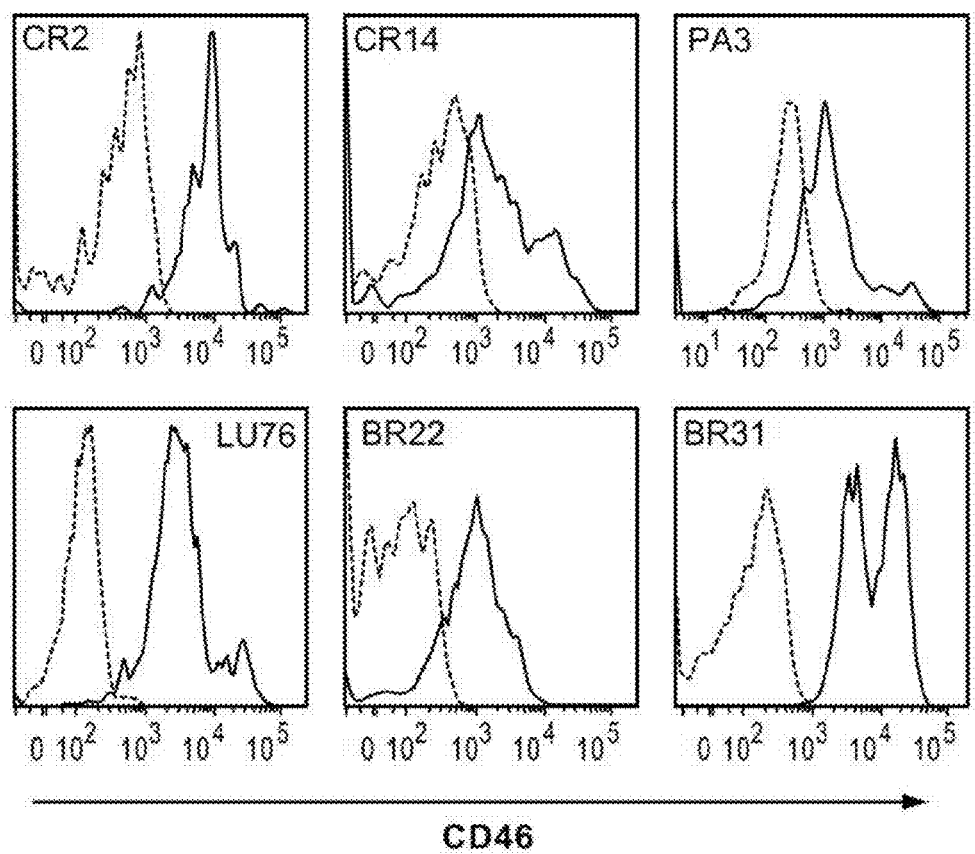

In the following detailed description, numerous specific details are set forth in order to provide a thorough understanding of the invention. However, it will be understood by those skilled in the art that aspects of the present invention may be practiced without these specific details. In other instances, well-known methods, procedures, and components have not been described in detail so as not to obscure the present invention.

Characterizing therapeutically significant aspects of tumor initiation and growth to identify and define treatment strategies and provide therapeutically effective targets has proven extremely difficult. In the past the inability to develop successful therapeutic regimens for the treatment of various cancers could, at least in part, be attributed to a lack of understanding of the underlying forces driving tumor growth and recurrence and limitations in research techniques and tools. Yet with the development and validation of the cancer stem cell paradigm over the past several years, and an enhanced appreciation of the intricacies of tumor physiology brought about by increasingly effective research methodology, substantial clinical advances as exhibited by patient survival should be self-evident. Unfortunately, and with some notable exceptions, the expected improvements have not been recognized, particularly in the case of certain solid tumors.

In part, this relative lack of clinical success may be attributed to the misapplication of generally accurate and illuminating research techniques to ill-conceived or improperly defined cell populations that are commonly held to be tumorigenic. For example, while differential gene expression has been widely used to identify cancer-associated gene activity and to distinguish expressed proteins having potential therapeutic or diagnostic value, the technique has been of limited value in improving patient survival. This is because such analysis has often been conducted using genetic information obtained from a complex mixture of tumor cells or subpopulations sorted using non-specific or inappropriate cancer stem cell markers.

While these procedures may provide some insight as to generally expressed tumor associated gene products, they do little to identify specific, relevant markers of cancer stem cells that can be exploited to develop targeted therapeutics for the prevention of tumor initiation, propagation, recurrence and metastasis. That is, because of the poor quality of the starting material, such differential expression studies often implicate irrelevant or relatively insignificant genes and/or proteins (from an etiological standpoint) derived from phenotypically diverse and differentiated cells that prove generally ineffective as cancer stem cell markers upon further study. Conversely, through the identification of specific cancer stem cell markers, including tumor initiating cell associated markers (TICAM), tumor perpetuating cell associated markers (TPCAM) and tumor progenitor cell associated markers (TProgAM), the present invention provides, among other aspects, for the uniform and reproducible interrogation, recognition, stratification, characterization, sorting, enrichment and/or isolation of highly pure tumorigenic cell subpopulations that, in turn, allow for the identification of cancer stem cell specific therapeutic targets and proteins or genes of prospective diagnostic utility.

More generally, in accordance with the teachings herein the inventors have discovered a series of markers that may be used independently, in combination or collectively to accurately identify, sort enrich and/or and characterize cancer stem cells from a wide variety of tumors. Using selected biochemical techniques, the novel association of the disclosed markers with specific, self-renewing malignant cells in the tumor architecture provides for interrogation, identification, stratification, characterization, enrichment, isolation, or purification of phenotypically distinct cells or tumor cell subpopulations that are capable of perpetual self-renewal and tumor recapitulation. In contrast to the prior art, and as evidenced by the Examples below, the disclosed markers are capable of recognizing or identifying tumor initiating cells from a variety of tumors. The enrichment or isolation of these marker-defined, relatively homogeneous cell populations in turn allows for the extensive characterization of the constituent cancer stem cells, including the elucidation of potential therapeutic targets and screening of pharmaceutical compounds. In other embodiments the cells and compositions of the instant invention may be used in conjunction with animal models such as non-traditional xenograft (NTX™) models to facilitate research and drug development efforts. Moreover, the disclosed markers may further be used in clinical and non-clinical settings for the diagnosis, prognosis, theragnosis, classification, monitoring and management of proliferative disorders as well as providing associated kits or other articles of manufacture.

While certain features of the invention have been illustrated and described, many modifications, substitutions, changes, and equivalents will now occur to those of ordinary skill in the art. It is, therefore, to be understood that the appended claims are intended to cover all such modifications and changes as fall within the true spirit of the invention.

II. Selected Abbreviations

CSC, cancer stem cells; ETP, early tumor progenitor cells; FACS, fluorescence activated cell sorting; LTP, late tumor progenitor cells; MACS, magnetic-assisted cell sorting; TIC, tumor initiating cells; TICAM, tumor initiating cell associated marker; TPC, tumor perpetuating cells; TPCAM, tumor perpetuating cell associated marker; TProg, tumor progenitor cells; TProgAM, tumor progenitor cell associated marker; NTX, non-traditional xenograft;

III. Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

As used herein the term "tumor initiating cells" (TIC) shall be held to mean tumorigenic cells or populations thereof that are capable of at least significant proliferation capacity and an ability to initiate and recapitulate tumors in immunocompromised mice when transplanted. In this regard tumor initiating cell populations will comprise both tumor perpetuating cells and highly proliferative tumor progenitor cells.

For purposes of the instant disclosure, "tumor perpetuating cells" or "cancer stem cells" (TPC or CSC) may be used interchangeably and are defined as cells that can undergo self-renewal and have abnormal proliferation and/or differentiation properties resulting in the ability to form a tumor. Functional features of tumor perpetuating cells are that they are tumorigenic; they can give rise to additional tumorigenic cells by self-renewal; and they can also fully recapitulate a heterogeneous tumor mass by giving rise to tumor progenitor and non-tumorigenic tumor cells. More specifically, TPC can completely recapitulate the composition of tumor cells existing within a tumor and have unlimited self-renewal capacity as demonstrated by serial transplantation (two or more passages through mice) of low numbers of isolated cells.

With respect to the instant invention the term "tumor progenitor cells" (TProg) refer to tumorigenic cells or populations thereof that are progeny of TPC and possess the capacity for at least some tumor recapitulation and limited self-renewal when cultured in vitro or passaged through a compatible animal host. Certain TProg cells or populations may be referred to as highly proliferative herein. As discussed in more detail below, TProg cell populations comprise both "early tumor progenitor cells" (ETP) and "late tumor progenitor cells" (LTP) that may be distinguished by phenotype (e.g., cell surface markers or genetic profile) and different capacities to recapitulate tumor cell architecture.

In the instant application a "tumor initiating cell associated marker" (TICAM) shall be held to comprise any marker that is associated with a tumor initiating cell or cell subpopulation and allows for the identification, characterization and optional isolation or enrichment thereof.

As used herein a "tumor perpetuating cell associated marker" (TPCAM) shall be held to comprise any marker that is associated with a tumor perpetuating cell or cell subpopulation and allows for the identification, characterization and optional isolation or enrichment thereof. It will be appreciated that TICAM and TPCAM are not mutually exclusive and that an individual marker may comprise both simultaneously.

For the purposes of the instant application a "tumor progenitor cell associated marker" (TProgAM) comprises any marker that is associated with a tumor progenitor cell or cell subpopulation and allows for the identification, characterization and optional isolation or enrichment thereof. It will be appreciated that TICAM and TProgAM are not mutually exclusive and that an individual marker may comprise both simultaneously.

As used herein, particularly in reference to an isolated cell or isolated cell population, the term "tumorigenic" refers to a cell derived from a tumor that is capable of forming a tumor, when dissociated and transplanted into a suitable animal model such as an immunocompromised mouse.

In the instant application a "non-tumorigenic cell" (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in immunocompromised mice, even when transplanted in excess cell numbers.

For the purposes of the instant application the terms "selecting," "sorting," "partitioning" "sectioning" or "isolating" selected cells, cell populations or cell subpopulations may be used interchangeably and mean, unless otherwise dictated by context, that a selected cell or defined subset of cells are removed from a tissue sample and separated from other cells and contaminants that are not within the parameters defining the cell or cell population. An isolated cancer stem cell will be generally free from contamination by other cell types and have the capability of self-renewal and tumor recapitulation allowing the generation of differentiated progeny in most cases. However, when the process or treatment results in a cell population it is understood that it is impractical to provide compositions of absolute purity. In such cases the cell population is "enriched" for the selected cells that then exist in the presence of various contaminants (including other cell types) that do not materially interfere with the function or properties of the selected cell subpopulation.

As used herein and applied to cells or cell populations, the term "enriched" may be construed broadly and held to mean any processed or treated cell population that contains a higher percentage of a selected cell type than is found in an untreated, otherwise equivalent cell population or sample. In some preferred embodiments enriching a cell population refers to increasing the percentage by about 10%, by about 20%, by about 30%, by about 40%, by about 50% or greater than 50% of one type of cell in a population of cells as compared to the starting population of cells. In other preferred embodiments enriched cell populations of the instant invention will comprise at least 30%, 40%, 50%, 60%, 70%, 80%, 85%, 90%, 95%, 98%, or 99% of the selected cell type. In yet other embodiments, an enriched preparation of tumor perpetuating cells may be described as comprising about 1% or greater or about 0.5% to about 40% of the total cell population contained in a preparation. By way of comparison, a non-enriched preparation of exemplary tumor cells would include only about 0.2% to about 2.0% or less of tumor perpetuating cells that are capable of giving rise to a secondary colony forming sphere or perpetuating a heterogeneous tumor in vivo. In some embodiments, the enriched preparations comprise a 100-fold, 200-fold, 500-fold, 1,000-fold, or up to a 2,000-fold or 10,000-fold to 20,000-fold enriched preparation of cancer stem cells capable of giving rise to secondary colonies or perpetuating a heterogeneous tumor in vivo, starting with low cell numbers.

In other aspects of the invention the term "substantially pure," with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, refer to a population of cells that contain fewer than about 20%, more preferably fewer than about 15%, 10%, 8%, 7%, most preferably fewer than about 5%, 4%, 3%, 2%, 1%, or less than 1%, of cells that are not tumor initiating cells.

A "marker" or "cell marker" as used herein in the context of a cell or tissue, means any trait or characteristic in the form of a chemical or biological entity (including phenotypic and genotypic traits or determinants) that is identifiably associated with, or specifically found in or on a particular cell, cell population or tissue including those identified in or on a tissue or cell population affected by a disease or disorder. Markers may be morphological, functional or biochemical in nature and may be genotypic or phenotypic. In preferred embodiments the marker is a phenotypic determinant such as a cell surface antigen that is differentially or preferentially expressed (or is not) by specific cell types (e.g., TPCs) or by cells under certain conditions (e.g., during specific points of the cell cycle or cells in a particular niche). In still other preferred embodiments the marker may comprise genotypic determinant such as a particular gene or genetic entity or locus that is differently regulated (up or down) in a specific cell or discrete cell population (e.g., mRNA transcription levels), a gene that is differentially modified with regard to its physical structure and chemical composition or a protein or collection of proteins physically associated with a gene that show differential chemical modifications. Markers contemplated herein are specifically held to be positive or negative and may denote a cell or cell subpopulation by its presence (positive) or absence (negative).

Similarly the term "marker phenotype" in the context of a tissue, cell or cell population (e.g., a stable TPC phenotype) means any marker or combination of markers that may be used to characterize, identify, quantify, separate, isolate, purify or enrich a particular cell or cell population. In specific preferred embodiments, the marker phenotype is a cell surface phenotype which may be determined by detecting or identifying the expression of a combination of cell surface markers. In other preferred embodiments the marker with will comprise a genotypic marker.

"Positive," "low" and "negative" expression levels as they apply to markers or marker phenotypes are defined as follows. Cells with negative expression (i.e. "−") are herein defined as those cells expressing less than, or equal to, the 95th percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95th percentile of expression observed with an isotype control antibody using the FMO staining procedure described above are herein defined as "positive" (i.e. "+"). As defined herein there are various populations of cells broadly defined as "positive." First, cells with low expression (i.e. "lo") are generally defined as those cells with observed expression above the 95th percentile determined using FMO staining with an isotype control antibody and within one standard deviation of the 95th percentile of expression observed with an isotype control antibody using the FMO staining procedure described above. Cells with "high" expression (i.e. "hi") may be defined as those cells with observed expression above the 95th percentile determined using FMO staining with an isotype control antibody and greater than one standard deviation above the 95th percentile of expression observed with an isotype control antibody using the FMO staining procedure described above. In other embodiments the 99th percentile may preferably be used as a demarcation point between negative and positive FMO staining and in particularly preferred embodiments the percentile may be greater than 99%.

The term "lineage" as used herein describes cells with a common ancestry. For example, cells that are derived from the same tumor initiating cell may be of the same lineage though the progeny have differentiated into various classes of cells.

For the purposes of the instant disclosure the terms "binding agent," "binding molecule" and "binding entity" are synonymous unless otherwise dictated by circumstance and may be used interchangeably. In the context of the instant invention the binding agent binds, interacts, recognizes, reacts, or otherwise preferably associates with a selected marker on a defined cell or cell subpopulation. For the purposes of the instant invention binding agents may comprise genotypic binding agents or phenotypic binding agents depending on the type of marker they tend to associate with. Exemplary binding agents can include, but are not limited to, an antibody or fragment thereof, an antigen, an aptamer, a nucleic acid or derivative thereof (e.g., DNA, RNA, miRNA, siRNA, antisense constructs, etc.), intercalating dyes, a protein (e.g. receptor, enzyme, enzyme inhibitor, enzyme substrate, ligand), a peptide, a lectin, a fatty acid or lipid and a polysaccharide. It will be appreciated that both genotypic and phenotypic binding agents may be associated with reporters or other detection aids. In a selected embodiment a compatible binding agent may comprise the hemagglutinin protein of measles virus or CD46 binding fragment thereof. In other particularly preferred embodiments the binding agent or entity comprises an antibody or fragment thereof. Exemplary genotypic and phenotypic binding agents are discussed in more detail below.

As set forth herein the term "antibody" is used in the broadest sense and specifically covers synthetic antibodies, monoclonal antibodies, oligoclonal or polyclonal antibodies, multiclonal antibodies, recombinantly produced antibodies, intrabodies, multispecific antibodies, bispecific antibodies, monovalent antibodies, multivalent antibodies, human antibodies, humanized antibodies, chimeric antibodies, primatized antibodies, Fab fragments, F(ab') fragments, single-chain FvFcs (scFvFc), single-chain Fvs (scFv), anti-idiotypic (anti-Id) antibodies, any other immunologically active antibody fragments and engineered reactive peptides (e.g. adnectins) so long as they exhibit the desired biological activity (i.e., marker association or binding). In a broader sense, the antibodies of the present invention include immunoglobulin molecules and immunologically active fragments of immunoglobulin molecules, i.e., molecules that contain an antigen binding site, where these fragments may or may not be fused to another immunoglobulin domain including, but not limited to, an Fc region or fragment thereof. Further, as outlined in more detail herein, the terms antibody and antibodies specifically include Fc variants, including full length antibodies and variant Fc-Fusions comprising Fc regions, or fragments thereof, optionally comprising at least one amino acid residue modification and fused to an immunologically active fragment of an immunoglobulin.

As used herein the term "epitope" refers to that portion of the target marker or antigen capable of being recognized and specifically bound by a particular antibody. When the marker is a polypeptide such as a cell surface receptor, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. Additionally an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

The term "derivative" as used herein refers to molecules, including proteins and nucleic acids which have been modified through standard molecular biology methodology or chemically, for example but not limited to by techniques such as ubiquitination, labeling (a fluorophore), pegylation (derivatization with polyethylene glycol) or addition of other molecules.

The term "functional derivative" and "mimetic" are used interchangeably, and refer to compounds that possess a biological activity (either functional or structural) that is substantially similar to a biological activity of the entity or molecule for which it's a functional derivative. The term functional derivative is intended to include the fragments, variants, analogues or chemical derivatives of a molecule.

As used herein, "variant" with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide). A "variant" of an antibody for example, is meant to refer to a molecule substantially similar in structure and function, e.g., where the variant retains the ability to bind with a selected antigen or a fragment thereof yet has an altered biochemical effect.

A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules not found in the other, or if the sequence of amino acid residues is not identical.

A "fragment" of a molecule, is meant to refer to any contiguous polypeptide or nucleotide subset of the molecule. Fragments of, for example, a transmembrane protein may comprise constructs that only include the extracellular domains or some portion thereof. With respect to the instant invention marker fragments or derivatives may include any immunoreactive or immunologically active portion of a selected marker.

An "analog" of a molecule such as a marker is meant to refer to a molecule similar in function to either the entire molecule or to a fragment thereof. As used herein, a molecule is said to be a "chemical derivative" of another molecule when it contains additional chemical moieties not normally a part of the molecule. Such moieties can improve the molecule's solubility, absorption, biological half life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., Mack Publ., Easton, Pa. (1990).

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. The term "substantially homologous" refers to sequences that are at least 90%, at least 95% identical, at least 97% identical or at least 99% identical. Homologous sequences can be the same functional gene in different species.

As used herein, the term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-100 amino acid residues (e.g., a heavy or light chain variable region of an antibody). In the context of amino acid sequences, "substantial similarity" further includes conservative substitutions of amino acids. Thus, a polypeptide is substantially similar to a second polypeptide, for example, where the two peptides differ by one or more conservative substitutions. The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

Determination of homologs of the genes or polypeptides of the present invention can be easily ascertained by the skilled artisan. The terms "homology" or "identity" or "similarity" are used interchangeably herein and refers to sequence similarity between two peptides or between two nucleic acid molecules. Homology and identity can each be determined by comparing a position in each sequence that can be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the present application.

As used herein, the terms "subject" or "patient" may be used interchangeably and refer to any living organism which can be administered any derived pharmaceutical compositions of the present invention and in which cancer or a proliferative disorder can occur. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" also includes living organisms susceptible to conditions or disease states as generally disclosed, but not limited to, throughout this specification. Examples of subjects include humans, dogs, cats, cows, goats, and mice, including transgenic species. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

As used herein the term "patient sample" shall be held to mean any tissue obtained from or provided by a subject or patient. In preferred embodiments the patient sample will comprise a tumor sample obtained using art recognized techniques. In other selected embodiments the patient sample will comprise a bodily fluid such as blood, serum, urine, tears, lymphatic fluid, etc, that may contain tumor cells or circulating tumor cells.

The term "effective amount" as used herein refers to the amount of an agent and/or a pharmaceutical composition required to retard, reduce or ameliorate at least one symptom of the disease or disorder. For example, an effective amount of a potential drug compound is the amount of required to reduce the rate of tumor growth of, or tumor frequency initiated by, tumor initiating cells implanted in a test animal. Thus, an effective amount is also the amount sufficient to prevent the development of a disease symptom, or to reduce a symptom or reduce the rate of symptom progression.

The terms "malignancy," "neoplasia" and "cancer" are used interchangeably herein and refer to diseases or disorders that are characterized by uncontrolled, hyperproliferative or abnormal growth or metastasis of cells. In other aspects the term is also intended to include any disease of an organ or tissue (e.g., colorectal, pancreatic, breast, etc.) in mammals characterized by poorly controlled or uncontrolled multiplication of normal or abnormal cells in that tissue and its effect on the body as a whole. Disorders within the scope of the definition comprise benign neoplasms, dysplasias, hyperplasias as well as neoplasms showing metastatic growth or any other transformations like e.g. leukoplakias which often precede an episode or recurrence of cancer.

As used herein, the term "refractory" is most often determined by failure to reach clinical endpoint, e.g., response, extended duration of response, extended disease-free, survival, relapse-free survival, progression-free survival and overall survival. Another way to define being refractory to a therapy is that a patient has failed to achieve a response to a therapy such that the therapy is determined to not be therapeutically effective.

As used herein, the phrase "diagnostic agent" refers to any molecule, compound, and/or substance used for the purpose of diagnosing a disease or disorder. In preferred embodiments the diagnostic agent shall comprise a binding agent associated with a reporter. Other non-limiting examples of diagnostic agents include antibodies, antibody fragments, or other proteins, including those conjugated to a detectable agent. As used herein, the term "detectable agent" or "reporter" refer to any molecule, compound and/or substance that is detectable by any methodology available to one of skill in the art. Non-limiting examples of detectable agents or reporter molecules include dyes, fluorescent tags, gases, metals, or radioisotopes. As set forth herein, "diagnostic agent" "imaging agent" and "reporter" or "reporter molecule" are equivalent and may be used interchangeably unless otherwise dictated by context.

As used herein, the term "treating" includes preventing the progression and/or reducing or reversing at least one adverse effect or symptom of a condition, disease or disorder associated with inappropriate proliferation, survival and/or differentiation of cells such as in, for example, cancer.

As used herein, the terms "administering" and "introducing" are used interchangeably herein and refer to the placement of the pharmaceutical compositions as disclosed herein into a subject by a method or route which results in at least partial localization of the pharmaceutical compositions at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions of the present invention comprising pyrazoloanthrones and optionally other agents or material other than directly into the central nervous system, such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, or be biologically inert.

IV. Tumorigenic Cell and Cell Subpopulations

In particularly preferred embodiments the present invention provides for the identification, stratification, characterization, enrichment and/or isolation of, respectively, tumor initiating cells (TIC), tumor perpetuating cells (TPC) and tumor progenitor cells (TProg) through the novel use of selected marker or marker combinations as set forth herein. With respect to the cancer stem cell paradigm, each of the aforementioned cell subpopulations are tumorigenic to a greater or lesser extent and, as such, are responsible for tumor growth, maintenance, metastasis and recurrence. Significantly, the instant invention allows such cell subpopulations to be identified and optionally derived from a variety of different tumor types and stages of cancer. As such, accounting for and eliminating these cells are likely critical for the effective management and treatment of a variety of diverse neoplasia. In this regard these cells or enriched cell subpopulations, alone or in combination, can be effectively employed in pharmaceutical research and development activities to identify novel therapeutic targets optimized for the suppression or depletion of tumor initiating cancer stem cells.

Figure 27A:
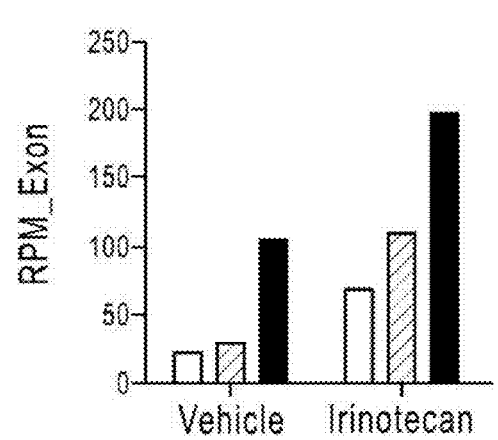
FIGS. 27A-27D present graphical depictions of representative gene expression for NOTUM (FIG. 27A), APCDD1 (FIG. 27B), REG1A (FIG. 27C) and MUC20 (FIG. 27D) associated with NTG cells, TProg cells and TPC, respectively, within an exemplary colorectal tumor.
Figure 27B:
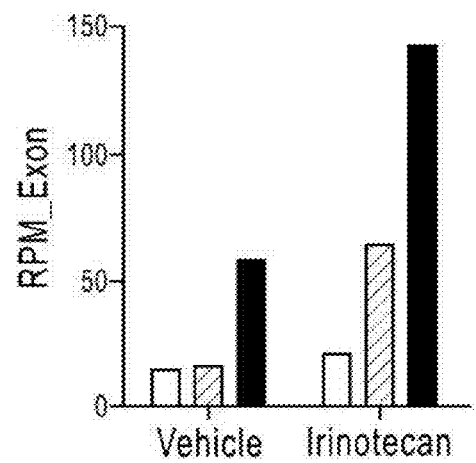
Figure 27C:
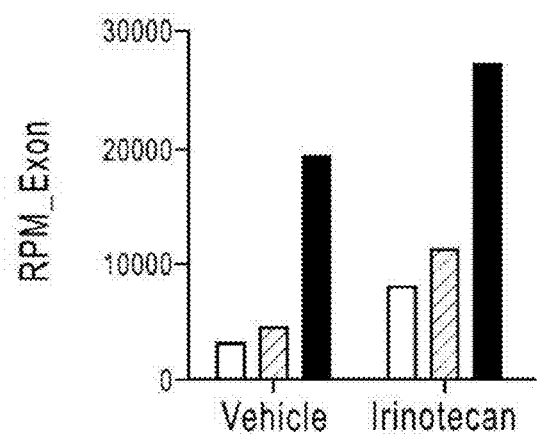
Figure 27D:
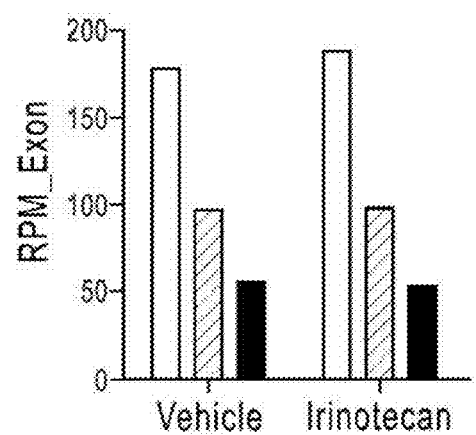

As has been demonstrated for blood and hematopoietic diseases, a hierarchy of cells likely exists within many solid tumors wherein distinct tumor cell subpopulations possess different proliferation and differentiation potential. Most solid tumors, such as in colorectal cancer, are heterogeneous in their composition, and consist of cells that have properties of stem cells and terminally differentiated cells. That is, tumor perpetuating cells (TPC) uniquely possess self-renewal properties, whereas progenitors, their progeny and non-tumorigenic cells are generally committed to die in the course of time, which may range on the order of hours to weeks. This process is consistent with the differentiation process during organogenesis and tissue homeostasis. Such heterogeneity is manifested by the high relative expression of stem cell-related genes and proteins in the TPC subpopulation of tumor cells, and low expression of such genes and proteins in the NTG cell population. In contrast, NTG cells typically express relatively high levels of genes/proteins associated with terminally differentiated progeny, such as MUC2 or MUC20, which are genes preferentially expressed by functional secretory cells (e.g. goblet [G] and enteroendocrine [eE] cells) in the intestine in the case of colorectal cancer-derived NTG cells (FIG. 27D).

More specifically, as illustrated in FIG. 26, cell populations isolated using the markers disclosed herein support the hypothesis that in tumors there exists significant differentiation capacity and cells are generally able to engage these differentiation programs. TPC (i.e. CSC) lie at the top of the cellular hierarchy in cancer, but TPC identity may have the phenotypic appearance of a normal stem or normal progenitor cell, depending on the patient tumor analyzed. In colorectal cancer, tumor cells with the $ESA^+$ $CD46^{hi}$ $CD324^+$ phenotype represent tumor initiating cells; a population encompassing both TPC and TProg cells. In tumors where there exist NTG cells having the gene expression repertoire of secretory cell fates, the TProg that lie in the middle of the differentiation pathway from a TPC to an NTG cell also express CD66c. Those $CD66c^+$ cells that also express high levels of CD46 and CD324 comprise early tumor progenitor cells, which have significant proliferative capacity, but do not efficiently confer tumorigenicity in carefully performed serial transplantation experiments. These TProg also express intermediate levels of genes associated with TPC and NTG cells, respectively. In summary, TPC exhibit the classical characteristics defining stem cells, whereas tumor progenitor cells exhibit similar characteristics, minus the ability to self-renew as demonstrated by serial transplantation of defined and highly purified cells in immunocompromised animals.

As previously alluded to, tumor initiating cell populations encompass both tumor perpetuating cells and highly proliferative tumor progenitor cells, which together generally comprise a unique subpopulation (i.e. 0.1-40%) of a bulk tumor or mass. For the purposes of the instant disclosure the terms tumor perpetuating cells and cancer stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As will be discussed in more detail below, fluorescence-activated cell sorting (FACS) using appropriate cell surface markers is a reliable method to isolate highly enriched tumor cell subpopulations (>99% purity) due, at least in part, to its ability to discriminate between single cells and clumps of cells (i.e. doublets, etc.).

Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and/or are demonstrably inefficient at reinitiating serial tumorigenesis in subsequent transplants. In contrast, TPC (or CSC) subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, demonstration of differential proliferation/differentiation capacity in vitro using colony forming cell assays, transcriptional profiling, and characterization of drug resistance, although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while generally maintaining the capacity for multilineage differentiation. Tumor perpetuating cells are thus capable of generating both tumorigenic progeny (i.e., tumor initiating cells: TPC and TProg) and non-tumorigenic (NTG) progeny often consisting of different terminally differentiated cell lineages (e.g. goblet cells or enterocytes in the case of colorectal cancer). As defined above a non-tumorigenic cell refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

For purposes of the instant disclosure, TProg are also categorized as tumor initiating cells due to their limited ability to generate tumors in mice. TProg are progeny of TPC and are typically capable of a finite number of non-self-renewing cell divisions. Moreover, as will be seen in the Examples below, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and generate tumors that do not typically reflect the heterogeneity of the parental tumor. Notwithstanding the foregoing distinctions, it has also been shown that various TProg populations can, on rare occasion, gain self-renewal capabilities normally attributed to stem cells and themselves become TPC. In any event, both types of tumor-initiating cells are likely represented in the typical tumor mass of a single patient and, as will be shown in the Examples below, are subject to identification, characterization, separation and/or enrichment or isolation as set forth herein.

More generally, TPC are more tumorigenic, relatively more quiescent and often more chemoresistant than the TProg (both ETP and LTP), NTG cells and the tumor-infiltrating non-TPC derived cells (e.g. fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC). The ability to identify, characterize and separate or enrich these distinct cell subpopulations as disclosed herein is critical in understanding tumor etiology and subsequently identifying novel compounds or modulators that may form the basis for more effective therapeutic treatments.

As explained in more detail below, virtually all colorectal, pancreatic, non-small cell lung, triple-negative breast, ovarian, and small cell lung tumor cells are ESA$^+$ CD24$^+$ CD34$^-$ and thus these markers have little utility in identifying tumor cell subpopulations. Surprisingly, it has been discovered that the disclosed TICAM, TPCAM and TProgAM are particularly effective markers for identifying, characterizing and optionally isolating or enriching selected tumorigenic cell populations. For example, in one particularly preferred embodiment comprising colorectal cancer, it has been demonstrated that CD46$^{hi}$ CD324$^+$ CD66c$^-$ cells are able to generate fully heterogeneous tumors consisting, in part, of CD46$^{hi}$ CD324$^+$ CD66c$^-$ and CD66c$^+$ cells. This is significant because, although CD46$^{hi}$ CD324$^+$ CD66c$^+$ cells are tumorigenic, they do not have the ability to efficiently generate CD46$^{hi}$ CD324$^+$ CD66c$^-$ cells and are unable to efficiently fuel tumor growth through serial transplantation. These data, combined with the observations that the cells with the a) ability to consistently generate heterogeneous tumors upon serial transplantation; b) most colony forming cell potential; and c) potential to generate CD66c cells and protein in vitro are CD46$^{hi}$ CD324$^+$ CD66c$^-$ cells supports the hypothesis that CD46$^{hi}$ CD324$^+$ CD66c$^+$ cells are daughters of CD46$^{hi}$ CD324$^+$ CD66c$^-$ cells with restricted proliferation capacity and potential.

The general reduction in in vivo tumorigenicity and in vitro colony forming potential along with a reduced ability to generate CD66c as cells lose expression of CD324 supports the hypothesis that CD46$^{hi}$ CD324$^-$ CD66$^+$ cells represent a late tumor progenitor (LTP) cell population that has some residual proliferative ability, but generally has no capacity for self-renewal. Finally, in support of the cellular hierarchy laid out in FIG. 26A, CD46$^-$ cells are also CD324$^+$ and are generally CD66c$^-$ as well. These NTG cells likely represent the terminally differentiated progeny, which in the colon include goblet cells (G) and enteroendocrine (eE) cells of the secretory lineage or enterocytes (E) of the absorptive lineage. Gene expression of the isolated cell subpopulations supports this hypothesis, as CD46$^-$ cells express many genes attributed to terminally differentiated secretory and/or absorptive cell types typical of colorectal tissue.

Unlike many conventional prior art therapeutic agents, novel compounds and compositions identified and developed in accordance with the present invention preferably reduce the frequency of tumor initiating cells upon administration to a subject regardless of the form or specific target (e.g., genetic material, cell surface protein, etc.) of the selected modulator. It will be appreciated that the reduction in tumor initiating cell frequency may occur as a result of a) elimination, depletion, sensitization, silencing or inhibition of tumor initiating cells; b) controlling the growth or expansion of tumor initiating cells; c) interrupting the initiation, propagation, maintenance, or proliferation of tumor initiating cells; or d) by otherwise hindering the survival, regeneration and/or metastasis of the tumorigenic cells. With selected modulators the reduction in the frequency of tumor initiating cells occurs as a result of a change in one or more physiological pathways. Pathway intervention or modulation, whether by reduction or elimination of the tumor initiating cells or by modifying their potential (e.g., induced differentiation, niche disruption) or otherwise interfering with their ability to exert affects on the tumor environment or other cells, in turn allows for the more effective treatment of neoplastic disorders by inhibiting tumorigenesis, tumor maintenance and/or metastasis and recurrence.

As will be discussed in more detail below and shown in the Examples, preferred methods used to assess such a reduction in the frequency of tumor initiating cells comprise limiting dilution analysis, either in vitro or in vivo, using either bulk tumor cells or tumor cell subpopulations characterized and isolated in accordance with the present invention. Preferably, the assessment employs Poisson distribution statistical analysis or otherwise assesses the frequency of measurable binary events such as the ability to generate tumors in vivo or not independent of rate. While such limiting dilution analysis comprise preferred methods of calculating a reduction of tumor initiating cell frequency, other, less demanding methods may also be used to effectively determine the desired values, albeit slightly less accurately, and are entirely compatible with the teachings herein. It is also possible to determine reduction of frequency through well-known flow cytometric or immunohistochemical means assessing the respective tumor cell subpopulations based upon their profile of marker expression, as laid out in the instant invention. As to all the aforementioned methods see, for example, Dylla et al. 2008, PMID: 18560594 & Hoey et al. 2009, PMID: 19664991; each of which is incorporated herein by reference in its entirety.

V. Sources of Tumor Initiating Cells

Except where otherwise required, the invention can be practiced with tumor initiating cells of any vertebrate species. Included are cancer stem cells from humans as well as non-human primates, domestic animals such as livestock, those typically used in research such as mice and rats and other non-human mammals.

Those skilled in art will appreciate that the aforementioned cells and cell subpopulations may be obtained from a variety of tumors at different clinical or pathological stages. Moreover, as will be illustrated in the Examples below the starting heterogeneous cell populations may be obtained from a primary tumor sample or biopsy taken directly from the patient or from secondary tumors that have been passaged in vivo or cultured in vitro. In particularly preferred embodiments the tumor cell populations to be interrogated, analyzed, characterized and/or enriched are derived from tumors arising from either bulk tumor material that contain TIC, or enriched TIC populations that have been implanted in immunocompromised mice. In other embodiments the tumor sample will be obtained from a non-traditional xenograft (NTX) tumor bank. Whichever tumor source is selected, the tumors are preferably handled in accordance with good laboratory practices and may be dissociated into single cell suspensions using art recognized mechanical and enzymatic dissociation techniques prior to being interrogated, characterized, separated and/or isolated.

Exemplary tumors which may be used as a source of cells, either directly or indirectly through in vitro or in vivo culturing or passaging, include, but are not limited to, sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, mesothelioma, Ewing's tumor, lymphangioendotheliosarcoma, synovioma, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, astrocytic tumors (e.g., diffuse, infiltrating gliomas, anaplastic astrocytoma, glioblastoma, gliosarcoma, pilocytic astrocytoma, pleomorphic xanthoastrocytoma), oligodendroglial tumors and mixed gliomas (e.g., oligodendroglioma, anaplastic oligodendroglioma, oligoastrocytoma, anaplastic oligoastrocytoma), ependymal tumors (e.g., ependymoma, anaplastic ependymoma, myxopapillary ependymoma, subependymoma), choroid plexus tumors, neuroepithelial tumors of uncertain origin (astroblastoma, chordoid glioma, gliomatosis cerebri), neuronal and mixed-neuronal-glial tumors (e.g., ganglioglioma and gangliocytoma, desmoplastic infantile astrocytoma and ganglioglioma, dysembryoplastic neuroepithelial tumor, central neurocytoma, cerebellar liponeurocytoma, paraganglioglioma), pineal parenchymal tumors, embryonal tumors (medulloepithelioma, ependymoblastoma, medulloblastoma, primitive neuroectodemmal tumor, atypical teratoid/rhabdoid tumor), peripheral neuroblastic tumors, tumors of cranial and peripheral nerves (e.g., schwannoma, neurinofibroma, perineurioma, malignant peripheral nerve sheath tumor), meningeal tumors (e.g., meningeomas, mesenchymal, non-meningothelial tumors, haemangiopericytomas, melanocytic lesions), germ cell tumors, tumors of the sellar region (e.g., craniopharyngioma, granular cell tumor of the neurohypophysis), hemangioblastoma, melanoma, and retinoblastoma.

In particularly preferred embodiments the tumor sample will be obtained from a human colorectal, esophageal, breast, non-small cell lung, small cell lung, pancreatic, melanoma, ovarian, kidney, liver, prostate or head and neck tumors.

Further, as alluded to above the enriched cell populations of the instant invention may be derived from primary tumors obtained directly from subjects suffering from a neoplastic disorder. However, in other embodiments isolated cell populations are obtained from patient-derived tumors that have been cultured in vitro or passaged through non-human animals (e.g., in a non traditional xenograft model). With regard to the present invention, and as described in more detail and in the Examples below, a NTX tumor bank was developed and maintained using art recognized techniques. The NTX tumor bank, comprising a large number of discrete tumor cell lines, was propagated in immunocompromised (e.g., NOD/SCID) mice through multiple passages of heterogeneous tumor cells originally obtained from numerous cancer patients afflicted by a variety of solid tumor malignancies. The continued availability of a large number of discrete early passage NTX tumors having well defined lineages greatly facilitate the identification and isolation of TPC as set forth herein as they allow for the reproducible and repeated characterization of cells purified from the cell lines.

More particularly, the existence of such models allows for consistent verification that the identified or isolated cells or cell subpopulations (as defined by marker phenotype) are actually TIC in that the TPC components are most accurately defined retrospectively according to their ability to generate phenotypically and morphologically heterogeneous tumors in mice that recapitulate the patient tumor sample from which the cells originated. That is, the ability to use small populations of enriched or isolated cells to generate fully heterogeneous tumors in mice is strongly indicative of the fact that the isolated cells comprise TPC and validates associated markers and putative therapeutic targets. In such work the use of minimally passaged NTX cell lines greatly simplifies in vivo experimentation and provides readily verifiable results. Moreover, early passage NTX tumors also respond to conventional therapeutic agents such as irinotecan or gemcitabine, which provides clinically relevant insights into underlying mechanisms driving tumor growth, resistance to current therapies and tumor recurrence.

VI. Defining Tumorigenic Cell Populations

In preferred embodiments the present invention provides for the identification, characterization and, optionally, the enrichment or isolation of selected tumor initiating cells or cell subpopulations. This analysis and/or physical enrichment of the cancer stem cell populations is accomplished by differential cell analysis using one or more markers (i.e., TICAM, TPCAM and TProgAM) that are phenotypically heterogeneous with regard to different cell populations. As previously discussed it will be appreciated that any trait, determinant or discernible characteristic, or combinations thereof, that allows for the differentiation of various cell populations constitutes a marker that may be used in accordance with the teachings herein. Thus, while in preferred embodiments such markers are phenotypic or genotypic determinants such as cell surface proteins or regulatory genetic elements, other characteristics or traits may function to differentiate the cell subpopulations and are expressly contemplated as be within the scope of the invention. For example, in addition to cell surface phenotyping, it may be useful to quantitate or characterize cell subpopulations based on certain tumor perpetuating cell characteristics. These attributes can be determined, for instance, by measuring the ability of the cells to self-renew and proliferate in culture; or by determining the presence of particular activated pathway(s) in these cells. Thus, in preferred embodiments a nucleic acid construct may be introduced into a cell or population of cells, where the construct comprises sequences encoding a detectable marker, and wherein the marker is operably linked to a transcriptional response element regulated by or associated with the selected pathway (e.g., one that covers the expression of a cell surface protein TICAM). As the pathway is activated the detectable marker is expressed, and indicates that the cell or cell subpopulation comprises tumor perpetuating cells. In some embodiments of the invention, the detectable marker is a fluorescent protein, e.g. green fluorescent protein (GFP) and variants thereof. Viable cells expressing GFP can be sorted, in order to isolate or enrich for the cell subpopulations of interest. In this aspect of the invention, the disclosed methods may be used to enrich for tumor perpetuating cells.

As disclosed herein, certain aspects of the present invention are directed to identifying or characterizing and, optionally, enriching or isolating tumor initiating cells or cell subpopulations thereof (e.g., TPC and/or TProg). In this respect the inventors have surprisingly discovered selected markers and/or marker combinations that allow for the rapid and effective identification, characterization and optionally, the enrichment or isolation of tumor initiating cells or populations thereof. As discussed briefly above a "marker", as used herein in the context of a cell or tissue, means any characteristic in the form of a chemical or biological entity or determinant (e.g., phenotypic or genotypic) that is identifiably associated with, or specifically found in or on a particular cell, cell population or tissue including those identified in or on a tissue or cell population affected by a disease or disorder. As manifested, markers may be morphological, functional or biochemical in nature. In preferred embodiments the marker is a cell surface antigen that is differentially or preferentially expressed by specific cell types (e.g., TPCs) or by cells under certain conditions (e.g., during specific points of the cell life cycle or cells in a particular niche).

It will be appreciated that markers, marker combinations or phenotypic or genotypic determinants may vary as to specific cells or cell subpopulations or with regard to cell lifecycles or hierarchy. In some embodiments markers will comprise stable or transitory characteristics, whether phenotypic, genotypic, morphological, functional or biochemical (e.g., enzymatic) particular to a specific cell type or population.

In particularly preferred embodiments compatible markers are proteins or polypeptides and, more preferably, possess one or more epitopes or active sites that allow for the association of binding molecules including, but not limited to, antibodies or immunoreactive fragments thereof, ligands, substrates or enzymes. However, for the purposes of the instant application a marker may consist of any molecule or metabolite associated with a cell including, but not limited to, proteins (peptides and polypeptides), lipids, polysaccharides, nucleic acids and steroids. In particularly preferred embodiments the marker of interest will be located on the surface of the cell at the appropriate time but in other embodiments the marker may be located or positioned intercellularly or intracellularly (e.g., on the nucleus). Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes, ability to migrate under particular conditions, and the ability to differentiate along particular lineages. As discussed herein it will be further appreciated that compatible markers may be detected by any method available to one of ordinary skill in the art. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to, fluorescent proteins, enzymes, chromomeric proteins, resistance genes and the like. Specific preferred markers will be discussed in more detail below.

The information thus derived from such markers is useful in theragnosis, prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. Clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Whichever markers are ultimately chosen to identify or characterize the selected cell subpopulations, the actual monitoring or analysis may be conducted using any one of a number of standard techniques well known to one of skill in the art. For example, cell surface marker expression can be assayed by immunoassays including, but not limited to, western blots, immunohistochemistry, radioimmunoassays, ELISA (enzyme linked immunosorbent assay), "sandwich" immunoassays, immunoprecipitation assays, precipitation reactions, gel diffusion precipitation reactions, immunodiffusion assays, agglutination assays, complement-fixation assays, immunoradiometric assays, fluorescent immunoassays, immunofluorescence, protein A immunoassays, laser capture microdissection, massively multiparametric mass cytometry, flow cytometry, and FACS analysis. In certain embodiments the amount of cancer stem cells in a test sample from a subject may be determined by comparing the results to the amount of cancer stem cells in a reference sample (e.g., a sample from a subject who has no detectable cancer) or to a predetermined reference range, or to the patient him/herself at either an earlier or later time point (e.g., prior to, or during therapy).

In specific embodiments, the cancer stem cell population is obtained from a tumor sample from a patient and is characterized by flow cytometry. As is well known in the art and demonstrated in the appended Examples, this method exploits the differential expression of certain surface markers on cancer stem cells relative to the bulk of the tumor. Labeled antibodies (e.g., fluorescent antibodies) can be used to react with, or binding agents recognizing other binding agents (i.e., secondary binding agents) that recognize, the markers on cells in the sample for the purpose of enriching or isolating cells by any number of methods including magnetic separation or FACS. In some embodiments, a combination of cell surface markers are utilized in order to further define or quantify the cancer stem cells in the sample in situ (e.g. by immunofluorescence or immunohistochemistry) or using methods analyzing single cells following tumor dissociation (e.g. flow cytometry or massively multiparametric mass cytometry). For example, both positive and negative cell sorting may be used to assess various TPC subpopulations or quantify the amount of cancer stem cells in the sample. The number or frequency of cancer stem cells in the sample might also be determined by transplanting un-enriched tumor cells in limiting dilution into immunocompromised mice, followed by the analysis of the frequency of tumorigenesis, independent of rate, by the different dilutions using Poisson distribution statistics. Moreover, as demonstrated in the Examples below specific tumor types can be characterized by assessing the frequency and nature of cells expressing tumor perpetuating cell and/or tumor progenitor cell markers. Preferably the tumors comprise tumor initiating cells identified using the markers disclosed herein, including those markers demonstrated to be coexpressed with respective TIC populations (i.e. TICAM), such as those described herein and whose presence may be confirmed through isolation and transplant in immunocompromised mice.

In other selected embodiments the interrogation, identification and/or characterization of tumor initiating cells in a tissue sample such as a solid tissue sample (e.g. a solid tumor biopsy) or a blood or serum sample (e.g., comprising circulating tumor cells) is determined using immunohistochemistry or immunofluorescence techniques. As known in the art, these methods exploit the differential expression of certain surface markers on tumor initiating cells relative to the bulk of the tumor. Antibodies (e.g., antibodies conjugated to a fluorophore) can be used to react with the cell subpopulation of interest. These antibodies may be directly labeled, or detected with secondary binding agents that detect the primary antibody. In preferred embodiments a combination of certain cell surface markers are used to further define and, if desired, quantify cancer stem cells in the un-dissociated sample (i.e. in situ). Further, such staining techniques allow for visualization of selected tumor cell subpopulations by assessing the expression of certain markers that distinguish the cancer stem or progenitor cells of interest. Such techniques facilitate the localization of cancer stem and/or progenitor cells within the context of the tumor, allowing spatial characteristics such as the distance from blood vessels to be established.

In other selected embodiments the interrogation, identification and/or characterization of tumor initiating cells in a tissue sample such as a solid tissue sample (e.g. a solid tumor biopsy) or blood or serum sample (e.g., comprising circulating tumor cells) is determined using quantitative RT-PCR techniques. As known in the art, these methods exploit the differential expression of certain genes expressed by TPC relative to TProg, NTG cells and/or the bulk of the tumor. Nucleic acid primer/probe sets can be used to react with cDNA from the cell subpopulation(s) of interest. These primer/probe sets may be specific to genes associated with particular tumor cell subpopulations, detecting the amount of messenger RNA present in an enriched or isolated cell population. In preferred embodiments a combination of certain primer/probe sets is used to further define and, if desired, quantify cancer stem cells in the un-dissociated sample (i.e. in situ). Further, such mRNA quantification techniques allow for enumeration of selected tumor cell subpopulations by assessing the expression of certain genes that distinguish the cell populations of interest. Such techniques facilitate the identification and/or quantification of TPC and/or TProg cells (i.e. TIC) within the context of the tumor, allowing assessment of TIC frequency and patient subtype.

Using the aforementioned art-recognized techniques for cell and cell population recognition and characterization in conjunction with the teachings herein one can readily identify the disclosed tumorigenic cell subpopulations. More particularly, as discussed extensively herein the present invention is predicated upon, at least in part, the heretofore unknown association between certain tumor initiating cell associated markers (TICAM) and tumor cell subpopulations or tumor initiating cells. These markers, whether by their absence or presence on the relevant cell populations, allow for the effective identification or characterization of tumor initiating cells and their respective TPC and TProg component subpopulations. Moreover, in preferred embodiments such as those set forth in the Examples below, these same markers allow for the rapid and efficient identification, separation, partitioning, sectioning, isolation or enrichment of defined tumor initiating cell populations or their respective TPC and/or TProg cell subpopulations. As set forth above and in accordance with the instant invention, TICAM shall be held to mean any marker or marker phenotype that allows for the identification, characterization and, optionally, isolation and enrichment of tumor initiating cells or cell populations. Similarly, marker or marker phenotypes that, by their presence or absence, may be used to identify or characterize and, optionally, isolate or enrich TPC or TProg or cell subpopulations comprise TPCAM or TProgAM, respectively, as defined previously. As explicitly noted above it will be understood that the three sets of markers (i.e. TICAM, TPCAM and TProgAM) are not mutually exclusive and that individual markers may be associated with different cell subpopulations (e.g., a single marker may be a TICAM and a TPCAM). In certain preferred embodiments such markers are proteins and even more preferably are cell surface proteins. In other selected embodiments the marker may comprise a genotypic anomaly or differential that may be interrogated, detected, or identified using a number of art recognized techniques in view of the teachings herein.

As previously alluded to preferred TICAMs compatible with the instant invention comprise CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

In another particularly preferred embodiment compatible TICAMs comprise CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

In yet other particularly preferred embodiments the marker will comprise CD46. In still other preferred embodiments the marker will comprise CD324. In yet other preferred embodiments the marker will comprise CD66c. In still other preferred embodiments a combination of CD46 marker and CD324 marker will be used to identify and, optionally, enrich or isolate tumorigenic cell subpopulations.

Those skilled in the art will appreciate that the particulars of each of the aforementioned TICAM may readily be found on the NCBI GenBank database and each relevant accession number and the associated record is hereby incorporated by reference herein. Accordingly, in view of the instant specification the skilled artisan would readily be able to identify and obtain the enumerated TICAMs (either from commercial sources or by producing them using standard biochemical techniques) in a form compatible with the instant invention.

With regard to the listed TICAM, FIGS. 12A-C provide exemplary tumor expression information in a tabular form while FIGS. 13-19 show expression data of the individual markers that are co-expressed on defined tumor initiating cell populations from several solid tumor types. In this respect it will be appreciated that, although the of tenets of the instant invention are most commonly exemplified or confirmed using the TICAM markers CD46 and CD324, the compatibility of other listed markers with the teachings herein is readily determined for specific tumors without undue experimentation. That is, despite the different etiology of the cancers and biology of the respective tissues in which these tumors arose, FIGS. 13-19 demonstrate that the compatibility and utility of a listed marker may be readily discerned using standard techniques. In view of these teachings and associated data one skilled in the art would easily be able to determine the optimal TICAM or combinations of TICAM to use to analyze or separate tumor initiating cell subpopulations from a particular type of tumor, or further use the TICAM to distinguish TPC from TProg as demonstrated using CD66c in colorectal cancer. The unexpected finding that a select set, but not all, of the disclosed markers are useful over a range of solid tumors merely underscores the novelty of the invention.

Moreover, a review of the tabular data set forth in FIGS. 12A-12C indicates an association of various TICAM with a number of different specific types of cancer. For example, based on the results of studies shown in FIGS. 12A-12C TICAM CD29, CD147, CD295, HER3 and Mer appear to be associated with melanoma CSC. As such, particularly preferred embodiments will comprise the enrichment of melanoma CSC comprising contacting a melanoma tumor cell population with a binding agent which preferably associates with at least one TICAM selected from the group consisting of CD29, CD147, CD295, HER3, Mer and combinations thereof and sorting said cells associated with said TICAM to provide an enriched melanoma tumorigenic cell population. Of course it will be appreciated that the resulting compositions and identified melanoma associated TICAM may be used in conjunction with the teachings herein to practice other aspects of the invention generally set forth in the context of the broader population of identified TICAM. Similarly, in view of the data set forth in FIGS. 12A-12C and as presented in the putative claims appended hereto, one of skill in the art could readily identify and use colorectal associated TICAM, breast associated TICAM, non-small cell lung cancer associated (NSCLC) TICAM, ovarian associated TICAM, pancreatic associated TICAM and small cell lung cancer (SCLC) TICAM. In this regard this TICAM subsets, which are not mutually exclusive, will be defined as follows:

"Colorectal associated TICAM" shall mean a TICAM selected from the group consisting of CA9, CCR10, CD9, CD49a, CD49b, CD49c, CD49f, CD51, CD55, CD63, CD73, CD81, CD82, CD98, CD99, CD104, CD136, CD151, CD155, CD275, c-Met, Eph-B4 and combinations thereof.

"Breast associated TICAM" shall mean a TICAM selected from the group consisting of CD49b, CD51, CD54, CD55, CD63, CD71, CD130, CD131, CD133, CD148, CD151, CD155, CD172a, CD221, CD230, CD244, CD245, CD275, CD318, CD349, CLEC4A, Eph-B4, Frizzled-1, HER3, IL-15R, Integrin-a8, Integrin b5, LDL-R, Leukotriene-B4R, LRP6, Nectin-4, Notch2, Plexin-B1, TROP-2, TREML1, ULBP2 and combinations thereof.

"NSCLC associated TICAM shall mean a TICAM selected from the group consisting of CCR4, CD9, CD13, CD15, CD24, CD26, CD29, CD46, CD49a, CD49b, CD49c, CD49f, CD51, CD58, CD66a, CD66c, CD66e, CD71, CD73, CD81, CD91, CD98, CD99, CD104, CD105, CD111, CD130, CD151, CD155, CD156, CD157, CD164, CD166, CD186, CD221, CD230, CD262, CD275, CD295, CD298, CD318, CD323, CD324, CD340, CLEC4A, Eph-B4, Frizzled-1, Glut-3, Glypican 5, HER3, IL-17R, Integrin a9b1, MMP14, Nectin-4, Notch2, NPC, Plexin-B2, Plexin-D1, Semaphorin 4B, TROP-2, TSPAN8 and combinations thereof.

"Ovarian associated TICAM" shall mean a TICAM selected from the group consisting of CCR10, CCRL2, CD15, CD24, CD32, CD56, CD66, CD66a/c/e, CD66c, CD71, CD91, CD102, CD111, CD117, CD133, CD141, CD146, CD151CD156, CD166, CD167a, CD177, CD196, CD221, CD234, CD265CD275, CD295, CD299, BMPR-1B, Cadherin-11, Claudin-3, DLL-1, DLL-3, Frizzled-3, HLA-A/B/C, HLA-A2, IL-17 RD, Jagged-2, Integrin a9b1, LAG-3, Lox-1MCSP, Mer, Nectin-4, NPC, PAR1, PD-L2, Plexin-B2, Plexin-D1, PNPLA2, Somatostatin-R2, TIMD4, VEGFR2 and combinations thereof.

"Pancreatic associated TICAM" shall mean a TICAM selected from the group consisting of CCR9, CCRL2, CD13, CD15, CD26, CD29, CD49b, CD49f CD51, CD54, CD55, CD66, CD66a, CD66a/c/e, CD66c, CD66e, CD71, CD99, CD104, CD108, CD155, CD172a, CD262, CD273, CD275, CD349, Eph-A2, Glut-2, Glypican 1, IL-17 RD, IL-20Ra, Integrin b5, LDL-R, Mer, PAR1, Plexin-B2, TREM2, TREML1, Vb9 and combinations thereof.

"SCLC associated TICAM" shall mean a TICAM selected from the group consisting CCR10, CD49c, CD51, CD66e, CD102, CD111, CD117, CD118, CD133, CD164, DLL-1, Glut-1, HER3, Integrin a9b1, Lox-1 and combinations thereof.

"Melanoma associated TICAM" shall mean a TICAM selected from the group consisting CD29, CD147, CD295, HER3, Mer and combinations thereof.

Pursuant to the instant disclosure it will be appreciated that any of the aforementioned TICAMs may be used, alone or in combination, to identify, characterize or, optionally, purify, separate, enrich or isolate defined tumorigenic cell populations using art-recognized techniques. In preferred embodiments the cell populations will comprise tumor initiating cells. In other preferred embodiments the cell populations identified or enriched using selected TICAM shall comprise tumor perpetuating cells and tumor progenitor cells. With respect to these latter embodiments, and as shown in the appended Examples, the TIC components may further be characterized and/or separated by contacting the TICAM-enriched population with binding agents to TPCAM and/or TProgAM, which provide for the isolation of these respective tumor initiating cell subpopulations.

For example, in particularly preferred embodiments it has been demonstrated that TIC may be identified and characterized through a combination of CD46 and CD324 and exhibit a CD46$^{hi}$ CD324$^+$ marker phenotype in several solid tumor types, including colorectal, pancreatic, triple-negative breast cancer and non-small cell lung cancer. Accordingly, in other particularly preferred embodiments, the isolated or enriched tumor cell subpopulations are obtained by contacting the TIC with binding agents for CD324 and CD46 wherein the binding agents may be contacted with the TIC in any order or simultaneously. Related preferred embodiments comprise isolated or enriched TIC populations comprising a CD46$^{hi}$ CD324$^+$ marker phenotype.

In another selected embodiment comprising TIC in colorectal cancer, it has been demonstrated that CD46$^{hi}$ CD324$^+$ CD66c$^-$ cells are able to generate fully heterogeneous tumors consisting, in part, of CD46$^{hi}$ CD324$^+$ CD66c$^-$ and CD66c$^+$ cells. This is significant because, although CD46$^{hi}$ CD324$^+$ CD66c$^+$ cells are tumorigenic, they do not have the ability to efficiently generate CD46$^{hi}$ CD324$^+$ CD66c$^-$ cells and are unable to efficiently fuel tumor growth through serial transplantation. Accordingly, other preferred embodiments of the instant invention comprise isolated or enriched TIC populations comprising a CD46$^{hi}$ CD324$^+$ marker phenotype. Colorectal tumor cells with this double positive phenotype are tumorigenic, comprise TPC and TProg, and can be identified, characterized or, optionally, purified, separated, enriched or isolated using TICAM disclosed herein (e.g., as per FIGS. 12 & 13). For example, contacting cells with binding agents against the TICAM CD82 or CD151 facilitates enrichment of TIC independent of using binding agents against CD46 and/or CD324, as cells expressing higher levels of CD82 or CD151 protein are inherently also enriched for TIC (i.e. CD46$^{hi}$ CD324$^+$ cells).

It will further be appreciated that the instant disclosure also identifies specific sets of TICAM in pancreatic, non-small cell lung, breast, small cell lung, melanoma and ovarian tumors; many of which are specific to these respective tumor types and are not differentially expressed on TIC from the other tumor types disclosed herein. These TICAM, used alone or in combination, can be used to identify, characterize, interrogate, recognize or distinguish tumor initiating cells from their respective tumor types due to their relatively high expression in the TIC subpopulation versus other cells in the respective tumor types. For example, LDL-R is preferentially expressed on TIC from pancreatic tumors and HER3 is preferentially expressed on TIC from non-small cell lung cancer tumors, and binding agents detecting these molecules facilitates their identification and characterization in the respective tumor types herein disclosed. In other preferred embodiments, the TICAM binding agent will be reporter activity driven by the promoter of genes encoding TICAM or the promoter of another gene regulated by the same transcriptional elements regulating expression of the given TICAM.

As disclosed herein a particularly preferred marker associated with tumorigenic cells is CD46 that has been found to act advantageously as a TICAM. As shown throughout the Examples below, the CD46 marker may be used, alone or in combination with other markers, to identify, characterize, interrogate, recognize or distinguish tumor initiating cells, tumor perpetuating cells or discrete cell subpopulations thereof. Further, in other preferred embodiments the CD46 marker may be used, alone or in combination with other markers, to effectively section, partition, isolate, purify or enrich tumorigenic cells or subpopulations thereof. Preferably the identification, characterization or isolation of the cancer stem cells or cell subpopulation will be effected with a binding agent that immunospecifically reacts with full length CD46 or a splice variant or isoform thereof. In other preferred embodiments the CD46 binding agent will comprise an antibody or immunoreactive fragment thereof. In other preferred embodiments the CD46 binding agent will be associated with a detectable reporter entity driven by the promoter of the gene encoding CD46 or the promoter of another gene regulated by the same transcriptional elements regulating CD46 expression.

CD46 is also known as membrane cofactor protein or MCP. It is a type 1 transmembrane protein that is widely expressed but has a number of isoforms as a result of alternate exon splicing and glycosylation. Recently Karosi et al., *Laryngoscope* 118: 1669-1676 (September 2008), which is incorporated herein by reference in its entirety, reported detecting fourteen isoforms of the molecule. The mRNA is transcribed from a single gene located at chromosome 1q32 and undergoes extensive alternative splicing to produce multiple transcripts encoding the various protein isoforms. Of the 14 exons comprising the gene, it appears that exons 1-6 are conserved in all CD46 protein isoforms, whereas exons 7 to 9 encode variably utilized serine-threonin-proline ("STP") rich regions, leading to the major hypervariability in the protein isoforms. Exons 11 and 12 encode the transmembrane region of CD46, while exons 13 and 14 encode the cytoplasmic tail of the protein. The longest mRNA transcript, variant A (NM_002389), contains sequences from all fourteen exons of the gene. Variable splicing of exons 7, 8, 9, and 13 is believed to yield the majority of CD46's fourteen isoforms, with the predominant observed protein isoforms of 66 and 56 kDa arising from alternative inclusion or exclusion of exon 8. Alternate inclusion/exclusion of exon 13 leads to changes in the encoded sequence of the cytoplasmic tail of the molecule, with the suggestion that these changes affect subcellular trafficking, stability, and the signaling properties of the protein.

As set forth in Karosi et al., CD46 mRNA isoform D comprises exons 1-6, 8-12 and 14 of the CD46 gene (equivalent to the sequence NM_153826, encoding the protein NP_722548), isoform F comprises exons 1-6, 9-12, and 14 (equivalent to the sequence NM_172353, encoding NP_758863), and isoform J comprises exons 1-6, 8, 10-12, and 14 (equivalent to the sequence NM_172356, encoding NP_758866). More specifically the CD46 molecule comprises four N-terminal short consensus repeat (SCR) modules ("Sushi" domains: 4 Cysteines in a 1-3, 2-4 linkage topology), where these SCR domains are encoded by the first six exons of the gene. The SCR2, 3, and 4 modules have the C3b/C4b binding and regulatory activity (discussed below), while the SCR1 module and sequences distal of SCR4 are not essential for complement regulatory function, The membrane-proximal extracellular sequence, encoded by the alternatively utilized exons 7-9 as well as exon 10, is heavily glycosylated, mainly via O-linked carbohydrates.

For the purposes of the instant disclosure the term "CD46" shall be held to mean any protein as set forth immediately above including any splice variant or immunoreactive fragment thereof as well as any nucleic acid sequence encoding such proteins, splice variants or fragments unless otherwise contextually dictated. Thus, as discussed above a "CD46 marker" would broadly include any detectable protein, peptide or nucleic acid sequence that constitutes or encodes for the CD46 antigen. In preferred embodiments the CD46 marker will comprise the full length glycoprotein (variant A) or reported splice variant or immunoreactive fragment thereof. Even more preferably the CD46 protein marker will be present on the cell surface of the selected tumorigenic cell population. In other preferred embodiments the CD46 marker will comprise a nucleic acid sequence (e.g., DNA or mRNA) encoding full length CD46, a splice variant or fragment thereof.

Another preferred marker that may optionally be used to characterize selected tumor initiating cell subpopulations in accordance with the teachings herein is human CD324 (hCD324) which has an exemplary nucleic acid sequence corresponding to GenBank Accession No: NM_004360 and an exemplary preproprotein amino acid sequence corresponding to GenBank Accession No: NP_004351 each of which is incorporated herein by reference. CD324 (also known as E-cadherin, uvomorulin, cadherin-1 or CAM 120/80) is a transmembrane protein that mediates calcium-dependent cell adhesion. It is specifically expressed in epithelial cells, where it is involved in maintaining their phenotype. The cytoplasmic domain of E-cadherin binds to β-catenin, which is itself bound to the actin filament networks of the cytoskeleton. This E-cadherin/β-catenin binding plays an essential role in stabilizing cell/cell adhesions of the epithelial tissue. The loss of E-cadherin can therefore reduce cell adhesion and increase the invasive capacity of cancer cells. A reduction in expression of E-cadherin or of β-catenin is generally associated with greater aggressiveness and dedifferentiation of the tumor, in particular with respect to gastrointestinal cancers. It has also been shown that patients having colorectal cancer and underexpressing E-cadherin have a more unfavorable prognosis than patients having a normal expression level.

Still another preferred marker that may be used in accordance with the present invention is CD66c (also called or NCA-90 or CEACAM6). Human CD66c (hCD66c) nucleic acid sequence corresponds to GenBank Accession No: NM_002483 while the amino acid sequence of the protein precursor (344 aa) corresponds to GenBank Accession No: NP_002474 each of which is incorporated herein by reference. The CD66c glycoprotein belongs to the immunoglobulin family, characterized by variable domains in the N-terminal part of the protein, and constant domains containing disulfide bridges inducing the formation of loops (Hammarstrom and Baranov 2001). CD66c is normally expressed at the surface of the granulocytes, macrophages and polynuclear neutrophils, but also by the epithelial cells in the colon, the lungs and the spleen (Audette et al., 1987; Kolbinger et al., 1989; von Kleist et al., 1972; Jantscheff et al., 2003). CD66c is also expressed in proliferating cells of hyperplastic colonic polyps and adenomas, compared with normal mucosa, as well as by many human cancers (Scholzel et al., Am J Pathol 157:1051-52, 2000; Kuroki et al., Anticancer Res 19:5599-5606, 1999).

Still yet another preferred marker that may be used in accordance with the present invention is EphB4 (also called or HTK, MYK1 and TYRO11). Human EPHB4 nucleic acid sequence corresponds to GenBank Accession No: NM_004444.4 while the amino acid sequence of the protein precursor (987 aa) corresponds to GenBank Accession No: NP_004435.3, each of which is incorporated herein by reference. The EphB4 receptor tyrosine kinase interacts with transmembrane ephrin-B family ligands residing on adjacent cells in a promiscuous fashion, leading to contact-dependent bidirectional signaling into neighboring cells (Fueller et al., 2003 J Cell Sci 116:2461). EphB4 has been demonstrated to play a role in heart morphogenesis and angiogenesis through regulation of cell adhesion and cell migration via its ligand EfnB2 (Erber et al., 2006 EMBO J 25:628).

Another preferred marker that may be used in accordance with the present invention is CD151 (also called GP27, MER2, RAPH, SFA1, PETA-3 or TSPAN24). Human CD151 nucleic acid sequence corresponds to GenBank Accession No: NM_001039490.1 while the amino acid sequence of the protein precursor (253 aa) corresponds to GenBank Accession No: NP_001034579.1, each of which is incorporated herein by reference. CD151 can be found complexed with CD9, CD81, alpha3beta1, alpha5beta and alpha6beta4 integrins, and other tetraspanin superfamily proteins. CD151 has been suggested to regulated integrin trafficking and/or function and its expression has been shown to enhance cell motility, invasion and metastasis of cancer cells (Wang et al., 2003 Biochem Soc Trans 39:547).

Another preferred marker that may be used in accordance with the present invention is CD275 (also called B7H2, GL50, B7RP1, ICOSL, LICOS and B7RP-1). Human ICOSLG (i.e. CD275) nucleic acid sequence corresponds to GenBank Accession No: NM_015259.4 while the amino acid sequence of the protein precursor (302 aa) corresponds to GenBank Accession No: NP_056074.1, each of which is incorporated herein by reference. CD275 has been shown to be a T-cell-specific cell surface receptor that acts as a costimulatory signal for T-cell proliferation and cytokine secretion; also inducing B-cell proliferation and differentiation into plasma cells. Its expression has also been linked to the activation and expansion of T-regulatory cells (Martin-Orozco et al. 2010 Cancer Res 70:9581), thus it appears to be involved in immunomodulation.

Another preferred marker that may be used in accordance with the present invention is CD15 (also called Lewis-X, ELFT, SSEA-1, FUC-TIV and FUTIV). Human FUT4 (i.e. CD15) nucleic acid sequence corresponds to GenBank Accession No: NM_000148.3 while the amino acid sequence of the protein precursor (365 aa) corresponds to GenBank Accession No: NP_000139.1, each of which is incorporated herein by reference. CD15 is a fucosyltransferase that transfers fucose to N-acetyllactosamine polysaccharides to generate fucosylated carbohydrate structures (Larsen et al., 1990 Proc Natl Acad Sci USA 87:6674).

Another preferred marker that may be used in accordance with the present invention is CD26 (also called DPP4, ADABP, ADCP2 or TP103). Human CD26 nucleic acid sequence corresponds to GenBank Accession No: NM_001935.3 while the amino acid sequence of the protein precursor (766 aa) corresponds to GenBank Accession No: NP_001926.2, each of which is incorporated herein by reference. CD26 is a cell surface glycoprotein receptor that co-stimulates T-cell receptor (TCR)-mediated T-cell activation by binding at least ADA, CAV1, IGF2R, and PTPRC. A serine exopeptidase with dipeptidyl peptidase activity that regulates various physiological processes by cleaving peptides in the circulation, including many chemokines, mitogenic growth factors, neuropeptides and peptide hormones, CD26 may also play a role in migration and metastasis, as it regulates lymphocyte-epithelial cell adhesion (Abbott et al., 1999 FEBS Lett 458:278; Salgado et al., 2000 Cytokine 12:1136; Gines et al., 2002 Biochem J 361:203). In association with FAP, CD26 may also be involved in the pericellular proteolysis of the extracellular matrix (ECM) during the migration and invasion of endothelial cells.

Still another preferred marker that may be used in accordance with the present invention is CD111 (also called HVEC, SK-12, CLPED1, nectin-1, PRR1 or Poliovirus receptor-related protein-1). Human PVRL1 (i.e. CD111) nucleic acid sequence corresponds to GenBank Accession No: NM_002855.4 while the amino acid sequence of the protein precursor (517 aa) corresponds to GenBank Accession No: NP_002846.3, each of which is incorporated herein by reference. CD111 promotes intercellular contact by forming homophilic or heterophilic trans-dimers. Heterophilic interactions have been detected between CD111 and CD113 and between CD111 and CD114 (Lopez et al., 1995 Gene 155:261). CD111 also interacts with several viruses, including herpes simplex virus 1 (HHV-1), herpes simplex virus 2 (HHV-2), and pseudorabies virus (PRV) envelope glycoprotein D, functioning as an entry receptor (Krummenacher et al., 1998 J Virol 72:7064; Takahashi et al., 1999 J Cell Biol 145:539; Reymond et al., 2001 J Biol Chem 276:43205; and Liu et al., 2005 J Proteome Res 4:2070).

Still yet another preferred marker that may be used in accordance with the present invention is Nectin-4 (also called LNIR and PRR4). Human PVRL4 (i.e. Nectin-4) nucleic acid sequence corresponds to GenBank Accession No: NM_030916.2 while the amino acid sequence of the protein precursor (510 aa) corresponds to GenBank Accession No: NP_112178.2, each of which is incorporated herein by reference. Nectin-4 promotes intercellular contact by forming homophilic or heterophilic trans-dimers (Reymond et al., 2001 J Biol Chem 276:43205). Heterophilic interactions have been detected between Nectin-4 and CD111. Nectin-4 has been shown to be shed as a result of proteolytic cleavage by ADAm17/TACE (Fabre-Lafay et al., 2005 J Biol chem. 280:19543).

It will further be appreciated that the invention also provides TICAM that can be used as antigens for cancer vaccines to stimulate an immune response against cells expressing these markers. This can be in the form of soluble TICAM coupled with adjuvants administered to a patient. Alternatively the TICAM can also be used to stimulate specific cell populations isolated from a patient, ex vivo. For example, the antigen itself can be used to activate some cells populations (eg. antigen presenting cells). In other embodiments T cell receptors specific to these antigens can be engineered and transduced into other isolated cell populations (eg., T cells). These cell populations can then be infused back into the patient to stimulate immune responses against target cells expressing these antigens (eg. TPC's, TProg's).

VII. Binding Agents

As discussed throughout the instant application the disclosed markers or determinants are preferably detected, recognized or interrogated by a binding agent as defined herein. Construed broadly for the purposes of the present invention a compatible binding agent may essentially comprise any entity or molecule that preferably associates with a marker and is detectable. More specifically and a defined above the binding agents of the instant invention may comprise phenotypic binding agents that associate with amino acid based marker manifestations and genotypic binding agents that preferably associate with nucleic acid based manifestations of the disclosed markers. In this regard the binding agent may take on many forms including, but not limited to small molecules, peptides, proteins and nucleic acids including DNA and RNA. More particularly the binding agents of the present invention may comprise a receptor, enzyme, enzyme inhibitor, enzyme substrate, ligand, lectin, fatty acid, aptamer, lipid or polysaccharide. For example, in a selected embodiment a compatible binding agent may comprise the hemagglutinin protein of measles virus or CD46 binding fragment thereof. In other particularly preferred embodiments the binding agent or entity comprises an antibody or fragment thereof. In yet other preferred embodiments the binding agent may comprise a marker specific small molecule binding agents that could disrupt receptor-ligand interactions, receptor-activation or dimerization/multimerization, co-receptor binding, or other myriad intracellular processes. In view of the instant disclosure the selection of compatible binding agents is well within the purview of one skilled in the art without undue experimentation.

As indicated, selected embodiments of the instant invention will comprise genotypic binding agents that react, associate, identify or otherwise recognize nucleic acid markers that are preferably differentially expressed in one form or another. Such markers may include, but are not limited to: specific sequences such as SNPs; amplifications, rearrangements, deletions or insertions, translocations, or inversions in the genomic DNA; changes in the size, sequence, number of repeats, or the density of DNA microsatellites, also termed simple sequence repeats; changes in the number of methylated or otherwise chemically modified bases in the DNA; or changes in the types of proteins associated with the DNA or the chromatin structure of the DNA due to chemical modifications of the associated histones. RNA markers may include, but are not limited to: specific RNA transcripts that are non-coding (i.e., pre- pri- and processed miRNAs, long or short non-coding RNAs), coding RNAs and their precursors (i.e., hnRNAs and mRNAs), alternatively spliced RNAs, or unique posttranscriptional chemical modifications or editing of the RNA nucleotide residues. Any and all of these nucleic acid markers may be used to define tumorigenic populations if their positive or negative occurrence, either being unique to the tumorigenic population or by changes in relative proportions to their frequency of occurrence in non-tumorigenic populations, is detected and/or quantified.

Both DNA and/or RNA markers may be detected by a variety of art recognized binding agents that may be used in nucleic acid hybridization, amplification, and/or sequencing methods including but not limited to: fluorescence in situ hybridization (FISH); comparative genomic hybridization (CGH); methods of PCR or RT-PCR amplification in non-quantitative, semi-quantitative, or quantitative forms coupled with detection by either electrophoretic analysis, or by hybridization using solution-based or solid phase arrayed or bead-bound probes composed of oligonucleotides or other chemically similar compounds (i.e., LNAs, peptide nucleic acids), or by use of chromogenic, fluorogenic, or luminescent dyes specifically linked to the probes or to the amplified or starting nucleic acid, or by use of such dyes capable of intercalating in the hybridized or amplified nucleic acid structures; the method of detection of specific nucleic acid sequences based upon incorporation of modified nucleotides into the amplified or hybridized product subsequently analyzable by specific proteins binding the modified nucleic acid residue or nucleic acid structure (i.e., apatamers); the methods of detection of specific nucleic acids sequences based upon signal amplification, such as branched DNA assays; the methods of detecting changes in DNA-modification or in changes of DNA-associated proteins by chromatin immunoprecipitation (ChIP) and its associated derivatives (ChIP-CHIP or ChIP-Seq) or by sequencing-based strategies including but not limited to ChiP-Seq or bisulfate sequencing; or the methods of detecting changes in the abundance of the nucleic acid markers using sequencing techniques including but not limited to SAGE, MPSS, and RNA-seq.

In still other genotypic binding agent embodiments the regulatory elements of TICAMs can be engineered through recombinant DNA technologies to direct expression of various intracellular modulators and introduced into tumor cells via viral vectors, or various transducing or transfecting agents. In one manifestation, TICAM regulatory element induced expression of a fluorescent or chromogenic protein could be used to identify TICAM-expressing cells without directly detecting expression of the TICAM itself. Alternatively, TICAM regulatory elements could enable selective expression of a cell-surface expressed biotin, or other agent which would permit selective indirect labeling and/or physical retention of TICAM-expressing cells. In another manifestation, TICAM regulatory elements could direct the expression of a drug resistance gene to facilitate drug-induced positive selection of a TICAM-expressing population. In another manifestation, TICAM regulatory elements could direct the expression of a drug-sensitizing gene, apoptosis-inducing gene, or cytotoxin to selectively deplete the TICAM expressing population. These approaches could be useful in the detection, isolation, and evaluation of the contribution to tumorigenicity of various TICAM expressing cells.

In other instances particularly preferred embodiments of the instant invention comprise phenotypic binding agents in the form of antibodies. The term "antibody" herein is used in the broadest sense and specifically covers synthetic antibodies, monoclonal antibodies, oligoclonal or polyclonal antibodies, multiclonal antibodies, recombinantly produced antibodies, intrabodies, multispecific antibodies, bispecific antibodies, monovalent antibodies, multivalent antibodies, human antibodies, humanized antibodies, chimeric antibodies, primatized antibodies, Fab fragments, F(ab') fragments, single-chain FvFcs (scFvFc), single-chain Fvs (scFv), anti-idiotypic (anti-Id) antibodies and any other immunologically active antibody fragments so long as they exhibit the desired biological activity (i.e., marker association or binding). In a broader sense, the antibodies of the present invention include immunoglobulin molecules and immunologically active fragments of immunoglobulin molecules, i.e., molecules that contain an antigen binding site, where these fragments may or may not be fused to another immunoglobulin domain including, but not limited to, an Fc region or fragment thereof. Further, as outlined in more detail herein, the terms "antibody" and "antibodies" specifically include Fc variants as described herein, including full length antibodies and variant Fc-Fusions comprising Fc regions, or fragments thereof, optionally comprising at least one amino acid residue modification and fused to an immunologically active fragment of an immunoglobulin.

Moreover, while all five classes of antibodies (i.e. IgA, IgD, IgE, IgG, and IgM) and all isotypes (i.e., IgG1, IgG2, IgG3, IgG4, IgA1, and IgA2), as well as variations thereof, are within the scope of the present invention, preferred embodiments comprising the IgG class of immunoglobulin will be discussed in some detail solely for the purposes of illustration. It will be understood that such disclosure is, however, merely demonstrative of exemplary compositions and methods of practicing the present invention and not in any way limiting of the scope of the invention or the claims appended hereto.

Within the context of the instant invention it will be appreciated that compatible antibodies specific for the disclosed TICAM are often commercially available (e.g., from Life Technologies or BioLegend, Inc.). In any event, antibodies or their derivatives and/or their fragments can be provided by methods that are well known to the person skilled in the art and include hybridoma technology in normal or transgenic mice or in rabbits, or phage display antibody technology. In one embodiment, genetic immunization is used. This technique comprises administration of a nucleic acid sequence, or a functional equivalent thereof, encoding at least one antigen of interest, to a non-human animal. The encoded antigen(s) is/are produced by the animal, which stimulates the animal's immune system against said antigen(s). In other embodiments antigens in the form of proteins or peptides are injected directly with and without adjuvants. However the immunogen is introduced an immune response against said antigen(s) is elicited in the animal. Subsequently, T-cells, B-cells and/or antibodies specific for an antigen of interest are preferably obtained from said animal. The T-cells, B-cells and/or antibodies are optionally further processed. In one preferred embodiment, an obtained B-cell of interest is used in hybridoma technology wherein said obtained B-cell is fused with a tumor cell in order to produce a hybrid antibody producing cell.

More particularly preferred embodiments of the invention employ monoclonal antibodies as binding agents. In preferred embodiments, antibody-producing cell lines are prepared from cells isolated from the immunized animal. After immunization, the animal is sacrificed and lymph node and/or splenic B cells are immortalized by means well known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. If fusion with myeloma cells is used, the myeloma cells preferably do not secrete immunoglobulin polypeptides (a non-secretory cell line). Immortalized cells are screened using CD46, or an immunoreactive portion thereof. In a preferred embodiment, the initial screening is performed using an enzyme-linked immunoassay (ELISA) or a radioimmunoassay.

More generally, discrete monoclonal antibodies consistent with the present invention can be prepared using a wide variety of techniques known in the art including hybridoma, recombinant techniques, phage display technologies, yeast libraries, transgenic animals (e.g. a XenoMousem® or HuMAb Mouse®) or some combination thereof. For example, monoclonal antibodies can be produced using hybridoma techniques such as broadly described above and taught in more detail in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) each of which is incorporated herein. Using the disclosed protocols, antibodies are preferably raised in mammals by multiple subcutaneous or intraperitoneal injections of the relevant antigen and an adjuvant. As previously discussed, this immunization generally elicits an immune response that comprises production of antigen-reactive antibodies (that may be fully human if the immunized animal is transgenic) from activated splenocytes or lymphocytes. While the resulting antibodies may be harvested from the serum of the animal to provide polyclonal preparations, it is generally more desirable to isolate individual lymphocytes from the spleen, lymph nodes or peripheral blood to provide homogenous preparations of monoclonal antibodies. Most typically, the lymphocytes are obtained from the spleen and immortalized to provide hybridomas.

More generally, methods of producing polyclonal and monoclonal antibodies are known to those of ordinary skill in the art. See, e.g., Coligan, Current Protocols in Immunology Wiley/Greene, N.Y., 1991; and Harlow and Lane, Antibodies: A Laboratory Manual Cold Spring Harbor Press, NY, 1989; Stites et al., (eds.) Basic and Clinical Immunology (4th ed.) Lange Medical Publications, Los Altos, Calif., and references cited therein; Goding, Monoclonal Antibodies: Principles and Practice (2d ed.) Academic Press, New York, N.Y., 1986; and Kohler and Milstein, Nature 256: 495-497, 1975. Other suitable techniques for antibody preparation include selection of libraries of recombinant antibodies in phage or similar vectors. See, Huse et al., Science 246: 1275-1281, 1989; and Ward et al., Nature 341: 544-546, 1989. Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), Antibody Engineering, 2nd Edition Freeman and Company, NY, 1995; McCafferty et al., Antibody Engineering, A Practical Approach, IRL at Oxford Press, Oxford, England, 1996, and Paul Antibody Engineering Protocols Humana Press, Towata, N.J., 1995. Each of the forgoing is incorporated herein by reference in its entirety.

No matter how obtained or which of the aforementioned forms the antibody binding agent takes (e.g., humanized, human, etc.) preferred embodiments of the disclosed agents may exhibit various characteristics. In this regard TICAM antibody-producing cells (e.g., hybridomas or yeast colonies) may be selected, cloned and further screened for desirable characteristics including, for example, robust growth, high antibody production and, as discussed in more detail below, desirable antibody characteristics such as affinity, epitope or domain specificity, etc. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

It will further be appreciated the disclosed antibodies will associate with, or bind to, discrete epitopes or determinants presented by the selected markers. As used herein the term epitope refers to that portion of the target antigen capable of being recognized and specifically bound by a particular antibody. When the antigen is a polypeptide such as CD46, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. Additionally an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731.

As used herein, the term "binning" refers to a method to group antibodies based on their antigen binding characteristics. The assignment of bins is somewhat arbitrary, depending on how different the observed binding patterns of the antibodies tested. Thus, while the technique is a useful tool for categorizing antibodies of the instant invention, the bins do not always directly correlate with epitopes and such initial determinations should be further confirmed by other art recognized methodology.

With this caveat one can determine whether a selected primary antibody (or fragment thereof) binds to the same epitope or cross competes for binding with a second antibody by using methods known in the art and set forth in the Examples herein. In selected embodiments, one allows the primary antibody of the invention to bind to the marker under saturating conditions and then measures the ability of the secondary antibody to bind to the same marker. If the test antibody is able to bind to the marker at the same time as the primary marker antibody, then the secondary antibody binds to a different epitope than the primary antibody. However, if the secondary antibody is not able to bind to the maker at the same time, then the secondary antibody binds to the same epitope, an overlapping epitope, or an epitope that is in close proximity to the epitope bound by the primary antibody. As known in the art, the desired data can be obtained using solid phase direct or indirect radioimmunoassay (RIA), solid phase direct or indirect enzyme immunoassay (EIA), sandwich competition assay, a Biacore™ system (i.e., surface plasmon resonance—GE Healthcare), a ForteBio® Analyzer (i.e., bio-layer interferometry—ForteBio, Inc.) or flow cytometric methodology. The term surface plasmon resonance, as used herein, refers to an optical phenomenon that allows for the analysis of real-time biospecific interactions by detection of alterations in protein concentrations within a biosensor matrix. In a particularly preferred embodiment, the analysis is performed using a Biacore or ForteBio instrument.

The term compete when used in the context of antibodies that compete for the same epitope means competition between antibodies is determined by an assay in which the antibody or immunologically functional fragment under test prevents or inhibits specific binding of a reference antibody to a common antigen. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

Besides epitope specificity the disclosed antibodies may be characterized using a number of different physical characteristics including, for example, binding affinities, melting temperature (Tm), and isoelectric points.

In this respect, the present invention further encompasses the use of antibodies that have a high binding affinity for the selected marker. An antibody of the invention is said to specifically bind its target antigen when the dissociation constant $K_d$ ($k_{off}/k_{on}$) is $\leq 10^{-8}$M. The antibody specifically binds antigen with high affinity when the $K_d$ is $\leq 5 \times 10^{-9}$M, and with very high affinity when the $K_d$ is $\leq 5\times 10^{-10}$M. In one embodiment of the invention, the antibody has a $K_d$ of $\leq 10^{-9}$M and an off-rate of about $1\times 10^{-4}$/sec. In one embodiment of the invention, the off-rate is $<1\times 10^{-5}$/sec. In other embodiments of the invention, the antibodies will bind to CD46 with a $K_d$ of between about $10^{-8}$M and $10^{-10}$M, and in yet another embodiment it will bind with a $K_d \leq 2\times 10^{-10}$M. Still other selected embodiments of the present invention comprise antibodies that have a disassociation constant or $K_d$ ($k_{off}/k_{on}$) of less than $10^{-2}$M, less than $5\times 10^{-2}$M, less than $10^{-3}$M, less than $5\times 10^{-3}$M, less than $10^{-4}$M, less than $5\times 10^{-4}$M, less than $10^{-5}$M, less than $5\times 10^{-5}$M, less than $10^{-6}$M, less than $5\times 10^{-6}$M, less than $10^{-7}$M, less than $5\times 10^{-7}$M, less than $10^{-8}$M, less than $5\times 10^{-8}$M, less than $10^{-9}$M, less than $5\times 10^{-9}$M, less than $10^{-10}$M, less than $5\times 10^{-10}$M, less than $10^{-13}$M, less than $5\times 10^{-11}$M, less than $10^{-12}$M, less than $5\times 10^{-12}$M, less than $10^{-13}$M, less than $5\times 10^{-13}$M, less than $10^{-14}$M, less than $5\times 10^{-14}$M, less than $10^{-15}$M or less than $5\times 10^{-15}$M.

In specific embodiments, an antibody of the invention that immunospecifically binds to CD46 has an association rate constant or $k_{on}$ rate (CD46 (Ab)+antigen $(Ag)_{on}{}^k \leftarrow$Ab-Ag) of at least $10^5 M^{-1} s^{-1}$, at least $2\times 10^5 M^{-1} s^{-1}$, at least $5\times 10^5 M^{-1} s^{-1}$, at least $10^6 M^{-1} s^{-1}$, at least $5\times 10^6 M^{-1} s^{-1}$, at least $10^7 M^{-1} s^{-1}$, at least $5\times 10^7 M^{-1} s^{-1}$, or at least $10^8 M^{-1} s^{-1}$.

In another embodiment, an antibody of the invention that immunospecifically binds to CD46 has a $k_{off}$ rate (CD46 (Ab)+antigen $(Ag)_{off}{}^k \leftarrow$Ab-Ag) of less than $10^{-1}$ $s^{-1}$, less than $5\times 10^{-1}$ $s^{-1}$, less than $10^{-2}$ $s^{-1}$, less than $5\times 10^{-2}$ $s^{-1}$, less than $10^{-3}$ $s^{-1}$, less than $5\times 10^{-3}$ $s^{-1}$, less than $10^{-4}$ $s^{-1}$, less than $5\times 10^{-4}$ $s^{-1}$, less than $10^{-5}$ $s^{-1}$, less than $5\times 10^{-5}$ $s^{-1}$, less than $10^{-6}$ $s^{-1}$, less than $5\times 10^{-6}$ $s^{-1}$, less than $10^{-7}$ $s^{-1}$, less than $5\times 10^{-7}$ $s^{-1}$, less than $10^{-8}$ $s^{-1}$, less than $5\times 10^{-8}$ $s^{-1}$, less than $10^{-9}$ $s^{-1}$, less than $5\times 10^{-9}$ $s^{-1}$ or less than $10^{-10}$ $s^{-1}$.

In other selected embodiments of the present invention anti-CD46 antibodies will have an affinity constant or $K_a$ ($k_{on}/k_{off}$) of at least $10^2 M^{-1}$, at least $5\times 10^2 M^{-1}$, at least $10^3 M^{-1}$, at least $5\times 10^3 M^{-1}$, at least $10^4 M^{-1}$, at least $5\times 10^4 M^{-1}$, at least $10^5 M^{-1}$, at least $5\times 10^5 M^{-1}$, at least $10^6 M^{-1}$, at least $5\times 10^6 M^{-1}$, at least $10^7 M^{-1}$, at least $5\times 10^7 M^{-1}$, at least $10^8 M^{-1}$, at least $5\times 10^8 M^{-1}$, at least $10^9 M^{-1}$, at least $5\times 10^9 M^{-1}$, at least $10^{10} M^{-1}$, at least $5\times 10^{10} M^{-1}$, at least $10^{11} M^{-1}$, at least $5\times 10^{11} M^{-1}$, at least $10^{12} M^{-1}$, at least $5\times 10^{12} M^{-1}$, at least $10^{13} M^{-1}$, at least $5\times 10^{13} M^{-1}$, at least $10^{14} M^{-1}$, at least $5\times 10^{14} M^{-1}$, at least $10^{15} M^{-1}$ or at least $5\times 10^{15} M^{-1}$ Once an protein or immunoglobulin binding agent of the invention has been produced by recombinant expression, it may be purified by any method known in the art for purification of an immunoglobulin molecule, or more generally, for purification of a protein, for example, by chromatography (e.g., ion exchange, affinity, particularly by affinity for the specific antigen after Protein A, and sizing column chromatography), centrifugation, differential solubility, or by any other standard technique for the purification of proteins. Further, antibody binding agents of the present invention may be fused to heterologous polypeptide sequences described herein or otherwise known in the art to facilitate purification. In particularly preferred embodiments the modulators of the instant invention will be purified, at least in part, using Protein A or Protein G affinity chromatography.

In other preferred embodiments, binding agents of the present invention, or fragments or derivatives thereof, are conjugated, coupled or otherwise associated with or to a diagnostic or detectable agent or reporter that may be a biological molecule (e.g., a peptide or nucleotide) or a small molecule or radioisotope. As set forth elsewhere herein such labeled binding agents can be useful for monitoring the development or progression of a hyperproliferative disorder or as part of a clinical testing procedure to determine the efficacy of a particular therapy including the disclosed modulators. In particularly preferred embodiments the disclosed binding agents associated with a reporter or detectable agent may be useful in identifying or characterizing and, optionally, enriching, isolating, sectioning, partitioning or purifying selected tumorigenic cell populations. Such populations may be used for a myriad of purposes including, but not limited to target identification, drug research and development, toxicology studies, etc.

Such diagnosis, detection and/or separation or enrichment can be accomplished by coupling or associating the binding agent to detectable substances including, but not limited to, various enzymes comprising for example horseradish peroxidase, alkaline phosphatase, beta-galactosidase, or acetylcholinesterase; prosthetic groups, such as but not limited to streptavidinlbiotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{151}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources. In particularly preferred embodiments the labeled binding agents may be used in flow cytometric analysis or FACS.

As discussed in more detail below, the binding agents can be associated with marker sequences, such as a peptide or fluorophore to facilitate purification of cell populations or separation or diagnostic procedures such as immunohistochemistry or FACS. In particularly preferred embodiments such labels shall comprise the MAXPAR™ reagent system (University of Toronto, Stemspec). In preferred embodiments, the marker amino acid sequence is a hexa-histidine peptide, such as the tag provided in a pQE vector (Qiagen), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

VIII. Analysis of Tumorigenic Cell Subpopulations

As discussed immediately above the markers disclosed herein provide for the differentiation of TPC and TProg (e.g., in colorectal cancer) and TIC and NTG cells in a variety of other neoplasias. Although isolation of live cells is requisite to demonstrate functional reconstitution, and thus definitively demonstrate tumor perpetuating capability (i.e. CSC identity), knowledge of TIC, their composite TPC and TProg cell, and NTG cell identity as discerned using the disclosed markers facilitates the discovery of genes and/or proteins associated with these respective cell populations, thereby enabling discovery of diagnostic and/or therapeutic target proteins.

In using the markers disclosed herein as tools to identify TIC, TPC, TProg and NTG tumor cell subpopulations, cells or genetic and/or proteomic material isolated from these cells can be identified and isolated through the use of art-recognized techniques such as magnetic separation, FACS (Example 2), laser capture microdissection or other techniques described above. Further, the isolated or enriched populations may be characterized and/or quantified using microarray technologies, next-generation whole transcriptome sequencing (Example 27), quantitative RT-PCR, mass spectrometry and technologies combining several aspects of these art recognized techniques, such as massively multi-parametric mass cytometry. Such technologies, when applied to analyze the respective tumor cell subpopulations disclosed herein, for example, may lead to the identification of additional TIC markers, including proteins, RNA markers (e.g. mRNA, micro-RNA, long or short non-coding RNA) that may be identifiable by fluorescence in situ hybridization (FISH) or PCR amplification, biochemical markers that can be visualized with chromogenic or fluorogenic dyes, physicochemical properties such as differential adherence to material substrates (i.e. glass, plastic, etc.), or expression of transcriptional regulators that can be identified using fluorescent or luminescent reporter gene constructs inserted into the genome using any number of transfection or viral transduction methods.

Those skilled in the art will appreciate that the cell populations disclosed herein can be enriched or isolated using any single marker, any combination of the select disclosed markers, or surrogate markers that associate with the expression of those markers disclosed herein (i.e. TICAM). As set forth immediately above tumor cell subpopulations can be enriched or isolated by contacting them with binding agents and then using magnetic separation, FACS, or any other technology able to separate the disclosed tumor cell subpopulations based on inherent physicochemical properties (i.e. their charge or differential adhesion to particular substrates) or physicochemical properties conferred to distinct tumor cell subpopulations via binding agents that associate with TICAM. Though magnetic separation techniques are common and generally successful at enriching populations of cells expressing a particular marker, samples enriched in this manner are commonly contaminated by a variety of dead cells, non-target cells and cell clumps. Similarly, cells obtained by depleting a population of cells with all markers except that not expressed on a target cell population (e.g. CD66c) are rarely pure.

Accordingly, particularly preferred embodiments of the instant application employ fluorescence-activated cell sorting (FACS) for cell enrichment or isolation, as flow cytometry allows rapid detailed analysis of single cells, and discriminates size and complexity of individual cells, enabling live versus dead, large versus small, single cell versus cell clumps, and more or less granular cells to be discriminated from one other. In addition to size & complexity parameters, emitted fluorescence can be measured via an array of reflective mirrors and bandpass filters, such that multiple light emission wavelengths from distinct fluorescent proteins, intracellular chemical reactions, retained dyes, or fluorochrome-conjugated antibodies can be interrogated in this manner on the order of many thousands of cells per second. Furthermore, using a flow cytometer with cell isolation capabilities (e.g. FACSAria; Becton Dickenson), single cells with distinct morphological, physicochemical and/or fluorescent characteristics can commonly be isolated to great purity (>99%). Using such techniques in accordance with the teachings herein, it was possible to characterize the heterogeneity of populations of single cells obtained from primary and metastatic tumors obtained directly from cancer patients and from NTX tumors grown in mice. Moreover, it was possible to maintain the viability of these cells during the process, enabling transplantation of as few as 3 cells per mouse in demonstrating the robust tumorigenicity of cell populations isolated using the markers disclosed herein.

Because the markers disclosed in the instant invention enable precise identification and isolation of TPC in colorectal cancer, for example, and distinguish these cells from TProg cells, NTG cells and stromal cells, the resulting tumorigenic cell populations provide for detection of protein-encoding genes, micro-RNAs, long or short non-coding RNAs and/or proteins associated with CSC. That is, these genetic and/or proteomic determinants of self-renewal, differentiation, proliferation and/or survival that are preferentially expressed by the relatively homogeneous tumorigenic cell subpopulations can be identified as discussed herein evaluated for use as prospective diagnostic markers that may truly predict disease severity, response to a particular therapeutic regimen or disease outcome based on their privileged expression by TPC (i.e. CSC) in colorectal cancer, for example. Similarly, markers disclosed herein that facilitate the isolation of TIC and NTG cells from pancreatic, non-small cell lung, triple-negative breast, ovarian, melanoma and ovarian cancer enable the discovery of better diagnostic markers associated with TIC.

The enriched or isolated solid tumor cell subpopulations provided for by the instant invention further allow for the precise elucidation cellular hierarchy and enhanced characterization of cell phenotypes. In this respect it will be understood that hematologic malignancies are among the best understood neoplastic malignancies precisely because the constituent cells are easy to obtain and the in vivo and in vitro assays to determine the fate and potential of these cells have been exhaustively developed. Similarly, oncology research has evolved to the point where, not only can the cells responsible for fueling tumor growth be identified, but they can be reliably isolated using the methods herein and their characteristics tested both in vivo and in vitro. Because tumor initiating cells (TIC) are preferably identified retrospectively by their ability to fuel tumor growth in vivo, techniques and instrumentation that facilitate isolation of competent TIC is essential for their precise identification. In this vein tumor perpetuating cells (i.e. the cancer stem cell subset of TIC), are best identified retrospectively based upon their ability to fuel heterogeneous tumor growth through at least two rounds of serial transplantation using small numbers of well defined cells as demonstrated herein for colorectal cancer.

Although primary transplants are sufficient to give an initial read on tumorigenicity, thus facilitating the retrospective identification of TIC and NTG cells, a single round of transplantation is not sufficient to definitively distinguish between TPC and TProg cells, as both populations are tumorigenic. As indicated herein TProg cells, as identified and disclosed herein for colorectal cancer, differ from TPC (i.e. CSC) in their inability to completely reconstitute tumor heterogeneity, but because TPC levels are typically low, this loss in heterogeneity (i.e. loss of TPC in tumors generated by TProg cells) can be difficult to observe. A second round of transplantation using small numbers of cells is needed to demonstrate the long-term reconstitution ability of TPC versus TProg cells, as the latter population of cells is devoid of self-renewal properties and its proliferation capacity should be exhausted prior to secondary and possibly tertiary transplantation. Done correctly, these serial transplantation experiments should use very small numbers of highly purified cells (<200 cells isolated by FACS) and tumors from primary transplants should be allowed to grow to >1,500 mm$^3$ independent of the time needed to reach this size, therein providing an opportunity for TProg cells to exhaust their proliferative capacity in vivo prior to secondary transplants. Such analysis is greatly facilitated by the techniques disclosed herein.

With respect to such matters it will be appreciated that a panel of markers is preferably used to precisely identify any defined population of stem and/or progenitor cells. More generally, cell populations defined by certain individual markers may not be pure but contain several different cell types, or cells with different potential, wherein additional markers are needed to parse apart the remaining heterogeneity. To determine whether a panel of markers is sufficient to precisely identify a particular cell population, the potential of that particular cell population is preferably demonstrated at the single cell level by single cell transplantation and/or lineage tracing in vivo. The above described serial transplantation methods enable identification of respective tumor cell subpopulations comprising TIC (TPC and TProg) and NTG cells.

When further modified to include the transplantation of at least 3 groups of mice with dilutions of identical cell populations isolated as described herein, one can also determine the actual frequency of TIC, or its constituent TPC or TProg cells, among the input population of cells. For example, this frequency is determined using Poisson distribution statistics, which enables the quantification of TIC among a known population of cells by empirically testing for the frequency of tumorigenicity (the functional demonstration of TIC capacity), independent of the rate at which tumors arise, using limiting dilutions of known input cell populations. The number of defined outcomes (i.e. tumors) achieved at each dilution of input cells is used to calculate the number of TIC among the input population of cells. In this manner, the true frequency of a cell with defined potential (i.e. tumorigenicity) can be assessed. It is important to note that Poisson distribution statistics gains its power from the defined events (i.e. tumorigenicity) being limited in number over the course of dilutions assessed in the experiment. As demonstrated herein for the CD46$^{hi}$ CD324$^+$ CD66c$^-$ cell population isolated from the colorectal NTX-CR4 patient-derived xenograft line, TIC appear to be represented at a 1 in 5 frequency within this population of cells (FIG. 22), whereas cells expressing other markers are nontumorigenic or very poorly tumorigenic. As evidence of the novelty of the instant invention demonstration of a 1 in 5 TIC frequency, as disclosed herein, represents a significant improvement over art recognized markers for other TIC populations, as cells with those markers demonstrate a 1:75 tumorigenic cell frequency in similar experiments (Dylla et al. 2008, PLoS ONE 3:e2428; Dalerba et al. 2011, Nature Biotechnology 29:1120).

It will further be appreciated that, in preferred embodiments, it is possible to quantify specific tumor cell subpopulations based on their marker profile, proteomics or gene expression profile. CSC and NTG cells, for example, may be detected and quantified in tumors following treatment with a prospective therapeutic agent that may then be compared with pre-treatment controls, the vehicle, an off-target agent, or standard of care chemotherapeutic agents. As discussed above, tumors may be dissociated and contacted with agents binding to the markers that define the respective tumor cell subpopulations, and the relative frequency of these cells can be assessed by flow cytometry. In accordance with the teachings herein this is demonstrated as set forth in the Examples below wherein CSC are enriched in colorectal and pancreatic tumors upon exposure to standard of care chemotherapeutic regimens involving irinotecan or gemcitabine, respectively (FIGS. 24 and 25).

With respect to limiting dilution analysis, in vitro enumeration of tumor initiating cell frequency may be accomplished by depositing characterized and/or fractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency; encompass the transplantation of human tumor cells from either untreated control or treated conditions, for example, into immunocompromised mice in serial dilutions and subsequently scoring each mouse as either positive or negative for tumor formation independent of the time required for tumor formation. As alluded to above the derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art recognized cell surface proteins known to enrich for tumor initiating cells (e.g., potentially compatible markers are set forth in Example 1 below) and thereby measure TIC levels from various samples. In still another compatible method one skilled in the art might enumerate TIC frequency in situ (i.e. tissue section) by immunohistochemistry or immunofluorescence using one or more antibodies or reagents that are able to bind cell surface proteins thought to demarcate these cells.

In vitro culture conditions have yet to mimic the physiological environment encountered in vivo; however, in vitro assays can serve as a decent surrogate for demonstration of functional reconstitution of a tumor in vivo by serial transplantation using the cell populations enriched or isolated using the markers disclosed herein. Specifically, cells of interest may be tested for functional properties such as proliferation and/or differentiation capacity in in vitro assays that might predict behavior in vivo. There exist examples where defined, serum-free media is able to maintain and expand tumorigenic cells in vitro (Dylla et al. 2008, PMCID: PMC2413402), demonstrating that tumorigenic cells can be maintained in vitro for at least brief periods of time. Such assays have typically been restricted to colony forming cell (CFC) or sphere forming assays, for example, which measure the ability of cell populations to initiate a colony (attached grouping of cells totally ≥50 cells) or a floating ball of cells of the same or greater cell number (i.e. sphere) (Bao et al. 2006, Nature 444:756). The number of CFC or spheres formed can serve as a proxy for TIC frequency. Moreover, upon dissociation of these colonies and/or spheres, the ability of the composite cells to subsequently reinitiate colonies or spheres can serve as a surrogate readout for self-renewal. In this manner, the frequency of CFC/sphere forming cells and degree of self-renewal under any various culture conditions can be used to identify and characterize the potential of tumor cell subpopulations such as those isolated using the markers herein disclosed.

Figure 23A:
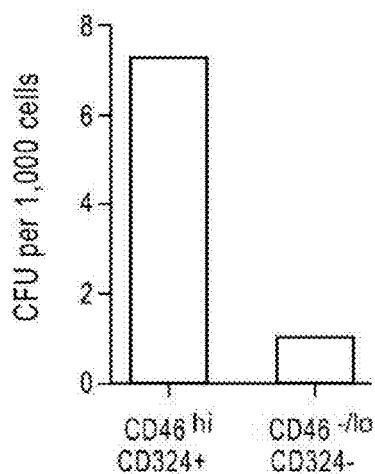
FIGS. 23A-23D graphically illustrate the ability of distinct isolated colorectal tumor cell subpopulations expressing various levels of CD46, CD324 and CD66c to form colonies, differentiate and produce soluble CD66c in vitro.
Figure 23B:
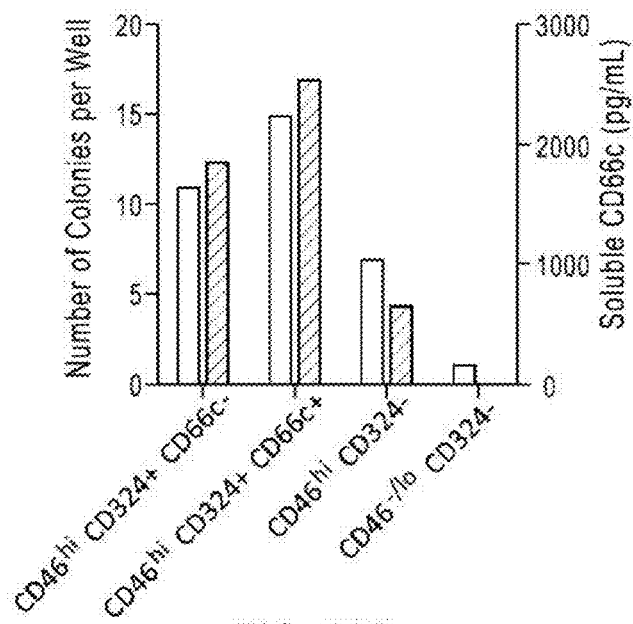
Figure 23C:
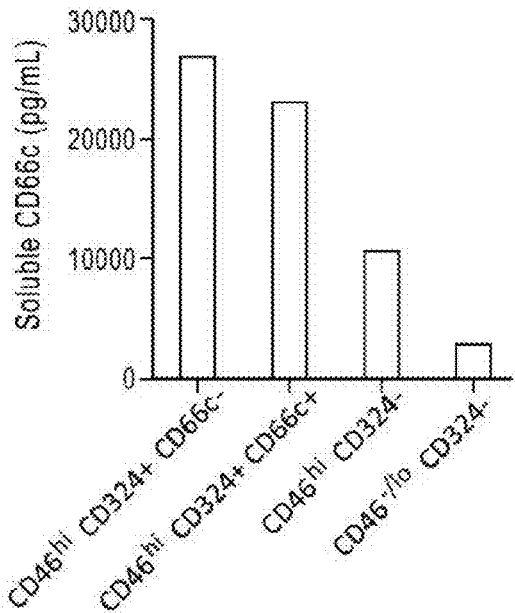

As is also standard in the art, differentiation might be facilitated by the culture of tumor cell subpopulations on different surfaces (e.g. glass or plastic; uncharged or alternating charges), attachment matrices (e.g. collagen or fibronectin in patterned or unorganized array), feeder cells, and/or addition of certain growth factors and/or fetal calf serum, for example, thereby allowing the experimental interrogation of the differentiation potential of said tumor cell subpopulations. Furthermore, genes, proteins and/or factors that impact stem and/or progenitor cell fate decisions such as self-renewal versus differentiation might also be interrogated by co-culture of the defined TIC with such factors or following transfection or transduction with genes and/or proteins of interest. For example, traditional CFC-like assays may be informative wherein these assays can be linked to a differentiation capacity readout such as the generation of TProg and/or NTG cell-associated gene products (e.g. CEACAM6), as demonstrated herein (FIGS. 23B and 23C). More clearly, cell differentiation potential might be measured in vitro based on the input of defined cell populations and monitoring differentiation processes that can be driven by culture conditions conducive to self-renewal or differentiation, followed by characterizing the resulting cells, proteins these cells are generating, and/or interrogating the resulting population's potential by in vivo transplantation. Other methods of characterization enabling the identification of cell populations expressing the markers disclosed herein include the use of high content imaging technologies. By utilizing parameters such as multispectral image analysis facilitating the identification of specific markers and their localization in live or fixed cells, parameters such as overall colony numbers, cell number per colony and quantification of cellular morphology among cells within the colony (e.g. nuclear to cytoplasmic ratio) can be analyzed, for example. Many of these analyses can also be done manually. In in vitro assays where markers indicative of TIC, their composite TPC or TProg cells, and/or NTG cells, respectively, are monitored by high-content, multispectral imaging, the number or frequency or the respective tumor cell subpopulations might be determined in vitro, and responses of these cells to various stimuli that may impact self-renewal or differentiation of these cell populations can be assessed.

As evidenced by the instant disclosure, the ability to passage and analyze enriched or isolated tumor initiating cell subpopulations in animals is a valuable and significant aspect of the instant invention. In this regard compatible animal hosts may comprise model organisms such as nematode, fruit fly, zebrafish; preferably a laboratory mammal such as a mouse (nude mouse, SCID mouse, NOD/SCID mouse, Beige/SCID mouse, FOX/SCID mouse), rat, rabbit, dog, pig, sheep or primate. Severely immunodeficient NOD-SCID mice are particularly suitable animal recipients of transplanted human cancer stem cells. Immunodeficient mice do not reject human tissues, and many such mouse strains have been characterized as hosts for in vivo studies of human hematopoiesis and tissue engraftment. McCune et al., Science 241: 1632-9 (1988); Kamel-Reid & Dick, Science 242: 1706-9 (1988); Larochelle et al., Nat. Med. 2: 1329-37 (1996). In particularly preferred embodiments the NOD/SCID or Beige/SCID mice can be further immunosuppressed using VP-16, antibodies against asialo-GM1 protein, radiation therapy, chemotherapy, or other immunosuppressive biological agents. Additional murine models capable of propagating xenografted human tumors include Nude.Beige, NOD/SCID/IL2Rg-/-, RAG2-/-/IL2Rg-/-, RAG1-/-/IL2Rg-/-, NOD/beta-2-microglobulin-/-, and athymic nude mice. Each of these murine model systems have severe deficiencies in adaptive immune responses, with further selective deficiencies in innate immunity which permit engraftment of tissues which would otherwise be rejected by the host immune system.

Typically, single-cell suspensions (or suspensions with a few aggregates of cells, such as 20,000 cells; ideally less than 100; preferably less than 10 cells) of the isolated cancer stem cells are prepared in a mixture comprising a 1:1 ratio of cell suspension and the matrix carrier Matrigel (Invitrogen), and transplanted into appropriate anatomical sites in the mice. General techniques for formulation and injection of cells may be found in Remington's Pharmaceutical Sciences, 20th ed. (Mack Publishing Co., Easton, Pa.). Suitable routes may include parenteral delivery, including intramuscular, subcutaneous, intramedullary injections, as well as intrathecal, direct intraventricular, intravenous, intraperitoneal, intranasal, intracerebral, or intraocular injections, for example. For injection, the cells of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art. As set forth herein once tumorigenicity is established, the animal model can be used for a wide array of biological and molecular assays to characterize the tumorigenic stem cells and the tumors that arise therefrom.

For example, in the case of treatment of advanced tumors, tumors are allowed to develop to the desired size, with animals having tumors exceeding the desired size range or those tumors that are insufficiently developed being eliminated. The selected animals are distributed at random to undergo the treatments and controls. Animals not bearing tumors may also be subjected to the same treatments as the tumor-bearing animals in order to be able to dissociate any toxicity from the test agent versus toxicity arising from tumor-associated material or responses to the said agent. Chemotherapy generally begins from 21-90 days after grafting, depending on the type of NTX tumor, and the animals are observed daily. The targeted cargo proteins can be administered to the animals, for example, by i.p. injection, intravenous injection, direct injection into the tumor (or into the organ having the tumor), or bolus infusion. The amount of test compound that is injected can be readily be determined by those of skill in the art. Typically the different animal groups are weighed about 1 or 2 times a week until the end of the trial. Tumors are measured once they are palpable and are monitored continuously by direct measurement using electronic calipers or 3D scanning about 1 or 2 times a week until the tumor reaches a pre-determined size and/or weight, or until the animal dies or is euthanized if this occurs before the tumor reaches the pre-determined size/weight. The animals are then sacrificed and not only is tissue is saved for RNA, DNA, protein, IHC and other analyses, but tumor cell subpopulations are enriched or isolated using the methods described herein for similar analyses of the respective populations.

IX. Analysis of Potential Therapeutic Compounds and Screening

The TICAM disclosed herein provide extremely effective methods for the identification, characterization, monitoring and separation or isolation of tumorigenic cell subpopulations. It will be appreciated that the disclosed observational techniques and highly defined cell subpopulations provide powerful tools that may be exploited to identify and validate therapeutic or diagnostic targets as will as pharmaceutical compounds for the treatment, prevention or diagnosis of selected disorders.

In one embodiment of the instant invention the isolated cells or cell populations may be subjected to genotypic or phenotypic analysis (e.g., Example 8 below). More particularly the isolated or enriched cells will be treated or prepared to provide genetic or proteomic material (i.e., information such as a transcriptome) using techniques known in the art. This prepared or treated material is then analyzed using modern techniques such as Next-Gen sequencing, mass spectrometry or mass cytometry to provide selected information about the tumorigenic cell or cell subpopulation such as nucleic acid expression, splice variant utilization, protein expression or morphology.

Further, the defined tumorigenic cell subpopulations disclosed herein may be used to evaluate or test candidate compounds in vitro and/or in vivo for their ability to reduce the amount of cancer cells and/or cancer stem cells, inhibit their proliferation or promote their differentiation. The ability of a candidate compound to stabilize or reduce the amount of cancer cells, cancer stem cells and/or increase immune cell (e.g., lymphocytes) recognition or inhibit their proliferation can be assessed by: detecting the expression of antigens on cancer cells, cancer stem cells and immune cells; detecting the proliferation cancer cells, cancer stem cells and immune cells; detecting the cancer cells and cancer stem cells using functional assays. In particularly preferred embodiments the analysis will comprise the identification, characterization and/or isolation and enrichment of tumorigenic cell subpopulations. Techniques known to those of skilled in the art can be used for measuring these activities. For example, cellular proliferation can be assayed by $^3$H-thymidine incorporation, quantification of ATP or trypan blue cell counts. Antigen expression can be assayed, for example, by immunoassays including, but are not limited to, competitive and non-competitive assay systems using techniques such as western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, immunofluorescence, flow cytometry, FACS analysis and multiparametric mass cytometry.

A potential pharmaceutical compound, pharmaceutical composition, or proposed regimen is preferably tested in vitro and then in vivo for the desired therapeutic or prophylactic activity prior to use in humans. For example, assays which can be used to determine whether administration of a specific compound is efficacious include assays in which a patient tissue sample (e.g., whole tumor or enriched cell subpopulations) is passaged in immunocompromised mice and exposed to, or otherwise contacted with, a compound of the invention, and the effect of such compound upon the tumor cells/tissue sample is observed. The tissue sample can be obtained by biopsy or resection from the patient. Efficacy may also be assessed by evaluating tumor-associated miR-NAs or proteins in the serum of tumor-bearing animals. Such tests allow the identification of the therapeutically most effective therapy (e.g., prophylactic or therapeutic agent) for each individual patient. Generally, a therapy is preferably tested in vitro and then in vivo for the desired therapeutic or prophylactic activity prior to use in humans.

More specifically the markers and associated cells, cultures, populations and compositions comprising the same, including progeny thereof, can be used to screen for or identify compounds or agents (e.g., drugs) that affect a function or activity of tumor initiating cells or progeny thereof. The invention therefore further provides systems and methods for evaluation or identification of a compound or agent that can affect a function or activity tumor initiating cells or progeny thereof by interfering with selected pathways or functions as displayed in the enriched populations. Such compounds and agents can be drug candidates that are screened for the treatment of a hyperproliferative disorder, for example. In one embodiment, a system or method includes enriched populations of tumor initiating cells and a compound or agent (e.g., drug), wherein the cells and compound or agent (e.g., drug) are in contact with each other.

In another preferred embodiment the method includes contacting tumor initiating cells and/or progeny thereof in vivo or in vitro with a test agent or compound; and determining if the test agent or compound modulates an activity or function of the tumor initiating cells. Exemplary activity or function that can be modulated include changes in cell morphology, expression of a marker, differentiation or dedifferentiation, maturation, proliferation, viability, apoptosis or cell death.

In some embodiments it will be advantageous to screen for and select compounds that may impact more than one tumorigenic subpopulation. Thus, if overall survival is to be impacted by therapeutic regimens, the targets of these drugs will be best selected based on their expression on or in, primarily TPC, but also TProg. One might expect that selected targeting of TPC would result in the eventual regression of a tumor, but this may take some time to occur, as TProg are herein demonstrated in colorectal cancer to have significant proliferative capacity. Therapeutic targets not only expressed by TPC, but also by TProg may be better drug candidates as both the self-renewing component of the tumor and the highly proliferative TProg compartment might be eradicated in parallel, resulting in noticeable tumor regression and prolonged overall survival. These drug targets may be, for example, genes, proteins, micro-RNA, and/or long or short non-coding RNAs. Drug targets may also include ligands that are not expressed by the TPC or TProg, but which bind receptors on TPC or TProg and which are critical for the self-renewal of TPC or proliferation of TProg.

More generally, contacting, when used in reference to cells or a cell culture or method step or treatment, means a direct or indirect interaction between the enriched or selected tumorigenic cells or cell subpopulations with another referenced entity. A particular example of a direct interaction is physical interaction. Moreover, such contact may take place in vitro or in vivo (i.e. a test compound administered to an NTX animal). A particular example of an indirect interaction is where a composition acts upon an intermediary molecule that in turn acts upon the referenced entity (e.g., cell or cell culture).

In this aspect of the invention modulates indicates influencing an activity or function of tumor initiating cells or progeny cells in a manner compatible with detecting the effects on cell activity or function that has been determined to be relevant to a particular aspect (e.g., metastasis or proliferation) of the tumor initiating cells or progeny cells of the invention. Exemplary activities and functions include, but are not limited to, measuring morphology, developmental markers, differentiation, proliferation, viability, cell respiration, mitochondrial activity, membrane integrity, protein secretion, gene expression, migration or expression of markers associated with certain conditions. Accordingly, a compound or agent (e.g., a drug candidate) can be evaluated for its effect on tumor initiating cells or progeny cells, by contacting such cells or progeny cells with the compound or agent and measuring any modulation of expression, an activity or function of tumor initiating cells or progeny cells as disclosed herein or would be known to the skilled artisan.

Methods of screening and identifying agents and compounds include those suitable for high throughput screening, which include arrays of cells (e.g., microarrays) positioned or placed, optionally at pre-determined locations or addresses. High-throughput robotic or manual handling methods can probe chemical interactions and determine levels of expression of many, for example, genes, protein and/or metabolic activity in a short period of time. Techniques have been developed that utilize molecular signals (e.g., fluorophores) and automated analyses to process information at a very rapid rate (see, e.g., Pinhasov et al., Comb. Chem. High Throughput Screen. 7:133 (2004)). For example, microarray technology has been extensively utilized to probe the expression of thousands of genes at once, while ChIP on chip analyses provide information on the interactome of specific proteins with nucleic acid elements of the genome (see, e.g., Mocellin and Rossi, Adv. Exp. Med. Biol. 593:19 (2007)).

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Such screening methods (e.g., high-throughput) can identify active agents and compounds rapidly and efficiently. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, phage display libraries, fully human antibody or antibody fragment yeast display libraries (e.g., Adimab, LLC), siRNA libraries, and adenoviral transfection vectors. In other preferred embodiments the method comprises screening a chemical compound library of interest for activity in a culture comprising an enriched preparation tumorigenic cells. Such a chemical library may include the Spectrum™ Collection library, the Lopac™ Collection library, the Prestwick Chemical Library® and the Maybridge® Collection library (each are libraries of compounds for screening).

Further, compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In such embodiments parameters to be measured comprise quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells. (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

Besides the aforementioned embodiments the instant invention may also be used for the screening and/or refinement of regenerative medicine products comprising stem cells. As used herein the term "regenerative medicine product" shall mean any diagnostic, theragnostic, prophylactic or therapeutic product or device or kit comprising stem cells. Preferably such products will comprise compositions of stem cells that will be administered to a subject in need thereof. Moreover, the stem cells included in such products may be derived from any art recognized source and generated using well known techniques.

In this respect cell products derived from embryonic, iPS and adult stem cells are becoming an increasingly available and popular avenue of therapy for many diseases. Stem cells hold great promise in that replacing damaged or deficient cell populations, such as pancreatic insulin-producing beta cells, myocardiocytes, etc. may cure patients and address unmet medical needs and/or circumvent the need for constant monitoring and treatment as is the case for patients with Type I diabetes. However, a major concern with these cell products is their safety: particularly ensuring that such stem cell compositions lack tumor forming capacity. To that end the TICAM disclosed herein may be used to identify regenerative medicine products comprising such tumorigenic cells, and may also be used to eliminate or deplete such tumorigenic cells thereby ensuring the cell products are safe for human administration. In this regard the TICAM of the instant invention may be used in much the same way that present biologic products are screened for viral contamination during production. Those of skill in the art will appreciate well known methodology and commercially available products may readily be employed to implement these aspects of the instant invention in view of the present disclosure.

X. Diagnostic Uses

In another preferred aspect, the present invention provides a method of diagnosing cancer or detecting a cancerous or pre-cancerous cell comprising obtaining a blood or serum sample, bulk tumor cells or tumor cell subpopulations enriched or purified from a subject's tumor (e.g. TIC, TPC, TProg, NTG cells, tumor stroma, or whole tumor tissue) and assessing the frequency of these tumor cell subpopulations and/or the genetic and/or proteomic molecular profile of these respective cell populations. Tumorigenic cells can also be isolated based on the TICAM disclosed herein and various methods of isolating tumorigenic cells from a subject, for example, a human, are known in the relevant field.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors and/or phenotype of constituent tumor cells originating from metastasizing cells of the primary tumor are analyzed in vivo. In another embodiment, the size and shape of secondary tumors are analyzed. In some embodiments, further ex-vivo analysis is performed. In another embodiment, the patient's tumor is transplanted into immunocompromised mice and grown as a xenograft such that the above embodiments analyzing cancer progression, pathogenesis and/or experiments to predict response to prospective or actual therapies are performed.

Other preferred embodiments of the invention also exploit the properties of the disclosed genotypic or phenotypic TICAM such as associated genes, proteins, micro-RNAs, or short and long non-coding RNAs obtained using cells enriched or isolated from TIC to quantify the relative number or frequency of TIC in a given specimen (e.g. tumor biopsy) based on the expression of TICAM in the sample versus the level of TICAM from a control specimen or a specimen obtained at a different point in time. In this manner, it may be possible to predict and/or actively assess response to therapy without directly assessing the actual number of TIC within the sample as described herein.

Any in vitro or in vivo assays known to one of ordinary skill in the art that can detect and/or quantify tumorigenic cells can be used to monitor the course of a disease in order to evaluate the impact of a selected treatment and/or regimen. These methods can be used to assess the impact in a research setting as well as in a clinical setting. The results of these assays then may be used to alter the dosing, drugs or timing of the treatment of a subject. The sample can be subjected to one or more pretreatment steps prior to the detection, isolation and/or measurement of the cancer stem cell population in the sample. In certain examples, a biological fluid is pretreated by centrifugation, filtration, precipitation, dialysis, or chromatography, or by a combination of such pre-treatment steps. In other examples, a tissue sample is pretreated by freezing, chemical fixation, paraffin embedding, dehydration, permeabilization, or homogenization followed by centrifugation, filtration, precipitation, dialysis, or chromatography, or by a combination of such pretreatment steps. In certain examples, the sample is pretreated by removing cells other than tumorigenic cell subpopulations from the sample, or removing debris from the sample prior to the determination of the amount of cancer stem cells in the sample.

Moreover, the sensitivity and accuracy of many diagnostic assays are degraded by the complexity of tumor cell types. In this regard it will be appreciated that tumors comprise transformed cancerous cells, normal human cells co-opted into supporting tumor growth including endothelial cells, adipose tissue, and other stromal cell types, and tumor-infiltrating immune cells which restrict tumor growth. These non-cancerous cells can constitute a significant proportion of the tumor mass, and in some cases comprise the majority of cells in a tumor. Accordingly such normal cells provide a significant background that can erode the sensitivity of diagnostic assays intended to survey the status of various features of cancerous cells within a tumor.

In terms of the instant invention the impact of background signal derived from non-cancerous stromal cell components can be minimized by selectively enriching cancerous tumor cells with TICAM-targeting molecules, thereby significantly reducing or eliminating background signal. This can be achieved by producing a single cell suspension of a primary patient tumor and contacting cells with a TICAM-binding agent, which is in turn bound to an agent that facilitates cell separation, including magnetic beads, fluorescent molecules, high-affinity binding agents including biotin or streptavidin, etc. Such an approach could significantly improve the accuracy of tests that survey populations of cells, including comparative genomic hybridization, targeted PCR for the identification of gene amplification or translocation, assessment of mRNA expression by qRT-PCR or array hybridization, or assessment of protein abundance by approaches including ELISA, immunoblot, and mass spectrometry.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors and/or phenotype of constituent tumor cells originating from metastasizing cells of the primary tumor is analyzed in-vivo. In another embodiment, the size and shape of secondary tumors are analyzed. In some embodiments, further ex-vivo analysis is performed. In another embodiment, the patient's tumor is transplanted into immunocompromised mice and grown as a xenograft such that the above embodiments analyzing cancer progression, pathogenesis and/or experiments to predict response to prospective or actual therapies are performed.

In certain examples, the tumorigenic cells in a subject or a sample from a subject may be assessed or characterized prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

XI. Articles of Manufacture

The present invention also provides kits for identifying, characterizing and/or enriching, or isolating tumorigenic cells or cell subpopulations as described herein. Such kits may be use used in a clinical setting for patient diagnostic purposes or in research for characterization and/or enrichment of tumorigenic cell populations. Kits according to the invention will comprise one or more containers comprising TICAM binding agents and a label or package insert on or associated with the container. Suitable containers include, for example, bottles, vials, syringes, 96 well plates, etc. The containers may be formed from a variety of materials such as glass or plastic. The container holds one or more compositions comprising binding agents that are effective for analyzing tumorigenic cells and optionally providing the enriched or isolated cells or cell subpopulations as described herein. Such kits will generally contain in a suitable container a formulation of one or more TICAM binding agents where in the case of multiple binding agents the binding agents may be in the same or different containers. The kits may also contain other pharmaceutically acceptable formulations, either for diagnosis or for labeling or modifying the enclosed binding agents.

More specifically the kits may have a single container that contains the one or more TICAM binding agent, with or without additional components, or they may have distinct containers for each component. Where combined reporters provided for conjugation, a single solution may be premixed, either in a molar equivalent combination, or with one component in excess of the other. Alternatively, the binding agent and any optional labeling agent of the kit may be maintained separately within distinct containers prior to administration to a subject or in vitro use. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the binding agent and any optional components to a subject, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. In particularly preferred embodiments any label or package insert indicates that the binding agent composition is used for in the diagnosis of cancer, for example colorectal cancer. In other preferred embodiments the enclosed instructions instructs or indicates how to use the components in an in vivo or in vitro research setting.

In still other embodiments the compounds (e.g., TICAM binding agents) or compositions (e.g., enriched TIC cell populations) may be used in conjunction with devices to detect, diagnose, profile, characterize or treat proliferative disorders. For example, in a preferred embodiments the disclosed TICAM could be used to detect, interrogate, capture, characterize or eliminate circulating tumor cells. (See, for example WO 2012/012801 which is incorporated herein in its entirety).

XII. Research Reagents

Other preferred embodiments of the invention also exploit the properties of the disclosed TICAM as an instrument useful for identifying, isolating, sectioning or enriching populations or subpopulations of tumor initiating cells through methods such as fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S.P.Ns. 20100184119, 20100273160, and 20110020221, each of which is incorporated herein by reference in its entirety). Compatible methods are further set forth in the Examples appended hereto.

XIII. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

All references or documents disclosed or cited within this specification are, without limitation, incorporated herein by reference in their entirety. Moreover, any section headings used herein are for organizational purposes only and are not to be construed as limiting the subject matter described.

XIV. Selected Embodiments of the Invention

In addition to the disclosure and Examples herein, the present invention is directed to selected embodiments specifically set forth in this section.

Putative Claims

1. A tumorigenic cell population enriched for expression of at least one TICAM.
2. The enriched tumorigenic cell population of claim 1 wherein said at least one TICAM is selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.
3. The enriched tumorigenic cell population of claim 2 wherein said at least one TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

4. The enriched tumorigenic cell population of claim 1 wherein said at least one TICAM is selected from the group consisting of CD46, CD324, CD66c and combinations thereof.

5. The enriched tumorigenic cell population of claim 1 wherein said cells have a marker phenotype comprising CD46$^{hi}$ CD324$^+$.

6. A composition comprising the enriched tumorigenic cell population of claim 1 and a carrier.

7. An isolated tumorigenic cell comprising at least one TICAM.

8. The cell of claim 7 wherein said at least one TICAM is selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

9. The cell of claim 8 wherein said at least one TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

10. The cell of claim 7 wherein said cell has a marker phenotype comprising CD46$^{hi}$ CD324$^+$.

11. A composition comprising the cell of claim 7 and a pharmaceutically acceptable carrier.

12. A method of detecting a tumorigenic cell, comprising the steps of:
  a. contacting a tumor cell population with a binding agent which preferably associates with at least one TICAM; and
  b. detecting said binding agent associated with said tumorigenic cell.

13. The method of claim 12, wherein said binding agent comprises a genotypic binding agent.

14. The method of claim 12 wherein said binding agent comprises a phenotypic binding agent.

15. The method of claim 12 wherein said phenotypic binding agent comprises a ligand.

16. The method of claim 12 wherein said phenotypic binding agent comprises an antibody.

17. The method of claim 16 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

18. The method of claim 16 wherein said antibody comprises a monoclonal antibody.

19. The method of claim 18 wherein said monoclonal antibody comprises a reporter molecule.

20. The method of claim 19 wherein said detecting step comprises fluorescence activated cell sorting, magnetic-assisted cell sorting, substrate-assisted cell sorting, laser capture microdissection, fluorometry, flow cytometry, mass cytometry or microscopy techniques.

21. The method of claim 12, wherein said tumor cell population is derived from a solid tumor.

22. The method of claim 21 wherein said solid tumor is obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, endometrial cancer and melanoma.

23. The method of claim 12 wherein said detected cell is a metastatic cell.

24. The method of claim 12 wherein said contacting step takes place in vivo.

25. The method of claim 24 wherein said contacting step takes place in an immunocompromised mouse.

26. A method for enriching a tumorigenic cell population comprising the steps of:
  a. contacting a tumor cell population with a binding agent which preferably associates with at least one TICAM; and
  b. sorting said cells associated with said TICAM to provide an enriched tumorigenic cell population.

27. The method of claim 26, wherein said binding agent comprises a genotypic binding agent.

28. The method of claim 26 wherein said binding agent comprises a phenotypic binding agent.

29. The method of claim 28 wherein said phenotypic binding agent comprises a ligand.

30. The method of claim 28 wherein said phenotypic binding agent comprises an antibody.

31. The method of claim 30 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

32. The method of claim 31 wherein said TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2 and VEGFR2.

33. The method of claim 31 wherein said antibody comprises a monoclonal antibody.

34. The method of claim 33 wherein said monoclonal antibody comprises a reporter molecule.

35. The method of claim 34 wherein said sorting step comprises fluorescence activated cell sorting, magnetic-assisted cell sorting, substrate-assisted cell sorting, laser capture microdissection, fluorometry, flow cytometry, mass cytometry or microscopy techniques.

36. The method of claim 26 wherein said tumor cell population is derived from a solid tumor.

37. The method of claim 36 wherein said solid tumor is obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head and neck cancer, endometrial cancer and melanoma.

38. The method of claim 26 wherein said enriched tumorigenic cell population has a marker phenotype comprising CD46$^{hi}$ CD324$^+$.

39. A composition comprising the enriched tumorigenic cell population of claim 38 and a carrier.

40. A method of sorting tumorigenic cells comprising the steps of:

a. contacting a tumor cell population with a binding agent which preferably associates with at least one TICAM; and b. sorting cells associated with said at least one TICAM.

41. The method of claim 40, wherein said binding agent comprises a genotypic binding agent.

42. The method of claim 40 wherein said binding agent comprises a phenotypic binding agent.

43. The method of claim 42 wherein said phenotypic binding agent comprises a ligand.

44. The method of claim 42 wherein said phenotypic binding agent comprises an antibody.

45. The method of claim 44 wherein said antibody preferably associates with a TICAM is selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD17, CD18, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

46. The method of claim 44 wherein said antibody comprises a monoclonal antibody.

47. The method of claim 46 wherein said monoclonal antibody comprises a reporter molecule.

48. The method of claim 40 wherein said sorting step comprises fluorescence activated cell sorting, magnetic-assisted cell sorting, substrate-assisted cell sorting, laser capture microdissection, fluorometry, flow cytometry, mass cytometry or microscopy techniques.

49. A method of determining if a cell obtained from a tumor sample is tumorigenic comprising the step of contacting the tumor cell with at least one TICAM binding agent.

50. The method of claim 49 wherein said TICAM is selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-7R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

51. The method of claim 49 wherein said contacting step comprises more than one TICAM binding agent.

52. The method of claim 49 wherein said tumor cell comprises a marker phenotype comprising $CD46^{hi}$ $CD324^+$.

53. A method of treating or diagnosing a disorder subject in need thereof comprising the steps of;
  a. obtaining a tumor sample from the subject; and
  b. contacting the tumor sample with at least one binding agent that preferably associates with a TICAM.

54. The method of claim 53, wherein said binding agent comprises a genotypic binding agent.

55. The method of claim 53 wherein said binding agent comprises a phenotypic binding agent.

56. The method of claim 55 wherein said phenotypic binding agent comprises a ligand.

57. The method of claim 55 wherein said phenotypic binding agent comprises an antibody.

58. The method of claim 57 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

59. The method of claim 58 wherein said TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

60. The method of claim 57 wherein said antibody comprises a monoclonal antibody.

61. The method of claim 60 wherein said monoclonal antibody comprises a reporter molecule.

62. The method of claim 53 wherein said sample comprises a blood or serum sample comprising circulating tumor cells.

63. The method of claim 62 wherein said disorder comprises a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, endometrial cancer and melanoma.

64. A method of determining the tumorigenicity of a cell comprising the step of contacting the cell with at least one TICAM binding agent.

65. The method of claim 64, wherein said binding agent comprises a genotypic binding agent.

66. The method of claim 64 wherein said binding agent comprises a phenotypic binding agent.

67. The method of claim 66 wherein said phenotypic binding agent comprises a ligand.

68. The method of claim 66 wherein said phenotypic binding agent comprises an antibody.

69. The method of claim 68 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

70. The method of claim 68 wherein said TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

71. The method of claim 68 wherein said antibody comprises a monoclonal antibody.

72. The method of claim 71 wherein said monoclonal antibody comprises a reporter molecule.

73. The method of claim 64 wherein said cell is present in a patient sample.

74. The method of claim 73 wherein said patient sample comprises a blood or serum sample comprising circulating tumor cells.

75. The method of claim 64 wherein said cell in contacted in vivo.

76. The method of claim 64 wherein said cell is present in a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, endometrial cancer and melanoma.

77. A method of determining whether a subject suffering from cancer is at risk of recurrence comprising the steps of:
   a. accessing a sample from the subject; and
   b. contacting the sample with at least one binding agent that preferably associates with a TICAM.

78. The method of claim 77, wherein said binding agent comprises a genotypic binding agent.

79. The method of claim 77 wherein said binding agent comprises a phenotypic binding agent.

80. The method of claim 79 wherein said phenotypic binding agent comprises an antibody.

81. The method of claim 80 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

82. The method of claim 81 wherein said TICAM is selected from the group consisting of CD46, CD324, CD66c and combinations thereof.

83. The method of claim 80 wherein said antibody comprises a monoclonal antibody.

84. The method of claim 83 wherein said monoclonal antibody comprises a reporter molecule.

85. The method of claim 77 wherein said contacting step takes place in vivo.

86. The method of claim 85 wherein said contacting step takes place in an immunocompromised mouse.

87. The method of claim 77 wherein said contacting step takes place in vitro.

88. The method of claim 77 wherein said accessing step comprises obtaining a patient sample from the subject.

89. The method of claim 88 wherein said patient sample comprises blood or serum comprising circulating tumor cells.

90. The method of claim 89 wherein said circulating tumor cells have a marker phenotype comprising $CD46^{hi}$ $CD324^+$.

91. The method of claim 75 wherein the subject has undergone a debulking procedure.

92. A kit useful for the diagnosis, characterization or monitoring of proliferative disorders comprising a receptacle comprising one or more TICAM binding agents and instructional materials for using the one or more TICAM binding agents to diagnose or monitor the proliferative disorder.

93. The kit of claim 92 wherein said one or more TICAM binding agents comprises a monoclonal antibody.

94. The kit of claim 93 wherein said monoclonal antibody is associated with a reporter molecule.

95. The kit of claim 92 wherein the receptacle comprises a readable plate.

96. A method of conducting genotypic or phenotypic analysis comprising the steps of:
   a. providing a tumorigenic cell or enriched tumorigenic cell population comprising one or more TICAM;
   b. treating said cell or cell population to provide genetic or proteomic material; and
   c. analyzing said genetic or proteomic material.

97. The method of claim 96 wherein material is genetic material.

98. The method of claim 97 wherein said genetic material comprises transcriptome material.

99. A method of screening potential pharmaceutical compounds comprising the steps of:
   a. exposing a tumorigenic cell or tumorigenic cell population to a candidate compound; and
   b. contacting the tumorigenic cell or tumorigenic cell population with at least one TICAM binding agent.

100. The method of claim 99 wherein said candidate compounds are small molecules.

101. The method of claim 99 further comprising the step of sorting said tumorigenic cell or tumorigenic cell population to provide a tumorigenic cell subpopulation.

102. The method of claim 101 wherein said sorting step comprises fluorescence activated cell sorting, magnetic-assisted cell sorting, substrate-assisted cell sorting, laser capture microdissection, fluorometry, flow cytometry, mass cytometry or microscopy techniques.

103. The method of claim 101 wherein said tumorigenic cell subpopulation is introduced into a non-human mammal.

104. A method of inducing cancer comprising the steps of:
   a. providing a tumorigenic cell population enriched for one or more TICAM; and
   b. introducing the tumorigenic cell population into a subject.

105. The method of claim 104 wherein said subject comprises a non-human mammal.

106. The method of claim 105 wherein said non-human mammal comprises an immunocompromised mouse or a humanized mouse.

107. A method of inducing cancer comprising the steps of:
   a. isolating a tumorigenic cell exhibiting one or more TICAM; and
   b. introducing isolated tumorigenic cell into a subject.

108. The method of claim 107 wherein said subject comprises a non-human mammal.

109. The method of claim 108 wherein said non-human mammal comprises an immunocompromised mouse or a humanized mouse.

110. A method a method of generating a tumor sample comprising the steps of:
   a. providing a tumorigenic cell or enriched tumorigenic cell population comprising one or more TICAM;
   b. introducing the tumorigenic cell or enriched tumorigenic cell population into a subject;
   c. allowing the tumorigenic cell or cell population to generate a tumor; and
   d. harvesting at least a portion of said tumor to provide the tumor sample.

111. The method of claim 110 wherein said subject is administered a candidate compound following step b.

112. The method of claim 110 wherein said tumor sample is heterogeneous.

113. An animal model for the analysis of pharmaceutical compounds or characterization of a proliferative disorder comprising a subject implanted with a tumorigenic cell or cell population purified or enriched for one or more TICAM.

114. The method of claim 113 wherein said subject comprises an immunocompromised mouse or a humanized mouse.

115. A method of producing an animal model for the analysis of pharmaceutical compounds comprising the step of introducing a tumorigenic cell or cell population purified or enriched for one or more TICAM.

116. The method of claim 115 wherein said subject comprises an immunocompromised mouse or a humanized mouse.

117. A method of monitoring cancer progression and/or pathogenesis in vivo, comprising the steps of:
 a. introducing one or more tumorigenic cells comprising one or more TICAM into a subject; and
 b. monitoring cancer progression and/or pathogenesis in the subject.

118. A method of determining whether a subject suffering from cancer is at risk of metastasis comprising the steps of:
 a. accessing a sample from the subject; and
 b. contacting the sample with at least one TICAM binding agent.

119. The method of claim 118, wherein said binding agent comprises a genotypic binding agent.

120. The method of claim 118 wherein said binding agent comprises a phenotypic binding agent.

121. The method of claim 120 wherein said phenotypic binding agent comprises a ligand.

122. The method of claim 120 wherein said phenotypic binding agent comprises an antibody.

123. The method of claim 122 wherein said antibody preferably associates with a TICAM selected from the group consisting of CA9, CCR4, CCR9, CCR10, CCRL2, CD9, CD13, CD15, CD24, CD26, CD29, CD32, CD46, CD49a, CD49b, CD49c, CD49f, CD51, CD54, CD55, CD56, CD58, CD63, CD66, CD66a, CD66a/c/e, CD66c, CD66e, CD71, CD73, CD81, CD82, CD91, CD98, CD99, CD102, CD104, CD105, CD108, CD111, CD117, CD118, CD130, CD131, CD133, CD136, CD141, CD146, CD147, CD148, CD151, CD155, CD156, CD157, CD164, CD166, CD167a, CD172a, CD177, CD186, CD196, CD221, CD230, CD234, CD244, CD245, CD262, CD265, CD273, CD275, CD295, CD298, CD299, CD317, CD318, CD323, CD324, CD340, CD349, BMPR-1B, Cadherin-11, c-Met, Claudin-3, Claudin-4, CLEC4A, DLL-1, DLL-3, Eph-A2, Eph-B2, Eph-B4, FOLR1, Frizzled-1, Frizzled-3, Glut-1, Glut-2, Glut-3, Glypican 1, Glypican 5, HLA-A/B/C, HLA-A2, HER3, IL-15R, IL-17R, IL-17 RD, IL-20Ra, Jagged-2, Integrin-a8, Integrin a9b1, Integrin b5, LAG-3, LDL-R, Leukotriene-B4R, Lox-1, LRP6, MCSP, M6PR, Mer, MMP14, Nectin-4, Notch2, NPC, OV6, P-Cadherin, PAR1, PD-L2, Plexin-B1, Plexin-B2, Plexin-D1, PNPLA2, Semaphorin 4B, Somatostatin-R2, TIMD4, TROP-2, TSPAN8, TREM2, TREML1, ULBP2, Vb9 and VEGFR2.

124. The method of claim 122 wherein said TICAM is selected from the group consisting of CA9, CCR4, CCR9, CCRL2, CD32, CD56, CD58, CD102, CD117, CD118, CD131, CD133, CD141, CD146, CD147, CD148, CD156, CD167a, CD177, CD196, CD234, CD244, CD245, CD265, CD299, CD323, CD349, BMPR-1B, Cadherin-11, Claudin-3, Claudin-4, CLEC4A, DLL-1, DLL-3, Eph-A2, Frizzled-1, Frizzled-3, Glut-1, Glut-3, Glypican 1, HLA-A/B/C, HLA-A2, IL-15R, IL-17R, IL-17 RD, Jagged-2, Integrin-a8, LAG-3, Leukotriene-B4R, Lox-1, LRP6, MCSP, M6PR, MMP14, Nectin-4, Notch2, NPC, OV6, P-Cadherin, PAR1, PD-L2, Plexin-B1, Plexin-B2, Plexin-D1, PNPLA2, Somatostatin-R2, TIMD4, TSPAN8, TREM2, TREML1, ULBP2, and VEGFR2.

125. The method of claim 122 wherein said antibody comprises a monoclonal antibody.

126. The method of claim 122 wherein said monoclonal antibody comprises a reporter molecule.

127. The method of claim 118 wherein said contacting step takes place in vivo.

128. The method of claim 127 wherein said contacting step takes place in an immunocompromised mouse or humanized mouse.

129. The method of claim 118 wherein said contacting step takes place in vitro.

130. The method of claim 118 wherein said sample comprises a solid tumor sample.

131. The method of claim 130 wherein said patient sample is obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, endometrial cancer and melanoma.

132. The method of claim 118 wherein said sample comprises cells exhibiting a marker phenotype comprising $CD46^{hi}$ $CD324^+$.

133. The method of claim 118 wherein the subject has undergone a debulking procedure.

134. A method of immunizing a subject comprising the steps of:
 a. providing a cell population enriched for one or more TICAM; and
 b. introducing the cell population into said subject.

135. The method of claim 134 wherein said subject comprises a competent immune system.

136. The method of claim 135 wherein said subject exhibits an immune response to the cell population.

137. The method of claim 136 wherein said cell population is engineered to express said TICAM.

138. A method for the detection and/or characterization of tumorigenic potential comprising the step of detecting secreted TICAM proteins or immunoreactive fragments thereof.

139. The method of claim 138 wherein said detecting step takes place in vivo.

140. The method of claim 138 wherein said detecting step takes place in vitro.

141. The method of claim 138 further comprising the step of quantifying the secreted proteins.

142. A method for identifying novel TICAMs comprising the steps of:
 a. exposing a tumor-bearing subject to chemotherapy;
 b. collecting composite tumor cell populations from said subject; and
 c. analyzing the cell populations for TICAM expression.

143. The method of claim 142 wherein said TICAM expression is elevated.

144. A method for detecting the presence of cancer stem cells in a regenerative medicine product comprising stem cells comprising the step of contacting said regenerative medicine product with at least one TICAM binding agent.

145. A method for the depletion or elimination of cancer stem cells from a regenerative medicine product comprising stem cells comprising the step of contacting said regenerative medicine product with at least one TICAM binding agent.

146. A method of generating an immune response in a subject in need thereof comprising the step of exposing the subject's immune system to one or more TICAM whereby the subject develops a protective immune response.

147. The method of claim 146 wherein the TICAM is in a soluble form.

148. The method of claim 146 wherein the TICAM is associated with a cell.

149. The method of claim 146 wherein the exposure takes place in vivo.

150. The method of claim 146 wherein the exposure takes place in vitro.

151. The method of claim 150 wherein the TICAM is in a soluble form.

152. A colorectal tumorigenic cell population enriched for expression of at least one colorectal associated TICAM.

153. A breast tumorigenic cell population enriched for expression of at least one breast associated TICAM.

154. A NSCLC tumorigenic cell population enriched for expression of at least one NSCLC associated TICAM.

155. An ovarian tumorigenic cell population enriched for expression of at least one ovarian associated TICAM.

156. A pancreatic tumorigenic cell population enriched for expression of at least one pancreatic associated TICAM.

157. A SCLC tumorigenic cell population enriched for expression of at least one SCLC associated TICAM.

158. A melanoma tumorigenic cell population enriched for expression of at least one melanoma associated TICAM

EXAMPLES

The present invention, thus generally described, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Characterization of Tumor Initiating Cell Populations

To characterize the cellular heterogeneity of solid tumors as they exist in cancer patients, elucidate the identity of tumor perpetuating cells (TPC; i.e. cancer stem cells: CSC) using particular phenotypic markers and identify clinically relevant diagnostic biomarkers and therapeutic targets, a large non-traditional xenograft (NTX™) tumor bank was developed and maintained using art recognized techniques. The NTX tumor bank, comprising a large number of discrete primary tumors, was propagated in immunocompromised mice through multiple passages of heterogeneous tumor cells originally obtained from cancer patients suffering from a variety of solid tumor malignancies. The availability of a large number of discrete early passage NTX tumor cell lines having well defined lineages greatly facilitate the identification and isolation of TPC as NTX tumor lines, the cells of which closely reflect the biology of a tumor taken directly from a patient, allow for the reproducible and repeated characterization of tumor cell subpopulations in vivo. More particularly, isolated or purified TPC are most accurately defined retrospectively according to their ability to generate phenotypically and morphologically heterogeneous tumors in mice that recapitulate the patient tumor sample from which the cells originated, while retaining their ability to fuel tumor growth in serial transplants of low cell numbers (i.e. <200 cells). Thus, the ability to use small populations of isolated cells to generate fully heterogeneous tumors in mice through at least two series of transplants is strongly indicative of the fact that the isolated cells comprise TPC. In such work the use of minimally passaged NTX cell lines that are never expanded in vitro (e.g. for the purpose of increasing cell numbers) greatly simplifies in vivo experimentation and provides verifiable results in a physiologically relevant setting. Moreover, early passage NTX tumors also respond to therapeutic agents such as irinotecan (i.e. Camptosar®), which provides clinically relevant insights into underlying mechanisms driving tumor growth, resistance to current therapies and tumor recurrence.

As the NTX tumor lines were established the constituent tumor cell phenotypes were analyzed using flow cytometry to identify discrete markers that might be used to identify, characterize, isolate, purify or enrich tumor initiating cells (TIC) and separate or analyze TPC and tumor progenitor cells within such populations. In this regard the inventors employed a proprietary proteomic based platform (i.e. PhenoPrint™ Array) that provided for the rapid characterization of cellular protein expression and the concomitant identification of potentially useful markers.

The PhenoPrint Array is a proprietary proteomic platform comprising hundreds of discrete binding molecules, many obtained from commercial sources, arrayed in 96 well plates wherein each well contains a distinct binding molecule in the phycoerythrin (PE) fluorescent channel. Other binding molecules in non-PE fluorescent channels are uniformly applied to all cells prior to their distribution into wells of the PhenoPrint Array for the purpose of identifying subpopulations within the tumor cell sample. The use of the PhenoPrint Array allows for the rapid identification of proteins or markers that prospectively distinguished TIC from non-tumorigenic (NTG) bulk tumor cells and tumor stroma (e.g., fibroblasts and endothelial cells). More specifically, proteins exhibiting heterogeneous cell surface expression over whole tumor cell samples allow for the identification, isolation and transplantation of distinct, and highly purified, TIC subpopulations based on differential protein expression. It will be appreciated that characterizing and enriching or isolating cell subpopulations (e.g., by flow cytometry or fluorescence activated cell sorting: FACS) based on marker phenotypes of the instant application allows for their transplant into immunocompromised mice, thereby facilitating the assessment of whether TIC were enriched in one tumor cell subpopulation versus another by functionally testing their tumorigenic capacity in vivo. When the PhenoPrint Array was used in combination with tissue dissociation, transplantation and stem cell techniques well known in the art (Al-Hajj et al., 2004, Dalerba et al., 2007 and Dylla et al., 2008, all supra, each of which is incorporated herein by reference in its entirety), it was possible to effectively identify relevant markers in accordance with the instant invention and subsequently isolate and transplant specific human tumor cell subpopulations with great efficiency.

In the instant case various patient-derived NTX tumor lines comprising human tumors were established in severely immunocompromised mice using art recognized techniques. Upon reaching 800-2,000 mm$^3$, tumors were resected from mice and dissociated into single cell suspensions using art recognized mechanical and enzymatic dissociation techniques involving the use of collagenase, hyaluronidase and DNAseI (see for example U.S.P.N. 2007/0292414 which is incorporated herein). Freshly resected patient tumors were similarly processed and analyzed wherever possible. Using standard flow cytometric techniques, individual tumor cells were characterized on a BD FACSCanto™ II flow cytometer (BD Biosciences) for the expression of hundreds of cell surface proteins. In contrast to most cell surface proteins that were uniformly expressed or absent, selected proteins including CD46, CD324 and those set forth in FIGS. 13-19 were, to a greater or lesser extent, positively and/or heterogeneously expressed on the surface of numerous primary human colorectal ("CR"), pancreatic ("PA"), triple negative breast ("BR"), non-small cell lung cancer ("LU"), breast ("BR"), ovarian ("OV"), small cell lung ("LU") cancer and melanoma ("SK") tumor cells. The heterogeneous expression of two of these markers, CD46 and CD324, are illustrated, respectively, in FIGS. 1A-1D and FIGS. 2A and 2B for several different tumor types. More particularly, FIGS. 1A-1D and FIGS. 2A and 2B depict flow cytometry-based protein expression data for individual tumor cells displayed as histogram plots wherein fluorescence minus one (FMO) staining using isotype control antibodies is shown in the gray, filled histograms and target antigen expression (i.e. CD46 and CD324) as determined using commercially available antigen-specific, PE-conjugated antibodies, is displayed using bold, black lines.

Figure 1C:
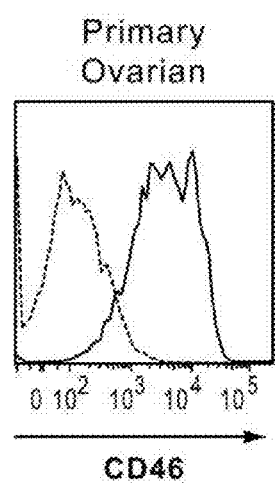
Figure 1D:
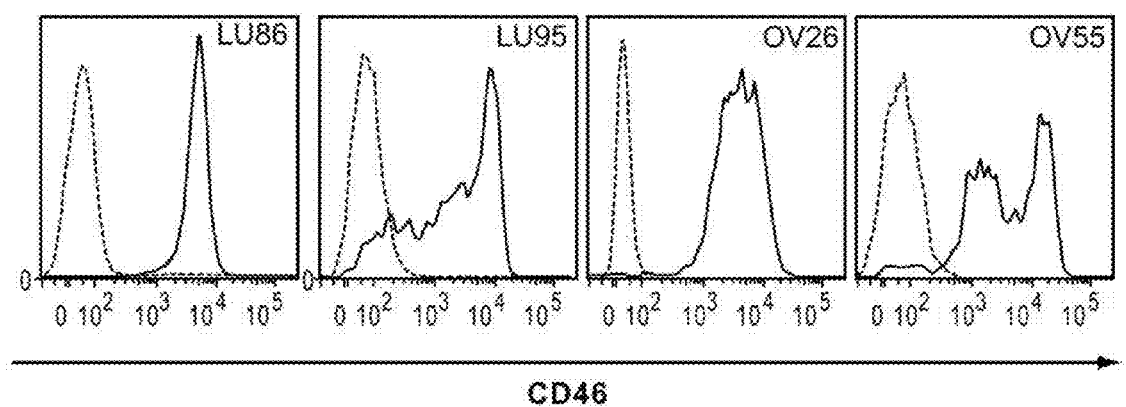

As may be seen in FIGS. 1A-1D and in accordance with the instant invention, CD46 expression was generally observed in subjects presenting with various types of solid tumors. Moreover, although the levels of expression varied it was generally above background staining. A review of the plots using tumor cells from freshly isolated patient tumors (i.e., primary tumors) reveals that CD46 expression was heterogeneous among live ESA$^+$ cells in tumors obtained from colorectal, pancreatic, non-small cell lung and ovarian cancer patients (FIGS. 1A and 1C). Similar heterogeneity was observed in, for example, patient-derived non-traditional xenograft (NTX) tumors established with colorectal, pancreatic, non-small cell lung, triple negative breast small cell lung and ovarian cancer patients (FIGS. 1B and 1D), with subpopulations generally demonstrating negative/lo or positive expression. Specifically, those cells positively expressing CD46 often had staining ranging from low levels to high levels as quantified using isotype control/FMO staining and standard flow cytometric methodology.

Figure 2A:
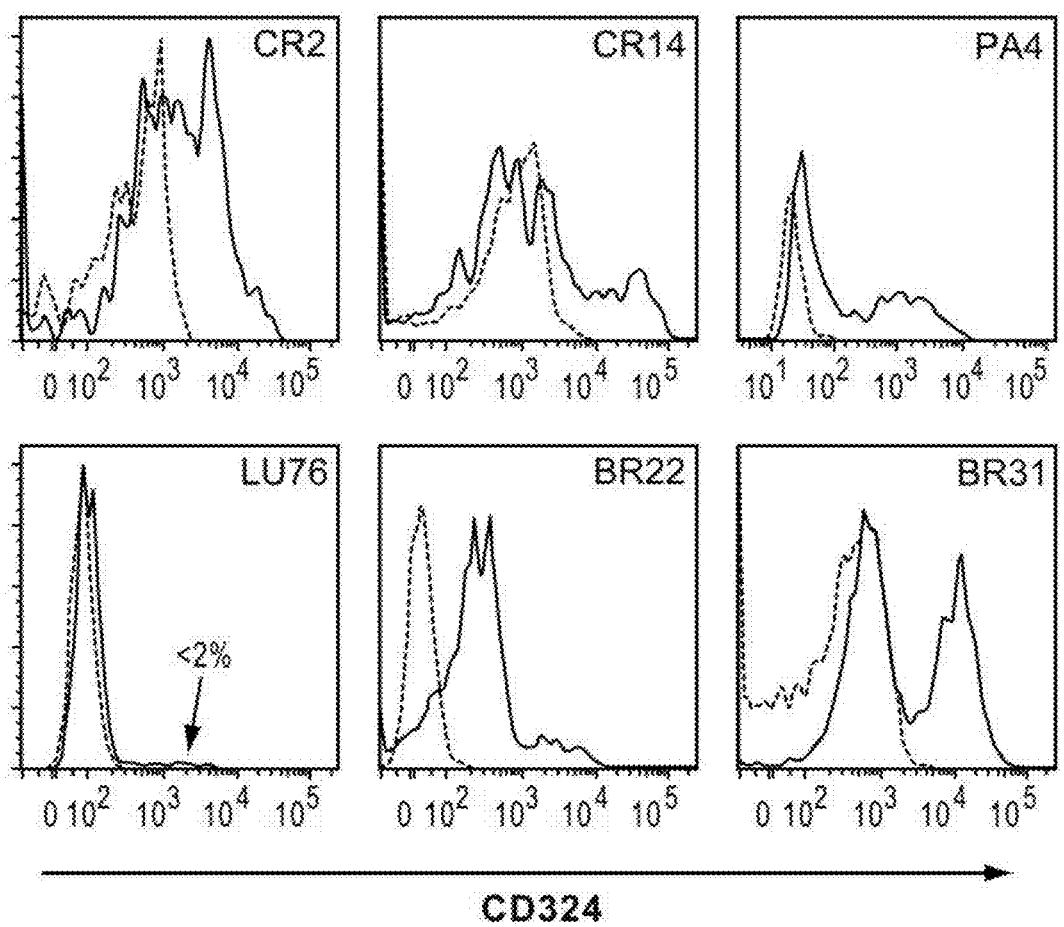
FIGS. 2A and 2B show graphical representations of flow cytometry-based protein expression data for individual tumor cells from various tumors displayed as histogram plots, wherein the background staining of isotype control antibodies is shown in the gray, filled histograms and CD324 expression is displayed by the bold, black line.
Figure 2B:
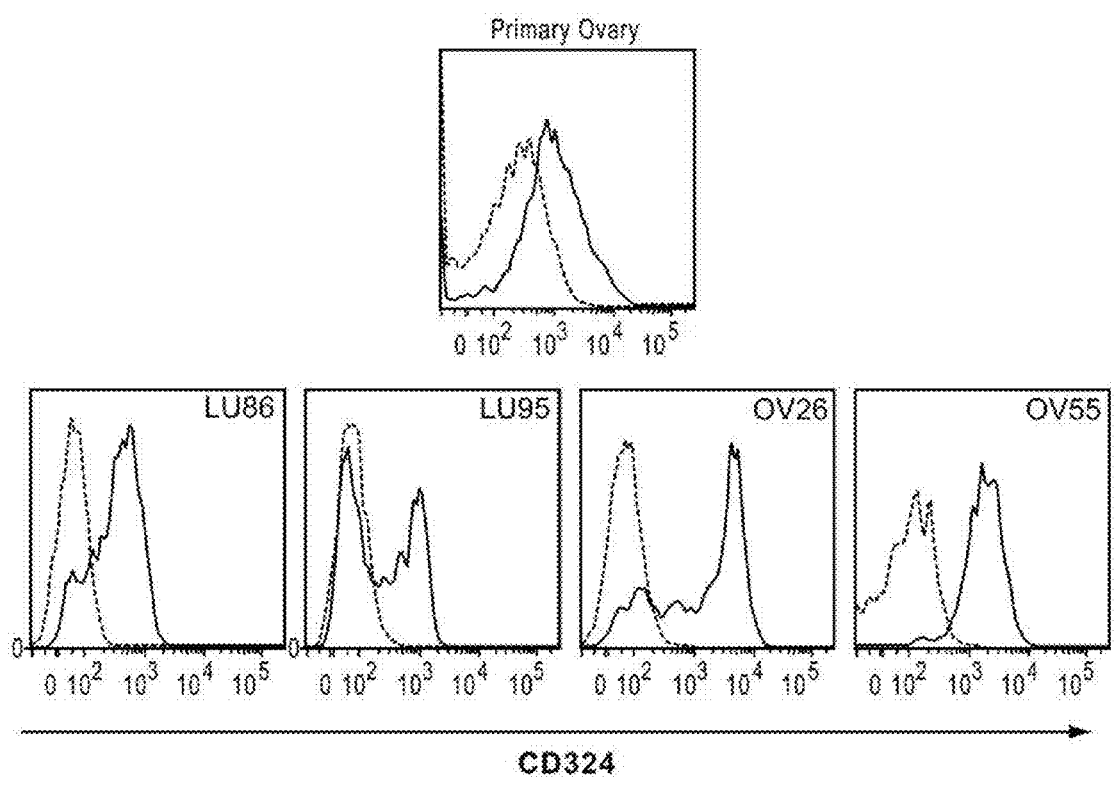

Similar observations were made using CD324 binding agents as seen in FIGS. 2A and 2B, wherein additional tumor cell subpopulations expressing CD324 were often observed to comprise a minority population. That is, those cells positively expressing CD324 generally presented a relatively diffuse or disseminated footprint ranging from low to high levels indicated relatively heterogeneous expression of the TICAM. It should be noted that in FIG. 2A the sample denoted LU76 does exhibit a long shoulder trending toward high levels of expression though it is difficult to discern given the size of the rendering.

Figure 3A:
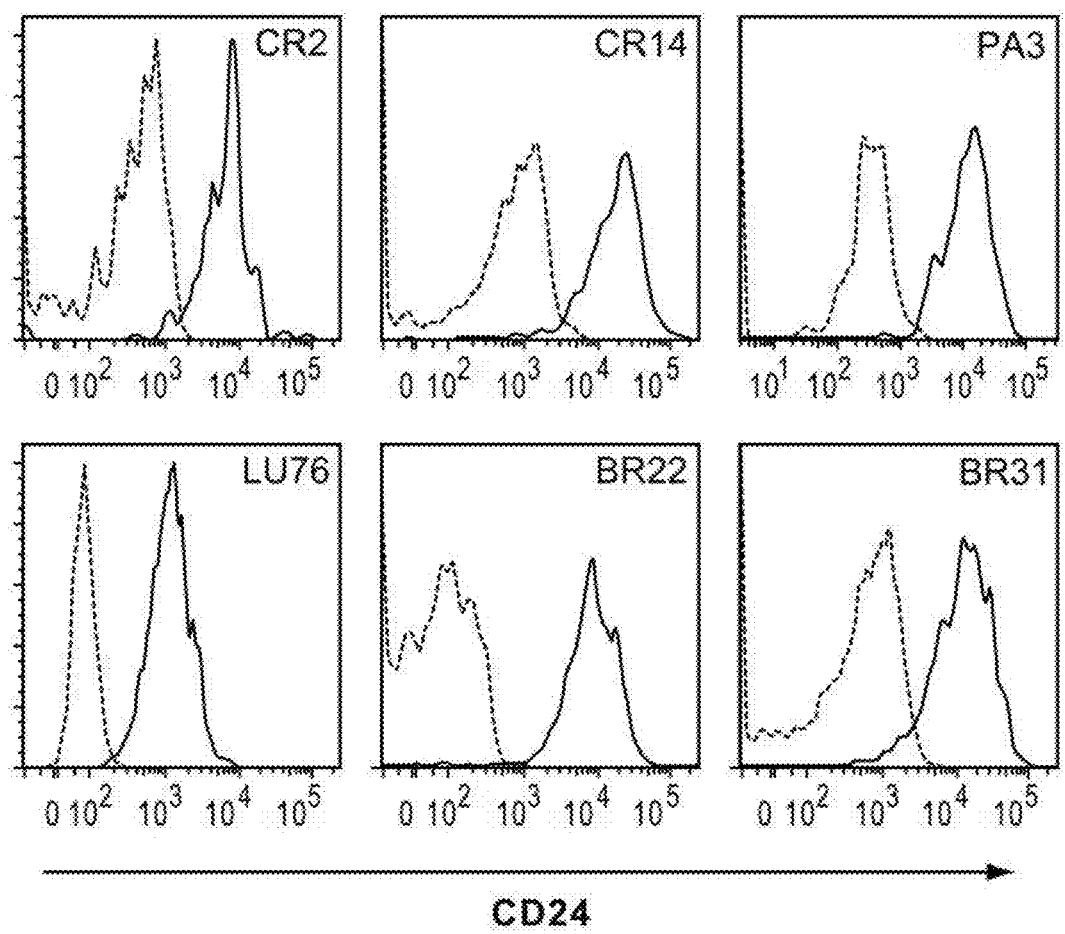
FIGS. 3A-3D depict flow cytometry-based expression data for individual tumor cells displayed as histogram plots, wherein the background staining of isotype control antibodies is shown in the gray, filled histograms and CD24 or CD34 expression are displayed by the bold, black line.
Figure 3B:
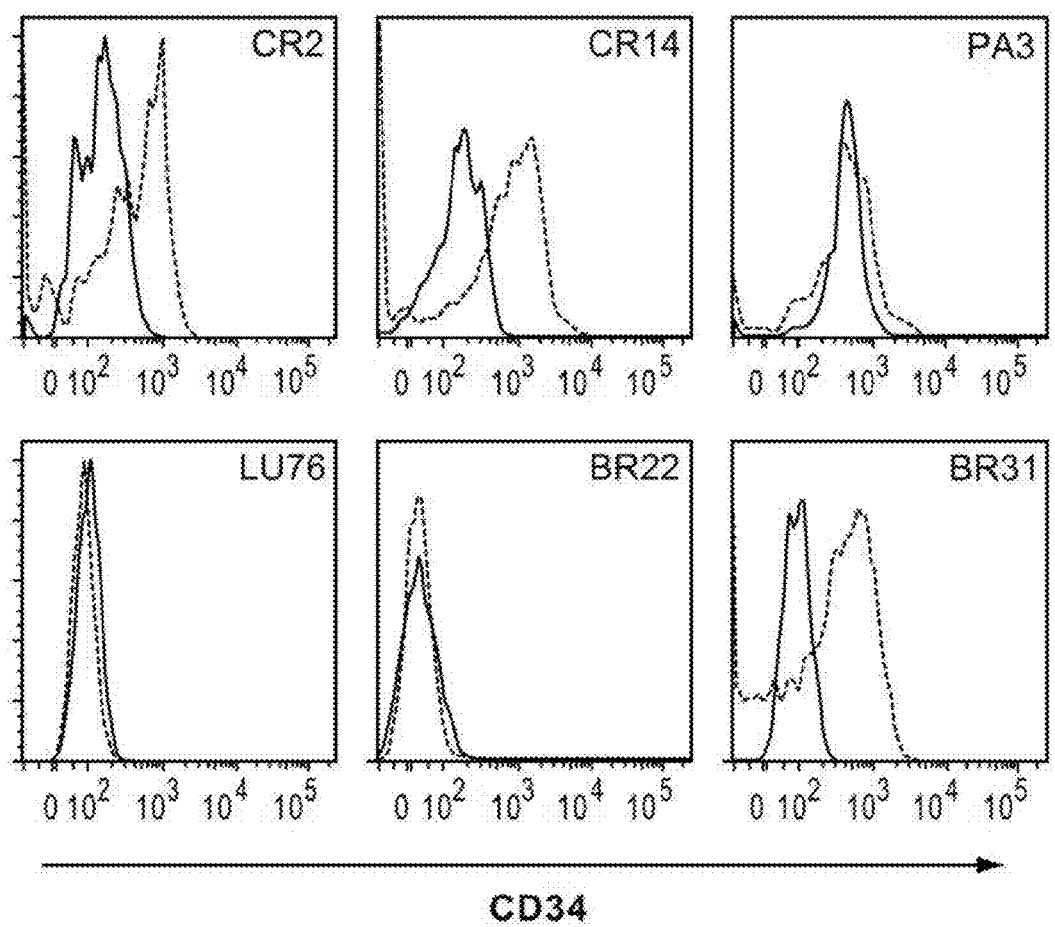
Figure 3C:
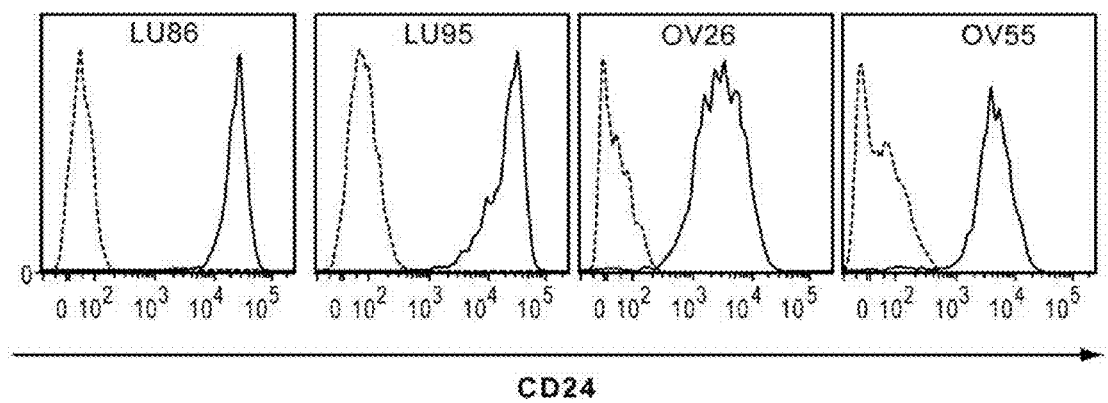
Figure 3D:
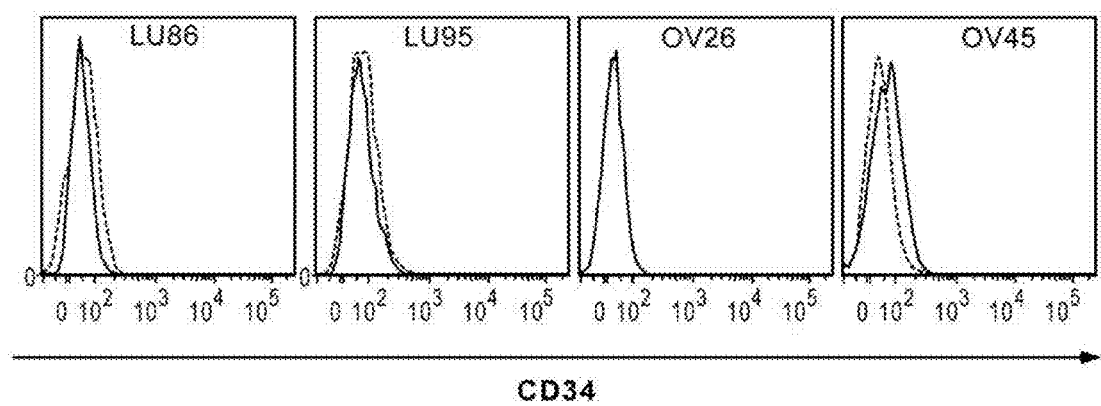
Figure 4A:
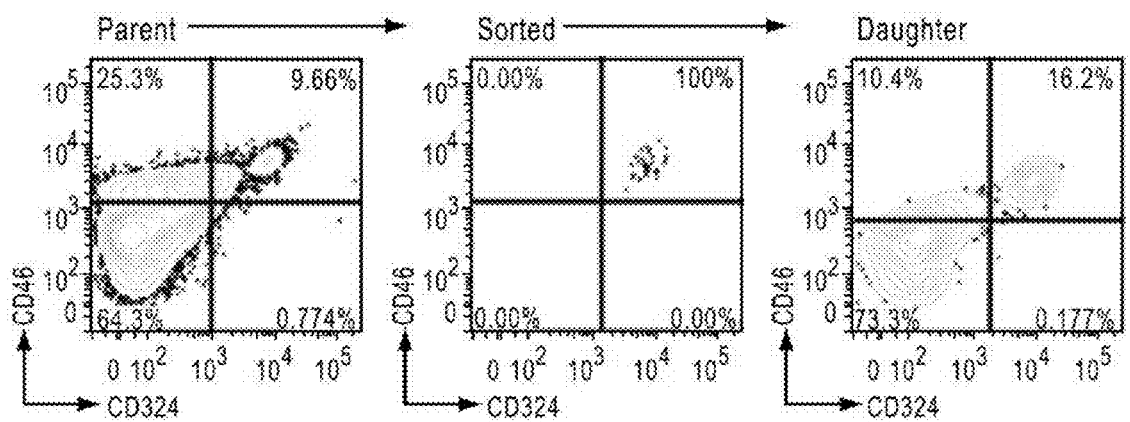
FIGS. 4A and 4B are scatter plots and a graphical representation demonstrating the tumorigenicity of isolated $CD46^{hi}$ $CD324^+$ cell populations from a representative colorectal tumor.
Figure 4B:
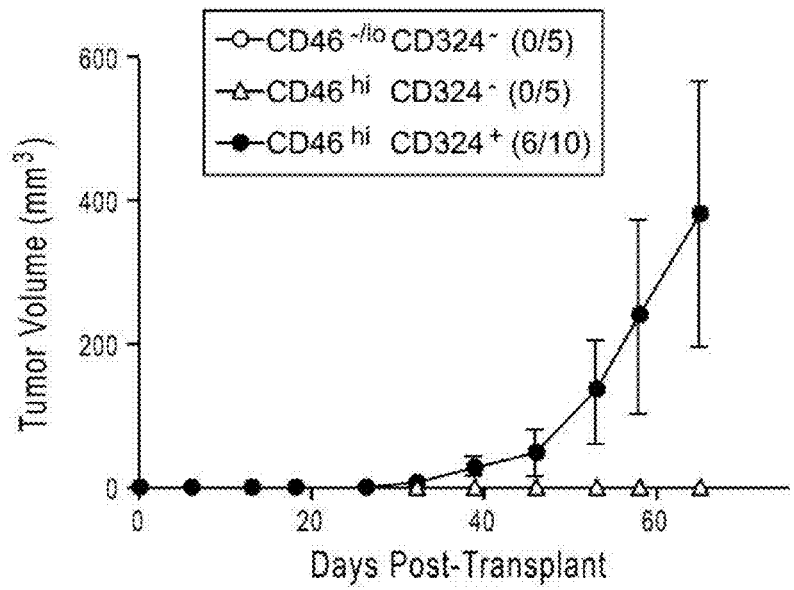
Figure 5A:
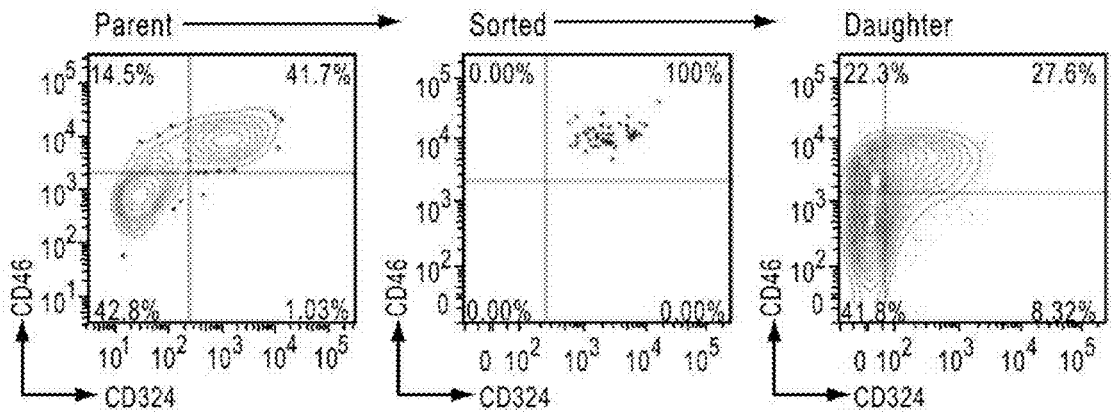
FIGS. 5A and 5B are scatter plots and a graphical representation demonstrating the tumorigenicity of isolated $CD46^{hi}$ $CD324^+$ cell populations from a representative pancreatic tumor.
Figure 5B:
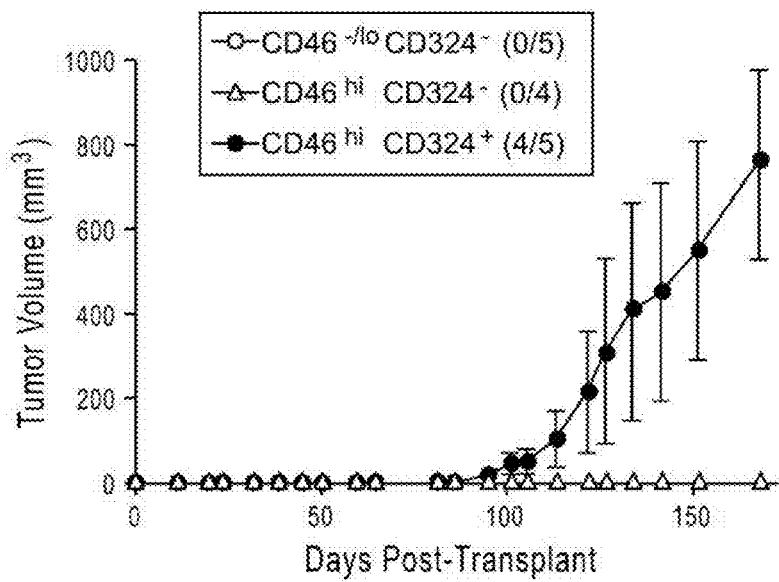
Figure 6A:
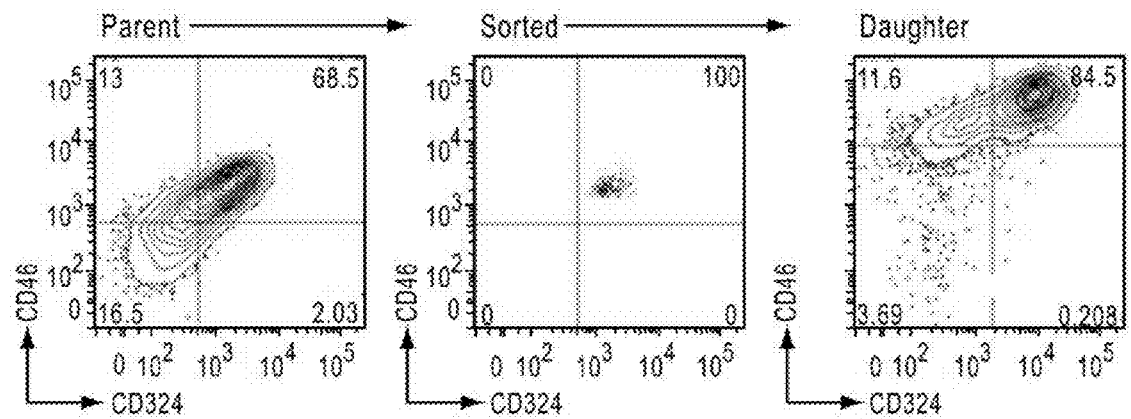
FIGS. 6A and 6B are scatter plots and a graphical representation demonstrating the tumorigenicity of isolated $CD46^{hi}$ $CD324^+$ cell populations from a representative non-small cell lung tumor.
Figure 6B:
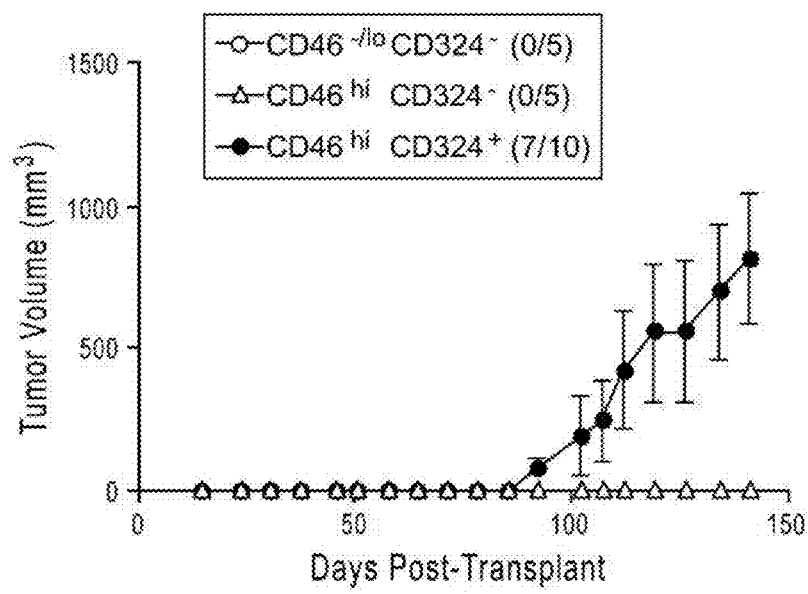
Figure 7A:
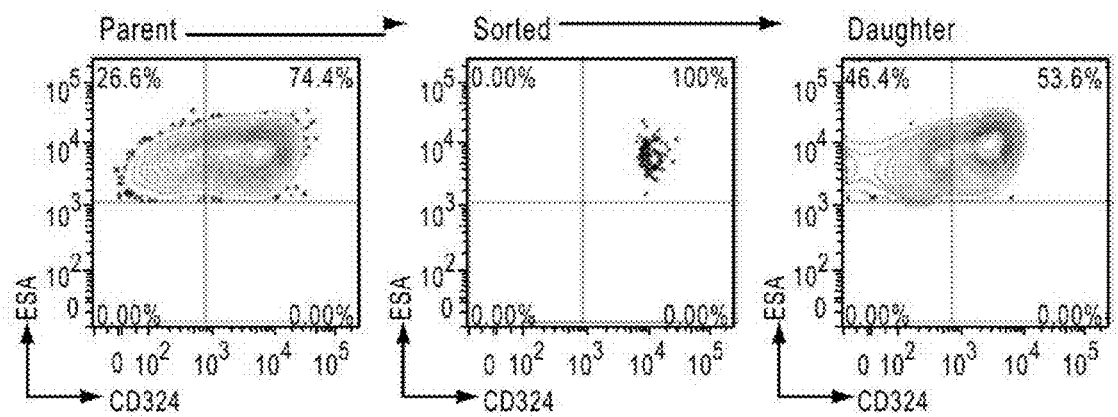
FIGS. 7A and 7B are scatter plots and a graphical representation demonstrating the tumorigenicity of isolated ESA$^+$ (CD46$^{hi}$) CD324$^+$ cell populations from a representative triple negative breast tumor.
Figure 7B:
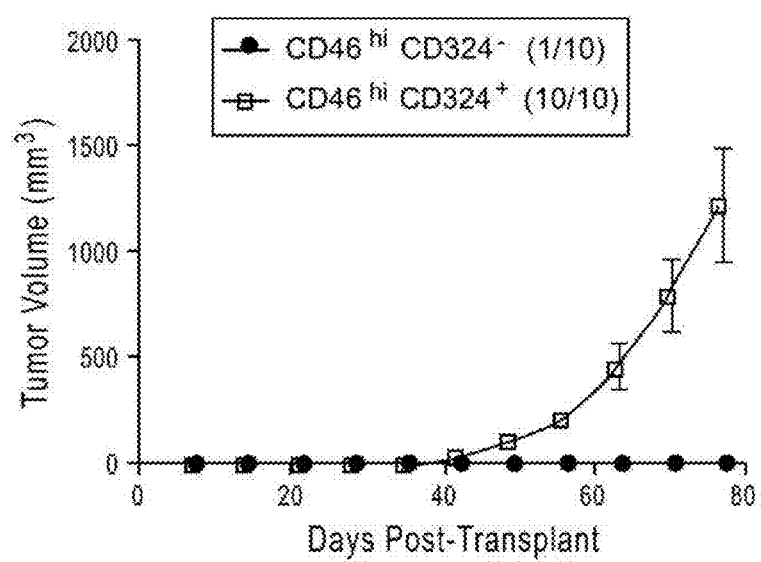
Figure 8A:
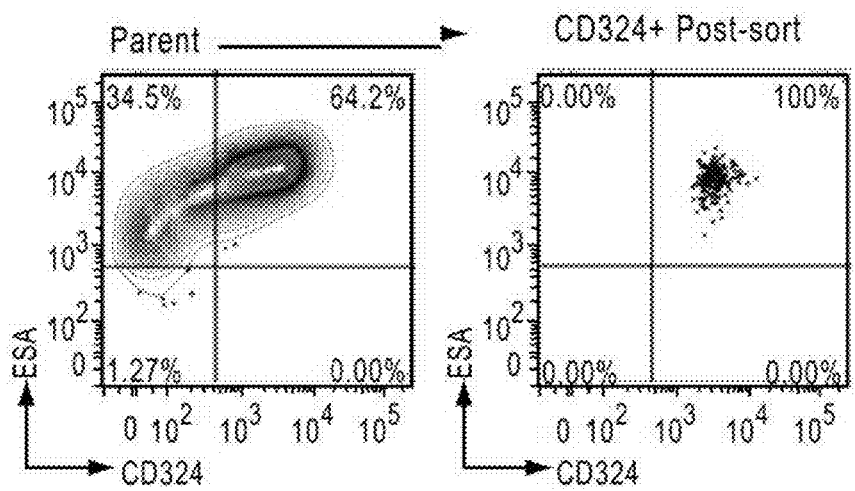
FIGS. 8A and 8B are scatter plots and a graphical representation demonstrating the tumorigenicity of isolated ESA$^+$ (CD46$^{hi}$) CD324$^+$ cell populations from a representative ovarian tumor.
Figure 8B:
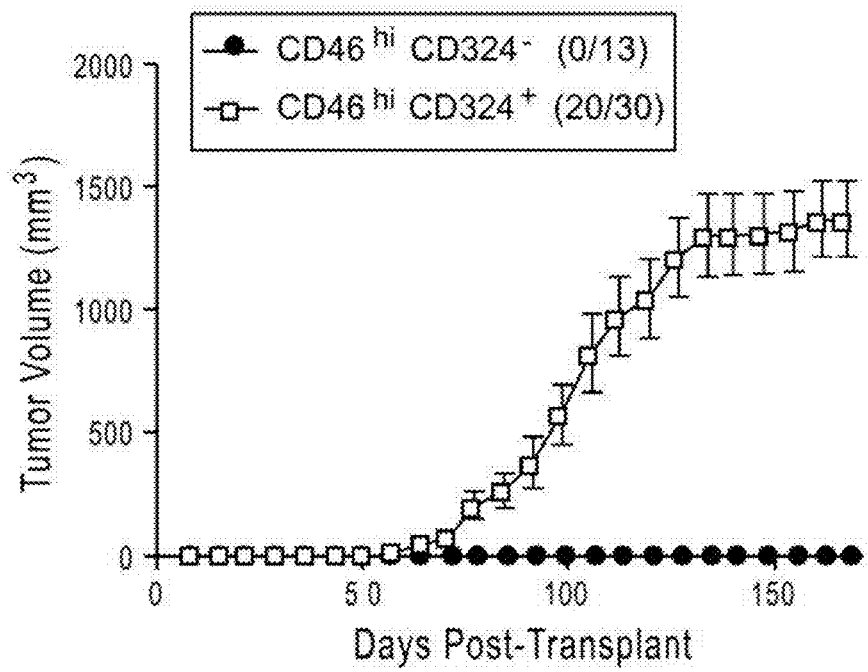
Figure 9A:
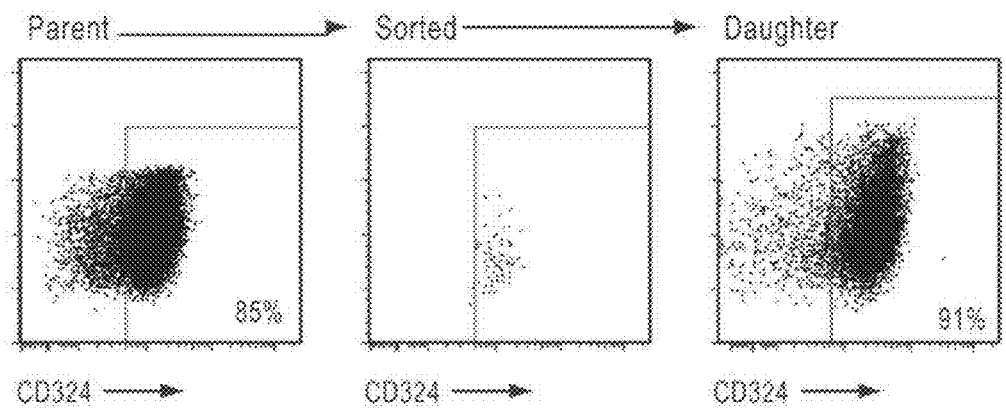
FIGS. 9A and 9B are scatter plots and a graphical representation demonstrating the tumorigenicity of isolated ESA$^+$ (CD46$^{hi}$ CD324$^+$ cell populations from a representative small cell lung tumor.
Figure 9B:
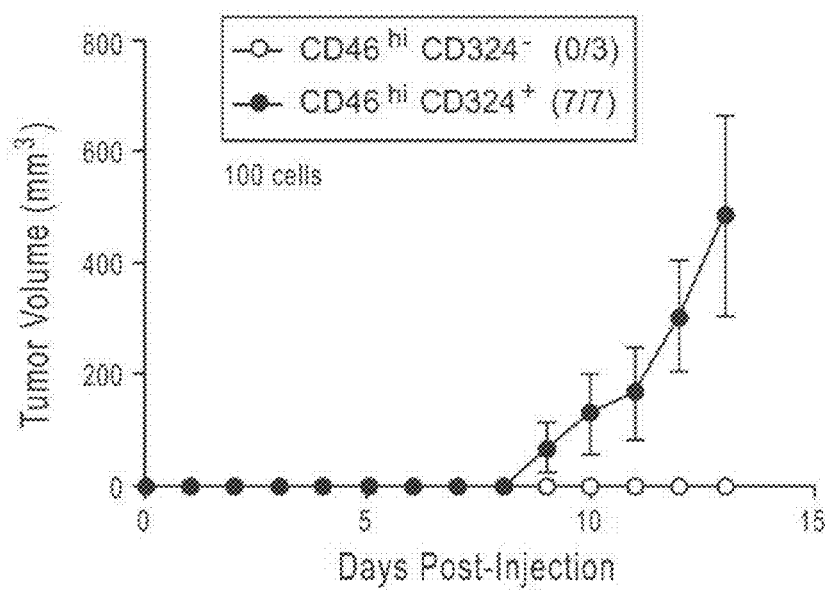
Figure 10A:
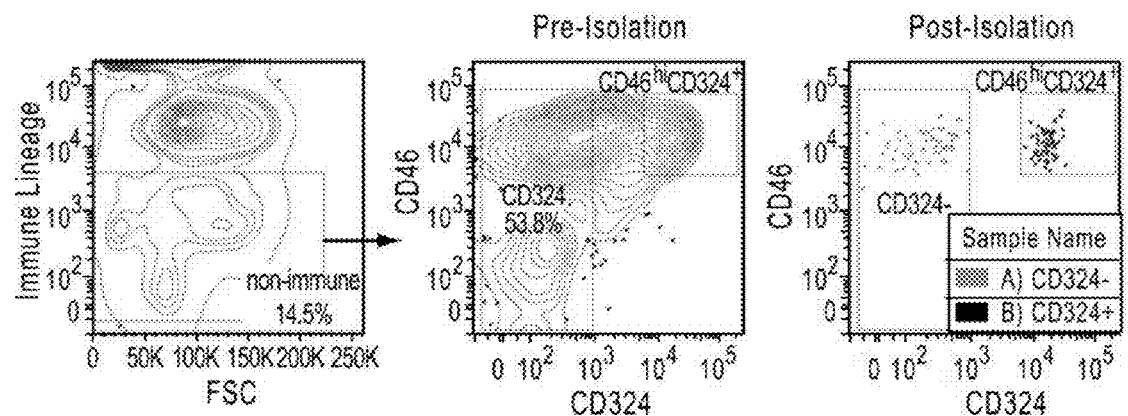
FIGS. 10A and 10B are scatter plots and a graphical representation demonstrating the tumorigenicity of isolated ESA$^+$ CD46$^{hi}$ CD324$^+$ cell populations from a representative melanoma tumor obtained directly from a patient undergoing tumor resection surgery.
Figure 10B:
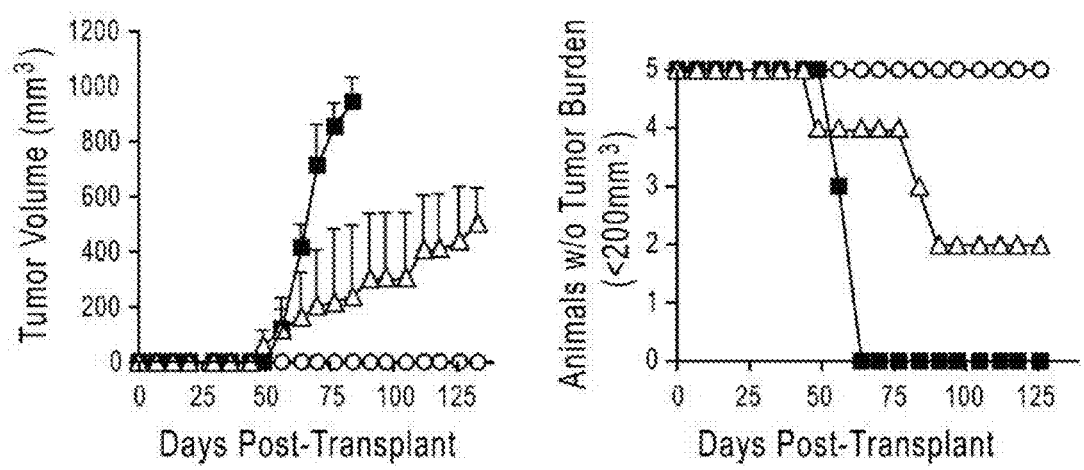
Figure 13:
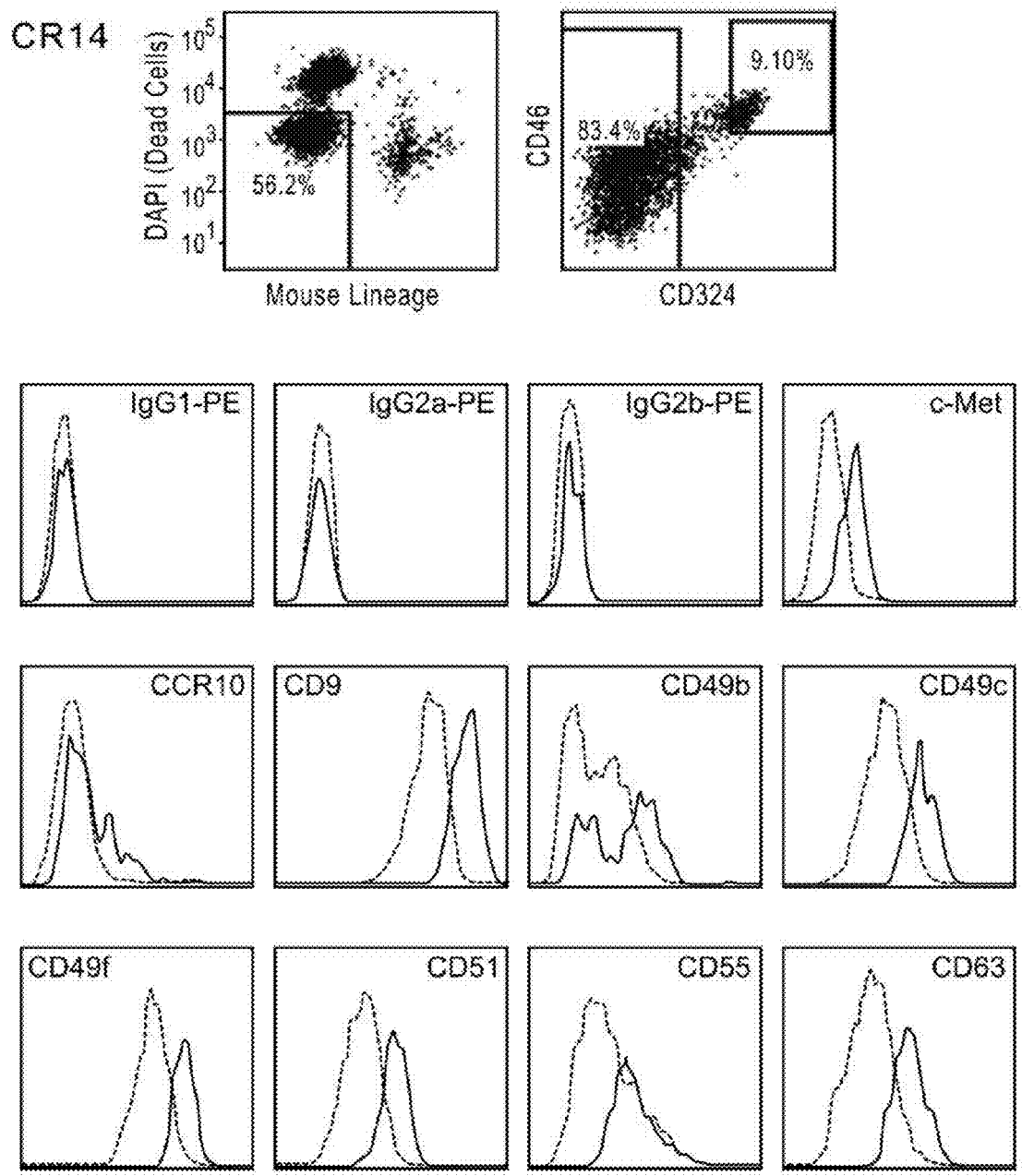
FIG. 13 provides graphical representations of flow cytometry-based protein expression data for individual colorectal tumor cells displayed as scatter plots (above) or histogram plots (below), wherein in the histogram plots show the denoted cell surface antigen expression on either the CD324$^-$ tumor cell subpopulation in gray, filled histograms or the CD46$^{hi}$ CD324$^+$ tumor initiating cell (TIC) subpopulation displayed by the bold, black line.
Figure 13:
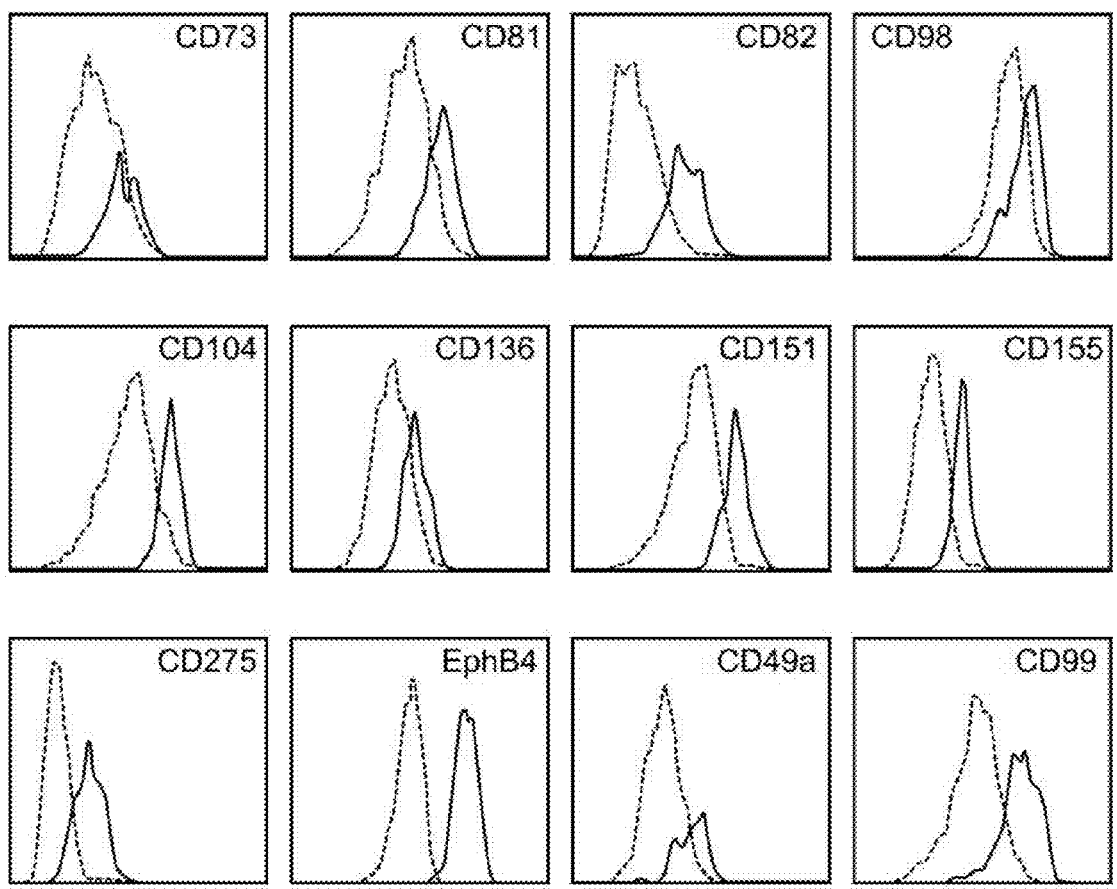
Figure 14:
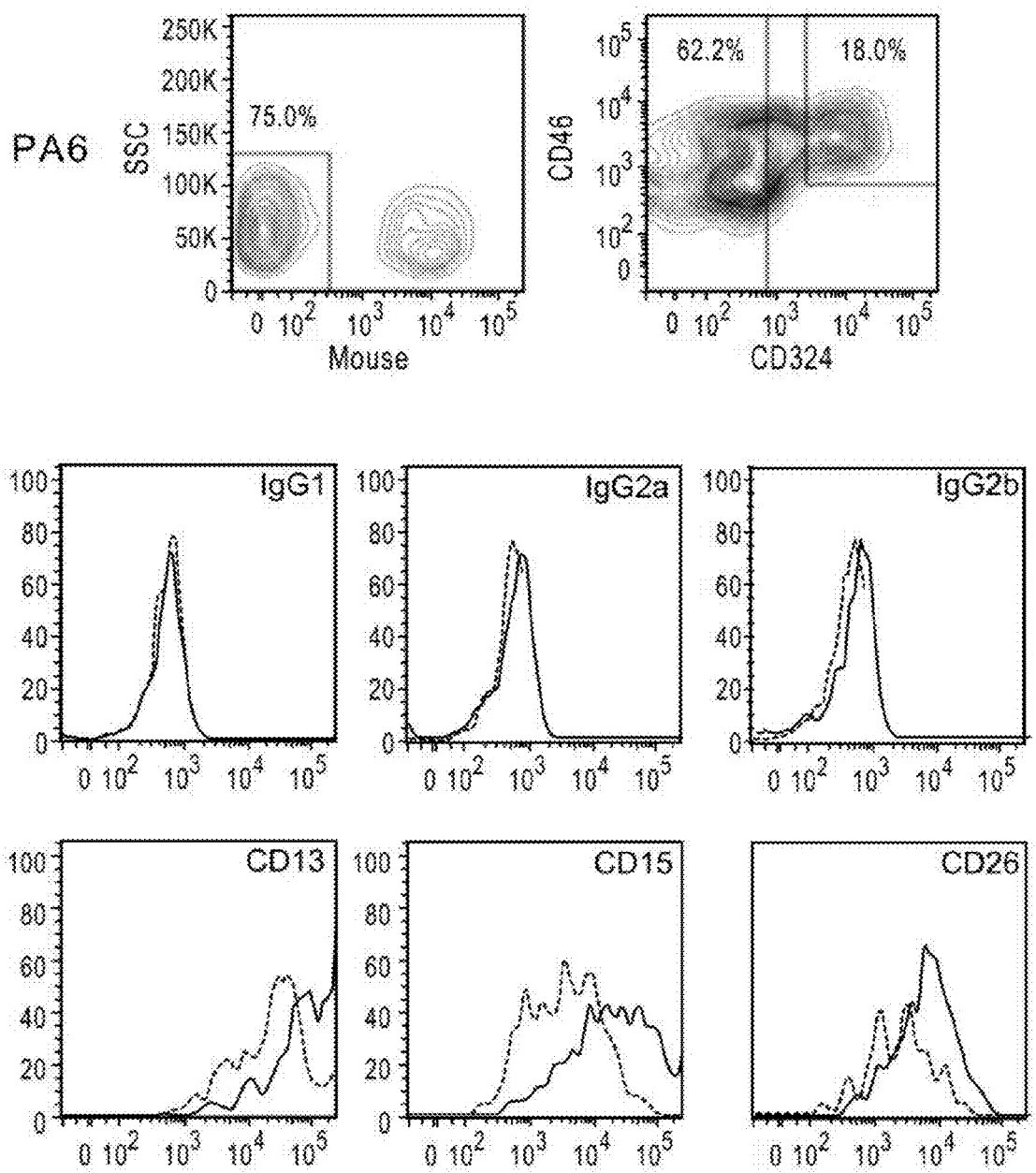
FIG. 14 graphically depicts flow cytometry-based protein expression data for individual pancreatic tumor cells displayed as contour plots (above) or histogram plots (below), wherein in the histogram plots show the denoted cell surface antigen expression on either the CD324$^-$ tumor cell subpopulation in gray, filled histograms or the CD46$^{hi}$ CD324$^+$ tumor initiating cell (TIC) subpopulation displayed by the bold, black line.
Figure 14:
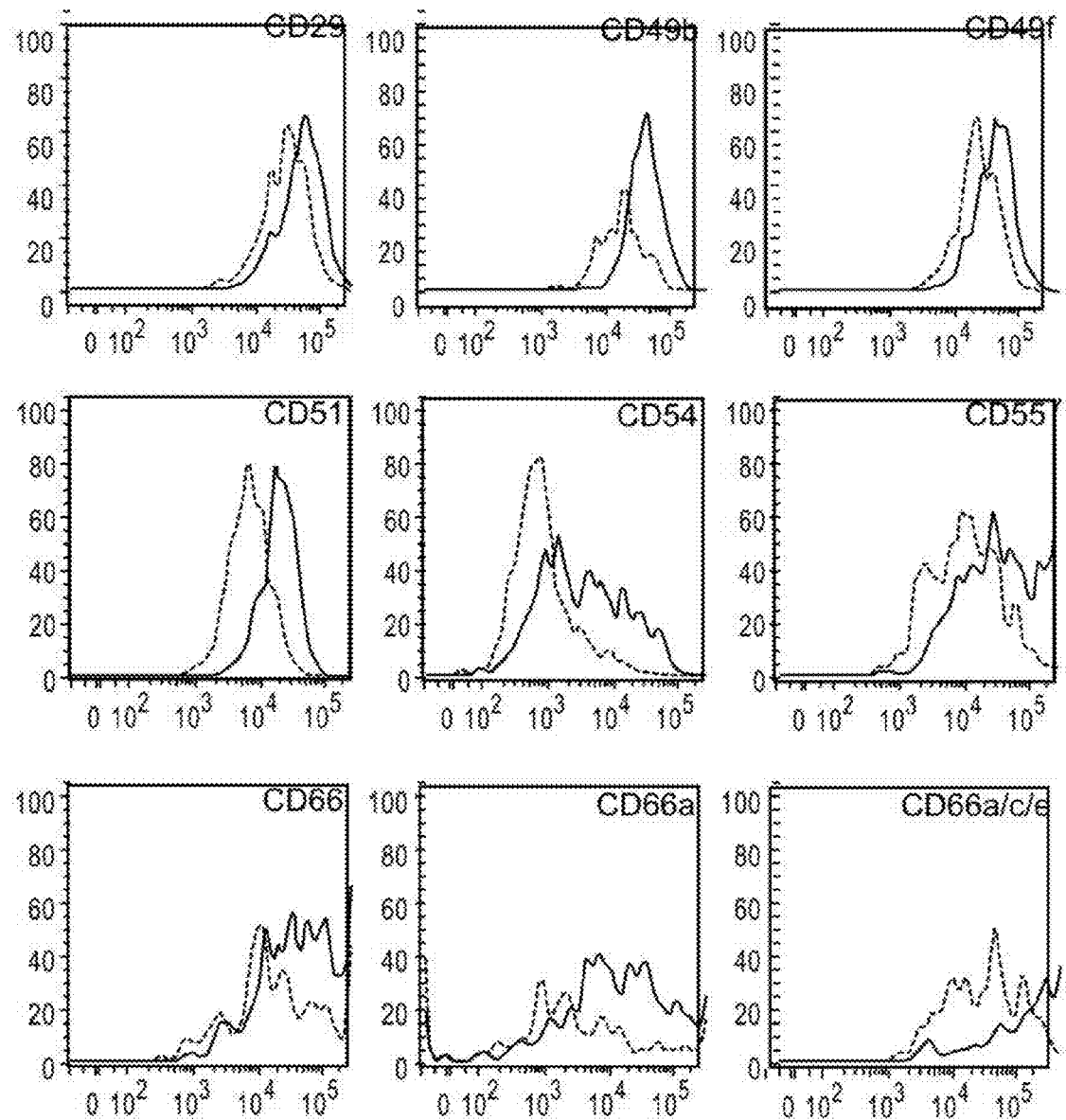
Figure 14:
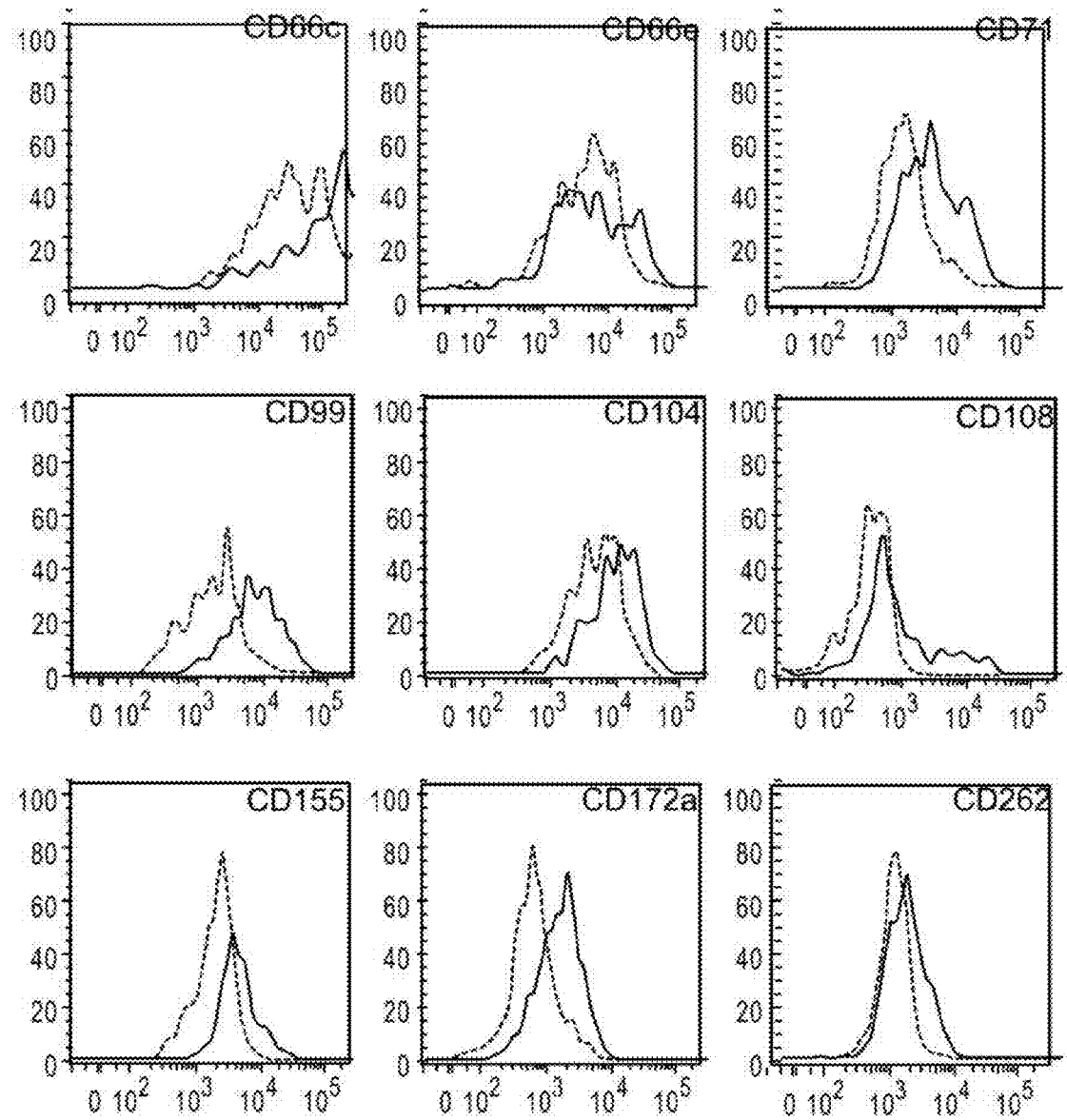
Figure 14:
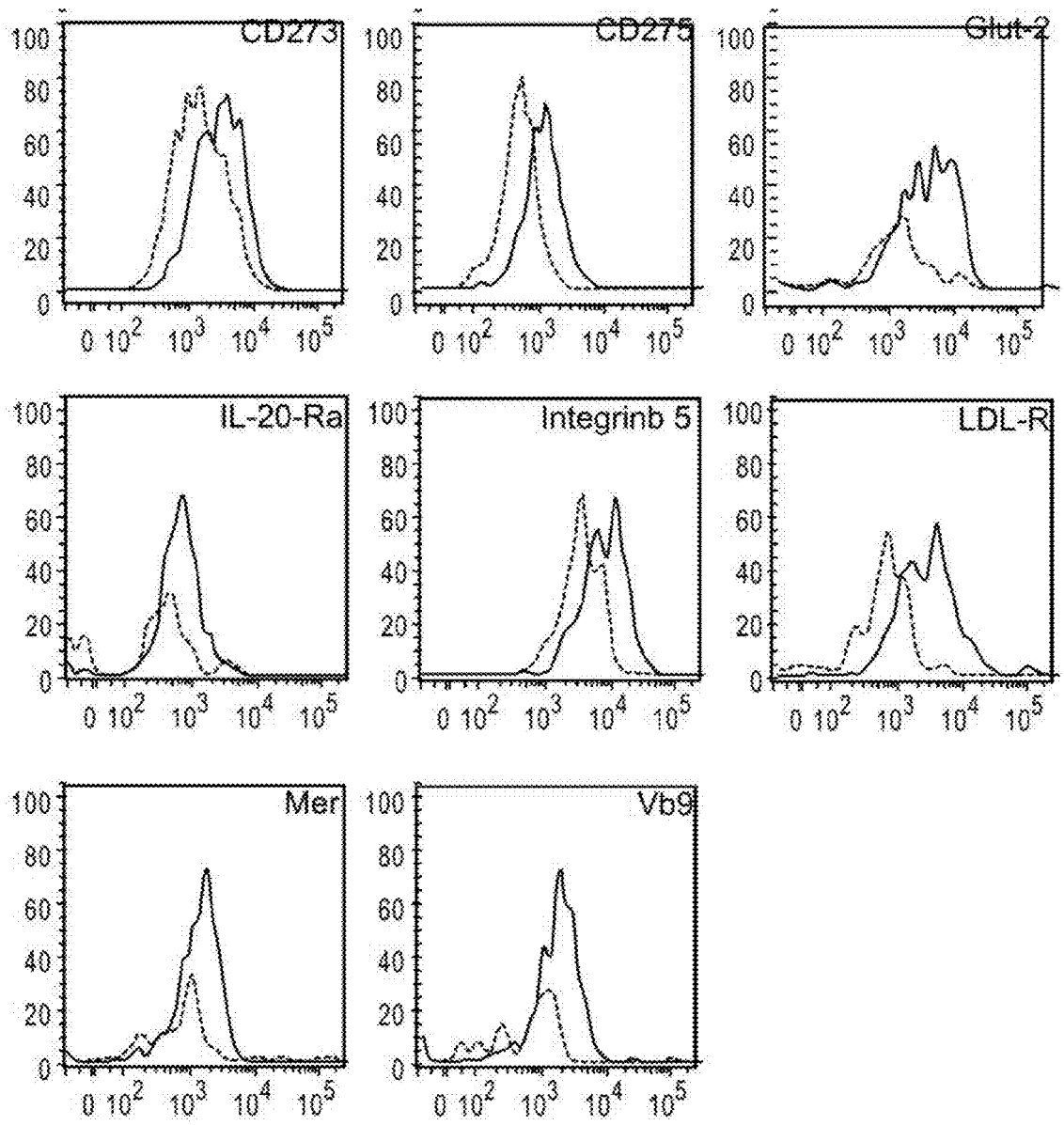
Figure 15:
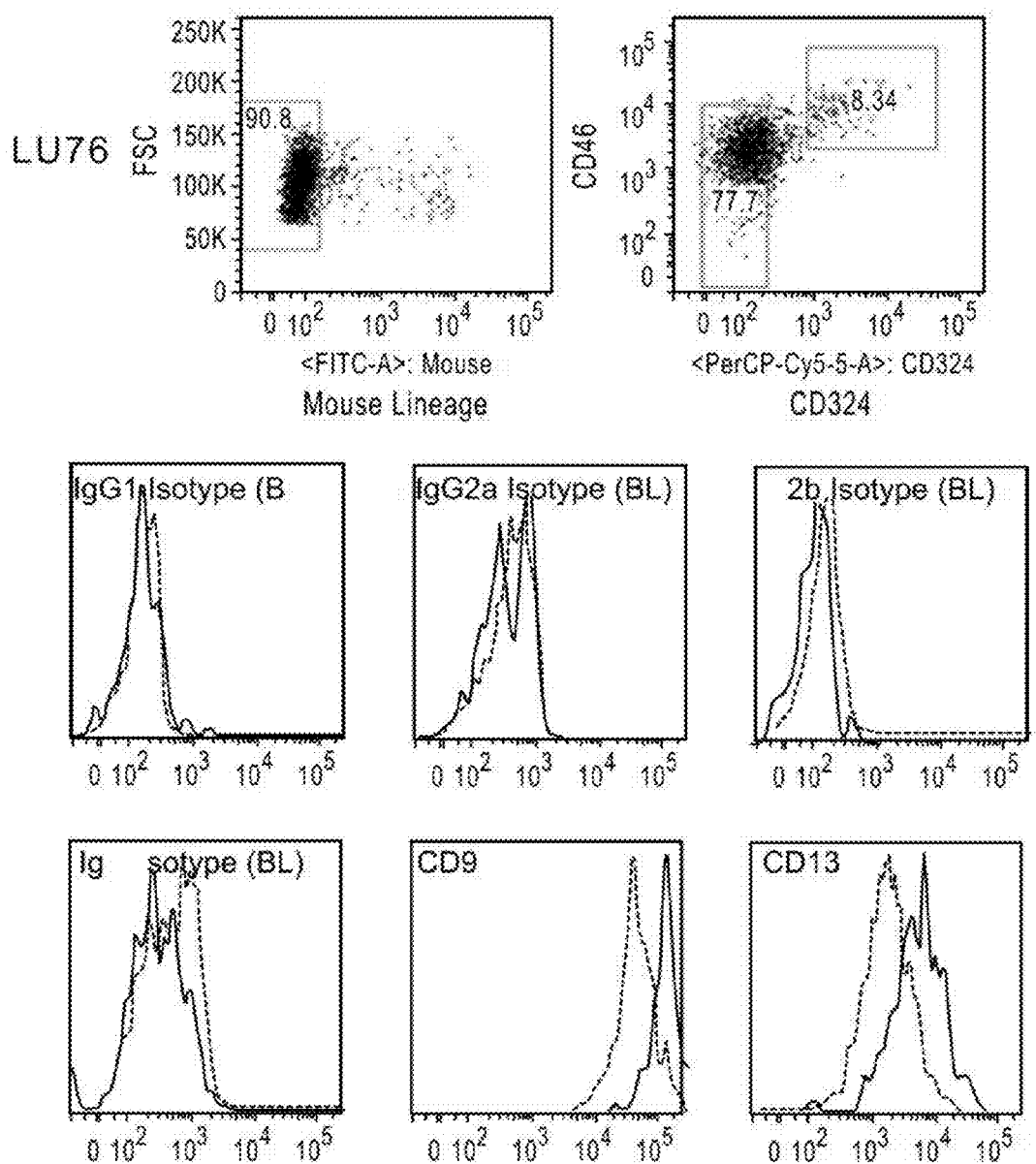
FIG. 15 shows graphical representations of flow cytometry-based protein expression data for individual non-small cell lung tumor cells displayed as scatter plots (above) or histogram plots (below), wherein in the histogram plots show the denoted cell surface antigen expression on either the CD324$^-$ tumor cell subpopulation in gray, filled histograms or the CD46$^{hi}$ CD324$^+$ tumor initiating cell (TIC) subpopulation displayed by the bold, black line.
Figure 15:
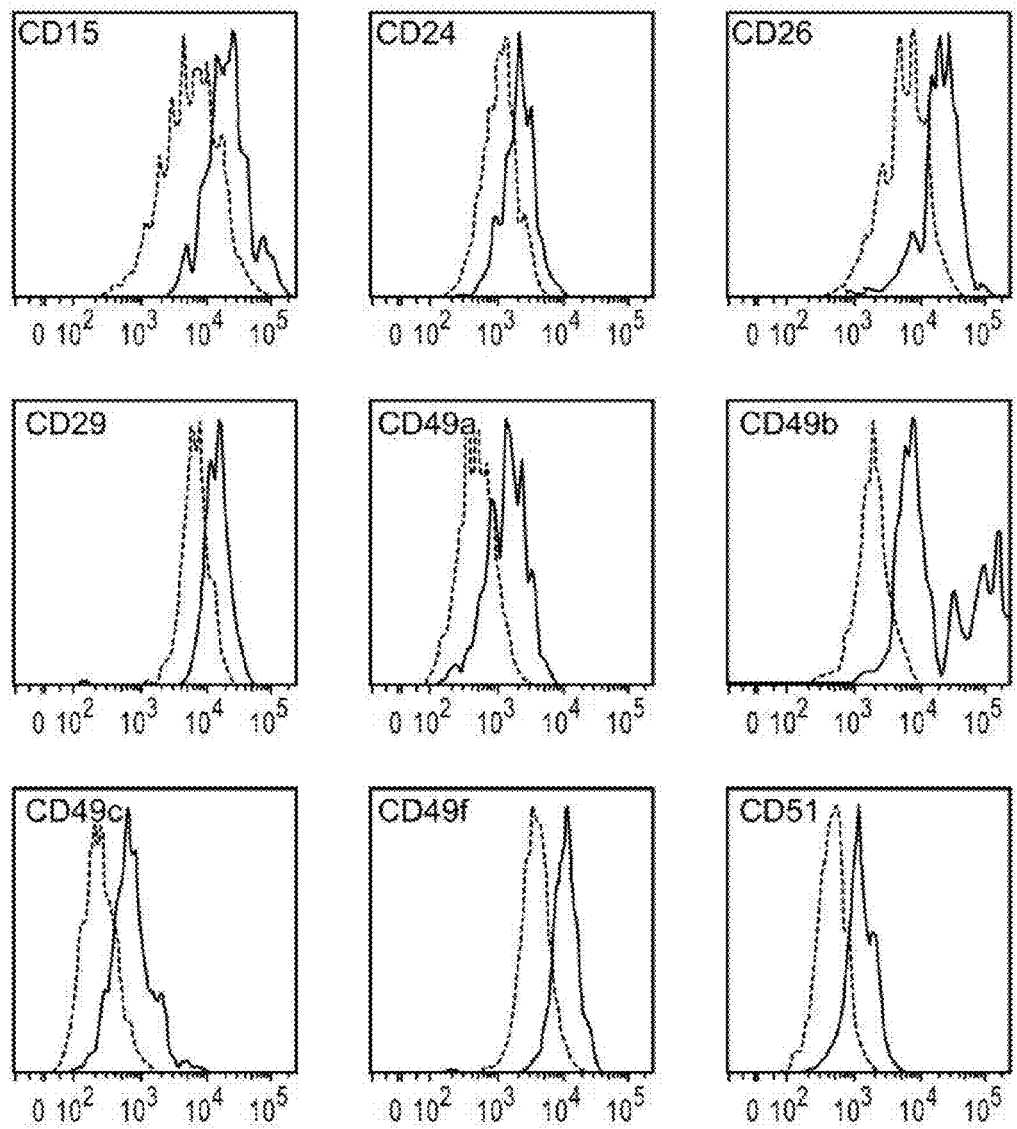
Figure 15:
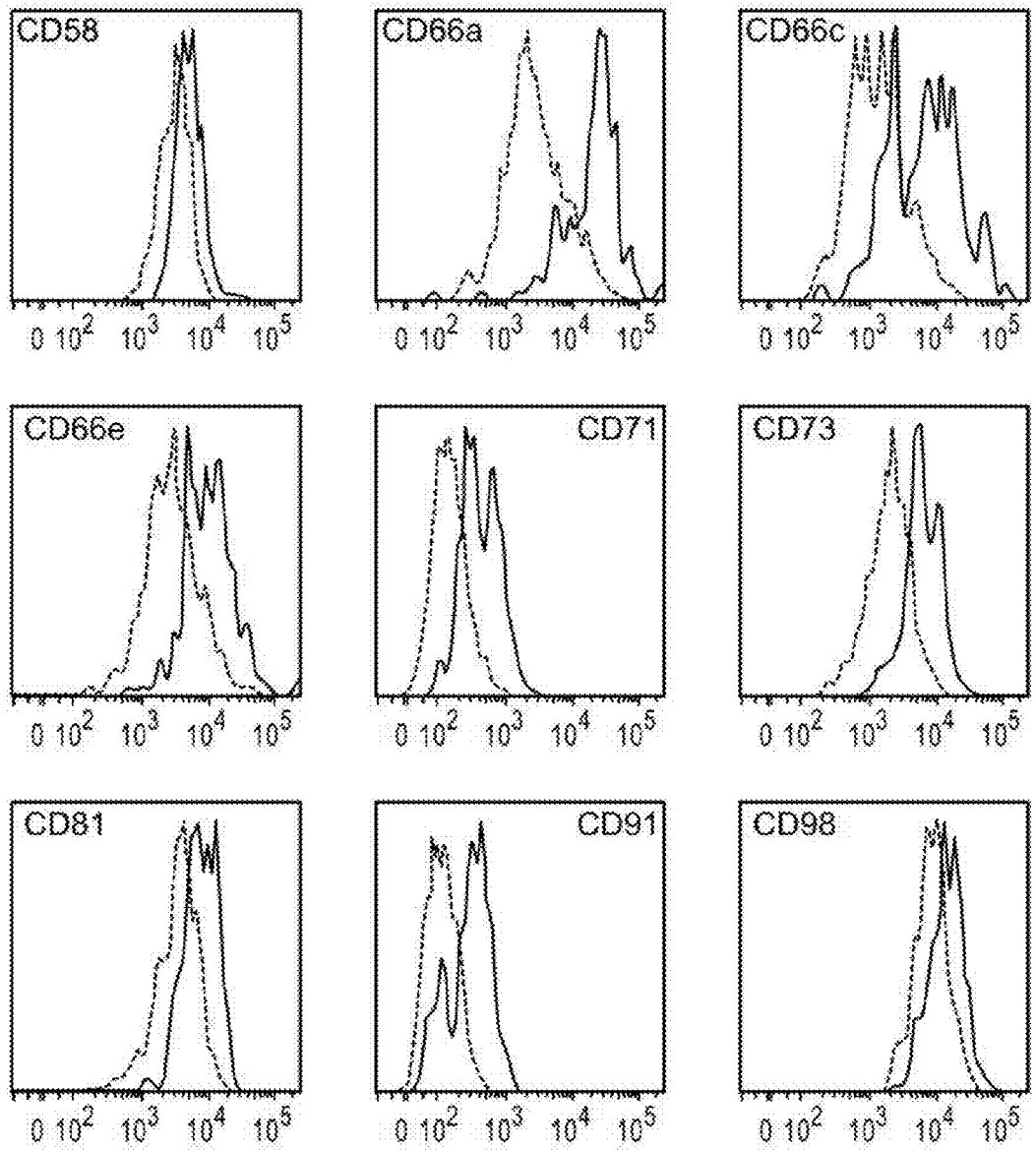
Figure 15:
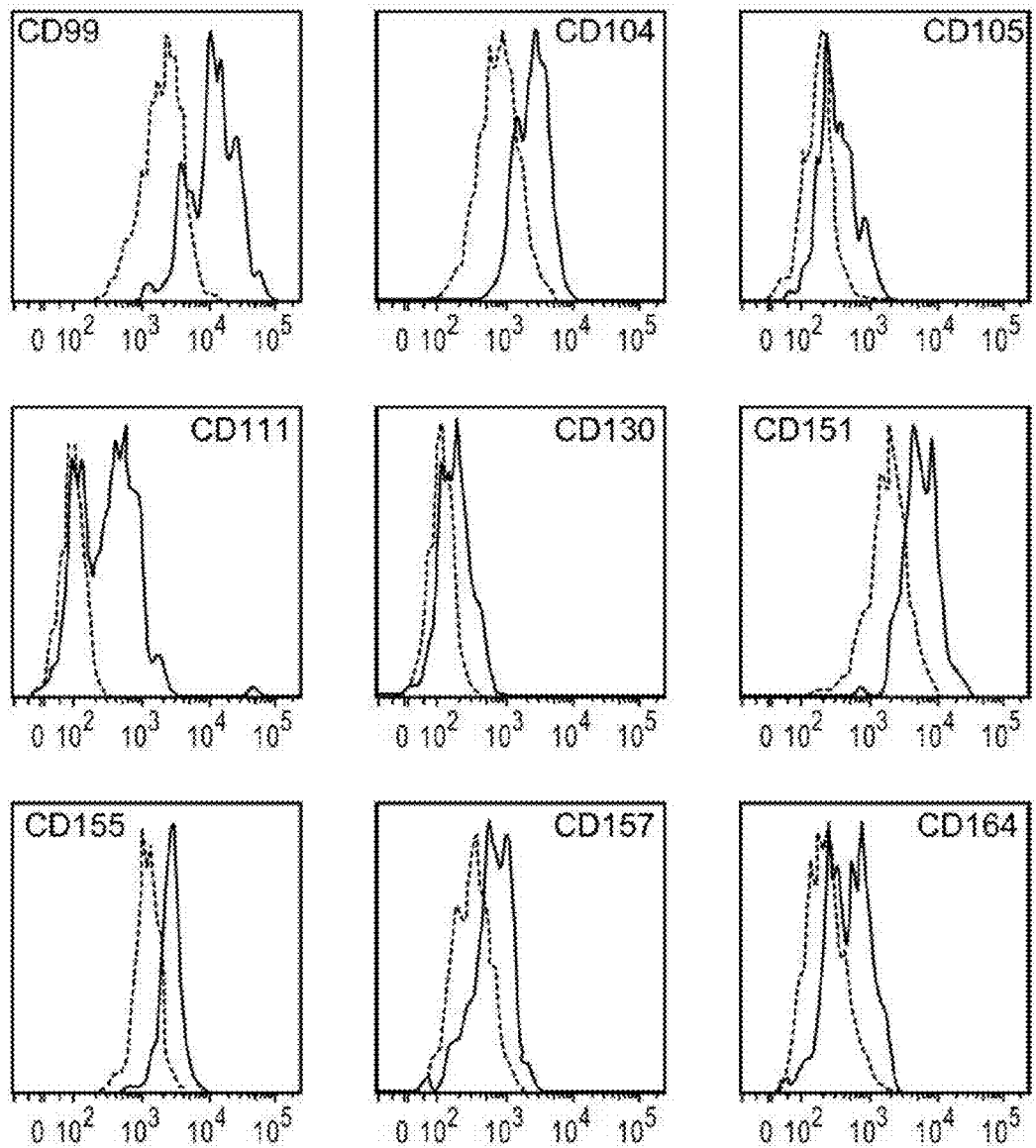
Figure 15:
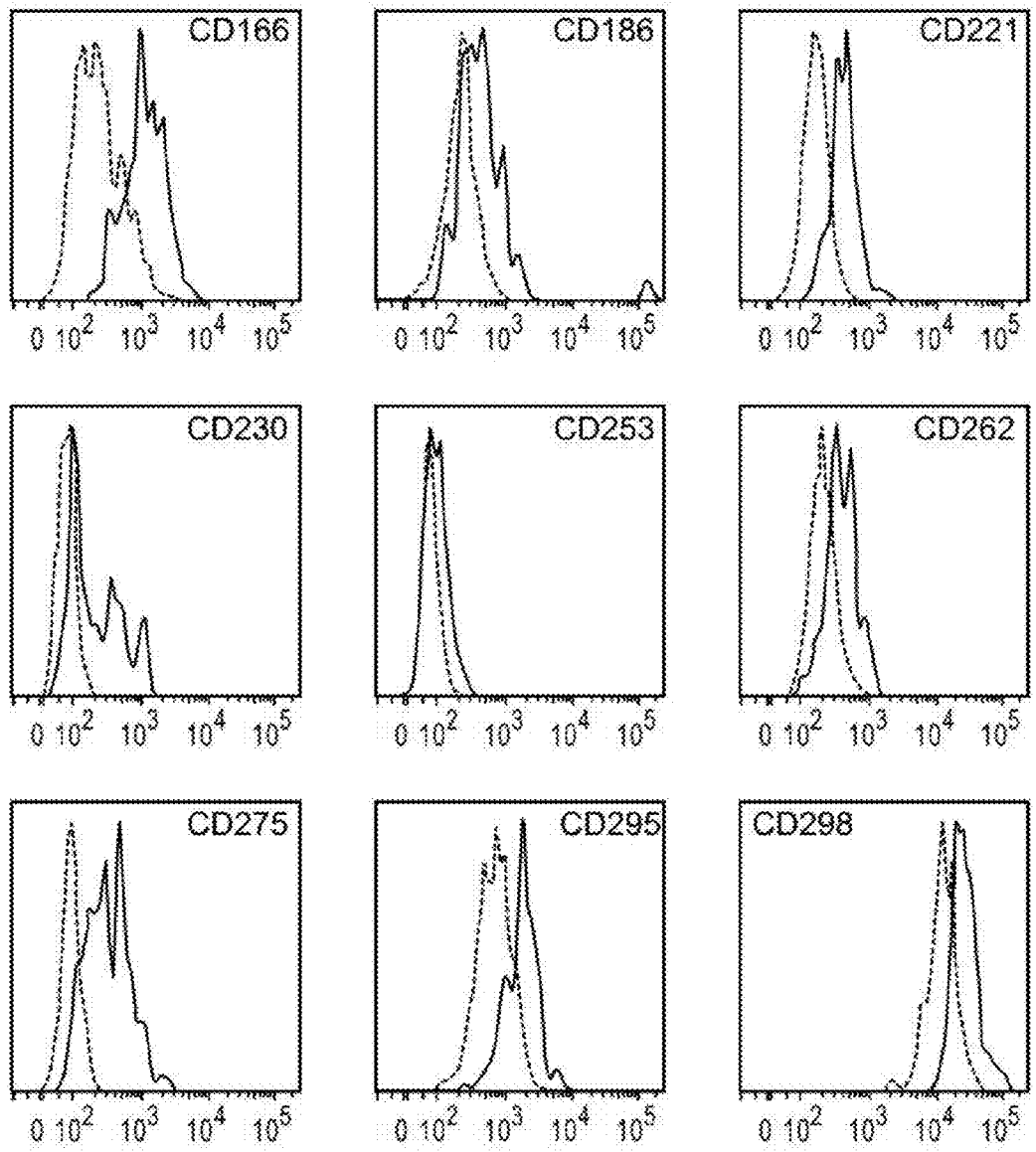
Figure 15:
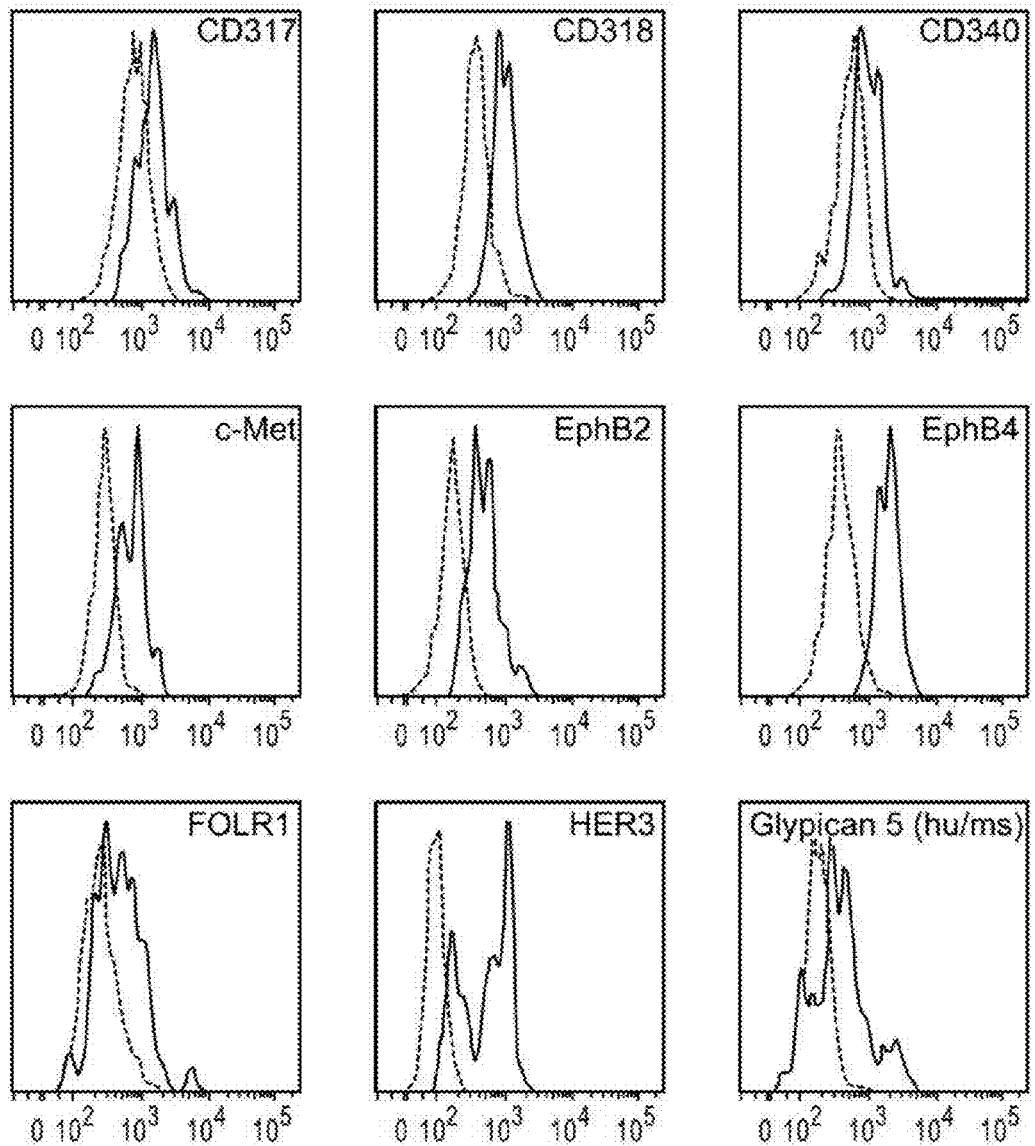
Figure 15:
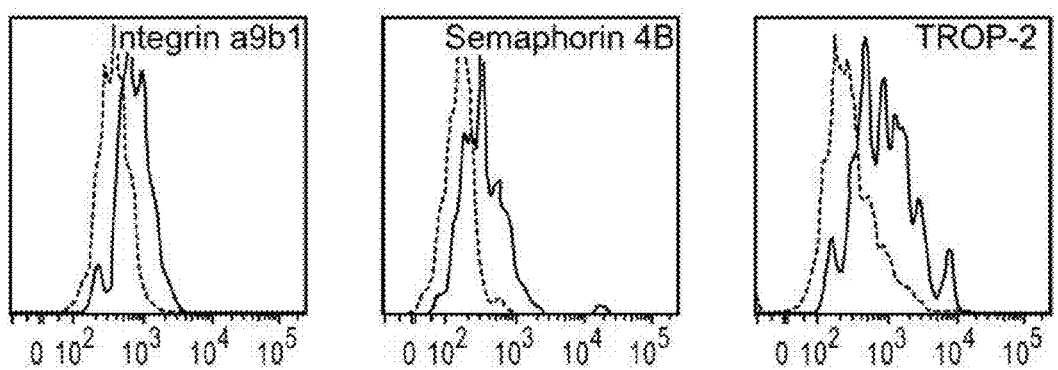
Figure 16:
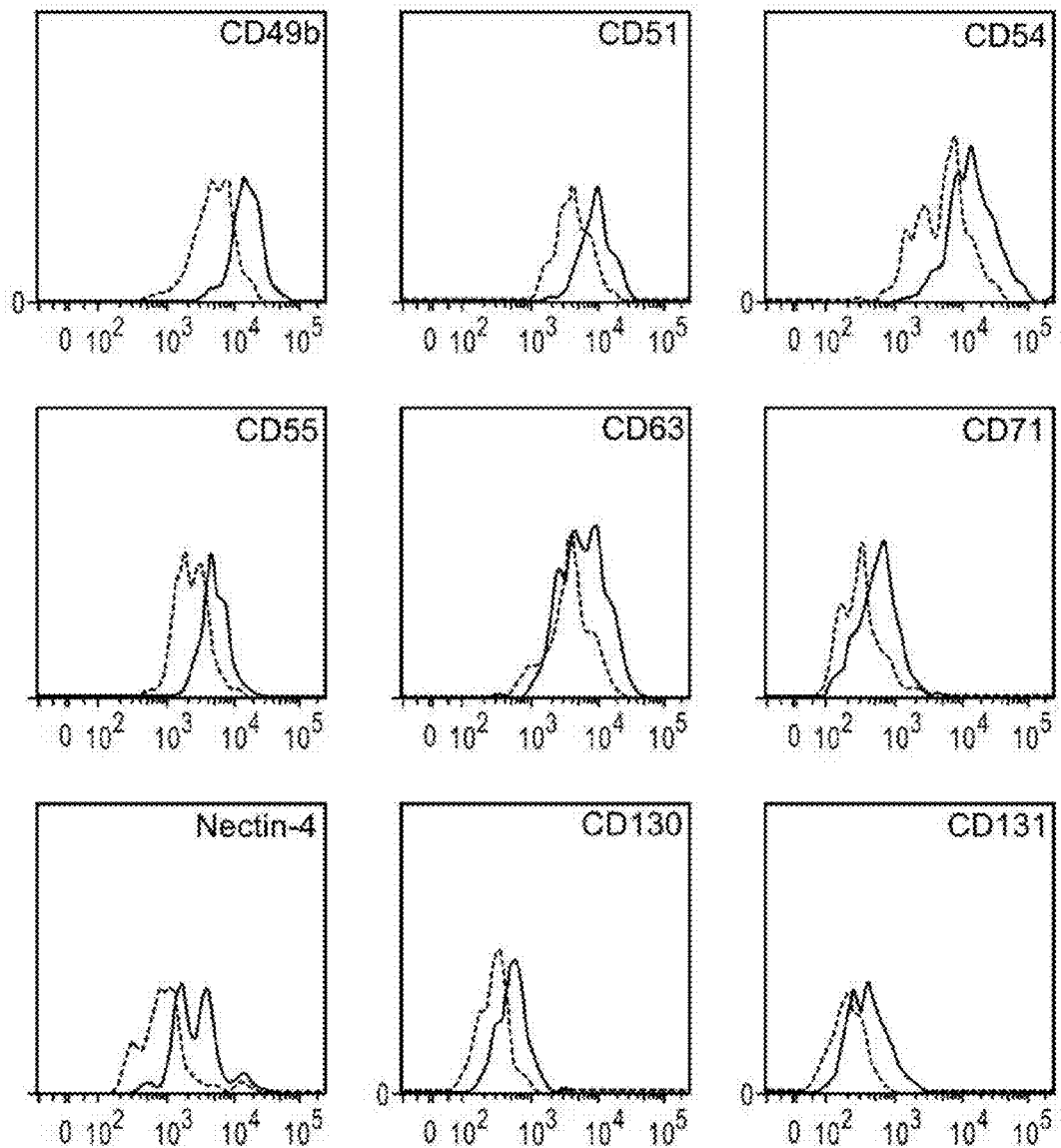
FIG. 16 provides graphical representations of flow cytometry-based protein expression data for individual triple-negative breast tumor cells displayed as histogram plots, which show the denoted cell surface antigen expression on either the CD324$^-$ tumor cell subpopulation in gray, filled histograms or the CD46$^{hi}$ CD324$^+$ tumor initiating cell (TIC) subpopulation displayed by the bold, black line.
Figure 16:
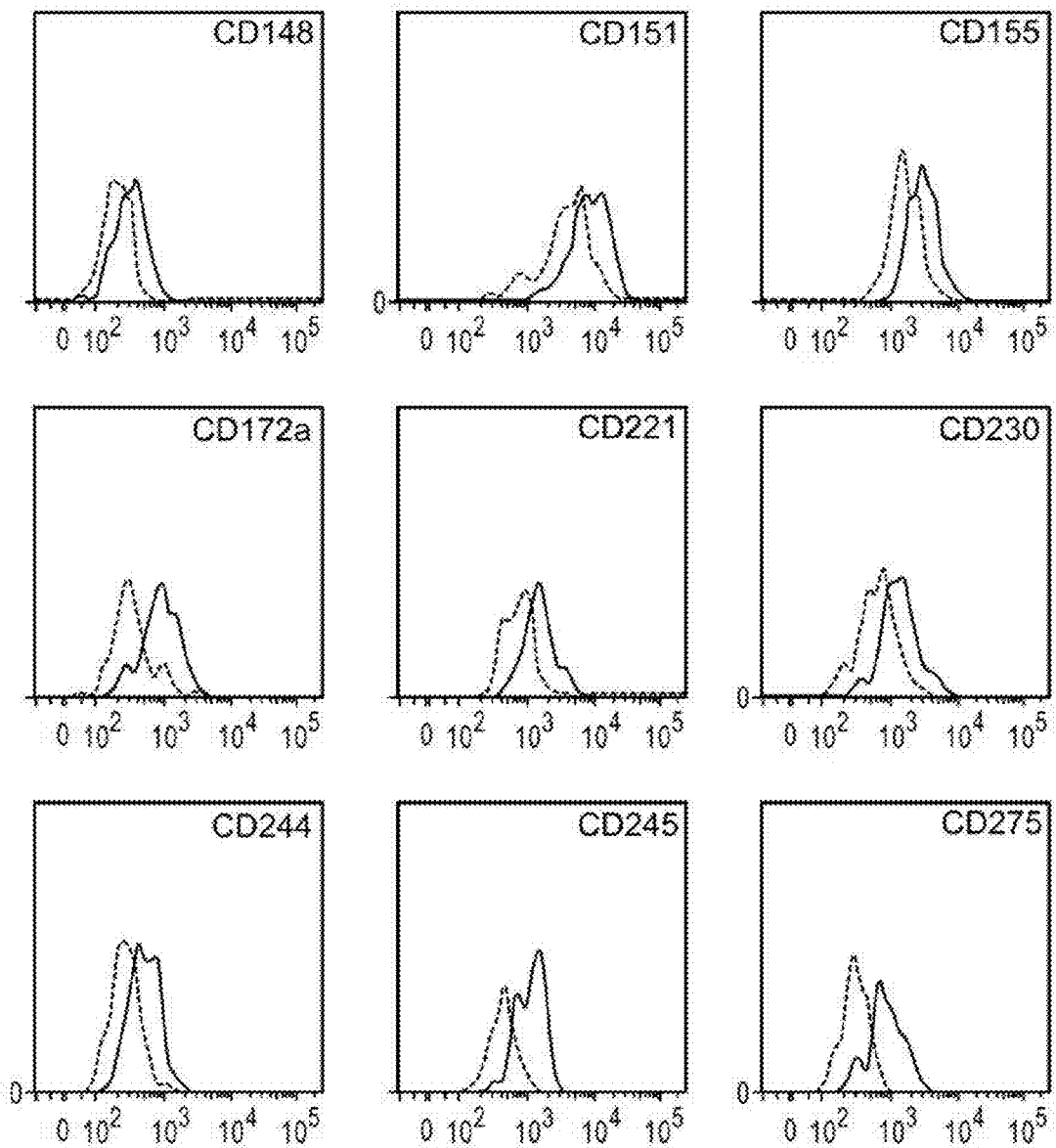
Figure 16:
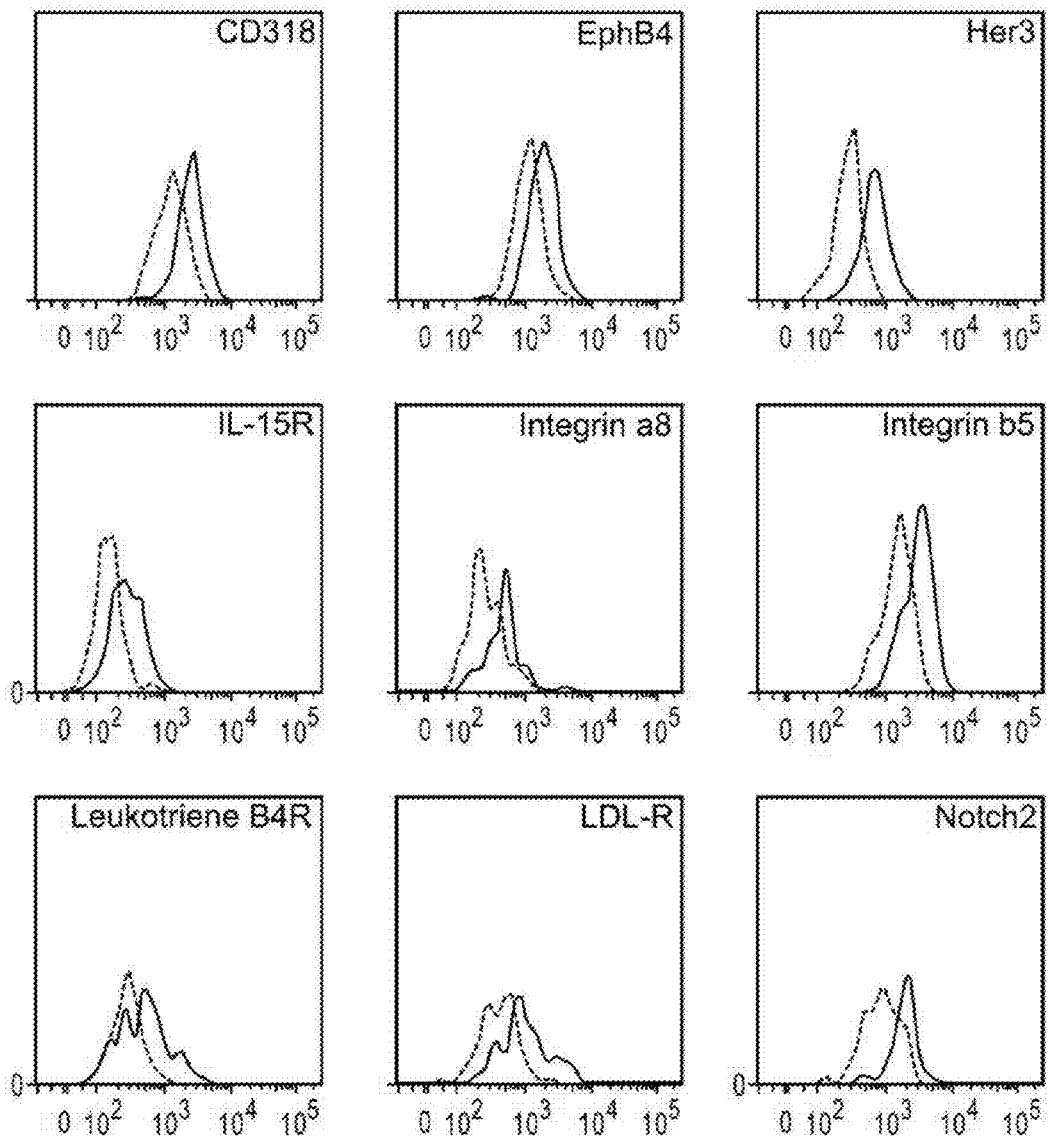
Figure 16:
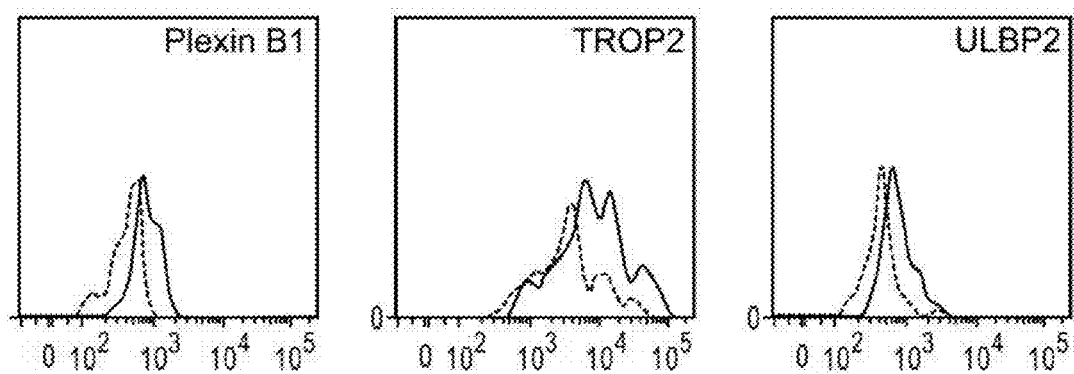
Figure 17:
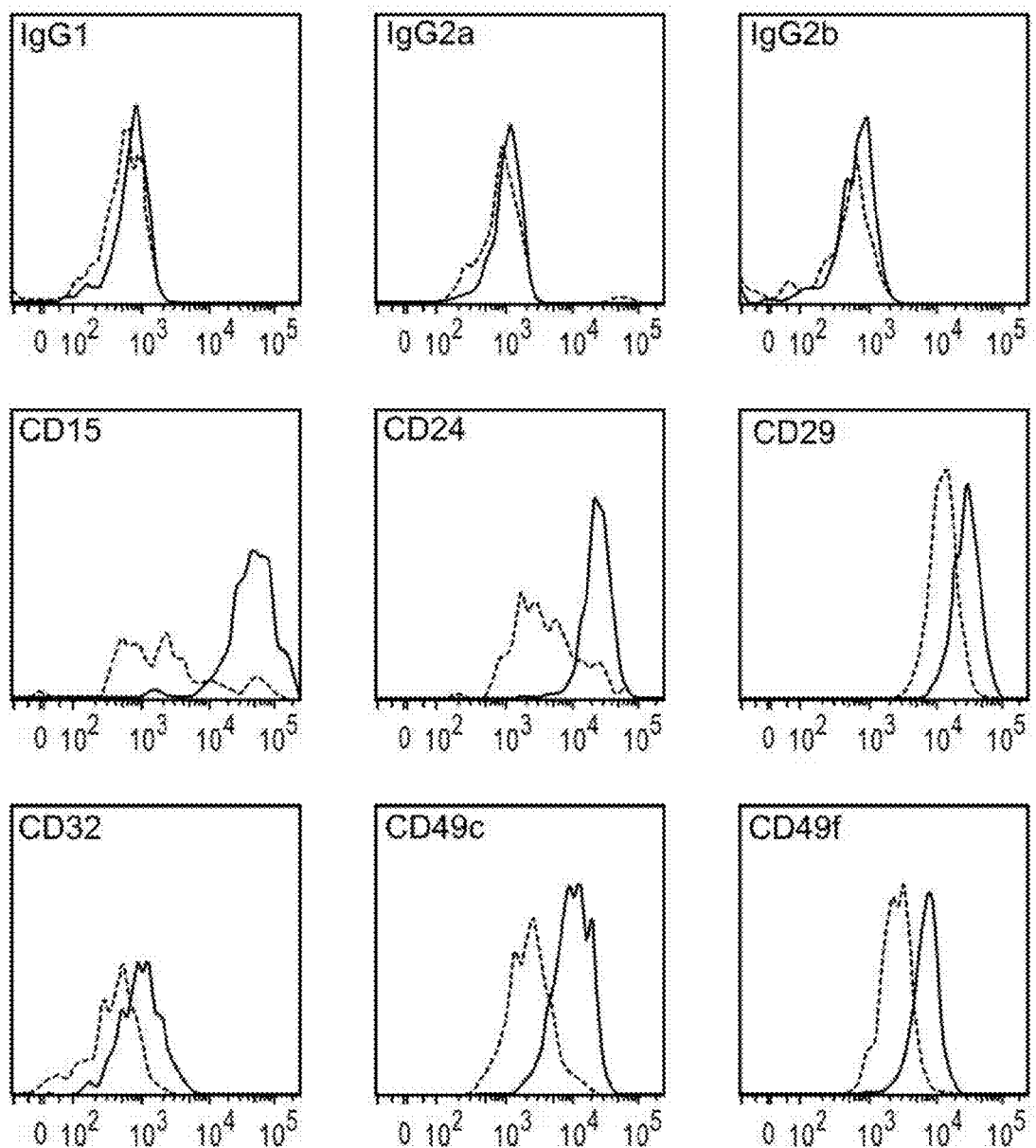
FIG. 17 depict graphical representations of flow cytometry-based protein expression data for individual ovarian tumor cells displayed as histogram plots, which show the denoted cell surface antigen expression on either the CD324$^+$ tumor cell subpopulation in gray, filled histograms or the CD46$^{hi}$ CD324$^+$ tumor initiating cell (TIC) subpopulation displayed by the bold, black line.
Figure 17:
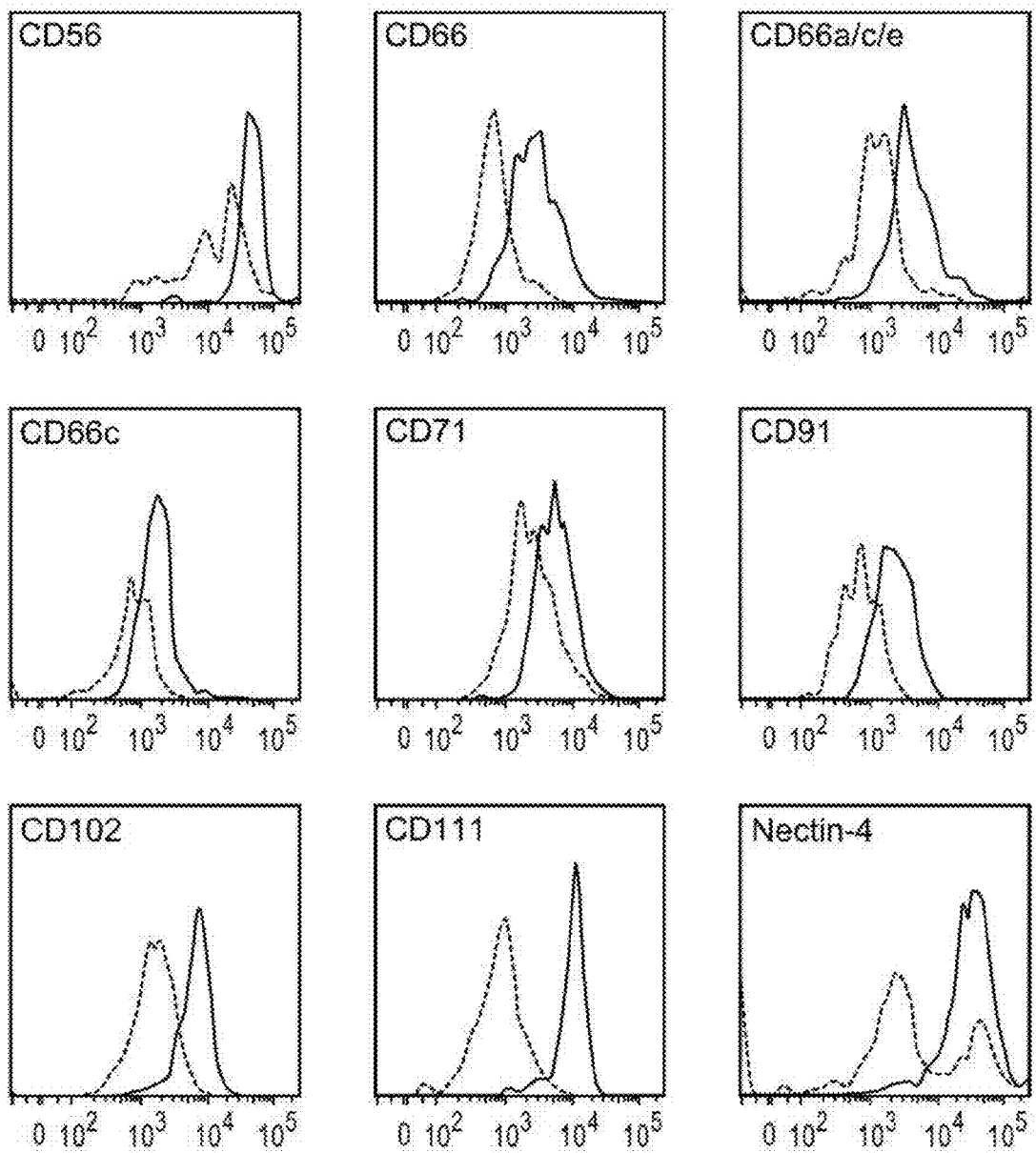
Figure 17:
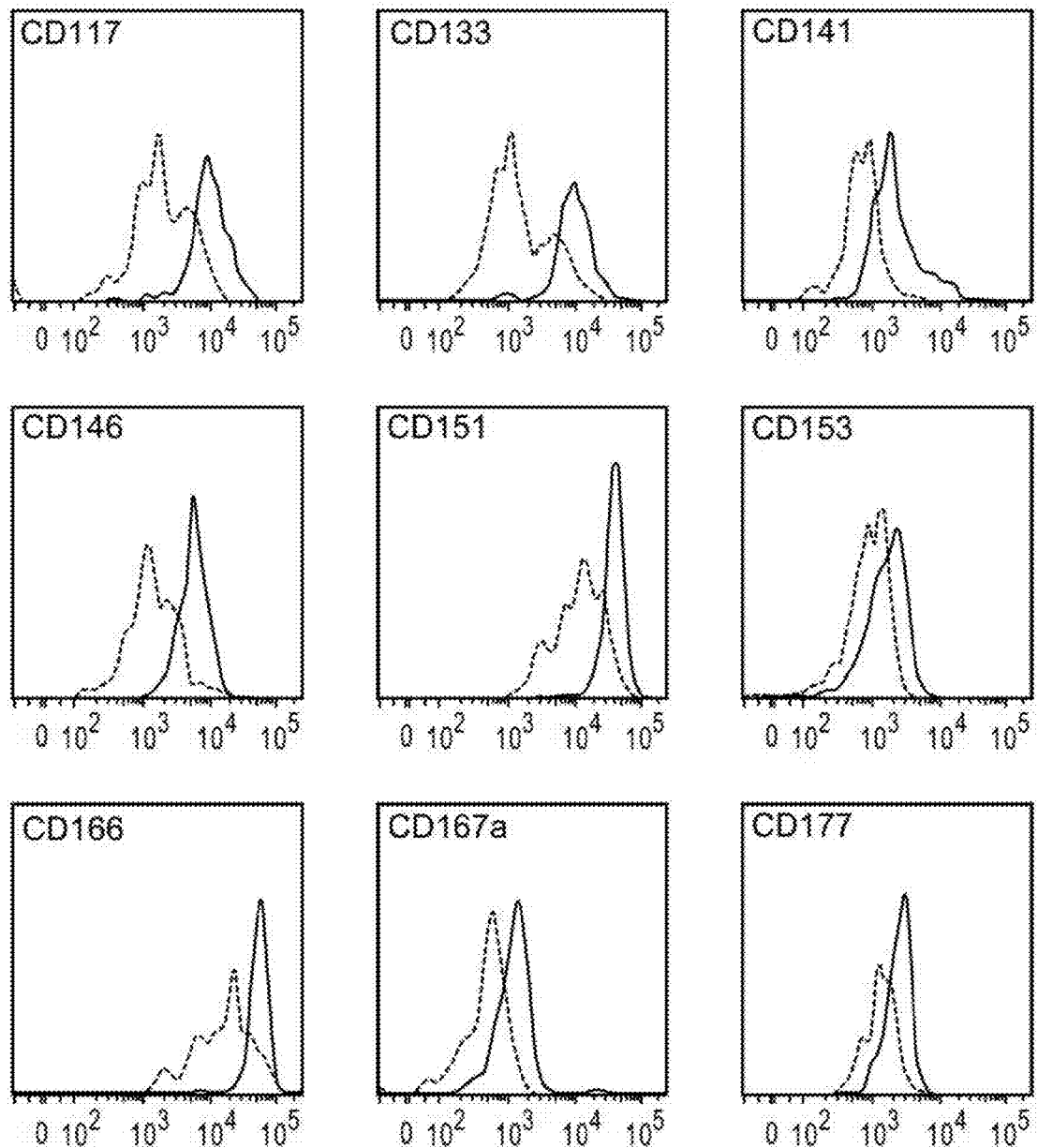
Figure 17:
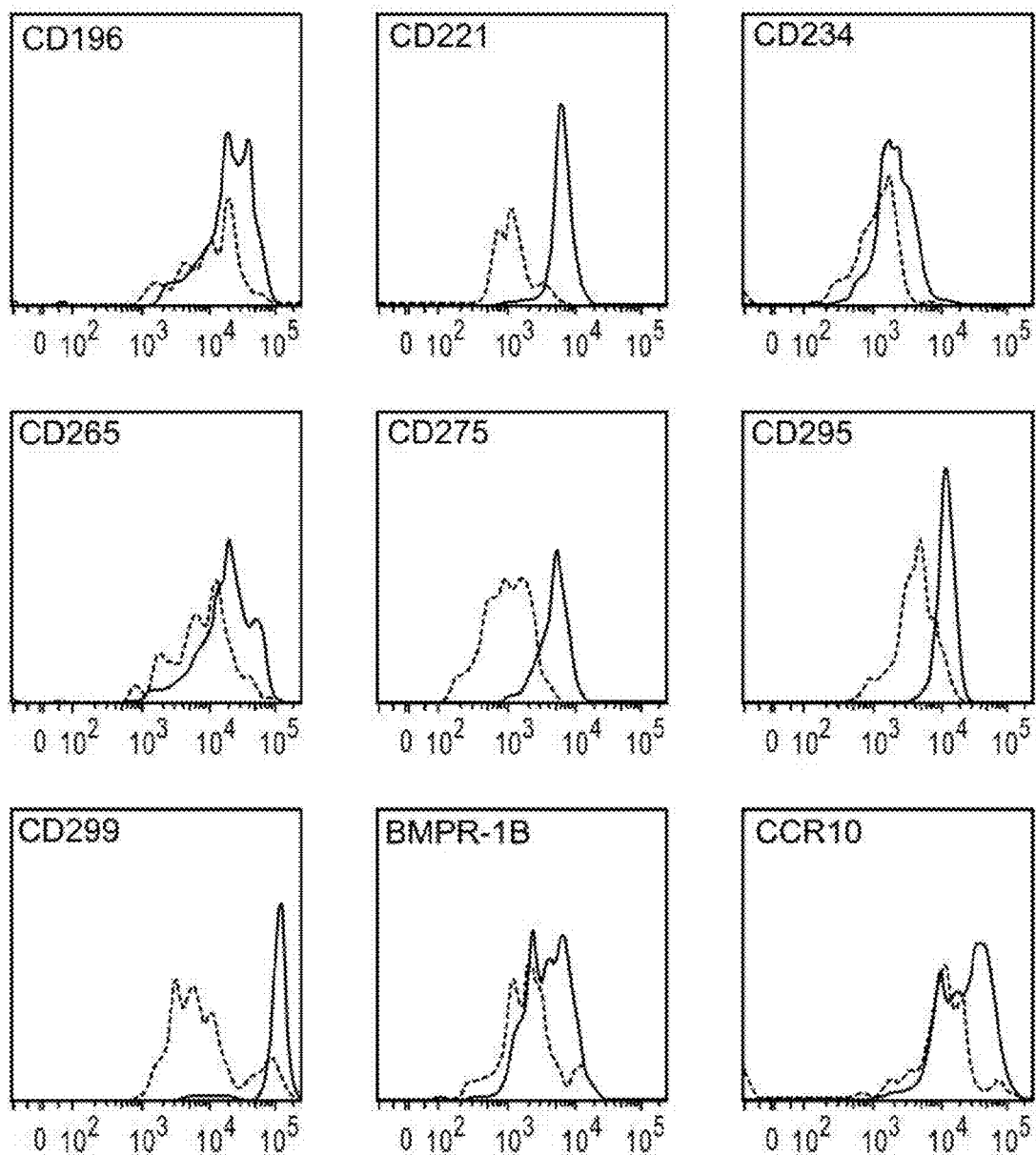
Figure 17:
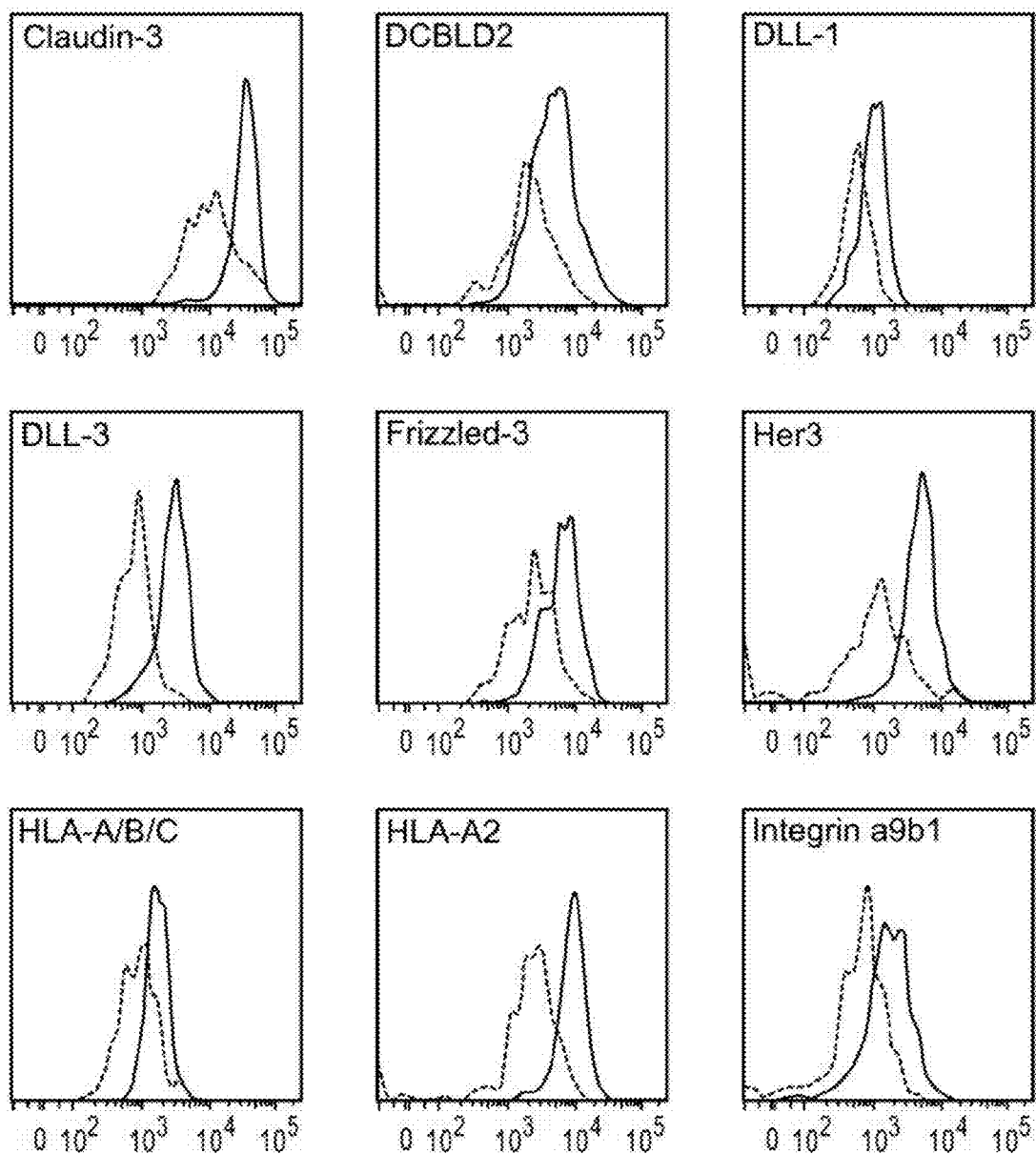
Figure 18:
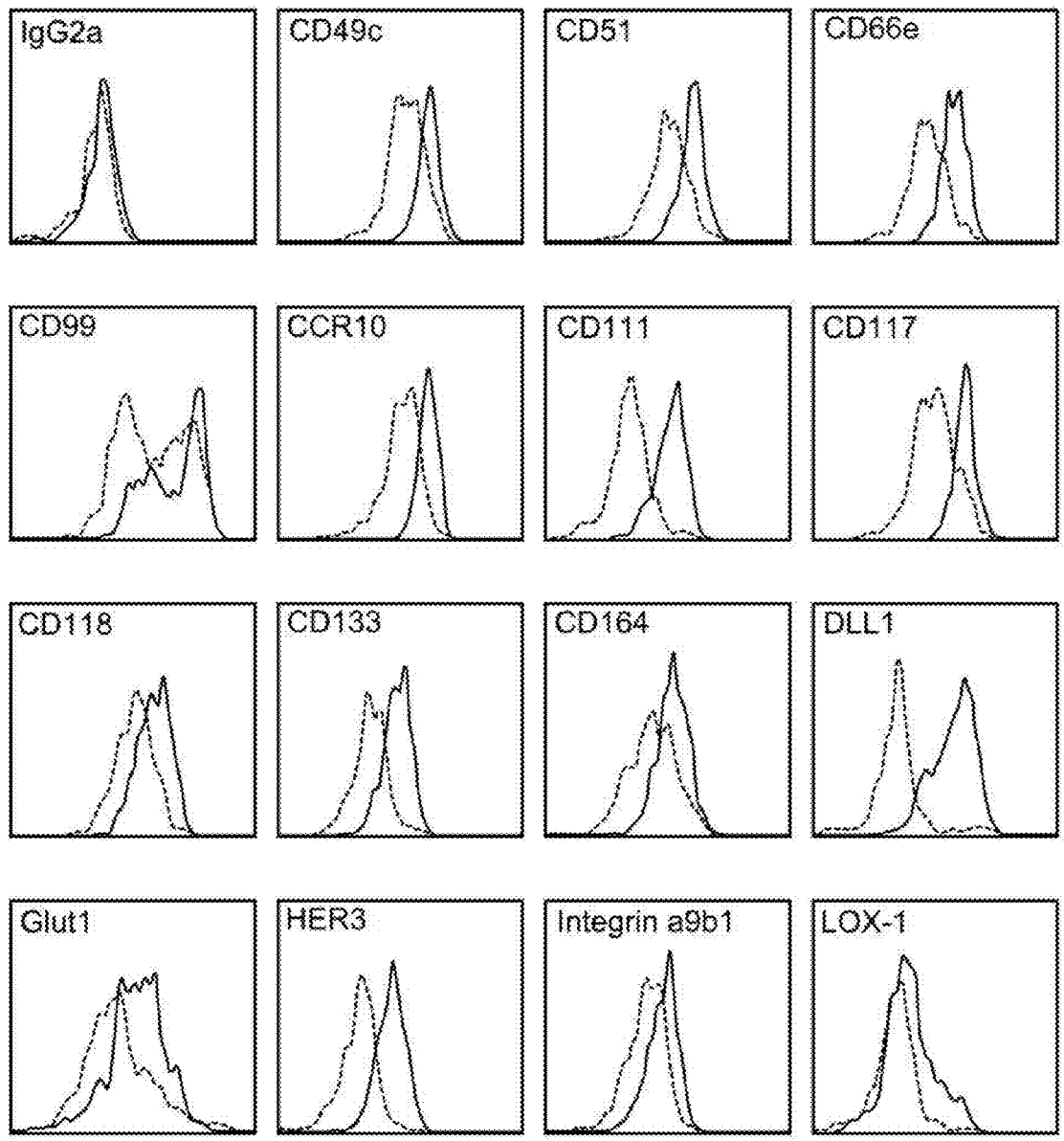
FIG. 18 shows graphical representations of flow cytometry-based protein expression data for individual small cell lung tumor cells displayed as histogram plots, which show the denoted cell surface antigen expression on either the CD324$^-$ tumor cell subpopulation in gray, filled histograms or the CD46$^{hi}$ CD324$^+$ tumor initiating cell (TIC) subpopulation displayed by the bold, black line.
Figure 19:
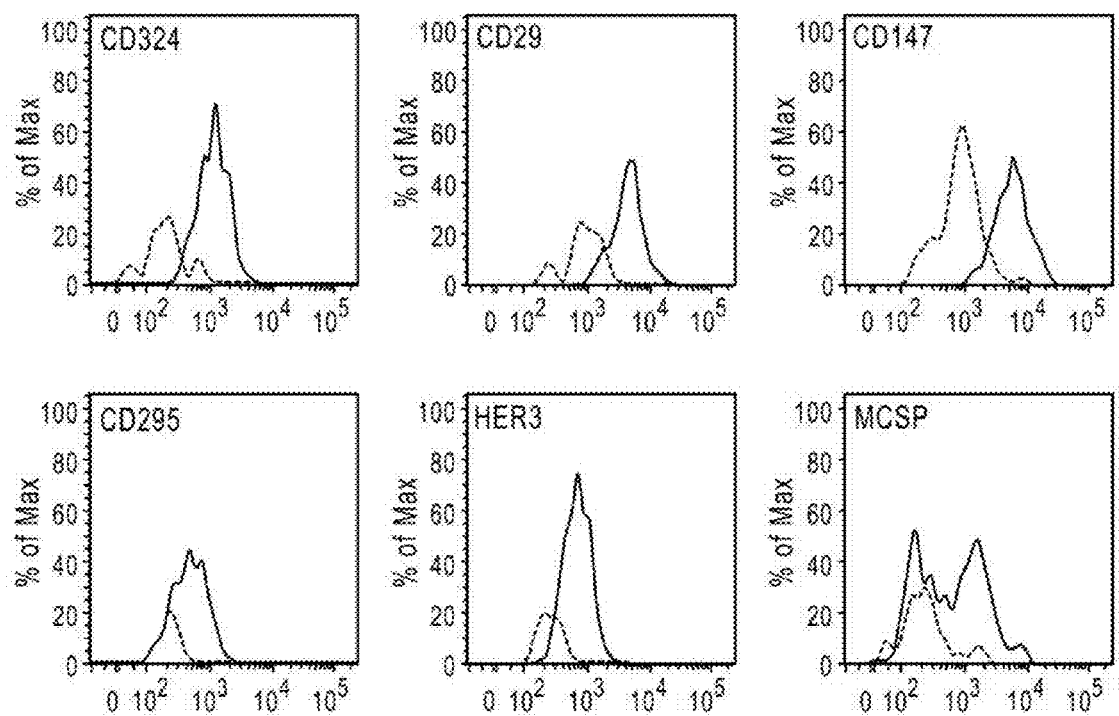
FIG. 19 depict graphical representations of flow cytometry-based protein expression data for individual melanoma tumor cells obtained directly from a patient and displayed as histogram plots, which show the denoted cell surface antigen expression on either the CD324$^+$ tumor cell subpopulation in gray, filled histograms or the CD46$^{hi}$ CD324$^+$ tumor initiating cell (TIC) subpopulation displayed by the bold, black line.

Surprisingly, and in contrast to accounts in the art, proteins generally thought to be associated only with a subpopulation of tumorigenic cells (e.g. CD24 and CD34) generally exhibited uniform expression as exemplified in FIGS. 3A and 3C (CD24) and FIGS. 3B and 3D (CD34) when measured using the flow cytometric techniques discussed above in similar solid tumor types. In this respect the use of binding agents reactive with both markers tended to provide relatively narrow, circumspect peaks indicative of homogeneous expression profiles. As such, these prior art markers may be incompatible with the teachings herein as far as providing preferred TICAMs.

In any event, the combined use of NTX tumor models that accurately recapitulate tumor physiology with the Pheno-Print Array flow cytometry analysis of tumor cells as described above demonstrate the possibility and utility in characterizing cell surface expression levels of many hundreds of tumor antigens, including CD46 and CD324. Unlike markers exhibiting homogeneous expression, the markers (e.g., TICAM or TPCAM) of the instant invention are generally heterogeneous across tumor cell subpopulations from numerous tumor types and thus provide a dramatic advantage when interrogating, identifying, characterizing and/or isolating or enriching TIC or components thereof.

Example 2

Enrichment for Tumor Initiating Cell

Populations by FACS and Transplantation

In tumors exhibiting heterogeneous expression of a particular protein or proteins of interest (e.g., CD46 and/or CD324), cells were enriched or isolated based on such markers and then transplanted into immunocompromised mice. More particularly, to determine whether high or low levels of surface CD46 and/or CD324 could be correlated with enhanced tumorigenicity, NTX tumor samples were disassociated using art recognized techniques and isolated using a FACSAria Flow Cytometer (BD Biosciences) as described in the previous Example to provide distinct marker enriched subpopulations that were subsequently transplanted into immunocompromised mice. In this regard isolated or enriched cell populations were injected subcutaneously into the mammary fat pad of recipient female immunocompromised NOD/SCID mice at doses typically ranging between 50 to 1,000 cells per mouse. When tumors arising from these transplants reached 800-2,000 mm$^3$, mice were euthanized and the tumors were removed and dissociated by enzymatic digestion to a single cell suspension for the purpose of phenotypic characterization to assess whether the constitution of cells was representative of the parental tumor from which the transplanted cells were originally isolated.

FIGS. 4-10 illustrate the results of representative experiments using freshly resected patient tumors or low passage, patient-derived NTX tumors derived from colorectal (FIGS. 4A and 4B), pancreatic (FIGS. 5A and 5B), non-small cell lung (FIGS. 6A and 6B), triple negative breast (FIGS. 7A and 7B), ovarian (FIGS. 8A and 8B), small cell lung (FIGS. 9A and 9B) and melanoma (FIGS. 10A and 10B) cancer patients. Specifically, cells expressing various levels of CD46 and/or CD324 were isolated by FACS and transplanted into immunocompromised mice to determine tumorigenicity as described above. As represented in FIG. 4A, colorectal tumor cells with the CD46$^{hi}$CD32$^+$ phenotype represent approximately 9% of all human ESA$^+$ cells, and following isolation by FACS (post-sort analysis shown in middle panel of FIG. 4A) and transplantation as described above, only cells with this phenotype were able to efficiently initiate tumorigenesis. Moreover, the phenotype of tumors initiated from these transplants ("Daughter" tumor) recapitulated that of the parental tumor. The kinetics of tumor growth following transplantation is shown in FIG. 4B.

As indicated, the above experiment was repeated using NTX lines or freshly resected tumors derived from, pancreatic, triple negative breast, non-small cell lung, ovarian, small cell lung and melanoma cancer patients to provide the representative data set forth in FIGS. 5-10. Using the aforementioned techniques $CD46^{hi}$ cells consistently generated heterogeneous tumors when transplanted into mice at cell numbers typically ranging from 50-250 cells, thereby indicating that this isolated subpopulation of cells is significantly enriched for TICs (FIGS. 4B-10B). Of note, human immune lineage-negative, $CD324^-$ and $CD46^{hi}$ $CD324^+$ tumor cell subpopulations were each isolated from a melanoma tumor removed from a patient less than 24 hours after surgery (FIG. 10A). Just 216 cells with the $CD324^-$ or $CD46^{hi}$ $CD324^+$ phenotype, respectively, were transplanted into NOD/SCID mice, whereas one million unfractionated tumor cells were also transplanted into a separate cohort of mice in parallel. While only 3 of 5 mice transplanted with one million unfractionated melanoma tumor cells developed tumors (FIG. 10B; white open triangles), all 5 mice transplanted with 216 $CD46^{hi}$ $CD324^+$ cells (black boxes) developed tumors. In contrast, none of the mice transplanted with $CD324^-$ cells (grey circles) developed tumors. It was thus surprisingly demonstrated that the tumorigenicity of this melanoma tumor was likely contained within the $CD46^{hi}$ $CD324^+$ tumor cell subpopulation, representing ~2% of all tumor cells analyzed ($CD46^{hi}$ $CD324^+$ cells represent 14.3% of the 14.5% of the tumor that was not stroma or immune cells). Similar results were observed with the various tested tumor types as shown by the data presented in FIGS. 4-9.

As further evidenced by the exemplary data shown in at tabular form in FIGS. 11A and 11B, numerous experiments of this nature have been performed using patient-derived NTX tumors and freshly resected patient tumors of different types (i.e., colorectal, small cell lung, non-small cell lung, pancreatic, breast, ovarian, and melanoma) to provide a representative data set. More particularly, FIGS. 11A and 11B show that the transplant of relatively few tumorigenic cells isolated or enriched using preferred TICAMs as taught herein and art recognized flow cytometry techniques can consistently produce tumors in immunocompromised mice. In this regard FIGS. 11A and 11B report the number of tumors generated per mice transplanted wherein the number of cells isolated by FACS and transplanted in each case are shown for the different patient-derived NTX tumors or freshly resected tumors (blank spaces indicate that tumorigenicity was tested for the given number of cells).

Significantly, tumorigenicity was consistently associated with the subpopulation of cells expressing CD46 and CD324, and the tumors generated by cells with $CD46^{hi}$ $CD324^+$ phenotype were analogous in composition to their parental tumors. Moreover, because all human cells within these solid tumors were epithelial specific antigen (ESA; EpCAM) positive and all, or at least the vast majority, were $CD24^+$ and $CD34^-$ (FIGS. 3A-3D), the tumor initiating cell (TIC) subpopulation from these tumors, and the vast majority of those tumors analyzed, can be identified using the phenotypic profile of $ESA^+$ $CD46^{hi}$ $CD324^+$ $CD24^+$ $CD34^-$. Yet, because ESA, CD24 and CD34 vary little in their surface expression and are of limited utility in defining tumor cell subpopulations, preferred TIC subpopulations disclosed herein may be identified phenotypically or genotypically as $CD324^+$ and, optionally, as $CD46^{hi}$.

Although CD46 and CD324 may each be used alone to enrich and characterize TIC subpopulations in accordance with the teachings herein, various aspects of the instant invention will use these markers in combination and, in alternate embodiments, optionally with additional markers to facilitate more precise stratification and isolation of tumor cell subpopulations (e.g., as shown in FIGS. 20 and 21). Conversely, tumor cells expressing either no, or low levels of, CD46 or CD324 were much less tumorigenic than their high or positive counterparts, respectively (e.g., as seen in FIGS. 4-11). Accordingly, and based on the data as presented herein, it was surprisingly found that subpopulations of tumor cells phenotypically or genotypically characterized as $CD324^+$ (and optionally $CD46^{hi}$) generally contain the vast majority of tumorigenic capability in most patients with the tumor types discussed above.

Example 3

Representative Cell Surface

Markers Expressed on Tumor Initiating Cells

Tumor initiating cells, like all cells, can express hundreds if not thousands of markers or antigens, preferably on their cell surface. As such, while CD46 and CD324 are preferred markers for TIC in many solid tumor indications as disclosed above, other concomitant markers may be used to identify and/or isolate the same tumor cell subpopulation independent of using molecules able to detect CD46 and/or CD324. Following confirmation of TIC populations using the cell surface marker profiles described above, the PhenoPrint Array was employed using reagents to identify proteins exhibiting comparable expression profiles to CD46 and/or CD324, indicating that they may be used as markers or TICAMs for the identification, characterization and/or enrichment of cancer stem cells.

To identify proteins that are associated with TIC cell populations or substantially co-express with CD46 and/or CD324, non-PE-conjugated antibodies against these antigens were included in all wells of the PhenoPrint Array and unique antibodies recognizing various distinct proteins of interest were arrayed and assessed using the fluorescent PE molecule substantially as set forth in Example 1. That is, flow cytometric analysis was conducted to detect proteins with higher expression within the human $CD46^{hi}$ $CD324^+$ (TIC) subfractions, for example, as compared to $CD46^{-/lo}$ (NTG) and/or $CD324^-$ subfractions of various xenografted tumors. More specifically flow cytometric analysis was conducted on cell subpopulations derived from colorectal (FIG. 13), pancreatic (FIG. 14), non-small lung (FIG. 15), breast (FIG. 16), ovarian (FIG. 17), small cell lung (FIG. 18) and melanoma (FIG. 19) tumors. A review of each of these FIGS. 13-19 show that they provide flow cytometry data for selected TICAMs that are expressed on the TIC subpopulation associated with each respective tumor. Data from all of these FIGS. 13-19 (along with additional studies—data not shown) are correlated and summarized in a tabular form in FIGS. 12A-12C to provide a comprehensive list of exemplary TICAMs in accordance with the instant invention.

Identification, characterization, enrichment and/or isolation of cells with substantial expression of each listed TICAM is indicative of TIC subpopulations which may be confirmed by the presence of $CD46^{hi}$ $CD324^+$ cells (i.e. TIC). In this regard, the markers of FIGS. 12-19 and other markers identified using similar techniques and correlated with expression of either CD46 or CD324 may be employed as TICAMs and effectively used to identify TIC as set forth herein. Accordingly, the markers set forth in FIGS. 12-19 may be used for the identification of TIC subpopulations and possess substantial utility for the interrogation, monitoring, enrichment and/or characterization of tumor cell subpopulations as well as in the clinic for the diagnosis, prognosis or monitoring a course of therapy. Moreover, as previously alluded to and presented in the appended claims hereto one of skill in the art could readily identify and use colorectal associated TICAM, breast associated TICAM, non-small cell lung cancer associated (NSCLC) TICAM, ovarian associated TICAM, pancreatic associated TICAM, small cell lung cancer (SCLC) TICAM and melanoma associated TICAM in accordance with the teachings herein.

Example 4

CD66c is an Effective TICAM for Selected TIC Subpopulations

While the majority of tumor cells are devoid of tumor forming ability and can thus be characterized as NTG, there is precedent in both normal cellular development and hematopoietic tumors for highly proliferative cells able to reconstitute a tissue and/or tumor upon transplantation, but which do not have self-renewal capacity (i.e. a finite lifespan) and thus are eventually exhausted: i.e. short-term reconstituting cells, transit amplifying cells or progenitor cells. In the context of cancer, cells with a progenitor cell phenotype might reacquire self-renewal properties normally restricted to stem cell populations and thereafter fulfill the definition of a TPC or CSC (Jamieson et al., N Engl J Med; 351, 2004, which is incorporated herein by reference in its entirety) in that these cells and their progeny will be long-lived; however, these mutagenic events that confer self-renewal properties to progenitor cells are rare. Nevertheless, because: a) the proliferative capacity of progenitor cells may be significant; b) immunocompromised mice must be euthanized once tumors reach ~1,500-2,000 mm$^3$; and c) the lifespan of immunocompromised mice is short relative to that of humans (~9-12 months for NOD/SCID mice), the ability of a TIC to generate tumors in mice is not a robust enough readout to demonstrate that the TIC is a TPC. As discussed in the art, demonstration of self-renewal capacity by a stem cell is preferably shown using serial transplants whenever possible.

To determine whether subpopulations of CD46$^{hi}$ CD324$^+$ cells were more or less tumorigenic and/or had differing potential, cells with this phenotype were systematically screened for heterogeneity to identify additional markers enabling cell isolation and transplantation experiments. Specifically, cell surface markers of interest and potential utility were identified using the PhenoPrint Array as set forth in previous examples discussed above. During the course of these experiments, CD66c was identified as a cell surface marker that commonly displayed heterogeneity among the CD46$^{hi}$ CD324$^+$ cell population (FIG. 20A) and enabled the isolation of two distinct subpopulations of CD46$^{hi}$ CD324$^+$ cells possessing different functional reconstitution capabilities. The respective populations transplanted at 200 cells per mouse are denoted in FIG. 20A. Colorectal tumors arising from the transplantation of CD66c$^-$ cell subset of CD46$^{hi}$ CD324$^+$ cells were fully heterogeneous and reflected the parental tumors from which they were derived (FIGS. 20B and 20C [black bar vs. white bar] and FIG. 21A). Surprisingly, and in contrast to tumors derived from the CD66c$^-$ subset of CD46$^{hi}$ CD324$^+$ cells, transplants with small numbers of the CD66c$^+$ subset did not generate fully heterogeneous tumors in that there were significantly less CD66c$^-$ cells present in tumors generated from CD46$^{hi}$ CD324$^+$ CD66c$^+$ cells (FIG. 20C [gray bar vs. white bar] and FIG. 21A), suggesting that these cells are tumor progenitor cells (TProg) with properties analogous to normal progenitor cells; i.e. significant proliferative capacity, but devoid of self-renewal capability and unable to dedifferentiate into CD46$^{hi}$ CD324$^+$ CD66c$^-$ cells.

Figure 21A:
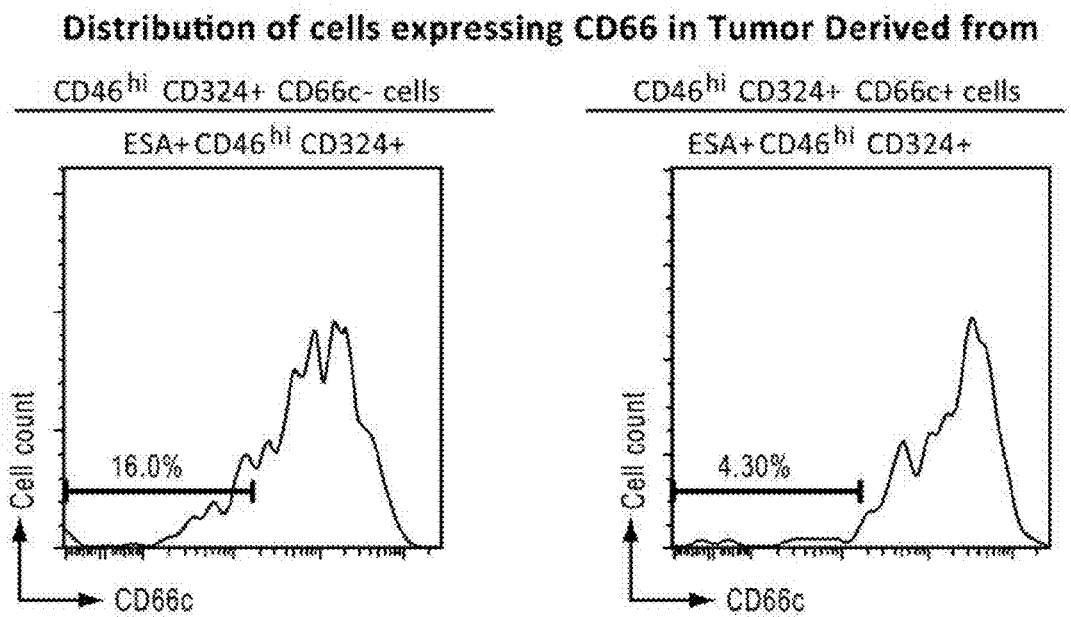
FIGS. 21A and 21B are histogram plots showing CD66c$^-$ expression on ESA$^+$ CD46$^{hi}$ CD324$^+$ tumor cells from colorectal tumors reconstituted in primary transplants by isolated colorectal tumor cell subpopulations obtained from the same tumor, and a graphical representation of tumorigenicity by the denoted tumor cell subpopulations in secondary transplants.
Figure 21B:
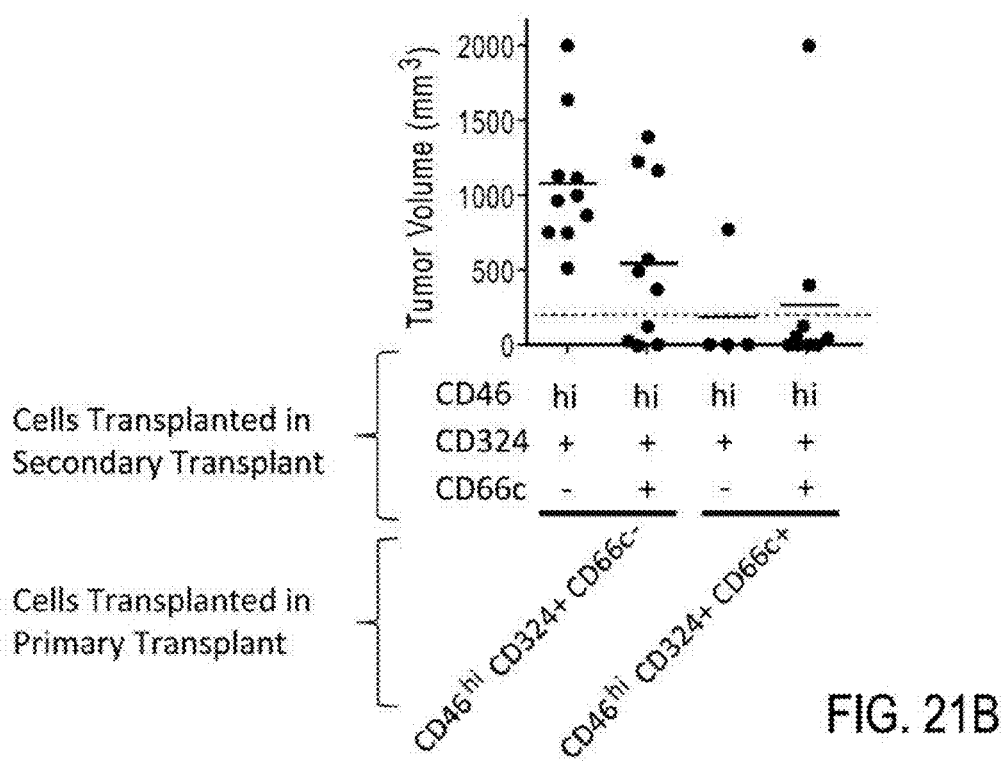

Serial transplantation of prospective TPC (CD46$^{hi}$ CD324$^+$ CD66c$^-$) and TProg (CD46$^{hi}$ CD324$^+$ CD66c$^+$) cells at low cell numbers confirmed the proposed identity of these tumor cell subpopulations, as CD46$^{hi}$ CD324$^+$ CD66c$^-$ cells arising from tumors generated by CD46$^{hi}$ CD324$^+$ CD66c$^-$ cells efficiently generated tumors upon serial transplantation of only 50 cells, whereas neither the CD66c$^-$ nor CD66c$^+$ cell subpopulations from tumors generated by CD46$^{hi}$ CD324$^+$ CD66c$^+$ cells could efficiently reinitiate tumors upon serial transplantation (FIGS. 21A and 21B). To be clear, 50 CD46$^{hi}$ CD324$^+$ CD66c$^+$ or 50 CD46$^{hi}$ CD324$^{hi}$ CD66c$^-$ cells isolated from tumors generated from 200 CD46$^{hi}$ CD324$^+$ CD66c$^+$ cells were rarely tumorigenic (FIG. 21B). Furthermore, identical experiments were done with tumors from different colorectal cancer patients with the same results. Surprisingly, these data are indicative of the fact that, in solid tumors from some colorectal cancer patients, CD46$^{hi}$ CD324$^+$ CD66c$^-$ cells are TPC and CD46$^{hi}$ CD324$^+$ CD66c$^+$ cells are TProg cells.

To determine the accuracy of the above described TPC phenotype in colorectal cancer, CD46$^{hi}$ CD324$^+$ CD66c$^-$ cells were isolated by FACS (pre- vs. post-FACS; FIGS. 22A vs. 22B, respectively) and transplanted in dilutions at 1,000, 200, 50, 20, 8 and 3 cells per mouse, respectively. Use of Poisson distribution statistics based on positive events being defined as successful tumorigenesis independent of rate resulted in the calculation that the true TIC frequency among CD46$^{hi}$ CD324$^+$ CD66c$^-$ TPC was roughly 1 in 5.4±2.5 cells (FIG. 22C). We have unexpectedly demonstrated in a representative colorectal NTX tumor that using the novel marker combination of CD46$^{hi}$ CD324$^+$ CD66c$^-$ facilitates a measurable enrichment in TIC frequency, and use of CD66c further facilitates the parsing of TIC subpopulations in some patients into TPC versus TProg. This development has significant implications in that not all TIC are equal and that only the TPC subpopulation in any given patient is the long-lived cancer stem cell truly driving disease progression and recurrence.

The combination of cell surface proteins used to enrich for TPC and TProg cell populations defined above in colorectal tumors has not been known to be associated with cells containing such activity in any tissue or neoplasm previously. This work represents a substantial improvement in the resolution of the method of isolating TIC and subpopulations thereof, and further improves techniques to identify, isolate and characterize distinct, highly enriched solid tumor cell subpopulations that exclusively contain tumor generating ability upon transplantation, distinguishing between tumorigenic cell subpopulations without or with self-renewal capacity: i.e. TProg and TPC, respectively. We further herein describe a method by which to enumerate TIC by transplanting human tumor cells in progressively lower dilutions of cell numbers and assessing the subsequent frequency, independent of rate, at which these dilutions of cells are able to initiate tumorigenesis in immunocompromised mice. Accordingly, while most cell surface markers identified using the proprietary PhenoPrint Array did not demonstrate an ability to enrich TIC populations from tumors using standard FACS protocols, distinct markers and combinations thereof could be used to identify at least two subpopulations of TIC, including TPC and TProg, which were functionally demonstrated as distinct and fulfilling the definitions standard in the art of a stem cell and a progenitor cell, respectively.

Example 5

TPC and TProg Cell Populations have Differing Potential

In vitro colony forming cell (CFC) assays have proven to have great utility in helping parse apart the differentiation potential of distinct cell populations in the hematopoietic cell hierarchy; however these assays are not amenable to epithelial tissues or solid tumor cells in that the assay conditions are not conducive to cell growth and/or differentiation. Using NTX tumor models in which many phenotypically distinct tumor cell subpopulations exist as they do in patient tumors, FACS and in vitro assay conditions that support either self-renewal or differentiation of TIC aid in the determination of the potential of defined tumor cell subpopulations. These in vitro CFC assays, at the very least, provide an effective advantage in the search for new markers defining tumor cell subpopulations, determining the differentiation potential of these respective tumor cell populations, and for the screening of anti-cancer agents.

To illustrate such aspects of the instant invention, single cells with the defined cell surface phenotypes of $CD46^{hi}$ $CD324^+$ (TIC) or $CD46^{-/lo}$ $CD324^-$ (NTG) were isolated from colorectal NTX tumors and deposited directly into 96-well plates in dilutions of 468, 162, 54, 18, 6 or 2 cells per well using a FACSAria flow cytometer (BD Biosciences). Cells were then cultured in defined serum-free conditions, as is standard in the art, for 15 days at 37° C./5% $CO_2$/5% $O_2$, and wells positive for colony formation were then scored as such (FIG. 23A). The frequency of colony-forming units for each population was finally determined utilizing L-Calc™ Software (Stemcell Technologies), utilizing the experimental setup information including: a) the number of individual wells initiated; b) the number of cells used to initiate each well; and c) the number of wells scored positive, independent of rate, from each dilution.

Colonies were observed in wells seeded with as few as 18 sorted $CD46^{hi}$ $CD324^+$ cells, while 162 cells were the fewest needed to observe a colony from sorted $CD46^{-/lo}$ $CD324^-$ cells. Colony forming cells were thus demonstrated to exist at frequencies of 7.3 and 1.1 per 1,000 cells for TIC and NTG cell populations, respectively (FIG. 23A). For the purposes of clarity, 1 in 137 $CD46^{hi}$ $CD324^+$ (TIC) cells formed colonies in vitro, while only 1 in 918 $CD46^{-/lo}$ $CD324^-$ (NTG) cells had this capacity. These results strongly indicate that colony-forming cells are significantly enriched in the $CD46^{hi}$ $CD324^+$ fraction of colorectal cancer cells and this activity correlates with tumorigenic capacity, as is also demonstrated above by in vivo transplantation.

To further assess the proliferative and differentiation potential of more distinct tumor cell subpopulations within colorectal tumors, cells expressing various combinations of CD46, CD324 and CD66c were sorted into plates containing standard serum-free media conditions that support stem cell self-renewal (Dylla et al., 2008, supra). The following cell populations were sorted from among single, live, human $ESA^+$ cells: $CD46^{-/lo}$ (NTG cells; predominantly also CD324), $CD46^{hi}$ $CD324^+$, $CD46^{hi}$ $CD324^+$ $CD66c^+$ and $CD46^{hi}$ $CD324^+$ $CD66c^-$. The ability of these respective tumor cell subpopulations to initiate colonies was then assessed 21 days after plating, as was the potential of these respective tumor cell subpopulations to generate soluble CD66c (i.e. CEACAM6) protein. CD66c is routinely shed from the cell surface, was readily measurable in the supernatant of the above described in vitro cultures, and was used as a surrogate marker of differentiation.

Specifically, 2,000 cells from NTX tumor CR33, for example, were sorted into flat-bottom 96-well Primaria plates (BD Biosciences) in serum-free media conditions and incubated in the environmental conditions noted above. After 21 days, colonies (defined as >50 cells per colony) of tightly packed, attached cells had formed and expanded in the wells. The number of colonies (white bars) in each well was counted manually and the concentration of CD66c protein in the supernatant (black bars) was measured by ELISA (FIG. 23B). The frequency of colony formation corresponded well with the frequency of tumorigenic cells observed in vivo. That is, $CD46^{-/lo}$ cells (i.e. NTG cells) generated only a single colony (1 in 2,000 cell frequency) and soluble CD66c protein was not detected in the media despite 21 days of culture (FIG. 23B). Just as $CD46^{hi}$ $CD324^-$ cells rarely demonstrate in vivo tumor initiation potential, we observed a small number of colonies in vitro and relatively low levels of CD66c were detected in the media. This is not surprising given that a subpopulation of $CD46^{hi}$ $CD324^-$ cells in many NTX tumors express CD66c, though these cells generally appear to be short-lived. Furthermore, $CD46^{hi}$ $CD324^+$ cells, regardless of CD66c expression, were better able to form colonies in vitro and generated significantly more soluble CD66c than either the $CD46^{-/lo}$ or the $CD46^{hi}$ $CD324^-$ tumor cell subpopulations (FIG. 23B). In addition, the amount of CD66c generated in the supernatant appeared to correlate with the number of colonies, suggesting that both $CD66^+$ and $CD66^-$ cell populations that were initially seeded into the wells were capable of generating CD66c. This is consistent with the observation that $CD66c^-$ cells are capable of generating $CD66c^+$ cells as demonstrated above in vivo.

Colony formation can serve as a surrogate for in vivo transplantation and determination of whether TIC are present in one tumor cell subpopulation versus another and is generally able to assess the potential of candidate stem and progenitor cell populations. However, even the best in vitro cell culture conditions do not mimic the physiological environment encountered in vivo. Furthermore, these serum-free culture conditions generally support self-renewal and prevent differentiation, but do not actively facilitate differentiation.

To better assess the differentiation potential of single cells with the defined cell surface phenotypes described above, the media conditions were modified to contain 10% fetal calf serum (FCS), so as to actively facilitate differentiation as is common in the art. Fourteen days later, media was removed and the amount of CD66c in the supernatant was assessed by ELISA. Although elevated levels of CD66c were expected in the media from $CD46^{hi}$ $CD324^+$ $CD66c^+$ cells, the fact that $CD46^{hi}$ $CD324^+$ $CD66c^-$ cells were able to generate similar levels of CD66c in vitro is consistent with the notion that $CD46^{hi}$ $CD324^+$ $CD66c^-$ cells can differentiate into $CD46^{hi}$ $CD324^+$ $CD66c^+$ cells (FIG. 23C). Expansion in media conditions supportive of self-renewal (i.e. in defined, serum-free media) as described above does not appear to be supportive of robust CD66c production; however, addition of FCS to the media facilitated differentiation and greatly aided the ability of cells to produce CD66c. Perhaps not surprisingly given the demonstration above that $CD46^{hi}$ $CD324^+$ $CD66c^-$ cells are often the only tumor cell subpopulation with self-renewal capacity (demonstrated by serial transplantation), the tumor cell subpopulation with the greatest CD66c production potential in vitro were also CD46$^{hi}$ CD324$^+$ CD66c$^-$ cells. Although this result was unexpected given that the cells seeded into the well were negative for CD66c protein expression, and Taqman qRT PCR analysis of this cell population shows little to no presence of the CD66c transcript (data not shown), these results confirm in vivo observations demonstrating that CD46$^{hi}$ CD324$^+$ CD66c$^-$ cells have the most proliferative and differentiation potential. This also implies that plating of CD46$^{hi}$ CD324$^+$ CD66c$^-$ cells in vitro results in progeny that express CD66c, and this process is augmented by cell growth conditions that promote differentiation.

Figure 23D:
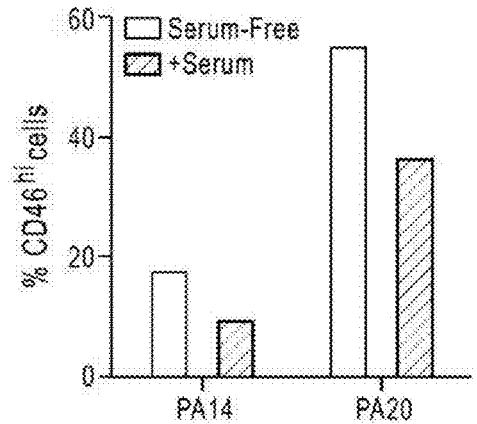

Induced differentiation of TIC in vitro by the addition of FCS is not only observed in with NTX colorectal cancer cells, as described above, but also with pancreatic cancer TIC. After fourteen days of pancreatic xenograft tumor cell culture without or with serum, the percentage of CD46$^{hi}$ cells (also predominantly CD324$^+$) was decreased on both NTX PA14 and PA20 tumor cells in conditions where FCS was present (FIG. 23D). This data further supports the use of CD46 and CD324 as markers to distinguish between less differentiated and more differentiated NTX-derived pancreatic cancer cells in vitro and supports the claim that these markers can serve distinguish between TIC and NTG cells in several epithelial tumor types.

This example demonstrates that TIC subpopulations (e.g. TPC & TProg) can be distinguished in vitro based upon their ability to initiate colonies, differentiate and produce proteins normally associated with differentiated cells. Moreover, culture conditions without or with FCS can also be developed that facilitate differentiation.

Example 6

Colorectal and Pancreatic Tumor Initiating Cells are Resistant to Standard of Care Chemotherapeutic Agents A central tenet of the cancer stem cell paradigm is that CSC are generally resistant to standard of care therapeutic regimens such as chemotherapy and radiation. To assess which colorectal and pancreatic tumor cell subpopulation was most resistant to standard of care regimens such as irinotecan or gemcitabine, respectively, mice were initiated with colorectal or pancreatic NTX tumors and then randomized once tumors reached approximately 180-350 mm$^3$. Mice then received twice weekly intraperitoneal dosing of 15 mg/kg irinotecan or 25 mg/kg gemcitabine, respectively, for a period of approximately 20 days before they were euthanized for tumor resection and cellular analysis.

Figure 24A:
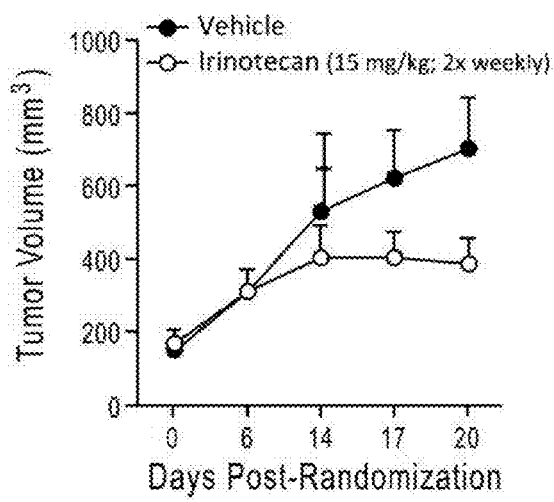
FIGS. 24A-24D provide data demonstrating the impact of standard of care chemotherapeutic agents on colorectal tumor cell subpopulations by showing the increase in relative frequency of CD46$^{hi}$ CD324$^+$ CD66$^-$ cells in irinotecan treated tumors.
Figure 24B:
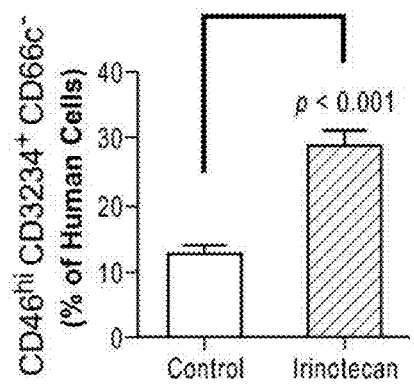
Figure 24C:
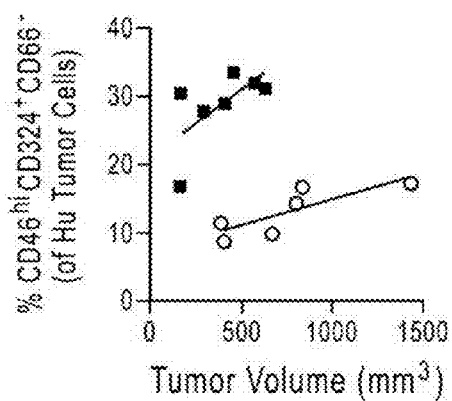
Figure 24D:
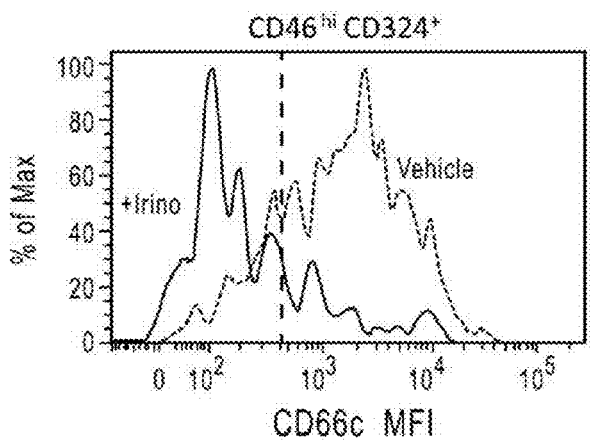

To assess chemoresistance of tumor cell subpopulations, in vivo cohorts of mice bearing NTX colorectal tumors were randomized into two groups, such that the average tumor volume for each group was roughly equal. The groups were then treated twice weekly with either 15 mg/kg irinotecan or an equivalent volume of vehicle buffer. Tumor volumes and animal health were monitored and recorded twice weekly, a day prior to each injection. In the case of colorectal tumors, the vehicle-treated tumors continued to grow while the irinotecan-treated tumors showed either retarded growth or a decrease in volume (FIG. 24A). When tumors in irinotecan-treated mice began to decrease in volume, all mice in the experiment were euthanized and tumors were harvested, dissociated into single-cell suspensions and their individual cell phenotypes were analyzed by flow cytometry using art recognized techniques. The frequency of cells with a TPC phenotype (CD46$^{hi}$ CD324$^+$ CD66c$^-$) among live human cells was determined to be more than 2.5-fold higher in tumors from irinotecan-treated mice, compared to saline-treated counterparts (FIGS. 24B and 24C). This is an indication that cells with the TPC phenotype (CD46$^{hi}$ CD324$^+$ CD66c$^-$) resist irinotecan-induced cytotoxicity while other tumor cell subpopulations succumb to irinotecan. In addition, among the CD46$^{hi}$ CD324$^+$ population of vehicle-treated tumors, most residual cells were CD66c$^+$; however, among the CD46$^{hi}$ CD324$^+$ population of irinotecan-treated mice, most residual cells were CD66c$^-$ (i.e. TPC or CSC) (FIG. 24D). This data indicates that cells with the TPC phenotype (i.e. CD46$^{hi}$ CD324$^+$ CD66c$^-$) are more resistant to irinotecan-mediated cytotoxicity than other tumor cell subpopulations, which include both the TProg subset of TIC (i.e. CD46$^{hi}$ CD324$^+$ CD66c$^+$) and NTG cells.

Figure 25A:
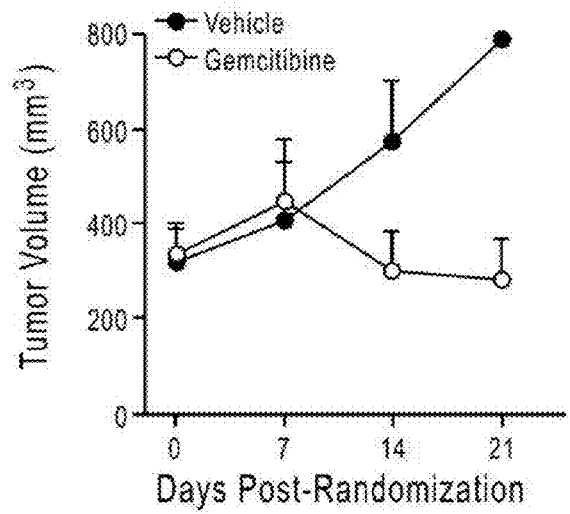
FIGS. 25A and 25B provide data demonstrating the impact of standard of care chemotherapeutic agents on pancreatic tumor cell subpopulations by showing the increase in relative frequency of CD46$^{hi}$ cells in gemcitabine treated tumors.
Figure 25B:
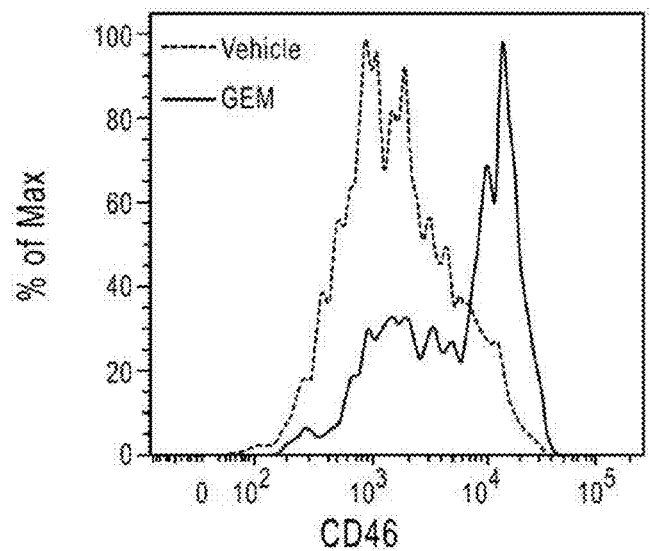

Analogous results were observed in a representative pancreatic NTX tumor, wherein residual pancreatic NTX tumors were removed during the course of gemcitabine treatment and the residual tumor cell subpopulations were analyzed based on their marker phenotype. As expected, pancreatic tumors from vehicle treated mice continued to grow unabated, while tumors from mice treated with gemcitabine decreased in volume in response to this chemotherapeutic agent (FIG. 25A). Harvested tumors were then dissociated and constituent single cells were analyzed by flow cytometry. As observed in colorectal cancer NTX tumors treated with irinotecan, gemcitabine treatment of pancreatic tumors resulted in enrichment for tumor cells expressing markers indicative of TIC (e.g. CD46). A representative example of CD46 expression in vehicle vs. gemcitabine treated tumors is shown in FIG. 25B. As with colorectal cancer, pancreatic TIC appear relatively resistant to the standard of care chemotherapeutic agent, gemcitabine.

We demonstrate here that not all tumor cell subpopulations are equally sensitive or resistant to standard of care chemotherapeutic agents such as irinotecan or gemcitabine. Moreover, we demonstrate in colorectal cancer that although TPC and TProg are both tumorigenic, TPC (i.e. CSC) are more resistant to chemotherapy. Our ability to precisely identify the most tumorigenic, chemoresistant subpopulation of tumors facilitates the identification of genes and proteins associated with tumorigenicity and chemoresistance and will therefore enable the identification of genes/proteins of great diagnostic and/or therapeutic utility.

Example 7

Hierarchy of Cells within Colorectal Tumors

As discussed above, TProg are categorized as a subpopulation of TIC due, in part, to their limited ability to generate tumors in mice. TProg are progeny of TPC and are typically capable of a finite number of non-self-renewing cell divisions. Moreover, there is precedent in the hematopoietic cell hierarchy, for example, for several distinct progenitor cell populations that maintain multilineage differentiation potential, but have differing capacity for proliferation prior to committing to defined cell fates. Representative examples of progenitors in the hematopoietic system are short-term reconstituting hematopoietic stem cells (ST-HSC) and multipotent progenitor (MPP) cells. Although both cell populations can fully reconstitute the hematopoietic system, neither can do so indefinitely (i.e. they lack of self-renewal capacity inherent to true stem cells) and ST-HSC can do so for a longer period of time than MPP (which are progeny of ST-HSC). Although the hierarchy of cells in both solid tissues and tumors originating in these tissues is ill-defined, a hierarchy of cells likely exists within many organs and tumors wherein distinct cell subpopulations possess different proliferation and differentiation potential. We demonstrate here for the first time that not only can TProg exist as a subset of TIC within colorectal cancer, but TProg cells may be further subdivided into early tumor progenitor (ETP) and late tumor progenitor (LTP) cells. Each of these respective TProg cell populations may be distinguished by phenotype (e.g., cell surface markers) and their progressively lesser capacity for proliferation and differentiation potential, and thus differing in their overall capacity to recapitulate certain tumor architecture.

Figure 26A:
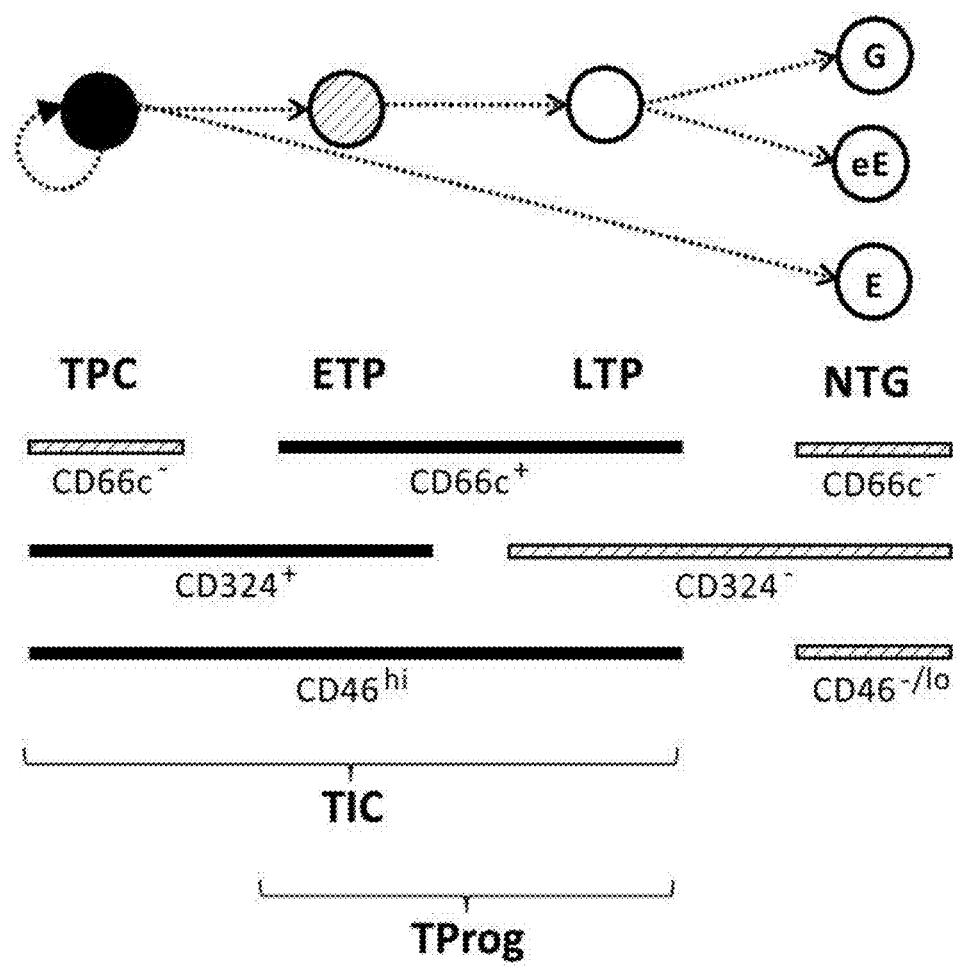
FIGS. 26A and 26B are schematic representations reflecting the cellular hierarchy in a subset of colorectal cancer patients as delineated by the instant disclosure.
Figure 26B:
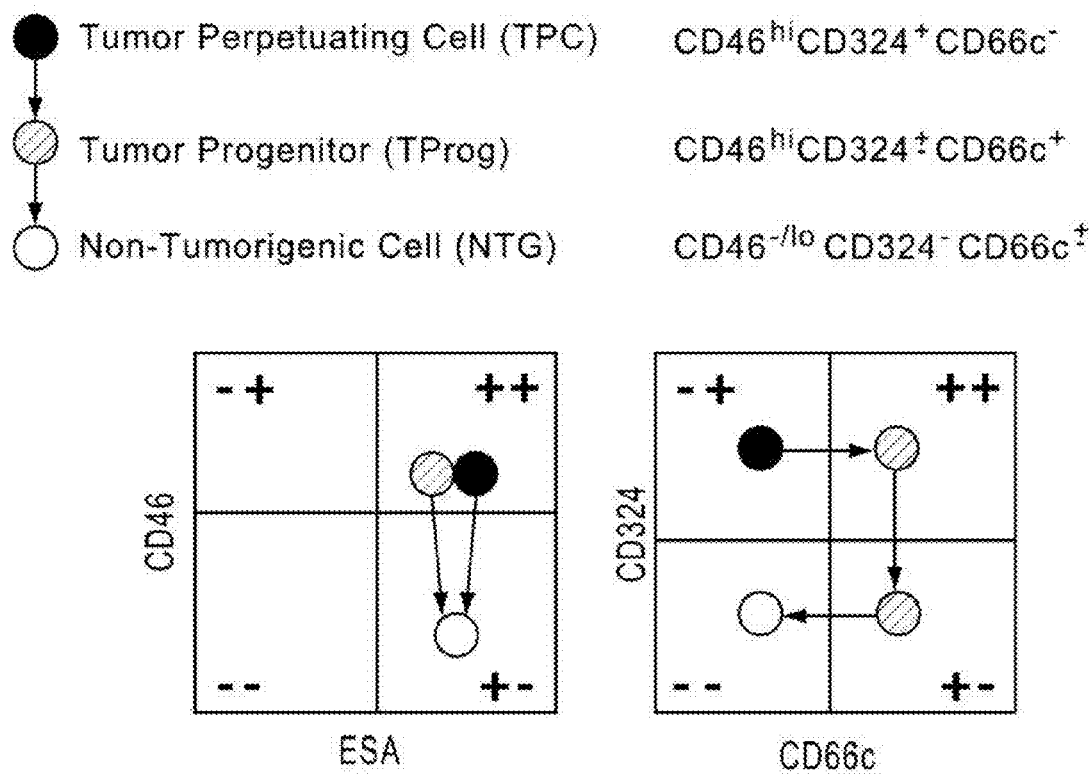

As illustrated in FIGS. 26A and 26B, the above described in vivo and in vitro data, together with tumor histomorphological observations, supports the hypothesis that in many tumors where there exists significant differentiation capacity and the ability to enact these differentiation programs, the TPC may reflect the identity of the normal colon stem cell, for example, which we herein propose has the identity of ESA$^+$ CD46$^{hi}$ CD324$^+$ CD66c$^-$ CD24$^+$ CD34$^-$. We have herein demonstrated that virtually all colorectal tumor cells are ESA$^+$ CD24$^+$ CD34$^-$ and thus these markers serve little utility in identifying tumor cell subpopulations. We further demonstrated that CD46$^{hi}$ CD324$^+$ CD66c$^-$ cells are able to generate fully heterogeneous tumors consisting, in part, of CD46$^{hi}$ CD324$^+$ CD66c$^-$ and CD66c$^+$ cells, whereas although CD46$^{hi}$ CD324$^+$ CD66c$^+$ cells are tumorigenic, they do not have the ability to generate CD46$^{hi}$ CD324$^+$ CD66c$^-$ cells and are unable to efficiently fuel tumor growth through serial transplantation. This data, combined with the observations that the cells with the a) ability to consistently generate heterogeneous tumors upon serial transplantation; b) most colony forming cell potential; and c) potential to generate CD66c cells and protein in vitro are CD46$^{hi}$ CD324$^+$ CD66c$^-$ cells supports the hypothesis that CD46$^{hi}$ CD324$^+$ CD66c$^+$ cells are daughters of CD46$^{hi}$ CD324$^+$ CD66c$^-$ cells with restricted proliferation capacity and potential. The further reduction in in vivo tumorigenicity, in vitro colony forming potential and reduced ability to generate CD66c as cells lose expression of CD324 supports the hypothesis that CD46$^{hi}$ CD324$^-$ CD66$^+$ cells represent a late tumor progenitor (LTP) cell population that has some residual proliferative ability, as has been demonstrated on occasion, but generally has no capacity for self-renewal. Finally, in support of the cellular hierarchy laid out in FIG. 26A, CD46$^-$ cells are also CD324$^-$ and are generally CD66c$^-$ as well. These NTG cells likely represent the terminally differentiated progeny, which in the colon include goblet cells (G) and enteroendocrine (eE) cells of the secretory lineage or enterocytes (E) of the absorptive lineage, which have been demonstrated to be present with specific histochemical stains such as mucicarmine to identify mucin-generating goblet cells. Gene expression of the isolated cell subpopulations also support this hypothesis as CD46$^-$ cells express many genes attributed to terminally differentiated secretory and/or absorptive cell types such as, for example, MUC20 (FIG. 27D).

The Examples above surprisingly document the existence of multiple populations of tumor initiating cells that are characterized by their differing abilities to generate tumors when implanted in mice and are associated with unique marker phenotypes. Moreover, the discrete subpopulations of TIC differ in their ability to self-renew and fully reconstitute a tumor. Tumor perpetuating cells (TPC), as they are defined here, fulfill the prevailing definition of a cancer stem cell (CSC) in their demonstrated capacity for self-renewal, as tested by serial transplantation with small numbers of well defined cells and analysis of resulting tumor heterogeneity. Conversely, tumor progenitor (TProg) cells, although tumorigenic in primary transplants, differ from true TPC or CSC in that they appear deficient of self-renewal capacity and their differentiation potential may, on occasion, be restricted. The above Examples also demonstrate the existence of discrete TProg cell populations with progressively less proliferation and differentiation potential: ETP and LTP. Knowledge of these cell identities in the context of cancer, and potentially normal tissue biology, facilitate their use to identify proteins and molecules of diagnostic and therapeutic utility. As diagrammed in FIGS. 26A and 26B, and documented in the instant disclosure, heterogeneous colorectal tumors comprising tumorigenic and NTG cell populations provide TPC, whose progeny progress from a CD46$^{hi}$ CD324$^+$ CD66c$^-$ phenotype to gain expression of CD66c (taking the identity of ETP) and eventually lose expression of CD324 (LTP phenotype). Finally, terminal differentiation is apparently accompanied by the concomitant loss of CD66c and CD46.

Example 8

Identification of Prospective Diagnostic and Therapeutic Targets from Enriched Tumor Initiating Cell Populations The established colorectal NTX tumor line SCRx-CR4, for example, was passaged as described in Example 1 and used to initiate tumors in immunocompromised mice. Once the mean tumor burden reached ~300 mm$^3$ the mice were randomized and treated with 15 mg/kg irinotecan or vehicle control (PBS) twice weekly for a period of at least twenty days before they were sacrificed. Tumors were then removed and TPC, TProg and NTG cells, respectively, were isolated generally using the technique set out in Example 2. More particularly, cell populations were isolated by FACS and immediately pelleted and lysed in Qiagen RLTplus RNA lysis buffer (Qiagen, Inc.). The lysates were then stored at −80° C. until used. Upon thawing, total RNA was extracted using the Qiagen RNeasy isolation kit (Qiagen, Inc.) following vendor's instructions, and quantified on the Nanodrop (Thermo Scientific) and a Bioanalyzer 2100 (Agilent) again using the vendor's protocols and recommended instrument settings. The resulting total RNA preparation was suitable for genetic sequencing and analysis.

Total RNA samples obtained from the respective cell populations isolated as described above from vehicle or irinotecan-treated mice were prepared for whole transcriptome sequencing using an Applied Biosystems SOLiD 3.0 (Sequencing by Oligo Ligation/Detection) next generation sequencing platform (Life Technologies), starting with ≥5 ng of total RNA per sample. The data generated by the SOLiD platform mapped to 34,609 genes from the human genome, was able to detect transcripts of interest along with verifiable measurements of transcript expression levels in all samples.

Generally the SOLiD3 next generation sequencing platform enables parallel sequencing of clonally-amplified RNA/DNA fragments linked to beads. Sequencing by ligation with dye-labeled oligonucleotides is then used to generate 50 base reads of each fragment that exists in the sample with a total of greater than 50 million reads per sample generating a much more accurate representation of the mRNA transcript level expression of proteins in the genome. The SOLiD3 platform is able to capture not only expression, but SNPs, known and unknown alternative splicing events, and potentially new exon discoveries based solely on the read coverage (reads mapped uniquely to genomic locations). Thus, use of this next generation platform allowed the determination of differences in transcript level expression as well as differences or preferences for specific splice variants of those expressed mRNA transcripts. Moreover, analysis with the SOLiD3 platform using a modified whole transcriptome protocol from Applied Biosystems only required approximately 5 ng of starting material pre-amplification. This is significant as extraction of total RNA from sorted cell populations where the TPC subset of cells is, for example, vastly smaller in number than the NTG or bulk tumors and thus results in very small quantities of usable starting material.

Duplicate runs of sequencing data from the SOLiD3 platform were normalized and transformed and fold ratios calculated, as is standard industry practice. In this manner, transcript gene expression levels (expressed as reads per million mapped to exons; RPM_Exon) were measured in NTG cells (white), TProg (gray) and TPC (black bars), which were isolated from SCRx-CR4 tumors (FIG. 27). Analysis of whole transcriptome data in this manner identified several proteins and potential therapeutic targets of interest, including APCDD1, Notum, REG1A and MUC20. An analysis of the data showed that these proteins of interest were up-regulated at the transcript level at least 2-fold greater than expression in NTG cells in vehicle and irinotecan-treated mice (FIG. 27A-C). Representative examples of prospective diagnostic and therapeutic target transcripts identified in this manner include NOTUM (FIG. 27A), APCDD1 (FIG. 27B), REG1A (FIG. 27C). Expression of these transcripts in TPC implies that these proteins are also preferentially expressed (i.e. APCDD1) or secreted (i.e. REG1A and NOTUM) by TPC cells at the protein level and that these proteins are critical for TPC maintenance and/or self renewal. It was concomitantly possible to identify transcripts preferentially expressed by NTG cell populations (e.g. MUC20; FIG. 27D), which may be used as markers to identify and/or enumerate terminally differentiated cells, and in so doing facilitate a negative selection where in tumors are depleted of their bulk tumor cell population such that the more tumorigenic components can been more easily identified and/or targeted with therapeutic regimens. Furthermore, because NTG cells are generally more numerous than their TProg and TPC counterparts, proteins expressed by these cell populations will be easier to detect, thus serving as biomarkers of disease burden and/or status.

Example 9

TICAM Define Tumorigenic Cell Populations

As further evidence that TICAM may be used to characterize, define and enrich tumorigenic cell populations, cells were sorted as previously described and the resulting phenotypically homogeneous subpopulations were implanted into immunocompromised mice. More specifically human tumor cells from the pancreatic tumor xenograft PA20 were isolated from mice using standard enzymatic digestion. The cells were then plated onto Primaria (Beckton Dickinson) treated plates and cultured as described above with fresh media twice weekly for 28 days. At this point the cultures were harvested enzymatically and phenotyped using TICAM antibodies in accordance with the instant teachings. Cells were then sorted and injected into NOD/SCID mice based upon their phenotype. In particular a total of 166 $CD46^{hi}CD324^+$ cells, a total of 166 $CD46^-$ $CD324^-$ and 166 unsorted cultured cells were transplanted, respectively, in the immunocompromised mice. The results are shown in FIG. 28 appended hereto.

Figure 28:
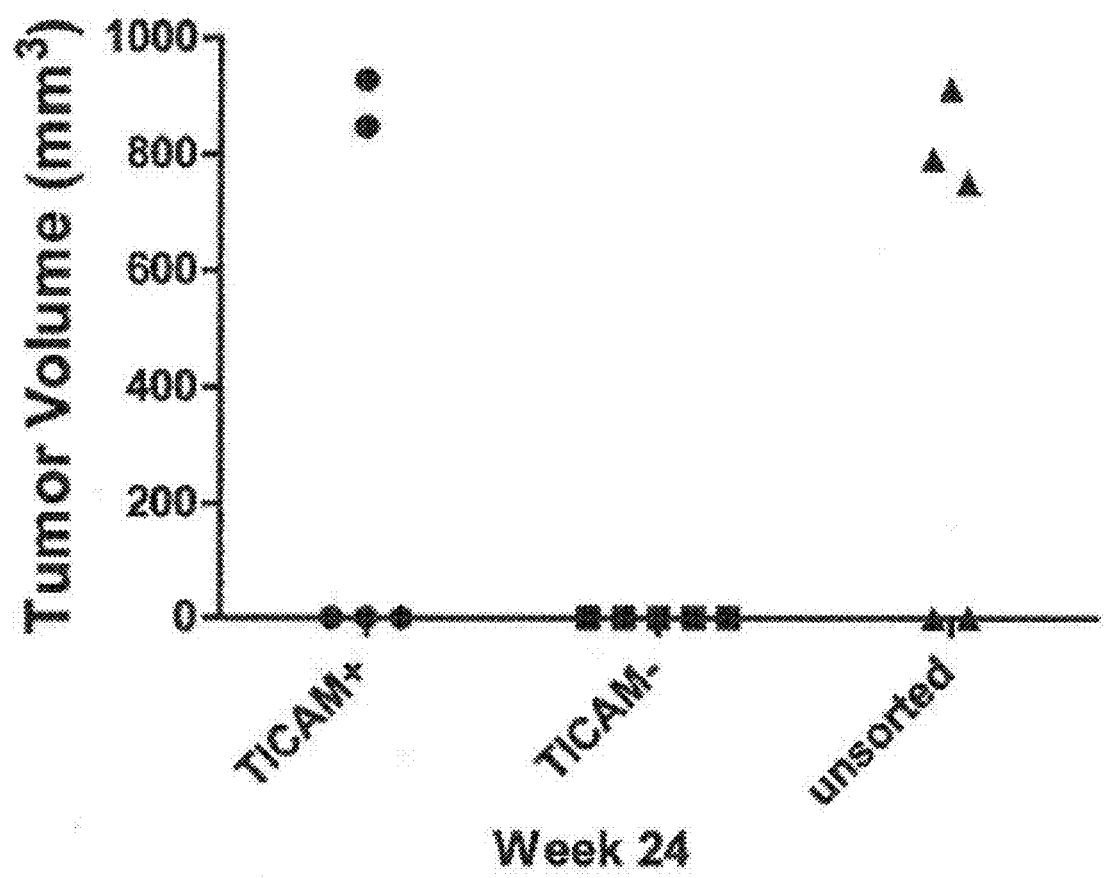
FIG. 28 illustrates the ability of disclosed TICAM to define tumorigenic cell subpopulations that retain the ability to recapitulate the parent tumor upon implantation in immunocompromised mice.

After 20 weeks in the mice FIG. 28 shows that tumors grew (as represented by measured tumor volume) only in mice implanted with the TICAM positive group and in mice implanted with the unsorted cells. Significantly, injecting human tumor cells into mice that were not phenotypically positive for TICAM resulted in no tumor-formation.

In order to determine if the implanted population maintained TICAM heterogeneity as it grew (i.e., recapitulated the parent tumor) or if it had become more homogenous as a result of culturing in vitro prior to implantation, tumors were harvested and phenotyped using the exemplary TICAM CD46 and CD324. The resulting phenotypes were heterogeneous and similar to the parental phenotype. Additionally, formalin fixed paraffin embedded histology obtained from these tumors were very similar to the parental histology (data not shown). These data further illustrate that the disclosed TICAM may be used to define and segregate tumor cell subpopulations as well as being to track TPC in vitro and in vivo. Moreover, the TICAM defined TPC prove able to give rise to tumors in vivo that are phenotypically and histologically indistinguishable from the parental tumor despite being cultured in vitro.

As discussed above, this ability to define, track and characterize tumor cell subpopulations in vitro and in vivo allows for the monitoring of tumorigenic cells as they are subject to different conditions. Because TICAM mark cells of primordial differentiation status, the retention or loss of these markers can be used to identify compounds that promote or inhibit cellular differentiation. For instance, tumor cells may be cultured in vitro under conditions favoring retention of TICAM expression and exposed to chemical or biological agents comprising potential therapeutic compounds. By monitoring the cells for loss of TICAM expression the methods of the instant invention provide an indication that the subject agent induces differentiation or otherwise reduces the frequency of the TPC. As previously indicated such compounds might prove to be useful as anti-cancer agents as an induction of differentiation and lineage commitment is often tied to a loss of replicative capacity. Conversely, tumor cells cultured in conditions favoring differentiation and lineage commitment may be exposed to various agents and monitored for retention of TICAM expression, indicating that the subject agent prevents differentiation and lineage commitment. Such compounds could be useful for the expansion of normal stem cells and could have utility in wound healing or anti-aging applications.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A method of producing an animal model comprising implanting a subject animal with an enriched tumorigenic cell population comprising tumorigenic cells and an anti-CD46 antibody associated with a detectable agent, wherein the tumorigenic cells have a marker phenotype comprising $CD46^{hi}$, and wherein the detectable agent comprises a fluorescent tag.

2. The method of claim 1, wherein the enriched tumorigenic cell population is derived from a solid tumor obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, and skin cancer.

3. The method of claim 2, wherein the subject animal is an immunodeficient mouse.

4. The method of claim 3, wherein the immunodeficient mouse is selected from the group consisting of a nude mouse, a SCID mouse, a NOD/SCID mouse and a Beige/SCID mouse.

5. The method of claim 1, wherein the enriched tumorigenic cell population further comprises an anti-CD324 antibody associated with a second detectable agent and wherein the tumorigenic cells have a marker phenotype comprising $CD46^{hi}CD324^+$.

6. The method of claim 5, wherein the tumorigenic cells have a marker phenotype comprising $CD46^{hi}CD324^+$ $CD66c^-$.

7. The method of claim 1, wherein the enriched tumorigenic cell population is derived from a tumor that has been passaged through a non-human mammal.

8. A method of producing an animal model comprising implanting a subject animal with an enriched tumorigenic cell population comprising tumorigenic cells having a marker phenotype comprising $CD46^{hi}CD324^+$, an anti-CD46 antibody associated with a first detectable agent, and an anti-CD324 antibody associated with a second detectable agent, wherein the detectable agent comprises a fluorescent tag.

9. The method of claim 8, wherein the subject animal is an immunodeficient mouse.

10. The method of claim 9, wherein the immunodeficient mouse is selected from the group consisting of a nude mouse, a SCID mouse, a NOD/SCID mouse and a Beige/SCID mouse.

11. The method of claim 8, wherein the enriched tumorigenic cell population is derived from a solid tumor obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, and skin cancer.

12. The method of claim 8, wherein the enriched tumorigenic cell population is derived from a tumor that has been passaged through a non-human mammal.

13. The method of claim 8, wherein the tumorigenic cells have a marker phenotype comprising $CD46^{hi}CD324^+$ $CD66c^-$.

14. A method of producing an immunodeficient mouse animal model comprising implanting an immunodeficient mouse with an enriched tumorigenic cell population comprising tumorigenic cells having a marker phenotype comprising $CD46^{hi}$ and an anti-CD46 antibody associated with a detectable agent, wherein the detectable agent comprises a fluorescent tag.

15. The method of claim 14, wherein the immunodeficient mouse is selected from the group consisting of a nude mouse, a SCID mouse, a NOD/SCID mouse and a Beige/SCID mouse.

16. The method of claim 14, wherein the enriched tumorigenic cell population is derived from a solid tumor obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, and skin cancer.

17. The method of claim 14, wherein the enriched tumorigenic cell population is derived from a tumor that has been passaged through a non-human mammal.

18. The method of claim 14, wherein the enriched tumorigenic cell population further comprises an anti-CD324 antibody associated with a second detectable agent and wherein the tumorigenic cells have a marker phenotype comprising $CD46^{hi}CD324^+$.

19. The method of claim 18, wherein the tumorigenic cells have a marker phenotype comprising $CD46^{hi}CD324^+$ $CD66c^-$.

20. A method of producing an immunodeficient mouse animal model comprising implanting an immunodeficient mouse with an enriched tumorigenic cell population comprising tumorigenic cells having a marker phenotype comprising $CD46^{hi}CD324^+$, an anti-CD46 antibody associated with a first detectable agent, and an anti-CD324 antibody associated with a second detectable agent, wherein the detectable agent comprises a fluorescent tag.

21. The method of claim 20, wherein the immunodeficient mouse is selected from the group consisting of a nude mouse, a SCID mouse, a NOD/SCID mouse and a Beige/SCID mouse.

22. The method of claim 20, wherein the enriched tumorigenic cell population is derived from a solid tumor obtained from a subject suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer, breast cancer, head & neck cancer, and skin cancer.

23. The method of claim 20, wherein the enriched tumorigenic cell population is derived from a tumor that has been passaged through a non-human mammal.

24. The method of claim 20, wherein the tumorigenic cells have a marker phenotype comprising $CD46^{hi}CD324^+$ $CD66c^-$.

\* \* \* \* \*

UNITED STATES PATENT AND TRADEMARK OFFICE
CERTIFICATE OF CORRECTION

PATENT NO.       : 9,778,264 B2                                                Page 1 of 1
APPLICATION NO.  : 14/454107
DATED            : October 3, 2017
INVENTOR(S)      : Dylla et al.

It is certified that error appears in the above-identified patent and that said Letters Patent is hereby corrected as shown below:

On the Title Page

At item (63) under the "Related U.S. Application Data," the text "said application No. 13,820,061 is a continuation of application No. PCT/US2011/050451, filed on Sep. 2, 2011." should be changed to
-- said application No. 13/820,061 is a 371 of PCT/US2011/050451, filed on Sep. 2, 2011. --

Signed and Sealed this
Twenty-seventh Day of February, 2018

Andrei Iancu
*Director of the United States Patent and Trademark Office*